US011414599B2

(12) United States Patent
Tong et al.

(10) Patent No.: US 11,414,599 B2
(45) Date of Patent: *Aug. 16, 2022

(54) POLYMERIZABLE COMPOUNDS AND THE USE THEREOF IN LIQUID-CRYSTAL DISPLAYS

(71) Applicant: MERCK PATENT GMBH, Darmstadt (DE)

(72) Inventors: Qiong Tong, Darmstadt (DE); Nico Schwebel, Fischbachtal (DE); Constanze Brocke, Gross-Gerau (DE); Kaja Christina Deing, Darmstadt (DE); Julian Vogt, Griesheim (DE); Elisabeth Meyer, Langenselbold (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/855,447

(22) Filed: Apr. 22, 2020

(65) Prior Publication Data

US 2020/0248078 A1  Aug. 6, 2020

Related U.S. Application Data

(62) Division of application No. 16/400,647, filed on May 1, 2019, now Pat. No. 11,225,606, which is a division of application No. 15/175,634, filed on Jun. 7, 2016, now Pat. No. 10,344,215.

(30) Foreign Application Priority Data

Jun. 9, 2015 (EP) .................... 15001706

(51) Int. Cl.
C09K 19/54 (2006.01)
C09K 19/30 (2006.01)
C07C 69/017 (2006.01)
C07C 67/08 (2006.01)
C07C 235/60 (2006.01)
C07C 231/12 (2006.01)
C09K 19/04 (2006.01)
C09K 19/12 (2006.01)

(52) U.S. Cl.
CPC ............ *C09K 19/542* (2013.01); *C07C 67/08* (2013.01); *C07C 69/017* (2013.01); *C07C 231/12* (2013.01); *C07C 235/60* (2013.01); *C09K 19/04* (2013.01); *C09K 19/3003* (2013.01); *C09K 19/3098* (2013.01); *C09K 2019/0448* (2013.01); *C09K 2019/0481* (2013.01); *C09K 2019/122* (2013.01); *C09K 2019/123* (2013.01); *C09K 2019/301* (2013.01); *C09K 2019/3004* (2013.01); *C09K 2019/3009* (2013.01); *C09K 2019/3016* (2013.01); *C09K 2019/3027* (2013.01); *C09K 2019/548* (2013.01)

(58) Field of Classification Search
CPC ..................................................... C09K 19/30
See application file for complete search history.

(56) References Cited

U.S. PATENT DOCUMENTS

| 4,746,721 | A | 5/1988 | Ueno et al. |
| 8,647,530 | B2 | 2/2014 | Kuriyama et al. |
| 8,765,013 | B2 | 7/2014 | Kurisawa et al. |
| 9,580,653 | B2 | 2/2017 | Archetti |
| 9,725,651 | B2 | 8/2017 | Hirata et al. |
| 10,077,401 | B2 | 9/2018 | Kobayashi |
| 10,323,186 | B2 | 6/2019 | Sudo et al. |
| 2004/0002576 | A1* | 1/2004 | Oguma ............... C08G 61/125 528/4 |
| 2010/0309423 | A1 | 12/2010 | Bematz |
| 2012/0292568 | A1 | 11/2012 | Kuriyama et al. |
| 2013/0299741 | A1 | 11/2013 | Zhong |
| 2015/0102259 | A1 | 4/2015 | Gotoh et al. |
| 2015/0322342 | A1* | 11/2015 | Archetti ............... C09K 19/32 252/299.62 |
| 2016/0046863 | A1 | 2/2016 | Archetti et al. |
| 2016/0053178 | A1 | 2/2016 | Hirschmann et al. |
| 2016/0075950 | A1 | 3/2016 | Kobayashi et al. |
| 2016/0376506 | A1 | 12/2016 | Saito |

FOREIGN PATENT DOCUMENTS

| EP | 2985334 A1 | 2/2016 |
| EP | 2990460 A1 | 3/2016 |
| JP | S62164722 A | 7/1987 |
| JP | 1180854 A2 | 7/1989 |
| JP | 2007063322 A | 3/2007 |
| JP | 2012240945 A | 12/2012 |

(Continued)

OTHER PUBLICATIONS

Partial European Search Report for EP16001079 dated Dec. 13, 2016.
English Abstract of JP5593890, Publication Date: Sep. 24, 2014.
Office action in corresponding European application No. 16001079.9 dated Oct. 26, 2018 (pp. 1-3).
Office Action in corresponding CN application 201610402361.8 dated Jun. 18, 2020 (pp. 1-122) and English translation of same (pp. 1-16).
Yousi et al: "Non-Spacer Side Chain Liquid Crystalline . . . ": Polymeric Materials Science and Engineering 1991, 5, 31-35 (with English Abstract).

(Continued)

Primary Examiner — Chanceity N Robinson
(74) Attorney, Agent, or Firm — Millen, White, Zelano and Branigan, P.C.; Harry B. Shubin

(57) ABSTRACT

The present invention relates to polymerizable compounds, to processes and intermediates for the preparation thereof, to liquid-crystal media comprising them, and to the use of the polymerizable compounds and liquid crystalline media for optical, electro-optical and electronic purposes, in particular in liquid crystalline displays, especially in liquid crystalline displays of the polymer sustained alignment type.

12 Claims, No Drawings

(56) References Cited

FOREIGN PATENT DOCUMENTS

| | | | | |
|---|---|---|---|---|
| JP | 2012241125 A | 12/2012 | | |
| JP | 5593890 B2 | 9/2014 | | |
| JP | 2014261948 A | * 12/2014 | | |
| WO | 2014090362 A1 | 6/2014 | | |
| WO | WO-2014090362 A1 | * 6/2014 | ............ | C09K 19/04 |
| WO | 14148472 A1 | 9/2014 | | |
| WO | 2014174929 A1 | 10/2014 | | |
| WO | WO-2014174929 A1 | * 10/2014 | ............ | C08F 218/12 |
| WO | 2015004947 A1 | 1/2015 | | |
| WO | 2015004954 A1 | 1/2015 | | |
| WO | 16104165 A1 | 6/2016 | | |
| WO | WO-2016104165 A1 | * 6/2016 | ............ | C08F 120/10 |

OTHER PUBLICATIONS

Notice for Reasons for Rejection JP application 2016-113209 dated Jun. 12, 2020 (pp. 1-12).
PTO form 892 is copending U.S. Appl. No. 16/400,647 dated Dec. 16, 2020 (1 page).
PTO form 892 is copending U.S. Appl. No. 16/400,647 dated May 25, 2021(1 page).
Notice of Reasons for Rejection in corresponding JP appln. No. 2021-016241 dispatched Feb. 8, 2022 (pp. 1-5).

* cited by examiner

POLYMERIZABLE COMPOUNDS AND THE USE THEREOF IN LIQUID-CRYSTAL DISPLAYS

The present invention relates to polymerizable compounds, to processes and intermediates for the preparation thereof, to liquid-crystal (LC) media comprising them, and to the use of the polymerizable compounds and LC media for optical, electro-optical and electronic purposes, in particular in LC displays, especially in LC displays of the polymer sustained alignment type.

One of the liquid-crystal display (LCD) modes used at present is the TN ("twisted nematic") mode. However, TN LCDs have the disadvantage of a strong viewing-angle dependence of the contrast.

In addition, so-called VA ("vertically aligned") displays are known which have a broader viewing angle. The LC cell of a VA display contains a layer of an LC medium between two transparent electrodes, where the LC medium usually has a negative dielectric anisotropy. In the switched-off state, the molecules of the LC layer are aligned perpendicular to the electrode surfaces (homeotropically) or have a tilted homeotropic alignment. On application of an electrical voltage to the two electrodes, a realignment of the LC molecules parallel to the electrode surfaces takes place.

Furthermore, OCB ("optically compensated bend") displays are known which are based on a birefringence effect and have an LC layer with a so-called "bend" alignment and usually positive dielectric anisotropy. On application of an electrical voltage, a realignment of the LC molecules perpendicular to the electrode surfaces takes place. In addition, OCB displays normally contain one or more birefringent optical retardation films in order to prevent undesired transparency to light of the bend cell in the dark state. OCB displays have a broader viewing angle and shorter response times compared with TN displays.

Also known are so-called IPS ("in-plane switching") displays, which contain an LC layer between two substrates, where the two electrodes are arranged on only one of the two substrates and preferably have intermeshed, comb-shaped structures. On application of a voltage to the electrodes, an electric field which has a significant component parallel to the LC layer is thereby generated between them. This causes realignment of the LC molecules in the layer plane.

Furthermore, so-called FFS ("fringe-field switching") displays have been reported (see, inter alia, S. H. Jung et al., Jpn. J. Appl. Phys., Volume 43, No. 3, 2004, 1028), which contain two electrodes on the same substrate, one of which structured in a comb-shaped manner and the other is unstructured. A strong, so-called "fringe field" is thereby generated, i.e. a strong electric field close to the edge of the electrodes, and, throughout the cell, an electric field which has both a strong vertical component and also a strong horizontal component. FFS displays have a low viewing-angle dependence of the contrast. FFS displays usually contain an LC medium with positive dielectric anisotropy, and an alignment layer, usually of polyimide, which provides planar alignment to the molecules of the LC medium.

FFS displays can be operated as active-matrix or passive-matrix displays. In the case of active-matrix displays, individual pixels are usually addressed by integrated, non-linear active elements, such as, for example, transistors (for example thin-film transistors ("TFTs")), while in the case of passive-matrix displays, individual pixels are usually addressed by the multiplex method, as known from the prior art.

Furthermore, FFS displays have been disclosed (see S. H. Lee et al., Appl. Phys. Lett. 73(20), 1998, 2882-2883 and S. H. Lee et al., Liquid Crystals 39(9), 2012, 1141-1148), which have similar electrode design and layer thickness as FFS displays, but comprise a layer of an LC medium with negative dielectric anisotropy instead of an LC medium with positive dielectric anisotropy. The LC medium with negative dielectric ansiotropy shows a more favourable director orientation that has less tilt and more twist orientation compared to the LC medium with positive dielectric anisotropy, as a result of which these displays have a higher transmission. The displays further comprise an alignment layer, preferably of polyimide provided on at least one of the substrates that is in contact with the LC medium and induces planar alignment of the LC molecules of the LC medium. These displays are also known as "Ultra Brightness FFS (UB-FFS)" mode displays. These displays require an LC medium with high reliability.

The term "reliability" as used hereinafter means the quality of the performance of the display during time and with different stress loads, such as light load, temperature, humidity, voltage, and comprises display effects such as image sticking (area and line image sticking), mura, yogore etc. which are known to the skilled person in the field of LC displays. As a standard parameter for categorising the reliability usually the voltage holding ration (VHR) value is used, which is a measure for maintaining a constant electrical voltage in a test display. The higher the VHR value, the better the reliability of the LC medium.

In VA displays of the more recent type, uniform alignment of the LC molecules is restricted to a plurality of relatively small domains within the LC cell. Disclinations may exist between these domains, also known as tilt domains. VA displays having tilt domains have, compared with conventional VA displays, a greater viewing-angle independence of the contrast and the grey shades. In addition, displays of this type are simpler to produce since additional treatment of the electrode surface for uniform alignment of the molecules in the switched-on state, such as, for example, by rubbing, is no longer necessary. Instead, the preferential direction of the tilt or pretilt angle is controlled by a special design of the electrodes.

In so-called MVA ("multidomain vertical alignment") displays, this is usually achieved by the electrodes having protrusions which cause a local pretilt. As a consequence, the LC molecules are aligned parallel to the electrode surfaces in different directions in different, defined regions of the cell on application of a voltage. "Controlled" switching is thereby achieved, and the formation of interfering disclination lines is prevented. Although this arrangement improves the viewing angle of the display, it results, however, in a reduction in its transparency to light. A further development of MVA uses protrusions on only one electrode side, while the opposite electrode has slits, which improves the transparency to light. The slitted electrodes generate an inhomogeneous electric field in the LC cell on application of a voltage, meaning that controlled switching is still achieved. For further improvement of the transparency to light, the separations between the slits and protrusions can be increased, but this in turn results in a lengthening of the response times. In so-called PVA ("patterned VA") displays, protrusions are rendered completely superfluous in that both electrodes are structured by means of slits on the opposite sides, which results in increased contrast and improved transparency to light, but is technologically difficult and makes the display more sensitive to mechanical influences ("tapping", etc.). For many applications, such as, for example, monitors and especially TV screens, however, a shortening of the response times and an improvement in the contrast and luminance (transmission) of the display are demanded.

A further development are displays of the so-called PS ("polymer sustained") or PSA ("polymer sustained alignment") type, for which the term "polymer stabilized" is also occasionally used. In these, a small amount (for example 0.3% by weight, typically <1% by weight) of one or more polymerizable, compound(s), preferably polymerizable monomeric compound(s), is added to the LC medium and, after filling the LC medium into the display, is polymerized or crosslinked in situ, usually by UV photopolymerization, optionally while a voltage is applied to the electrodes of the display. The polymerization is carried out at a temperature where the LC medium exhibits a liquid crystal phase, usually at room temperature. The addition of polymerizable mesogenic or liquid-crystalline compounds, also known as reactive mesogens or "RMs", to the LC mixture has proven particularly suitable.

Unless indicated otherwise, the term "PSA" is used hereinafter when referring to displays of the polymer sustained alignment type in general, and the term "PS" is used when referring to specific display modes, like PS-VA, PS-TN and the like.

Also, unless indicated otherwise, the term "RM" is used hereinafter when referring to a polymerizable mesogenic or liquid-crystalline compound.

In the meantime, the PS(A) principle is being used in various conventional LC display modes. Thus, for example, PS-VA, PS—OCB, PS-IPS, PS—FFS, PS—UB—FFS and PS-TN displays are known. The polymerization of the RMs preferably takes place with an applied voltage in the case of PS-VA and PS-OCB displays, and with or without, preferably without, an applied voltage in the case of PS-IPS displays. As can be demonstrated in test cells, the PS(A) method results in a pretilt in the cell. In the case of PS-OCB displays, for example, it is possible for the bend structure to be stabilized so that an offset voltage is unnecessary or can be reduced. In the case of PS-VA displays, the pretilt has a positive effect on response times. For PS-VA displays, a standard MVA or PVA pixel and electrode layout can be used. In addition, however, it is also possible, for example, to manage with only one structured electrode side and no protrusions, which significantly simplifies production and at the same time results in very good contrast at the same time as very good transparency to light.

Furthermore, the so-called posi-VA displays ("positive VA") have proven to be a particularly suitable mode. Like in classical VA displays, the initial orientation of the LC molecules in posi-VA displays is homeotropic, i.e. substantially perpendicular to the substrates, in the initial state when no voltage is applied. However, in contrast to classical VA displays, in posi-VA displays LC media with positive dielectric anisotropy are used. Like in the usually used IPS displays, the two electrodes in posi-VA displays are arranged on only one of the two substrates, and preferably exhibit intermeshed and comb-shaped (interdigital) structures. By application of a voltage to the interdigital electrodes, which create an electrical field that is substantially parallel to the layer of the LC medium, the LC molecules are transferred into an orientation that is substantially parallel to the substrates.

In posi-VA displays polymer stabilisation, by addition of RMs to the LC medium which are polymerized in the display, has also proven to be advantageous, as a significant reduction of the switching times could thereb< be realised.

PS-VA displays are described, for example, in EP 1 170 626 A2, U.S. Pat. Nos. 6,861,107, 7,169,449, US 2004/0191428 A1, US 2006/0066793 A1 and US 2006/0103804 A1. PS-OCB displays are described, for example, in T.-J-Chen et al., Jpn. J. Appl. Phys. 45, 2006, 2702-2704 and S. H. Kim, L.-C-Chien, Jpn. J. Appl. Phys. 43, 2004, 7643-7647. PS-IPS displays are described, for example, in U.S. Pat. No. 6,177,972 and Appl. Phys. Lett. 1999, 75(21), 3264. PS-TN displays are described, for example, in Optics Express 2004, 12(7), 1221.

Like the conventional LC displays described above, PSA displays can be operated as active-matrix or passive-matrix displays. In the case of active-matrix displays, individual pixels are usually addressed by integrated, non-linear active elements, such as, for example, transistors (for example thin-film transistors ("TFTs")), while in the case of passive-matrix displays, individual pixels are usually addressed by the multiplex method, as known from the prior art.

The PSA display may also comprise an alignment layer on one or both of the substrates forming the display cell. The alignment layer is usually applied on the electrodes (where such electrodes are present) such that it is in contact with the LC medium and induces initial alignment of the LC molecules. The alignment layer may comprise or consist of, for example, a polyimide, which may also be rubbed, or may be prepared by a photoalignment method.

In particular for monitor and especially TV applications, optimisation of the response times, but also of the contrast and luminance (thus also transmission) of the LC display continues to be demanded. The PSA method can provide significant advantages here. In particular in the case of PS-VA, PS-IPS, PS—FFS and PS-posi-VA displays, a shortening of the response times, which correlate with a measurable pretilt in test cells, can be achieved without significant adverse effects on other parameters.

Prior art has suggested biphenyl diacrylates or dimethacrylates, which are optionally fluorinated as RMs for use in PSA displays However, the problem arises that not all combinations consisting of an LC mixture and one or more RMs are suitable for use in PSA displays because, for example, an inadequate tilt or none at all becomes established or since, for example, the so-called "voltage holding ratio" (VHR or HR) is inadequate for TFT display applications. In addition, it has been found that, on use in PSA displays, the LC mixtures and RMs known from the prior art do still have some disadvantages. Thus, not every known RM which is soluble in LC mixtures is suitable for use in PSA displays. In addition, it is often difficult to find a suitable selection criterion for the RM besides direct measurement of the pretilt in the PSA display. The choice of suitable RMs becomes even smaller if polymerization by means of UV light without the addition of photoinitiators is desired, which may be advantageous for certain applications.

In addition, the selected combination of LC host mixture/RM should have the lowest possible rotational viscosity and the best possible electrical properties. In particular, it should have the highest possible VHR. In PSA displays, a high VHR after irradiation with UV light is particularly necessary since UV exposure is a requisite part of the display production process, but also occurs as normal exposure during operation of the finished display.

In particular, it would be desirable to have available novel materials for PSA displays which produce a particularly small pretilt angle. Preferred materials here are those which produce a lower pretilt angle during polymerization for the same exposure time than the materials known to date, and/or through the use of which the (higher) pretilt angle that can be achieved with known materials can already be achieved after a shorter exposure time. The production time ("tact time") of the display could thus be shortened and the costs of the production process reduced.

A further problem in the production of PSA displays is the presence or removal of residual amounts of unpolymerized RMs, in particular after the polymerization step for production of the pretilt angle in the display. For example, unreacted RMs of this type may adversely affect the properties of the display by, for example, polymerizing in an uncontrolled manner during operation after finishing of the display.

Thus, the PSA displays known from the prior art often exhibit the undesired effect of so-called "image sticking" or "image burn", i.e. the image produced in the LC display by temporary addressing of individual pixels still remains visible even after the electric field in these pixels has been switched off or after other pixels have been addressed.

This "image sticking" can occur on the one hand if LC host mixtures having a low VHR are used. The UV component of daylight or the backlighting can cause undesired decomposition reactions of the LC molecules therein and thus initiate the production of ionic or free-radical impurities. These may accumulate, in particular, at the electrodes or the alignment layers, where they may reduce the effective applied voltage. This effect can also be observed in conventional LC displays without a polymer component.

In addition, an additional "image sticking" effect caused by the presence of unpolymerized RMs is often observed in PSA displays. Uncontrolled polymerization of the residual RMs is initiated here by UV light from the environment or by the backlighting. In the switched display areas, this changes the tilt angle after a number of addressing cycles. As a result, a change in transmission in the switched areas may occur, while it remains unchanged in the unswitched areas.

It is therefore desirable for the polymerization of the RMs to proceed as completely as possible during production of the PSA display and for the presence of unpolymerized RMs in the display to be excluded as far as possible or reduced to a minimum. Thus, RMs and LC mixtures are required which enable or support highly effective and complete polymerization of the RMs. In addition, controlled reaction of the residual RM amounts would be desirable. This would be simpler if the RM polymerized more rapidly and effectively than the compounds known to date.

A further problem that has been observed in the operation of PSA displays is the stability of the pretilt angle. Thus, it was observed that the pretilt angle, which was generated during display manufacture by polymerizing the RM as described above, does not remain constant but can deteriorate after the display was subjected to voltage stress during its operation. This can negatively affect the display performance, e.g. by increasing the black state transmission and hence lowering the contrast.

Another problem to be solved is that the RMs of prior art do often have high melting points, and do only show limited solubility in many currently common LC mixtures, and therefore frequently tend to spontaneously crystallise out of the mixture. In addition, the risk of spontaneous polymerization prevents the LC host mixture being warmed in order to dissolve the polymerizable component, meaning that the best possible solubility even at room temperature is necessary. In addition, there is a risk of separation, for example on introduction of the LC medium into the LC display (chromatography effect), which may greatly impair the homogeneity of the display. This is further increased by the fact that the LC media are usually introduced at low temperatures in order to reduce the risk of spontaneous polymerization (see above), which in turn has an adverse effect on the solubility.

Another problem observed in prior art is that the use of conventional LC media in LC displays, including but not limited to displays of the PSA type, often leads to the occurrence of mura in the display, especially when the LC medium is filled in the display cell manufactured using the one drop filling (ODF) method. This phenomenon is also known as "ODF mura". It is therefore desirable to provide LC media which lead to reduced ODF mura.

Another problem observed in prior art is that LC media for use in PSA displays, including but not limited to displays of the PSA type, do often exhibit high viscosities and, as a consequence, high switching times. In order to reduce the viscosity and switching time of the LC medium, it has been suggested in prior art to add LC compounds with an alkenyl group. However, it was observed that LC media containing alkenyl compounds often show a decrease of the reliability and stability, and a decrease of the VHR especially after exposure to UV radiation. Especially for use in PSA displays this is a considerable disadvantage, because the photopolymerization of the RMs in the PSA display is usually carried out by exposure to UV radiation, which may cause a VHR drop in the LC medium.

There is thus still a great demand for PSA displays and LC media and polymerizable compounds for use in such displays, which do not show the drawbacks as described above, or only do so to a small extent, and have improved properties.

In particular, there is a great demand for PSA displays, and LC media and polymerizable compounds for use in such PSA displays, which enable a high specific resistance at the same time as a large working-temperature range, short response times, even at low temperatures, and a low threshold voltage, a low pretilt angle, a multiplicity of grey shades, high contrast and a broad viewing angle, have high reliability and high values for the "voltage holding ratio" (VHR) after UV exposure, and, in case of the polymerizable compounds, have low melting points and a high solubility in the LC host mixtures. In PSA displays for mobile applications, it is especially desired to have available LC media that show low threshold voltage and high birefringence.

The invention thus provides novel suitable materials, in particular RMs and LC media comprising the same, for use in PSA displays, which do not have the disadvantages indicated above or do so to a reduced extent.

In particular, the invention provides RMs, and LC media comprising them, for use in PSA displays, which enable very high specific resistance values, high VHR values, high reliability, low threshold voltages, short response times, high birefringence, show good UV absorption especially at longer wavelengths, enable quick and complete polymerization of the RMs, allow the generation of a low pretilt angle as quickly as possible, enable a high stability of the pretilt even after longer time and/or after UV exposure, reduce or prevent the occurrence of "image sticking" and "ODF mura" in the display, and in case of the RMs polymerize as rapidly and completely as possible and show a high solubility in the LC media which are typically used as host mixtures in PSA displays.

The invention further provides novel RMs, in particular for optical, electro-optical and electronic applications, and of suitable processes and intermediates for the preparation thereof.

In particular, it has been found, surprisingly, that the use of RMs of formula I as described hereinafter allows achieving the advantageous effects as mentioned above. These compounds are characterized in that they contain a mesogenic core with one or more polymerizable reactive groups and one or more alkoxy substituents attached thereto, and wherein preferably all polymerizable reactive groups have the same meaning.

It was surprisingly found that the use of these RMs, and of LC media comprising them, in PSA displays facilitates a quick and complete UV-photopolymerization reaction in particular at longer UV wavelengths in the range from 300-380 nm and especially above 320 nm, even without the addition of photoinitiator, leads to a fast generation of a large and stable pretilt angle, reduces image sticking and ODF mura in the display, leads to a high reliability and a high VHR value after UV photopolymerization, especially in case of LC host mixtures containing LC compounds with an alkenyl group, and enables to achieve fast response times, a low threshold voltage and a high birefringence.

In addition, the RMs according to the invention have low melting points, good solubility in a wide range of LC media, especially in commercially available LC host mixtures for PSA use, and a low tendency to crystallisation. Besides, they show good absorption at longer UV wavelengths, in particular in the range from 300-380 nm, and enable a quick and complete polymerization with small amounts of residual, unreacted RMs in the cell.

JP 2012-018215 A and WO 2014/174929 A1 disclose hybrid type RMs which contain at least two different polymerizable reactive groups and wherein the mesogenic core may also be substituted by an alkoxy group, but do neither disclose nor suggest RMs as disclosed and claimed hereinafter.

The invention relates to polymerizable compounds of formula I

P-Sp-Ar—R     I wherein
Ar is a group selected from the following formulae

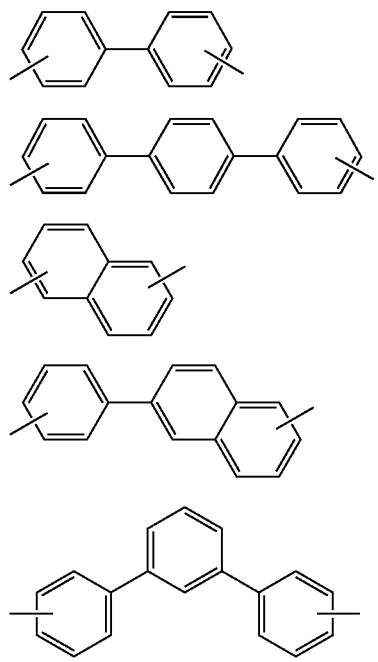

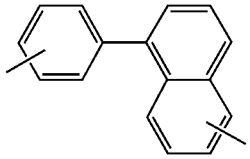

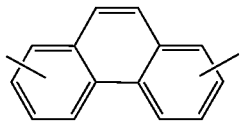

which is substituted by at least one group $L^a$, and is optionally further substituted by one or more groups L,
$L^a$ is an alkoxy group with 1 to 12 C atoms that is straight-chain or branched and is optionally fluorinated,
L is on each occurrence identically or differently F, Cl, —CN, P—Sp-, or straight chain, branched or cyclic alkyl having 1 to 25 C atoms, wherein one or more non-adjacent $CH_2$— groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F or Cl, or L has the meaning of $L^a$,
P is a polymerizable group,
Sp is a spacer group that is optionally substituted by one or more groups P, or a single bond,
R is P-Sp-, H or has one of the meanings given for L,
wherein, in case Ar is selected from formulae Ar1-Ar4, all groups P that are present in the compound have the same meaning.

The invention further relates to the use of compounds of formula I as polymerizable compounds in LC media and LC displays, especially in the LC medium, active layer or alignment layer of an LC display, wherein the LC displays are preferably PSA displays.

The invention further relates to methods for preparing compounds of formula I, and to novel intermediates used or obtained in these methods.

The invention furthermore relates to an LC medium comprising one or more compounds of formula I.

The invention furthermore relates to an LC medium comprising one or more polymerizable compounds, at least one of which is a compound of formula I.

The invention furthermore relates to an LC medium comprising
a polymerizable component A) comprising, preferably consisting of, one or more polymerizable compounds, at least one of which is a compound of formula I, and
a liquid-crystalline component B), hereinafter also referred to as "LC host mixture", comprising, preferably consisting of, one or more mesogenic or liquid-crystalline compounds.

The liquid-crystalline component B) of an LC medium according to the present invention is hereinafter also referred to as "LC host mixture", and preferably comprises one or more, preferably at least two mesogenic or LC compounds selected from low-molecular-weight compounds which are unpolymerizable.

The invention furthermore relates to an LC medium as described above and below, wherein the LC host mixture or component B) comprises at least one mesogenic or LC compound comprising an alkenyl group.

The invention furthermore relates to an LC medium or LC display as described above, wherein the compounds of formula I, or the polymerizable compounds of component A), are polymerized.

The invention furthermore relates to a process for preparing an LC medium as described above and below, comprising the steps of mixing one or more mesogenic or LC compounds, or an LC host mixture or LC component B) as described above and below, with one or more compounds of formula I, and optionally with further LC compounds and/or additives.

The invention furthermore relates to the use of compounds of formula I and LC media according to the invention in PSA displays, in particular the use in PSA displays containing an LC medium, for the production of a tilt angle in the LC medium by in-situ polymerization of the compound(s) of the formula I in the PSA display, preferably in an electric or magnetic field.

The invention furthermore relates to an LC display comprising one or more compounds of formula I or an LC medium according to the invention, in particular a PSA display, particularly preferably a PS-VA, PS—OCB, PS-IPS, PS—FFS, PS—UB—FFS, PS-posi-VA or PS-TN display.

The invention furthermore relates to an LC display comprising a polymer obtainable by polymerization of one or more compounds of formula I or of a polymerizable component A) as described above, or comprising an LC medium according to the invention, which is preferably a PSA display, very preferably a PS-VA, PS—OCB, PS-IPS, PS—FFS, PS—UB—FFS, PS-posi-VA or PS-TN display.

The invention furthermore relates to an LC display of the PSA type comprising two substrates, at least one which is transparent to light, an electrode provided on each substrate or two electrodes provided on only one of the substrates, and located between the substrates a layer of an LC medium that comprises one or more polymerizable compounds and an LC component as described above and below, wherein the polymerizable compounds are polymerized between the substrates of the display.

The invention furthermore relates to a process for manufacturing an LC display as described above and below, comprising the steps of filling or otherwise providing an LC medium, which comprises one or more polymerizable compounds as described above and below, between the substrates of the display, and polymerizing the polymerizable compounds.

The PSA displays according to the invention have two electrodes, preferably in the form of transparent layers, which are applied to one or both of the substrates. In some displays, for example in PS-VA, PS—OCB or PS-TN displays, one electrode is applied to each of the two substrates. In other displays, for example in PS-posi-VA, PS—IPS or PS—FFS or PS—UB-FFS displays, both electrodes are applied to only one of the two substrates.

In a preferred embodiment the polymerizable component is polymerized in the LC display while a voltage is applied to the electrodes of the display.

The polymerizable compounds of the polymerizable component are preferably polymerized by photo-polymerization, very preferably by UV photo-polymerization.

Unless stated otherwise, the compounds of formula I are preferably selected from achiral compounds.

As used herein, the terms "active layer" and "switchable layer" mean a layer in an electrooptical display, for example an LC display, that comprises one or more molecules having structural and optical anisotropy, like for example LC molecules, which change their orientation upon an external stimulus like an electric or magnetic field, resulting in a change of the transmission of the layer for polarized or unpolarized light.

As used herein, the terms "tilt" and "tilt angle" will be understood to mean a tilted alignment of the LC molecules of an LC medium relative to the surfaces of the cell in an LC display (here preferably a PSA display). The tilt angle here denotes the average angle (<90°) between the longitudinal molecular axes of the LC molecules (LC director) and the surface of the plane-parallel outer plates which form the LC cell. A low value for the tilt angle (i.e. a large deviation from the 90° angle) corresponds to a large tilt here. A suitable method for measurement of the tilt angle is given in the examples. Unless indicated otherwise, tilt angle values disclosed above and below relate to this measurement method.

As used herein, the terms "reactive mesogen" and "RM" will be understood to mean a compound containing a mesogenic or liquid crystalline skeleton, and one or more functional groups attached thereto which are suitable for polymerization and are also referred to as "polymerizable group" or "P".

Unless stated otherwise, the term "polymerizable compound" as used herein will be understood to mean a polymerizable monomeric compound.

As used herein, the term "low-molecular-weight compound" will be understood to mean to a compound that is monomeric and/or is not prepared by a polymerization reaction, as opposed to a "polymeric compound" or a "polymer".

As used herein, the term "unpolymerizable compound" will be understood to mean a compound that does not contain a functional group that is suitable for polymerization under the conditions usually applied for the polymerization of the RMs.

The term "mesogenic group" as used herein is known to the person skilled in the art and described in the literature, and means a group which, due to the anisotropy of its attracting and repelling interactions, essentially contributes to causing a liquid-crystal (LC) phase in low-molecular-weight or polymeric substances. Compounds containing mesogenic groups (mesogenic compounds) do not necessarily have to have an LC phase themselves. It is also possible for mesogenic compounds to exhibit LC phase behaviour only after mixing with other compounds and/or after polymerization. Typical mesogenic groups are, for example, rigid rod- or disc-shaped units. An overview of the terms and definitions used in connection with mesogenic or LC compounds is given in *Pure Appl. Chem.* 2001, 73(5), 888 and C. Tschierske, G. Pelzl, S. Diele, *Angew. Chem.* 2004, 116, 6340-6368.

The term "spacer group", hereinafter also referred to as "Sp", as used herein is known to the person skilled in the art and is described in the literature, see, for example, *Pure Appl. Chem.* 2001, 73(5), 888 and C. Tschierske, G. Pelzl, S. Diele, *Angew. Chem.* 2004, 116, 6340-6368, which is hereby incorporated by reference for its disclosure of spacer groups. As used herein, the terms "spacer group" or "spacer" mean, e.g., a flexible group, for example an alkylene group, which connects the mesogenic group and the polymerizable group(s) in a polymerizable mesogenic compound.

Above and below,

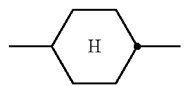

denotes a trans-1,4-cyclohexylene ring, and

and denotes a 1,4-phenylene ring.

In a group

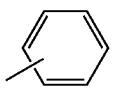

the single bond shown between the two ring atoms can be attached to any free position of the benzene ring.

Above and below "organic group" denotes a carbon or hydrocarbon group.

"Carbon group" denotes a mono- or polyvalent organic group containing at least one carbon atom, where this either contains no further atoms (such as, for example, —C≡C—) or optionally contains one or more further atoms, such as, for example, N, O, S, B, P, Si, Se, As, Te or Ge (for example carbonyl, etc.). The term "hydrocarbon group" denotes a carbon group which additionally contains one or more H atoms and optionally one or more heteroatoms, such as, for example, N, O, S, B, P, Si, Se, As, Te or Ge.

"Halogen" denotes F, Cl, Br or I.

—CO—, —C(=O)— and —C(O)— denote a carbonyl group, i.e.

A carbon or hydrocarbon group can be a saturated or unsaturated group. Unsaturated groups are, for example, aryl, alkenyl or alkynyl groups. A carbon or hydrocarbon radical having more than 3 C atoms can be straight-chain, branched and/or cyclic and may also contain spiro links or condensed rings.

The terms "alkyl", "aryl", "heteroaryl", etc., also encompass polyvalent groups, for example alkylene, arylene, heteroarylene, etc.

The term "aryl" denotes an aromatic carbon group or a group derived therefrom. The term "heteroaryl" denotes "aryl" as defined above, containing one or more heteroatoms, preferably selected from N, O, S, Se, Te, Si and Ge.

Preferred carbon and hydrocarbon groups are optionally substituted, straight-chain, branched or cyclic, alkyl, alkenyl, alkynyl, alkoxy, alkylcarbonyl, alkoxycarbonyl, alkylcarbonyloxy and alkoxycarbonyloxy having 1 to 40, preferably 1 to 20, very preferably 1 to 12, C atoms, optionally substituted aryl or aryloxy having 5 to 30, preferably 6 to 25, C atoms, or optionally substituted alkylaryl, arylalkyl, alkylaryloxy, arylalkyloxy, arylcarbonyl, aryloxycarbonyl, arylcarbonyloxy and aryloxycarbonyloxy having 5 to 30, preferably 6 to 25, C atoms, wherein one or more C atoms may also be replaced by hetero atoms, preferably selected from N, O, S, Se, Te, Si and Ge.

Further preferred carbon and hydrocarbon groups are $C_1$-$C_{20}$ alkyl, $C_2$-$C_{20}$ alkenyl, $C_2$-$C_{20}$ alkynyl, $C_3$-$C_{20}$ allyl, $C_4$-$C_{20}$ alkyldienyl, $C_4$-$C_{20}$ polyenyl, $C_6$-$C_{20}$ cycloalkyl, $C_4$-$C_{15}$ cycloalkenyl, $C_6$-$C_{30}$ aryl, $C_6$-$C_{30}$ alkylaryl, $C_6$-$C_{30}$ arylalkyl, $C_6$-$C_{30}$ alkylaryloxy, $C_6$-$C_{30}$ arylalkyloxy, $C_2$-$C_{30}$ heteroaryl, $C_2$-$C_{30}$ heteroaryloxy.

Particular preference is given to $C_1$-$C_{12}$ alkyl, $C_2$-$C_{12}$ alkenyl, $C_2$-$C_{12}$ alkynyl, $C_6$-$C_{25}$ aryl and $C_2$-$C_{25}$ heteroaryl.

Further preferred carbon and hydrocarbon groups are straight-chain, branched or cyclic alkyl having 1 to 20, preferably 1 to 12, C atoms, which are unsubstituted or mono- or polysubstituted by F, Cl, Br, I or CN and in which one or more non-adjacent $CH_2$ groups may each be replaced, independently of one another, by —C($R^x$)=C($R^x$)—, —C≡C—, —N($R^x$)—, —O—, —S—, —CO—, —CO—O—, —O—CO—, —O—CO—O— in such a way that O and/or S atoms are not linked directly to one another.

$R^x$ preferably denotes H, F, Cl, CN, a straight-chain, branched or cyclic alkyl chain having 1 to 25 C atoms, in which, in addition, one or more non-adjacent C atoms may be replaced by —O—, —S—, —CO—, —CO—O—, —O—CO—, —O—CO—O— and in which one or more H atoms may be replaced by F or Cl, or denotes an optionally substituted aryl or aryloxy group with 6 to 30 C atoms, or an optionally substituted heteroaryl or heteroaryloxy group with 2 to 30 C atoms.

Preferred alkyl groups are, for example, methyl, ethyl, n-propyl, isopropyl, n-butyl, isobutyl, s-butyl, t-butyl, 2-methylbutyl, n-pentyl, s-pentyl, cyclopentyl, n-hexyl, cyclohexyl, 2-ethylhexyl, n-heptyl, cycloheptyl, n-octyl, cyclooctyl, n-nonyl, n-decyl, n-undecyl, n-dodecyl, dodecanyl, trifluoromethyl, perfluoro-n-butyl, 2,2,2-trifluoroethyl, perfluorooctyl, perfluorohexyl, etc.

Preferred alkenyl groups are, for example, ethenyl, propenyl, butenyl, pentenyl, cyclopentenyl, hexenyl, cyclohexenyl, heptenyl, cycloheptenyl, octenyl, cyclooctenyl, etc.

Preferred alkynyl groups are, for example, ethynyl, propynyl, butynyl, pentynyl, hexynyl, octynyl, etc.

Preferred alkoxy groups are, for example, methoxy, ethoxy, 2-methoxy-ethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, n-decoxy, n-undecoxy, n-dodecoxy, etc.

Preferred amino groups are, for example, dimethylamino, methylamino, methylphenylamino, phenylamino, etc.

Aryl and heteroaryl groups can be monocyclic or polycyclic, i.e. they can contain one ring (such as, for example, phenyl) or two or more rings, which may also be fused (such as, for example, naphthyl) or covalently bonded (such as, for example, biphenyl), or contain a combination of fused and linked rings. Heteroaryl groups contain one or more heteroatoms, preferably selected from O, N, S and Se.

Particular preference is given to mono-, bi- or tricyclic aryl groups having 6 to 25 C atoms and mono-, bi- or tricyclic heteroaryl groups having 5 to 25 ring atoms, which optionally contain fused rings and are optionally substituted.

Preference is furthermore given to 5-, 6- or 7-membered aryl and heteroaryl groups, in which, in addition, one or more CH groups may be replaced by N, S or O in such a way that O atoms and/or S atoms are not linked directly to one another.

Preferred aryl groups are, for example, phenyl, biphenyl, terphenyl, [1,1':3',1"]terphenyl-2'-yl, naphthyl, anthracene, binaphthyl, phenanthrene, 9,10-dihydro-phenanthrene, pyrene, dihydropyrene, chrysene, perylene, tetracene, pentacene, benzopyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquin-oline, acridine, phenothiazine, phenoxazine, benzopyridazine, benzopyrimi-dine, quinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothiophene, benzothiadiazo-thiophene, or combinations of these groups.

The aryl and heteroaryl groups mentioned above and below may also be substituted by alkyl, alkoxy, thioalkyl, fluorine, fluoroalkyl or further aryl or heteroaryl groups.

The (non-aromatic) alicyclic and heterocyclic groups encompass both saturated rings, i.e. those containing exclusively single bonds, and also partially unsaturated rings, i.e. those which may also contain multiple bonds. Heterocyclic rings contain one or more heteroatoms, preferably selected from Si, O, N, S and Se.

The (non-aromatic) alicyclic and heterocyclic groups can be monocyclic, i.e. contain only one ring (such as, for example, cyclohexane), or polycyclic, i.e. contain a plurality of rings (such as, for example, decahydronaphthalene or bicyclooctane). Particular preference is given to saturated groups. Preference is furthermore given to mono-, bi- or tricyclic groups having 5 to 25 ring atoms, which optionally contain fused rings and are optionally substituted. Preference is furthermore given to 5-, 6-, 7- or 8-membered carbocyclic groups, in which, in addition, one or more C atoms may be replaced by Si and/or one or more CH groups may be replaced by N and/or one or more non-adjacent $CH_2$ groups may be replaced by —O— and/or —S—.

Preferred alicyclic and heterocyclic groups are, for example, 5-membered groups, such as cyclopentane, tetrahydrofuran, tetrahydrothiofuran, pyrroli-dine, 6-membered groups, such as cyclohexane, silinane, cyclohexene, tetrahydropyran, tetrahydrothiopyran, 1,3-dioxane, 1,3-dithiane, piperidine, 7-membered groups, such as cycloheptane, and fused groups, such as tetrahydronaphthalene, decahydronaphthalene, indane, bicyclo[1.1.1]-pentane-1,3-diyl, bicyclo[2.2.2]octane-1,4-diyl, spiro[3.3]heptane-2,6-diyl, octahydro-4,7-methanoindane-2,5-diyl.

Preferred substituents are, for example, solubility-promoting groups, such as alkyl or alkoxy, electron-withdrawing groups, such as fluorine, nitro or nitrile, or substituents for increasing the glass transition temperature (Tg) in the polymer, in particular bulky groups, such as, for example, t-butyl or optionally substituted aryl groups.

Preferred substituents, hereinafter also referred to as "L", are, for example, F, Cl, Br, I, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, straight-chain or branched alkyl, alkoxy, alkylcarbonyl, alkoxycarbonyl, alkylcarbonyloxy or alkoxycarbonyloxy each having 1 to 25 C atoms, in which one or more H atoms may optionally be replaced by F or Cl, optionally substituted silyl having 1 to 20 Si atoms, or optionally substituted aryl having 6 to 25, preferably 6 to 15, C atoms, wherein $R^x$ denotes H, F, Cl, CN, or straight chain, branched or cyclic alkyl having 1 to 25 C atoms, wherein one or more non-adjacent $CH_2$— groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F, Cl, P- or P-Sp-, and $Y^1$ denotes halogen.

"Substituted silyl or aryl" preferably means substituted by halogen, —CN, $R^0$, —OR$^0$, —CO—R$^0$, —CO—O—R$^0$, —O—CO—R$^0$ or —O—CO—O—R$^0$, wherein $R^0$ denotes H or alkyl with 1 to 20 C atoms.

Particularly preferred substituents L are, for example, F, Cl, CN, NO$_2$, CH$_3$, C$_2$H$_5$, OCH$_3$, OC$_2$H$_5$, COCH$_3$, COC$_2$H$_5$, COOCH$_3$, COOC$_2$H$_5$, CF$_3$, OCF$_3$, OCHF$_2$, OC$_2$F$_5$, furthermore phenyl.

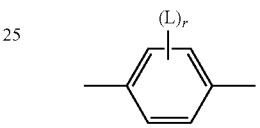

is preferably

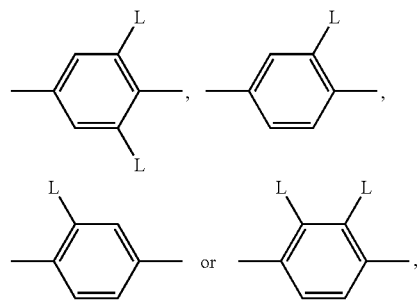

in which L has one of the meanings indicated above.

The polymerizable group P is a group which is suitable for a polymerization reaction, such as, for example, free-radical or ionic chain polymerization, polyaddition or polycondensation, or for a polymer-analogous reaction, for example addition or condensation onto a main polymer chain. Particular preference is given to groups for chain polymerization, in particular those containing a C=C double bond or —C≡C— triple bond, and groups which are suitable for polymerization with ring opening, such as, for example, oxetane or epoxide groups.

Preferred groups P and P$^{a,b}$ are selected from the group consisting of CH$_2$=CW$^1$—CO—O—, CH$_2$=CW$^1$—CO—,

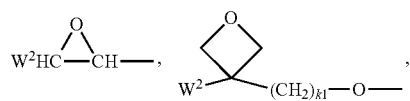

-continued

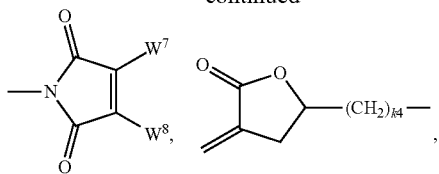

$CH_2=CW^2-(O)_{k3}-$, $CW^1=CH-CO-(O)_{k3}-$, $CW^1=CH-CO-NH-$, $CH_2=CW^1-CO-NH-$, $CH_3-CH=CH-O-$, $(CH_2=CH)_2CH-OCO-$, $(CH_2=CH-CH_2)_2CH-OCO-$, $(CH_2=CH)_2CH-O-$, $(CH_2=CH-CH_2)_2N-$, $(CH_2=CH-CH_2)_2N-CO-$, $HO-CW^2W^3-$, $HS-CW^2W^3-$, $HW^2N-$, $HO-CW^2W^3-NH-$, $CH_2=CW^1-CO-NH-$, $CH_2=CH-(COO)_{k1}\text{-Phe-}(O)_{k2}-$, $CH_2=CH-(CO)_{k1}\text{-Phe-}(O)_{k2}-$, $\text{Phe-CH}=CH-$, $HOOC-$, $OCN-$ and $W^4W^5W^6Si-$, in which $W^1$ denotes H, F, Cl, ON, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, which is optionally substituted by one or more radicals L as defined above which are other than P-Sp-, $k_1$, $k_2$ and $k_3$ each, independently of one another, denote 0 or 1, $k_3$ preferably denotes 1, and $k_4$ denotes an integer from 1 to 10.

Very preferred groups P and $P^{a,b}$ are selected from the group consisting of $CH_2=CW^1-CO-O-$, $CH_2=CW^1-CO-$,

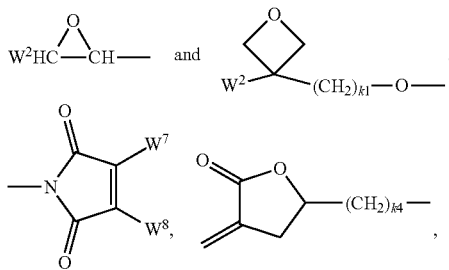

$CH_2=CW^2-O-$, $CH_2=CW^2-$, $CW^1=CH-CO-(O)_{k3}-$, $CW^1=CH-CO-NH-$, $CH_2=CW^1-CO-NH-$, $(CH_2=CH)_2CH-OCO-$, $(CH_2=CH-CH_2)_2CH-OCO-$, $(CH_2=CH)_2CH-O-$, $(CH_2=CH-CH_2)_2N-$, $(CH_2=CH-CH_2)_2N-CO-$, $CH_2=CW^1-CO-NH-$, $CH_2=CH-(COO)_{k1}\text{-Phe-}(O)_{k2}-$, $CH_2=CH-(CO)_{k1}\text{-Phe-}(O)_{k2}-$, Phe-CH=CH— and $W^4W^5W^6Si-$, in which $W^1$ denotes H, F, Cl, CN, $CF_3$, phenyl or alkyl having 1 to 5 C atoms, in particular H, F, $C_1$ or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, $C_1$ or alkyl having 1 to 5 C atoms, Phe denotes 1,4-phenylene, $k_1$, $k_2$ and $k_3$ each, independently of one another, denote 0 or 1, $k_3$ preferably denotes 1, and $k_4$ denotes an integer from 1 to 10.

Very particularly preferred groups P and $P^{a,b}$ are selected from the group consisting of $CH_2=CW^1-CO-O-$, in particular $CH_2=CH-CO-O-$, $CH_2=C(CH_3)-CO-O-$ and $CH_2=CF-CO-O-$, furthermore $CH_2=CH-O-$, $(CH_2=CH)_2CH-O-CO-$, $(CH_2=CH)_2CH-O-$,

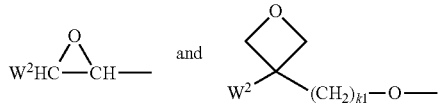

Further preferred polymerizable groups P and $P^{a,b}$ are selected from the group consisting of vinyloxy, acrylate, methacrylate, fluoroacrylate, chloro-acrylate, oxetane and epoxide, most preferably from acrylate and methacrylate.

If the spacer group Sp is different from a single bond, it is preferably of the formula Sp"-X", so that the respective radical P-Sp- conforms to the formula P-Sp"-X"—, wherein Sp" denotes alkylene having 1 to 20, preferably 1 to 12, C atoms, which is optionally mono- or polysubstituted by F, Cl, Br, I or CN and in which, in addition, one or more non-adjacent $CH_2$ groups may each be replaced, independently of one another, by —O—, —S—, —NH—, —N($R^0$)—, —Si($R^0R^{00}$)—, —CO—, —CO—O—, —O—CO—, —O—CO—O—, —S—CO—, —CO—S—, —N($R^{00}$)—CO—O—, —O—CO—N($R^0$)—, —N($R^0$)—CO—N($R^{00}$)—, —CH=CH— or —C≡C— in such a way that O and/or S atoms are not linked directly to one another, X" denotes —O—, —S—, —CO—, —CO—O—, —O—CO—, —O—CO—O—, —CO—N($R^0$)—, —N($R^0$)—CO—, —N($R^0$)—CO—N($R^0$)—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CY$^2$=CY$^3$—, —C≡C—, —CH=CH—CO—O—, —O—CO—CH=CH— or a single bond, $R^0$ and $R^{00}$ each, independently of one another, denote H or alkyl having 1 to 20 C atoms, and $Y^2$ and $Y^3$ each, independently of one another, denote H, F, $C_1$ or CN.

X" is preferably —O—, —S—, —CO—, —COO—, —OCO—, —O—COO—, —CO—NR$^0$—, —NR$^0$—CO—, —NR$^0$—CO—NR$^{00}$— or a single bond.

Typical spacer groups Sp and -Sp"-X"— are, for example, —(CH$_2$)$_{p1}$—, —(CH$_2$)$_{p1}$—O—, —(CH$_2$)$_{p1}$—O—CO—, —(CH$_2$)$_{p1}$—CO—O—, —(CH$_2$)$_{p1}$—O—CO—O—, —(CH$_2$CH$_2$O)$_{q1}$—CH$_2$CH$_2$—, —CH$_2$CH$_2$—S—CH$_2$CH$_2$—, —CH$_2$CH$_2$—NH—CH$_2$CH$_2$— or —(SiR$^0$R$^{00}$—O)$_{p1}$—, in which p1 is an integer from 1 to 12, q1 is an integer from 1 to 3, and $R^0$ and $R^{00}$ have the meanings indicated above.

Particularly preferred groups Sp and -Sp"-X"— are —(CH$_2$)$_{p1}$—, —(CH$_2$)$_{p1}$—O—, —(CH$_2$)$_{p1}$—O—CO—, —(CH$_2$)$_{p1}$—CO—O—, —(CH$_2$)$_{p1}$—O—CO—O—, in which p1 and q1 have the meanings indicated above.

Particularly preferred groups Sp" are, in each case straight-chain, ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methylimino-ethylene, 1-methylalkylene, ethenylene, propenylene and butenylene.

In another preferred embodiment of the invention the compounds of formula I and its subformulae contain a spacer group Sp that is substituted by one or more polymerizable groups P, so that the group Sp-P corresponds to Sp(P)$_s$, with s being >2 (branched polymerizable groups).

Preferred compounds of formula I according to this preferred embodiment are those wherein s is 2, i.e. compounds which contain a group Sp(P)$_2$. Very preferred compounds of formula I according to this preferred embodiment contain a group selected from the following formulae:

| | |
|---|---|
| —X-alkyl-CHPP | S1 |
| X-alkyl-CH((CH$_2$)$_{aa}$P)((CH$_2$)$_{bb}$P) | S2 |
| X—N((CH$_2$)$_{aa}$P)((CH$_2$)$_{bb}$P) | S3 |
| X-alkyl-CHP—CH$_2$—CH$_2$P | S4 |
| X-alkyl-C(CH$_2$P)(CH$_2$P)—C$_{aa}$H$_{2aa+1}$ | S5 |
| X-alkyl-CHP—CH$_2$P | S6 |
| X-alkyl-CPP—C$_{aa}$H$_{2aa+1}$ | S7 |
| X-alkyl-CHPCHP—C$_{aa}$H$_{2aa+1}$ | S8 | in which P is as defined in formula I,
  alkyl denotes a single bond or straight-chain or branched alkylene having 1 to 12 C atoms which is unsubstituted or mono- or polysubstituted by F, Cl or CN and in which one or more non-adjacent CH$_2$ groups may each, independently of one another, be replaced by —C(R$^0$)=C(R$^0$)—, —C≡C—, —N(R$^0$)—, —O—, —S—, —CO—, —CO—O—, —O—CO—, —O—CO—O— in such a way that O and/or S atoms are not linked directly to one another, where R$^0$ has the meaning indicated above,
aa and bb each, independently of one another, denote 0, 1, 2, 3, 4, 5 or 6,
  X has one of the meanings indicated for X", and is preferably O, CO, SO$_2$, O—CO—, CO—O or a single bond.

Preferred spacer groups Sp(P)$_2$ are selected from formulae S1, S2 and S3.

Very preferred spacer groups Sp(P)$_2$ are selected from the following subformulae:

| | |
|---|---|
| —CHPP | S1a |
| —O—CHPP | S1b |
| —CH$_2$—CHPP | S1c |
| —OCH$_2$—CHPP | S1d |
| —CH(CH$_2$—P)(CH$_2$—P) | S2a |
| —OCH(CH$_2$—P)(CH$_2$—P) | S2b |
| —CH$_2$—CH(CH$_2$—P)(CH$_2$—P) | S2c |
| —OCH$_2$—CH(CH$_2$—P)(CH$_2$—P) | S2d |
| —CO—NH((CH$_2$)$_2$P)((CH$_2$)$_2$P) | S3a |

Preferably in the compounds of formula I and its subformulae as described above and below all polymerizable groups P that are present in the compound have the same meaning, and very preferably denote acrylate or methacrylate.

Further preferred are compounds of formula I and its subformulae wherein the group Ar is selected from formulae Ar5, Ar 6 and Ar7, and the groups P present in the compound are identical or different.

In the compounds of formula I and its subformulae as described above and below, L$^a$ is preferably OCH$_3$, OC$_2$H$_5$, O(CH$_2$)$_2$CH$_3$, OC(CH$_3$)$_3$, OCF$_3$, OCF$_2$H or OCFH$_2$, very preferably OCH$_3$ or OCF$_3$, most preferably OCH$_3$.

In the compounds of formula I and its subformulae as described above and below, Ar is preferably selected from formulae Ar1, Ar2 and Ar5.

Preferred compounds of formula I are selected from the following subformulae

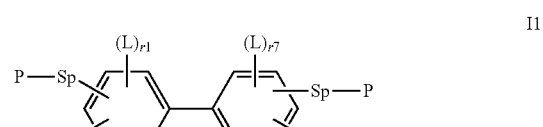

I1

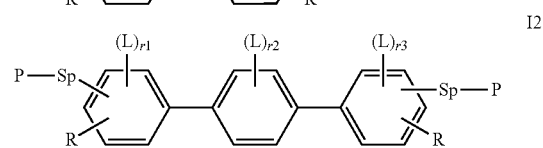

I2

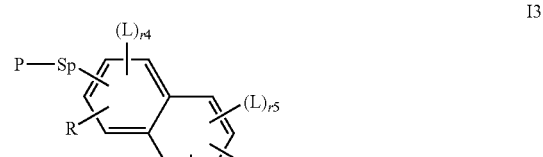

I3

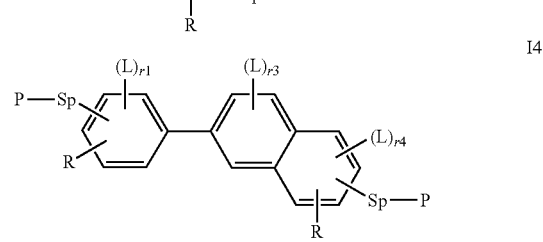

I4

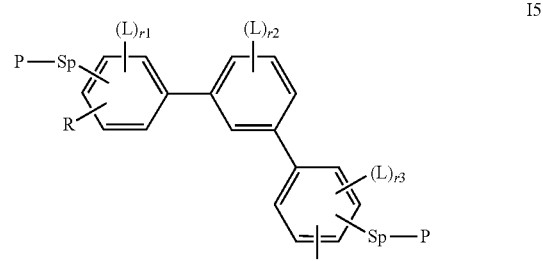

I5

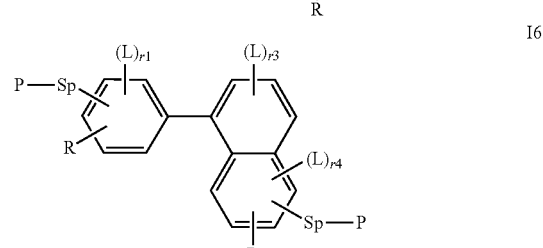

I6

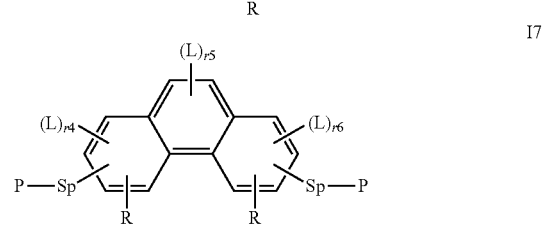

I7 wherein P, Sp, R and L have the meanings given in formula I, r1, r3, r7 are independently of each other 0, 1, 2 or 3,
r2 is 0, 1, 2, 3 or 4,
r4, r5, r6 are independently of each other 0, 1 or 2,
with r1+r7≥1, r1+r2+r3≥1, r4+r5≥1, r1+r3+r4≥1, and
wherein the compounds contain at least one substituent L that denotes $L^a$ as defined in formula I.

Preferred are compounds of formula I1-I7 wherein one of the two groups R is H and the other is P-Sp.

Further preferred are compounds of formula I1-I7 wherein both groups R denote H.

Further preferred are compounds of formula I1-I7 wherein both groups R denote P-Sp.

Very preferred are compounds of formula I1, I2 and I5.

Further preferred compounds of formula I and I1-I7 are selected from the following subformulae

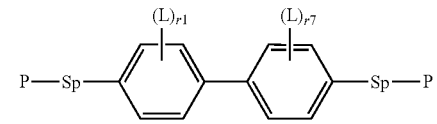
I1-1

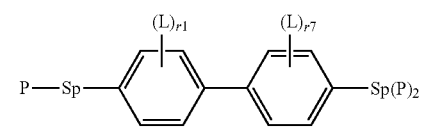
I1-2

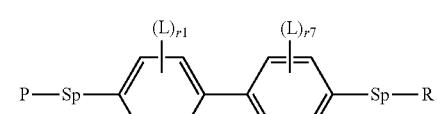
I1-3

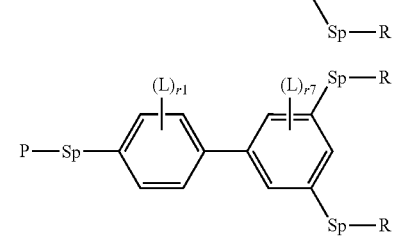
I1-4

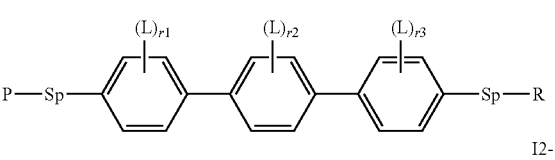
I2-1

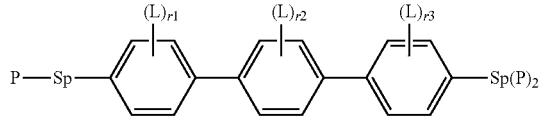
I2-1

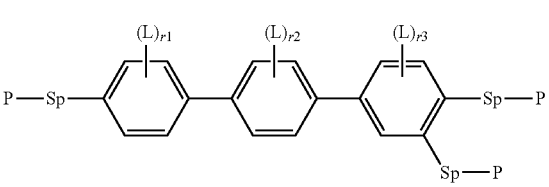
I2-3

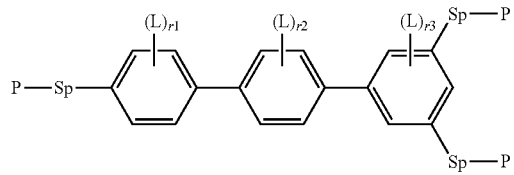
I2-4

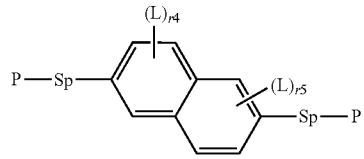
I3-1

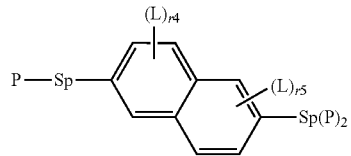
I3-2

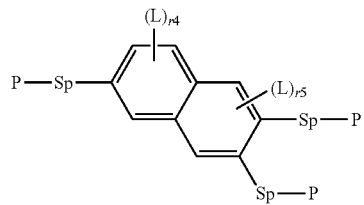
I3-3

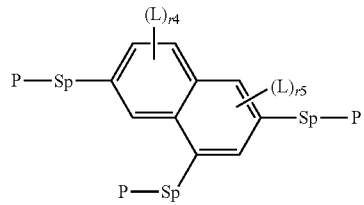
I3-4

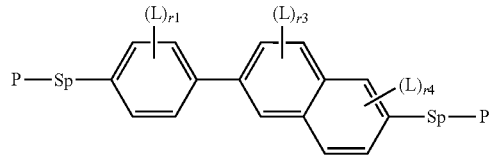
I4-1

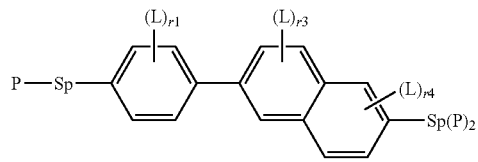
I4-2

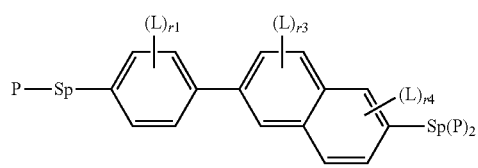
I4-3

I4-4
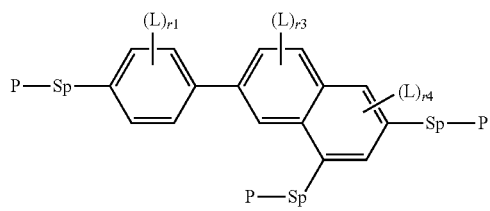
I4-5
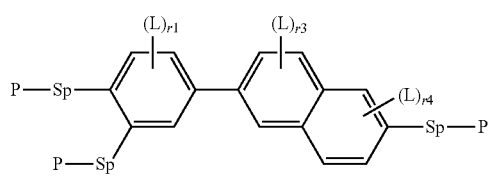
I4-6
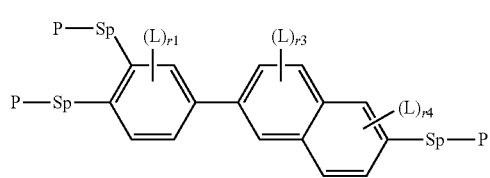
I4-7
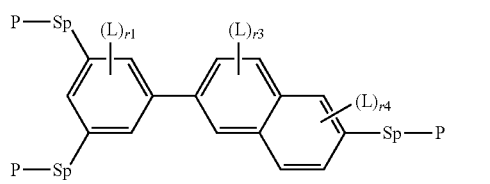
I5-1
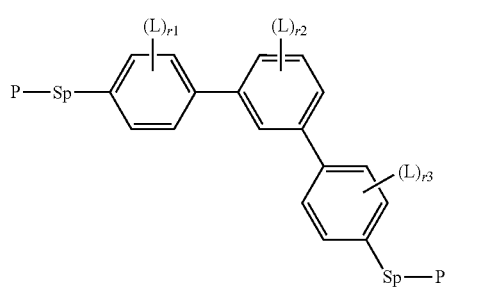
I5-2
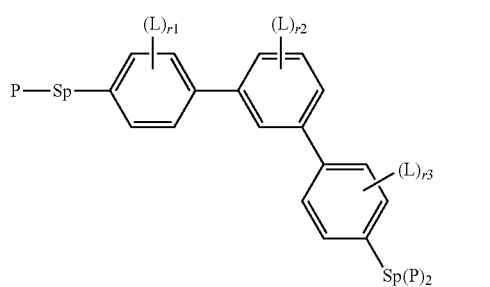
I5-3
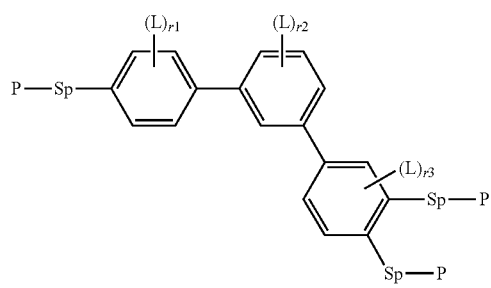
I5-4
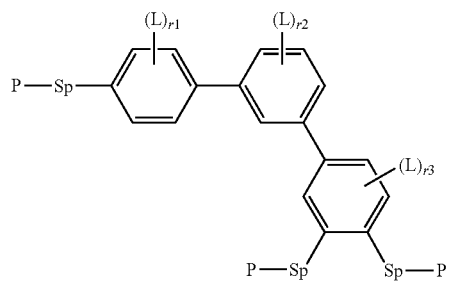
I5-5
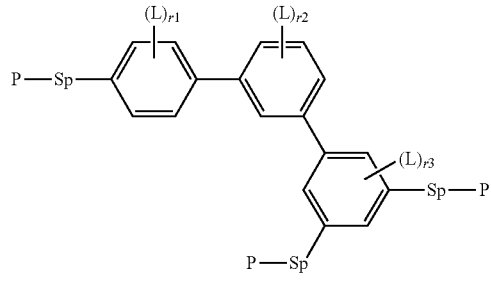
I6-1
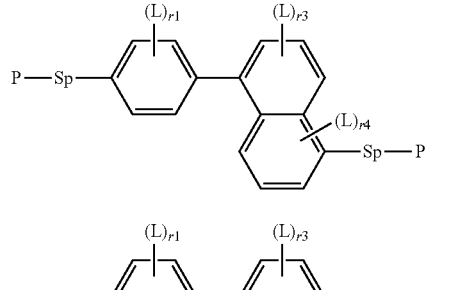
I6-2
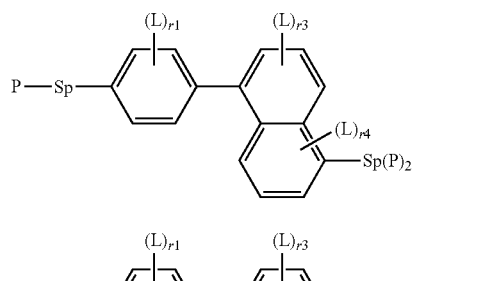
I6-3
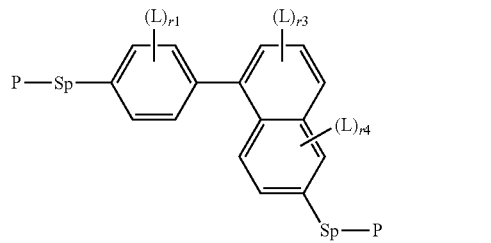

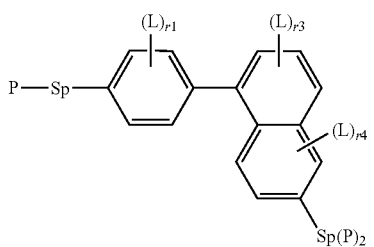
I6-4
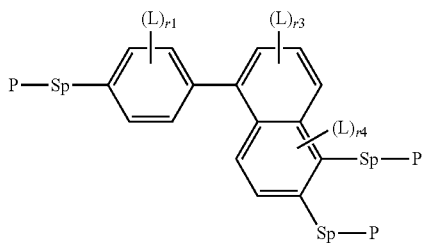
I6-5
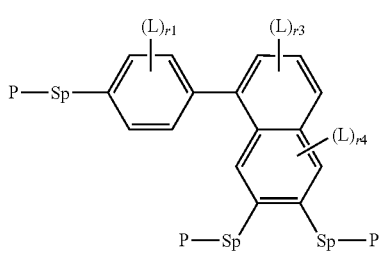
I6-6
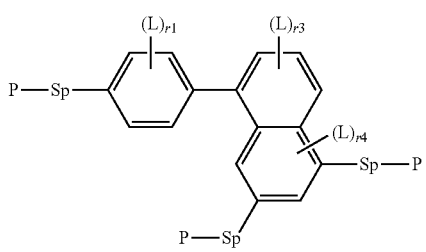
I6-7
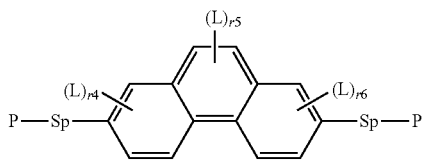
I7-1
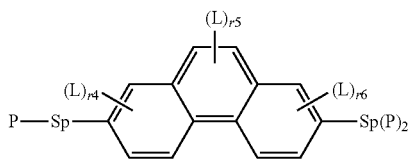
I7-2
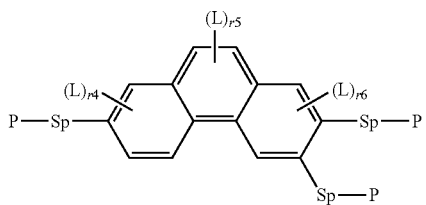
I7-3
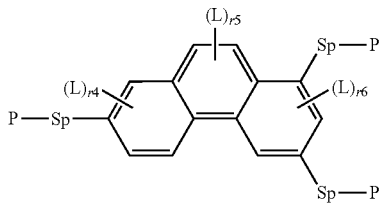
I7-4
wherein P, Sp, P(Sp)₂, L, r1-r7 have the meanings given in formula I or one of the preferred meanings as given above and below.
Preferably in formulae I1-2, I2-2, I3-2, I4-2, I5-2, I6-2, I6-4 and I7-2 the group -Sp(P)₂ is selected from formulae S1 to S8 or S1a to S3a as defined above.
Very preferred compounds of formula I are selected from the following subformulae:
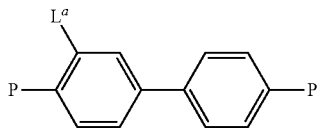
I1-1-1
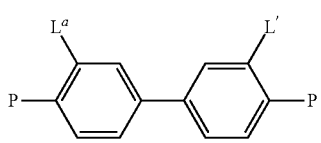
I1-2-2
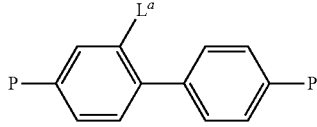
I1-1-3
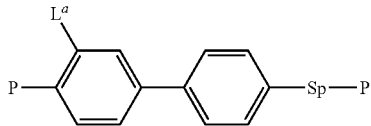
I1-1-4
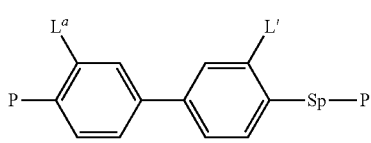
I1-1-5
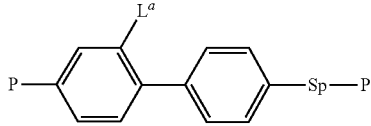
I1-1-6
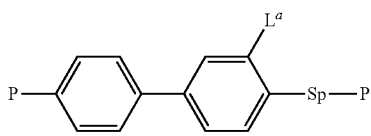
I1-1-7
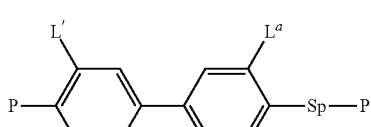
I1-1-8

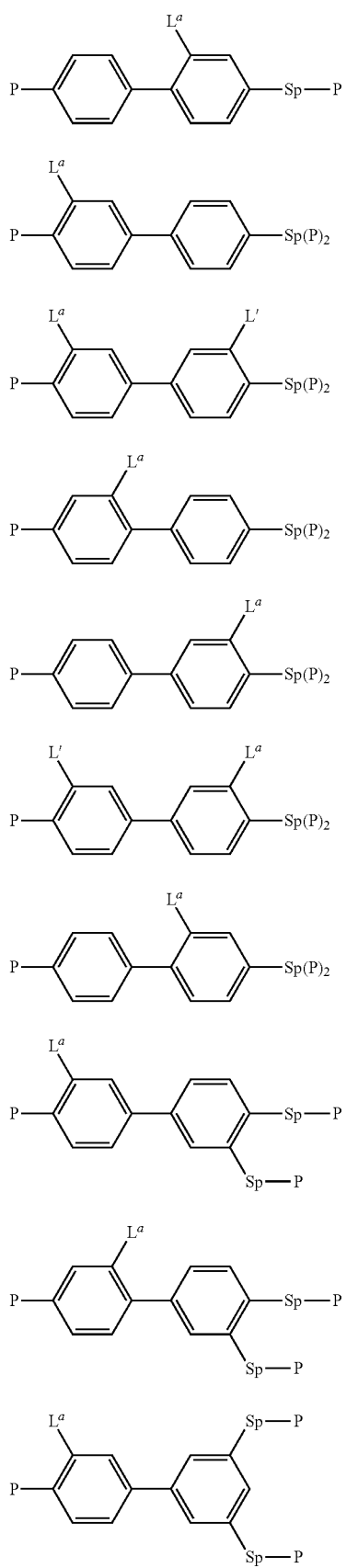
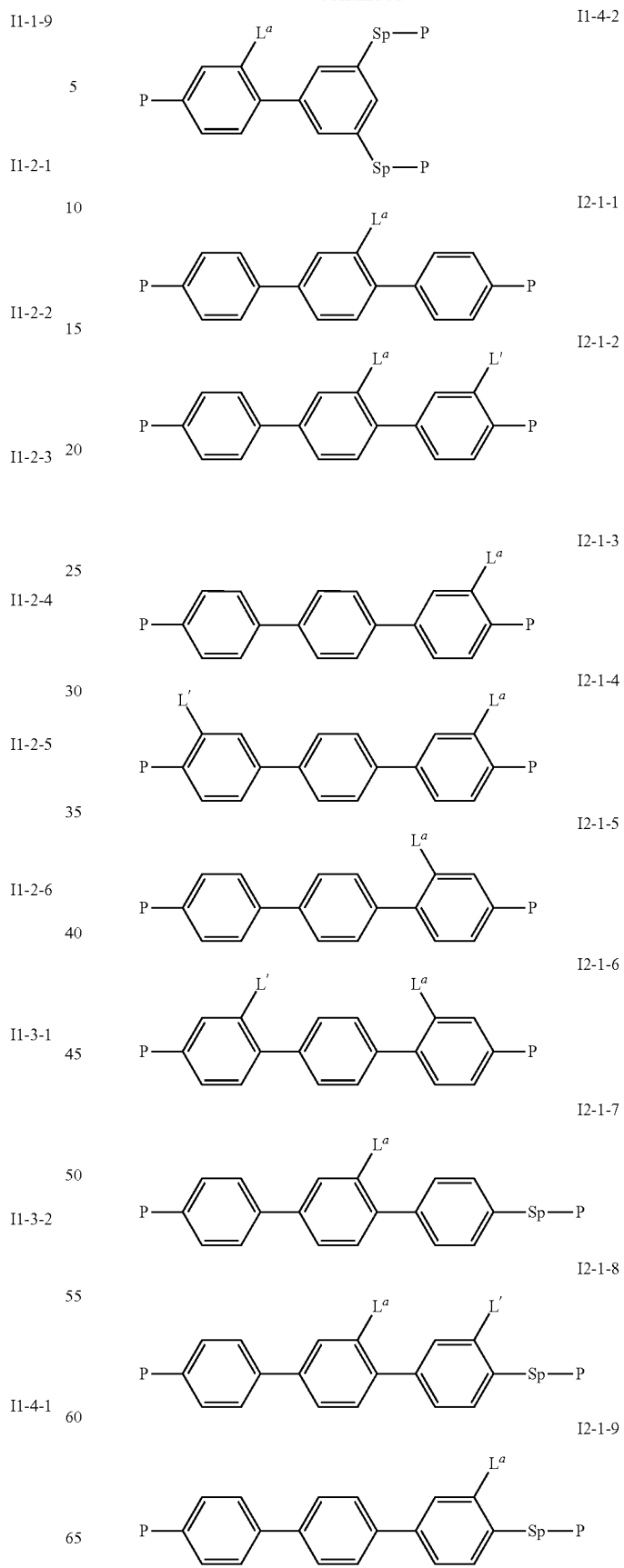

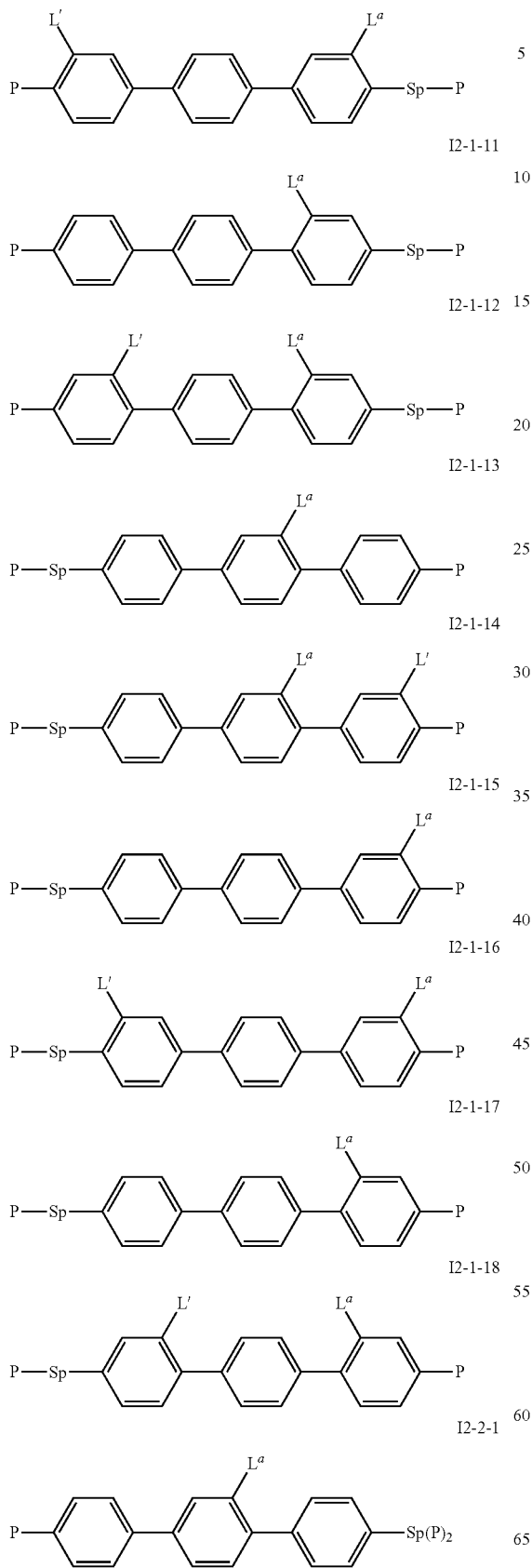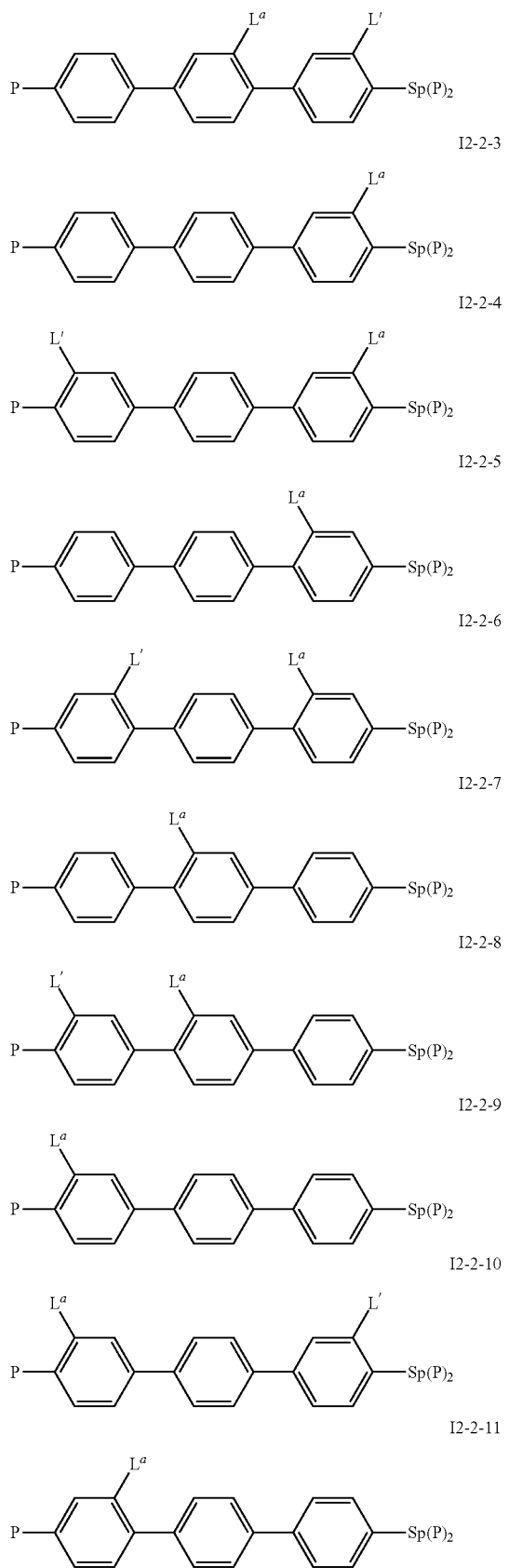

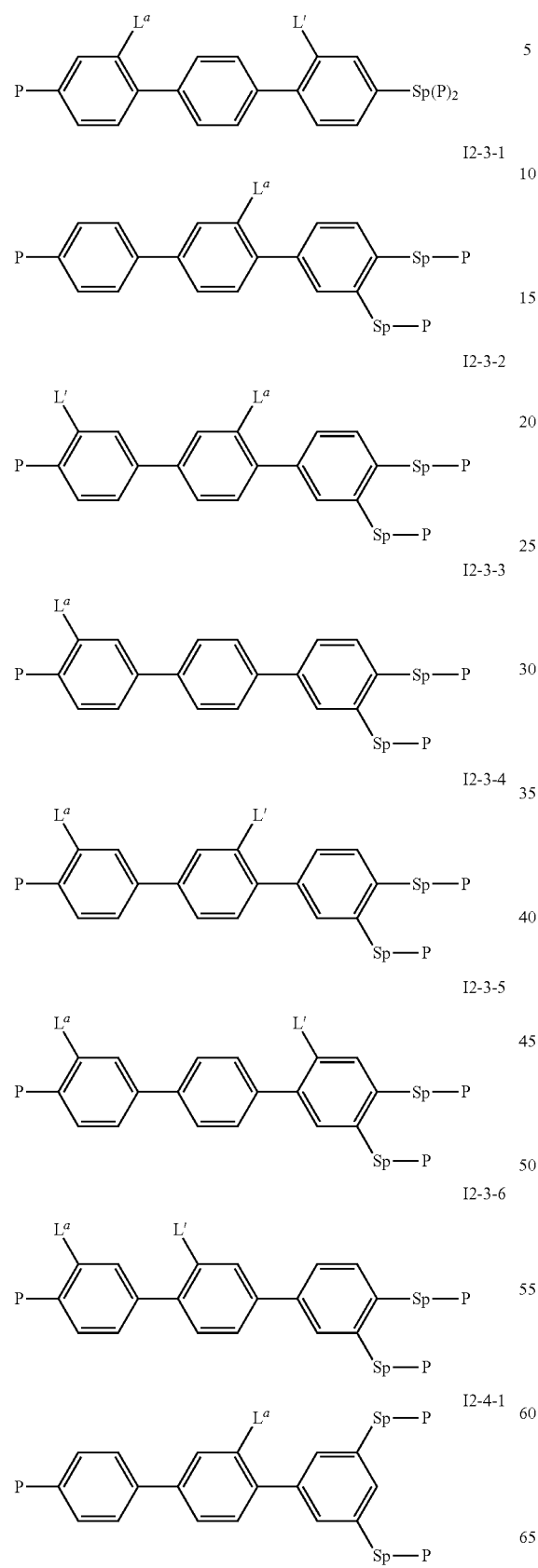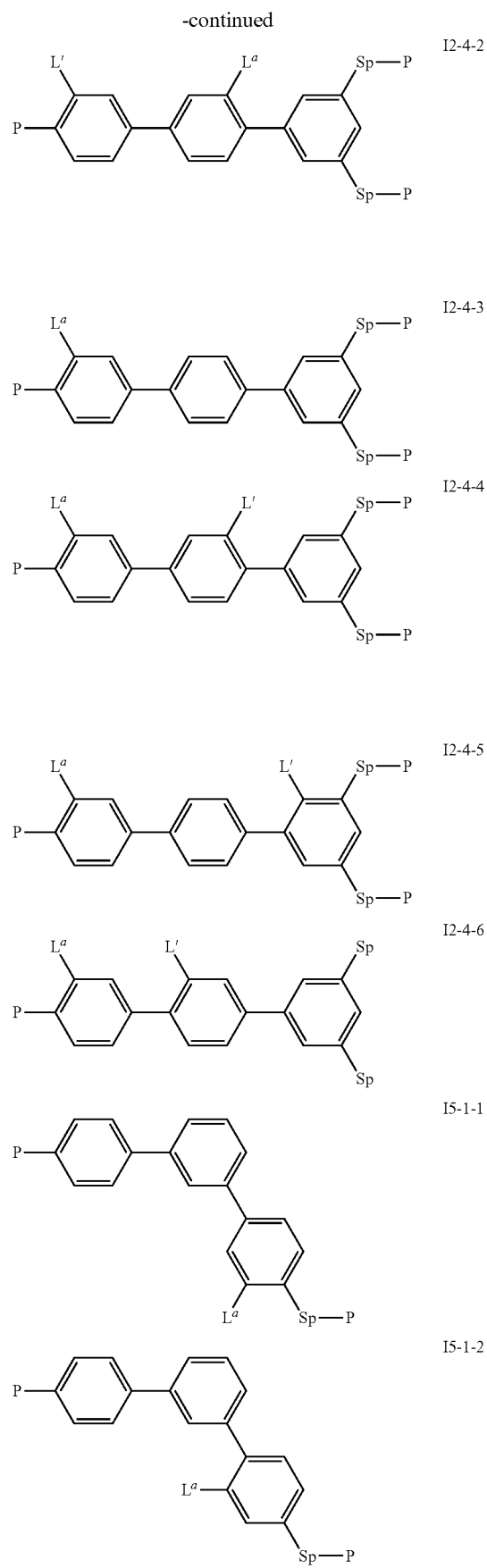

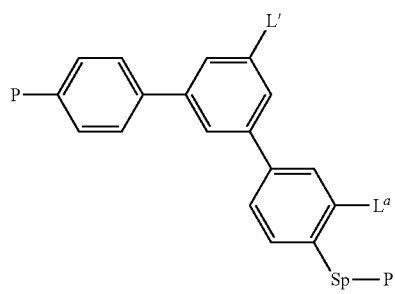
I5-1-3
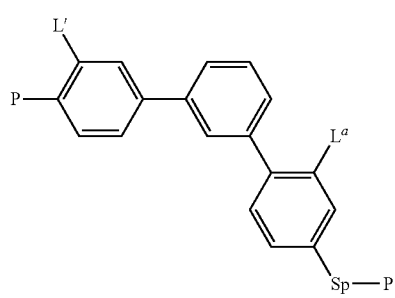
I5-1-4
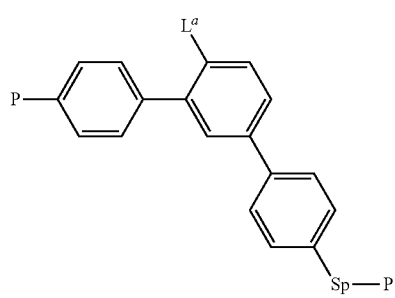
I5-1-5
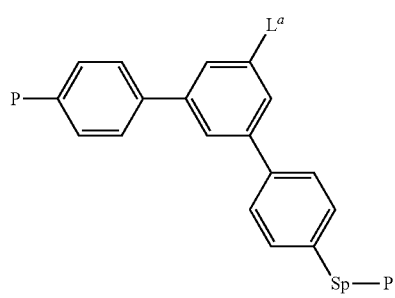
I5-1-6
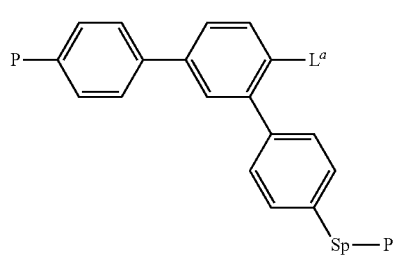
I5-1-7
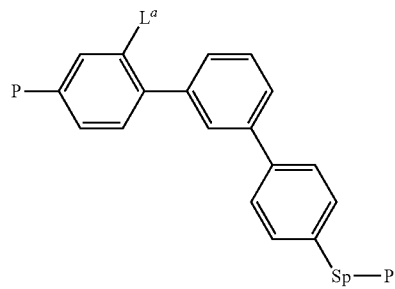
I5-1-8
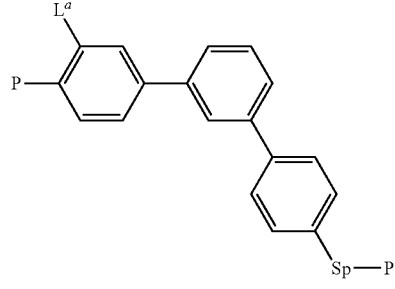
I5-1-9
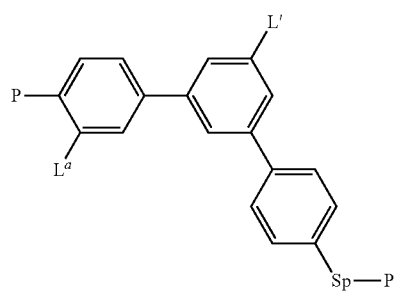
I5-1-10
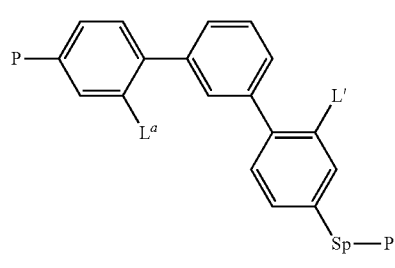
I5-1-11
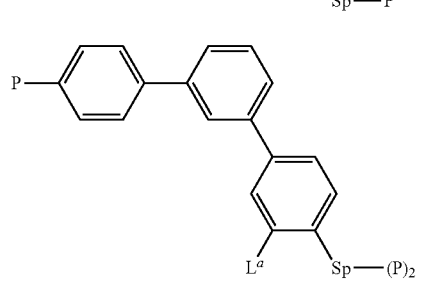
I5-2-1
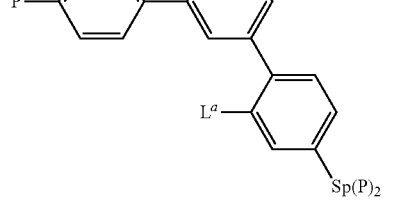
I5-2-2

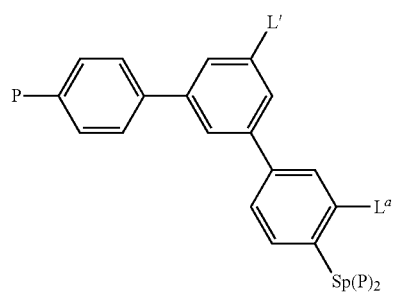
I5-2-3
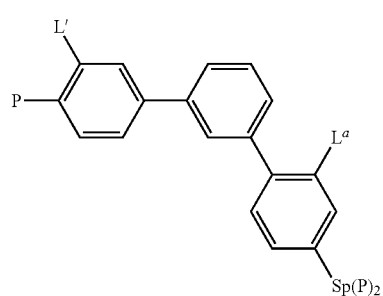
I5-2-4
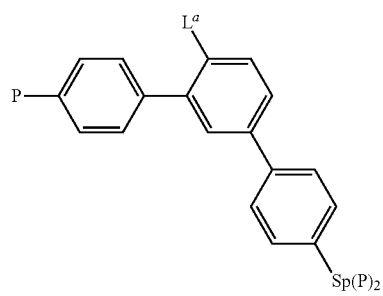
I5-2-5
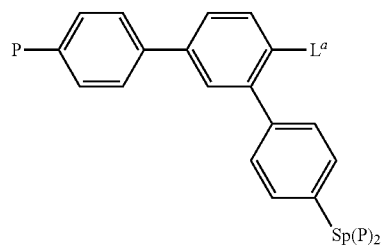
I5-2-7
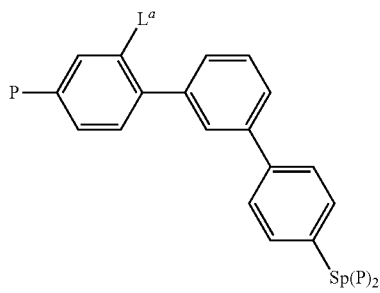
I5-2-8
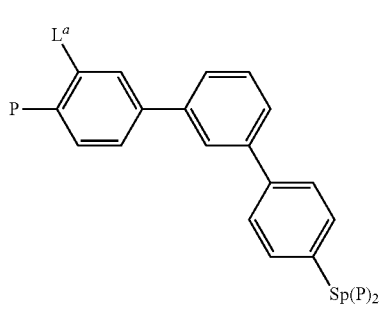
I5-2-9
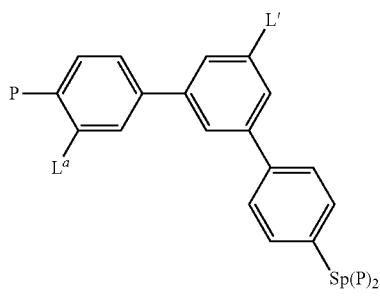
I5-2-10
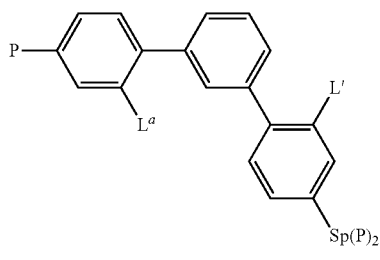
I5-2-11
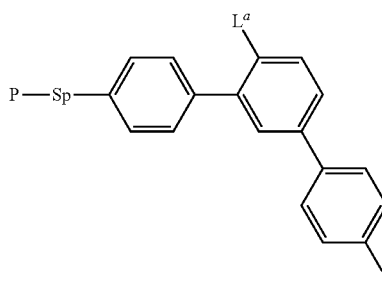
I5-3-1

-continued

I5-3-2

I5-3-3

I5-3-4

I5-3-5

I5-3-6

-continued

I5-3-7

I5-4-1

I5-4-2

I5-4-3

I5-4-4

I5-4-5
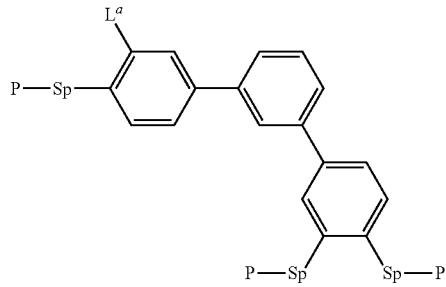

I5-4-6
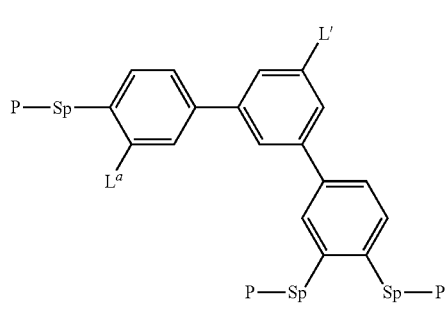

I5-4-7
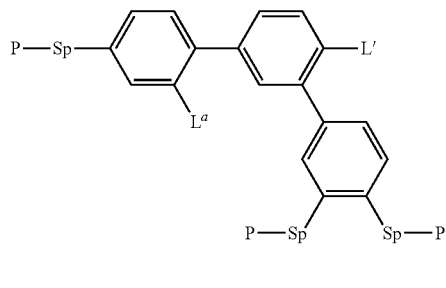

I5-5-1
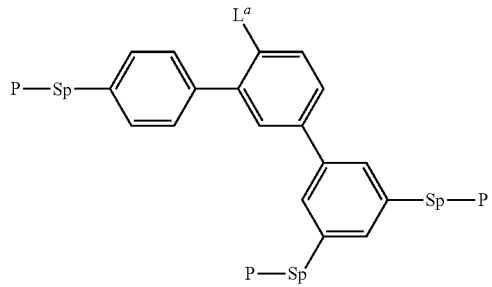

I5-5-2
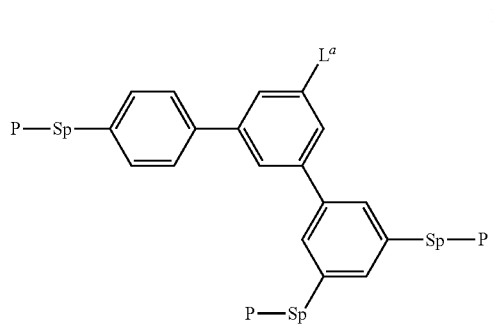

I5-5-3
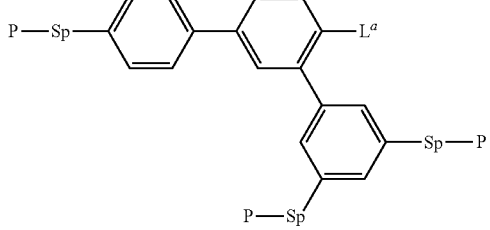

I5-5-4
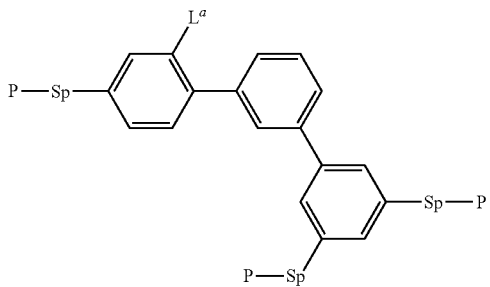

I5-5-5
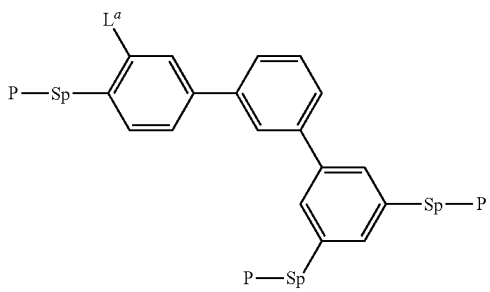

I5-5-6
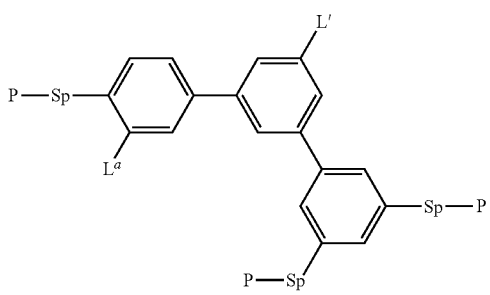

I5-5-7
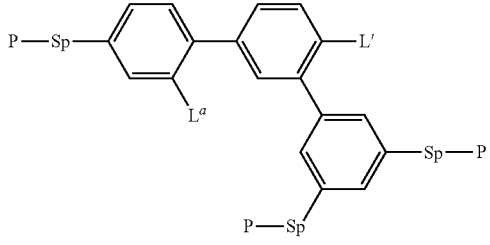

wherein P, Sp, Sp(P)$_2$ and L$^a$ have the meanings given above or below, with Sp being different from a single bond, and L' has one of the meanings given for L above or below.

Very preferred compounds of subformulae I1-1-1 to I5-5-7 are those wherein all groups P are identical and denote either an acrylate or methacrylate group, furthermore those wherein Sp is, —(CH$_2$)$_{p1}$—, —(CH$_2$)$_{p1}$—O—, —(CH$_2$)$_{p1}$—O—CO— or —(CH$_2$)$_{p1}$—CO—O—, in which p1 is an integer from 1 to 12, preferably 1 to 6, and the O— or CO-group is connected to the benzene ring, furthermore those wherein Sp(P)$_2$ is selected from formulae S1-S8, very preferably from subformulae S1a-S3a, furthermore those wherein L' is F or denotes L$^a$, preferably F, furthermore those wherein L$^a$ is OCH$_3$, OC$_2$H$_5$, O(CH$_2$)$_2$CH$_3$, OC(CH$_3$)$_3$ or OCF$_3$, very preferably OCH$_3$ or OCF$_3$, most preferably OCH$_3$.

Further preferred compounds of formula I and its subformulae are selected from the following preferred embodiments, including any combination thereof:

All groups P in the compound have the same meaning,
Ar is selected from formulae Ar1, Ar2, Ar3 and Ar4, and all groups P present in the compound have the same meaning,
Ar is selected from formulae Ar1, Ar2, Ar3, Ar4 and Ar5, and all groups P present in the compound have the same meaning,
Ar is selected from formulae Ar1, Ar2, Ar3, Ar4 and Ar6, and all groups P present in the compound have the same meaning,
Ar is selected from formulae Ar1, Ar2, Ar3, Ar4 and Ar7, and all groups P present in the compound have the same meaning,
Ar is selected from formulae Ar1, Ar2, Ar3, Ar4, A5 and Ar7, and all groups P present in the compound have the same meaning,
Ar is selected from formulae Ar1, Ar2, Ar3, Ar4, A6 and Ar7, and all groups P present in the compound have the same meaning,
Ar is selected of formula Ar5, and the groups P present in the compound can have the same or different meanings,
Ar is selected of formula Ar6, and the groups P present in the compound can have the same or different meanings,
Ar is selected of formula Ar7, and the groups P present in the compound can have the same or different meanings,
the compounds contain exactly two polymerizable groups (represented by the groups P),
the compounds contain exactly three polymerizable groups (represented by the groups P),
P is selected from the group consisting of acrylate, methacrylate and oxetane,
Sp, when being different from a single bond, is —(CH$_2$)$_{p2}$—, —(CH$_2$)$_{p2}$—O—, —(CH$_2$)$_{p2}$—CO—O—, —(CH$_2$)$_{p2}$—O—CO—, wherein p2 is 2, 3, 4, 5 or 6, and the O-atom or the CO-group, respectively, is connected to the benzene ring,
Sp(P)$_2$ is selected from subformulae S11-S31,
Sp, when being different from a single bond, is —(CH$_2$)$_{p2}$—, —(CH$_2$)$_{p2}$—O—, —(CH$_2$)$_{p2}$—CO—O—, —(CH$_2$)$_{p2}$—O—CO—, wherein p2 is 2, 3, 4, 5 or 6, and the O-atom or the CO-group, respectively, is connected to the benzene ring, and Sp(P)$_2$ is selected from formulae S1-S8, preferably from subformulae S11-S31,
R denotes P-Sp-,
R does not denote or contain a polymerizable group,
R does not denote or contain a polymerizable group and denotes straight chain, branched or cyclic alkyl having 1 to 25 C atoms, wherein one or more non-adjacent CH$_2$— groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F or C, L, when being different from L$^a$, denotes F, Cl or CN,
L$^a$ is OCH$_3$, OC$_2$H$_5$, OCF$_3$, OCF$_2$H or OCFH$_2$, very preferably OCH$_3$ or OC$_2$H$_5$, most preferably OCH$_3$,
r1, r2 and r3 denote 0 or 1,
r1, r2, r3, r4, r5 and r6 denote 0 or 1,
one of r1 and r7 is 0 and the other is 1,
r1 is 1, and r2 and r3 are 0,
r3 is 1 and r1 and r2 are 0,
one of r4 and r5 is 0 and the other is 1,
r4 and r6 are 0 and r5 is 1,
r1 and r4 are 0 and r3 is 1,
r1 and r3 are 0 and r4 is 1,
r3 and r4 are 0 and r1 is 1, The invention furthermore relates to compounds of formula II1-II7

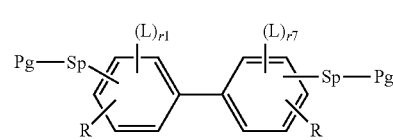

II1

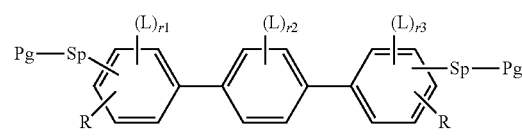

II2

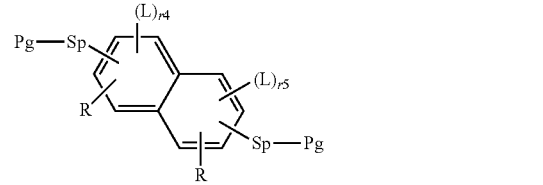

II3

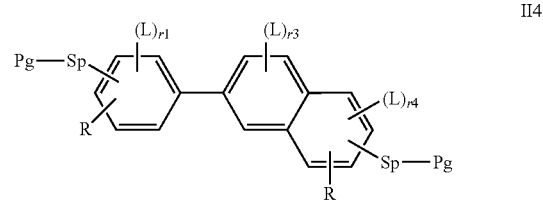

II4

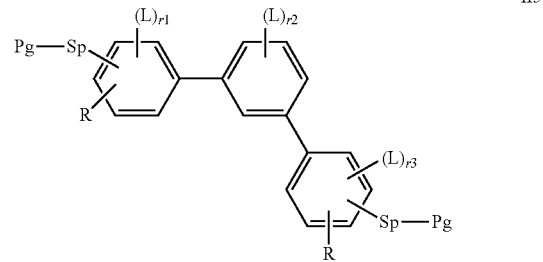

II5

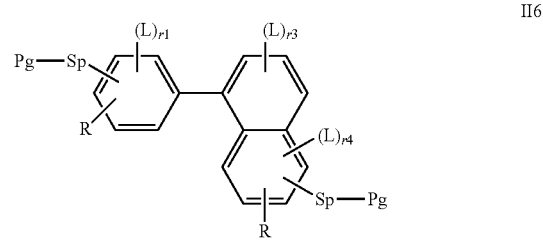

II6

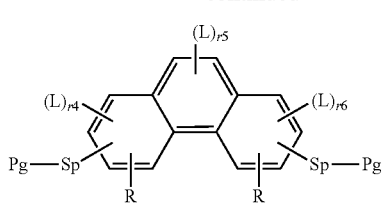

II7 wherein Sp, L, r$^{1-6}$ and q are as defined in formula I1-I7, R denotes H or Pg-Sp, and Pg denotes OH, a protected hydroxyl group or a masked hydroxyl group.

Preferred compounds of formula II1-II6 are selected from subformulae I1-I4 and I1a-I4a as defined above, wherein P is replaced by Pg.

Suitable protected hydroxyl groups Pg are known to the person skilled in the art. Preferred protecting groups for hydroxyl groups are alkyl, alkoxyalkyl, acyl, alkylsilyl, arylsilyl and arylmethyl groups, especially 2-tetrahydropyranyl, methoxymethyl, methoxyethoxymethyl, acetyl, triisopropylsilyl, tert-butyl-dimethylsilyl or benzyl.

The term "masked hydroxyl group" is understood to mean any functional group that can be chemically converted into a hydroxyl group. Suitable masked hydroxyl groups Pg are known to the person skilled in the art.

The compounds of formula II are suitable as intermediates for the preparation of compounds of the formula I and its subformulae.

The invention further relates to the use of the compounds of formula II as intermediates for the preparation of compounds of the formula I and its subformulae.

The compounds and intermediates of the formulae I and II and sub-formulae thereof can be prepared analogously to processes known to the person skilled in the art and described in standard works of organic chemistry, such as, for example, in Houben-Weyl, Methoden der organischen Chemie [Methods of Organic Chemistry], Thieme-Verlag, Stuttgart.

For example, compounds of formula I can be synthesized by esterification or etherification of the intermediates of formula II, wherein Pg denotes OH, using corresponding acids, acid derivatives, or halogenated compounds containing a polymerizable group P.

For example, acrylic or methacrylic esters can be prepared by esterification of the corresponding alcohols with acid derivatives like, for example, (meth)acryloyl chloride or (meth)acrylic anhydride in the presence of a base like pyridine or triethyl amine, and 4-(N,N-dimethylamino)pyridine (DMAP). Alternatively the esters can be prepared by esterification of the alcohols with (meth)acrylic acid in the presence of a dehydrating reagent, for example according to Steglich with dicyclohexylcarbodiimide (DCC), N-(3-dimethylaminopropyl)-N'-ethylcarbodiimide (EDC) or N-(3-dimethylaminopropyl)-N'-ethylcarbodiimide hydrochloride and DMAP.

Further suitable methods are shown in the examples.

For the production of PSA displays, the polymerizable compounds contained in the LC medium are polymerized or crosslinked (if one compound contains two or more polymerizable groups) by in-situ polymerization in the LC medium between the substrates of the LC display, optionally while a voltage is applied to the electrodes.

The structure of the PSA displays according to the invention corresponds to the usual geometry for PSA displays, as described in the prior art cited at the outset. Geometries without protrusions are preferred, in particular those in which, in addition, the electrode on the colour filter side is unstructured and only the electrode on the TFT side has slots. Particularly suitable and preferred electrode structures for PS-VA displays are described, for example, in US 2006/0066793 A1.

A preferred PSA type LC display of the present invention comprises:
  a first substrate including a pixel electrode defining pixel areas, the pixel electrode being connected to a switching element disposed in each pixel area and optionally including a micro-slit pattern, and optionally a first alignment layer disposed on the pixel electrode,
  a second substrate including a common electrode layer, which may be disposed on the entire portion of the second substrate facing the first substrate, and optionally a second alignment layer,
  an LC layer disposed between the first and second substrates and including an LC medium comprising a polymerizable component A and a liquid crystal component B as described above and below, wherein the polymerizable component A may also be polymerized.

The first and/or second alignment layer controls the alignment direction of the LC molecules of the LC layer. For example, in PS-VA displays the alignment layer is selected such that it imparts to the LC molecules homeotropic (or vertical) alignment (i.e. perpendicular to the surface) or tilted alignment. Such an alignment layer may for example comprise a polyimide, which may also be rubbed, or may be prepared by a photoalignment method.

The LC layer with the LC medium can be deposited between the substrates of the display by methods that are conventionally used by display manufacturers, for example the so-called one-drop-filling (ODF) method. The polymerizable component of the LC medium is then polymerized for example by UV photopolymerization. The polymerization can be carried out in one step or in two or more steps.

The PSA display may comprise further elements, like a colour filter, a black matrix, a passivation layer, optical retardation layers, transistor elements for addressing the individual pixels, etc., all of which are well known to the person skilled in the art and can be employed without inventive skill.

The electrode structure can be designed by the skilled person depending on the individual display type. For example for PS-VA displays a multi-domain orientation of the LC molecules can be induced by providing electrodes having slits and/or bumps or protrusions in order to create two, four or more different tilt alignment directions.

Upon polymerization the polymerizable compounds form a crosslinked polymer, which causes a certain pretilt of the LC molecules in the LC medium. Without wishing to be bound to a specific theory, it is believed that at least a part of the crosslinked polymer, which is formed by the polymerizable compounds, will phase-separate or precipitate from the LC medium and form a polymer layer on the substrates or electrodes, or the alignment layer provided thereon. Microscopic measurement data (like SEM and AFM) have confirmed that at least a part of the formed polymer accumulates at the LC/substrate interface.

The polymerization can be carried out in one step. It is also possible firstly to carry out the polymerization, optionally while applying a voltage, in a first step in order to produce a pretilt angle, and subsequently, in a second polymerization step without an applied voltage, to polymerize or crosslink the compounds which have not reacted in the first step ("end curing").

Suitable and preferred polymerization methods are, for example, thermal or photopolymerization, preferably photopolymerization, in particular UV induced photopolymerization, which can be achieved by exposure of the polymerizable compounds to UV radiation.

Optionally one or more polymerization initiators are added to the LC medium. Suitable conditions for the polymerization and suitable types and amounts of initiators are known to the person skilled in the art and are described in the literature. Suitable for free-radical polymerization are, for example, the commercially available photoinitiators Irgacure651®, Irgacure184®, Irgacure907®, Irgacure369® or Darocure1173® (Ciba AG). If a polymerization initiator is employed, its proportion is preferably 0.001 to 5% by weight, particularly preferably 0.001 to 1% by weight.

The polymerizable compounds according to the invention are also suitable for polymerization without an initiator, which is accompanied by considerable advantages, such, for example, lower material costs and in particular less contamination of the LC medium by possible residual amounts of the initiator or degradation products thereof. The polymerization can thus also be carried out without the addition of an initiator. In a preferred embodiment, the LC medium thus does not contain a polymerization initiator.

The LC medium may also comprise one or more stabilizers in order to prevent undesired spontaneous polymerization of the RMs, for example during storage or transport. Suitable types and amounts of stabilizers are known to the person skilled in the art and are described in the literature. Particularly suitable are, for example, the commercially available stabilizers from the Irganox® series (Ciba AG), such as, for example, Irganox® 1076. If stabilizers are employed, their proportion, based on the total amount of RMs or the polymerizable component (component A), is preferably 10-500,000 ppm, particularly preferably 50-50,000 ppm.

The polymerizable compounds of formula I do in particular show good UV absorption in, and are therefore especially suitable for, a process of preparing a PSA display including one or more of the following features:
- the polymerizable medium is exposed to UV light in the display in a 2-step process, including a first UV exposure step ("UV-1 step") to generate the tilt angle, and a second UV exposure step ("UV-2 step") to finish polymerization,
- the polymerizable medium is exposed to UV light in the display generated by an energy-saving UV lamp (also known as "green UV lamps"). These lamps are characterized by a relative low intensity (1/100-1/10 of a conventional UV1 lamp) in their absorption spectra from 300-380 nm, and are preferably used in the UV2 step, but are optionally also used in the UV1 step when avoiding high intensity is necessary for the process.
- the polymerizable medium is exposed to UV light in the display generated by a UV lamp with a radiation spectrum that is shifted to longer wavelengths, preferably 340 nm or more, to avoid short UV light exposure in the PS-VA process.

Both using lower intensity and a UV shift to longer wavelengths protect the organic layer against damage that may be caused by the UV light.

A preferred embodiment of the present invention relates to a process for preparing a PSA display as described above and below, comprising one or more of the following features:
- the polymerizable LC medium is exposed to UV light in a 2-step process, including a first UV exposure step ("UV-1 step") to generate the tilt angle, and a second UV exposure step ("UV-2 step") to finish polymerization,
- the polymerizable LC medium is exposed to UV light generated by a UV lamp having an intensity of from 0.5 mW/cm$^2$ to 10 mW/cm$^2$ in the wavelength range from 300-380 nm, preferably used in the UV2 step, and optionally also in the UV1 step,
- the polymerizable LC medium is exposed to UV light having a wavelength of 340 nm or more, and preferably 400 nm or less.

This preferred process can be carried out for example by using the desired UV lamps or by using a band pass filter and/or a cut-off filter, which are substantially transmissive for UV light with the respective desired wavelength(s) and are substantially blocking light with the respective undesired wavelengths. For example, when irradiation with UV light of wavelengths X of 300-400 nm is desired, UV exposure can be carried out using a wide band pass filter being substantially transmissive for wavelengths 300 nm<$\lambda$<400 nm. When irradiation with UV light of wavelength $\lambda$ of more than 340 nm is desired, UV exposure can be carried out using a cut-off filter being substantially transmissive for wavelengths $\lambda$>340 nm.

"Substantially transmissive" means that the filter transmits a substantial part, preferably at least 50% of the intensity, of incident light of the desired wavelength(s). "Substantially blocking" means that the filter does not transmit a substantial part, preferably at least 50% of the intensity, of incident light of the undesired wavelengths. "Desired (undesired) wavelength" e.g. in case of a band pass filter means the wavelengths inside (outside) the given range of $\lambda$, and in case of a cut-off filter means the wavelengths above (below) the given value of $\lambda$.

This preferred process enables the manufacture of displays by using longer UV wavelengths, thereby reducing or even avoiding the hazardous and damaging effects of short UV light components.

UV radiation energy is in general from 6 to 100 J, depending on the production process conditions.

Preferably the LC medium according to the present invention does essentially consist of a polymerizable component A), or one or more polymerizable compounds of formula I, and an LC component B), or LC host mixture, as described above and below. However, the LC medium may additionally comprise one or more further components or additives, preferably selected from the list including but not limited to co-monomers, chiral dopants, polymerization initiators, inhibitors, stabilizers, surfactants, wetting agents, lubricating agents, dispersing agents, hydrophobing agents, adhesive agents, flow improvers, defoaming agents, deaerators, diluents, reactive diluents, auxiliaries, colorants, dyes, pigments and nanoparticles.

Particular preference is given to LC media comprising one, two or three polymerizable compounds of formula I.

Preference is furthermore given to LC media in which the polymerizable component A) comprises exclusively polymerizable compounds of formula I.

Preference is furthermore given to LC media in which the liquid-crystalline component B) or the LC host mixture has a nematic LC phase, and preferably has no chiral liquid crystal phase.

The LC component B), or LC host mixture, is preferably a nematic LC mixture.

Preference is furthermore given to achiral compounds of formula I, and to LC media in which the compounds of component A and/or B are selected exclusively from the group consisting of achiral compounds.

Preferably the proportion of the polymerizable component A) in the LC medium is from >0 to <5%, very preferably from >0 to <1%, most preferably from 0.01 to 0.5%.

Preferably the proportion of compounds of formula I in the LC medium is from >0 to <5%, very preferably from >0 to <1%, most preferably from 0.01 to 0.5%.

Preferably the proportion of the LC component B) in the LC medium is from 95 to <100%, very preferably from 99 to <100%.

In a preferred embodiment the polymerizable compounds of the polymerizable component B) are exclusively selected from formula I.

In another preferred embodiment the polymerizable component B) comprises, in addition to the compounds of formula I, one or more further polymerizable compounds ("co-monomers"), preferably selected from RMs.

Suitable and preferred mesogenic comonomers are selected from the following formulae:

-continued in which the individual radicals have the following meanings:

- $P^1$, $P^2$ and $P^3$ each, independently of one another, denote an acrylate or methacrylate group,
- $Sp^1$, $Sp^2$ and $Sp^3$ each, independently of one another, denote a single bond or a spacer group having one of the meanings indicated above and below for Sp, and particularly preferably denote —$(CH_2)_{p1}$—, —$(CH_2)_{p1}$—O—, —$(CH_2)_{p1}$—CO—O—, —$(CH_2)_{p1}$—O—CO— or —$(CH_2)_{p1}$—O—CO—O—, in which p1 is an integer from 1 to 12, where, in addition, one or more of the radicals $P^1$-$Sp^1$-, $P^1$—$Sp^2$- and $P^3$—$Sp^3$- may denote $R^{aa}$, with the proviso that at least one of the radicals $P^1$-$Sp^1$-, $P^2$—$Sp^2$ and $P^3$—$Sp^3$- present is different from $R^{aa}$,
- $R^{aa}$ denotes H, F, Cl, CN or straight-chain or branched alkyl having 1 to 25 C atoms, in which, in addition, one or more non-adjacent $CH_2$ groups may each be replaced, independently of one another, by $C(R^0)$=$C(R^{00})$—, —C≡C—, —$N(R^0)$—, —O—, —S—, —CO—, —CO—O—, —O—CO—, —O—CO—O— in such a way that O and/or S atoms are not linked directly to one another, and in which, in addition, one or more H atoms may be replaced by F, Cl, CN or $P^1$—$Sp^1$-, particularly preferably straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms (where the alkenyl and alkynyl radicals have at least two C atoms and the branched radicals have at least three C atoms),
- $R^0$, $R^{00}$ each, independently of one another and identically or differently on each occurrence, denote H or alkyl having 1 to 12 C atoms,
- $R^y$ and $R^z$ each, independently of one another, denote H, F, $CH_3$ or $CF_3$,
- $X^1$, $X^2$ and $X^3$ each, independently of one another, denote —CO—O—, —O—CO— or a single bond,
- $Z^1$ denotes —O—, —CO—, —$C(R^yR^z)$— or —$CF_2CF_2$—,
- $Z^2$ and $Z^3$ each, independently of one another, denote —CO—O—, —O—CO—, —$CH_2O$—, —$OCH_2$—, —$CF_2O$—, —$OCF_2$— or —$(CH_2)_n$—, where n is 2, 3 or 4,
- L on each occurrence, identically or differently, denotes F, Cl, CN or straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, preferably F,
- L' and L" each, independently of one another, denote H, F or Cl,
- r denotes 0, 1, 2, 3 or 4,
- s denotes 0, 1, 2 or 3,
- t denotes 0, 1 or 2,
- x denotes 0 or 1.

Especially preferred are compounds of formulae M2, M13, M17, M22, M23, M24 and M30.

Further preferred are trireactive compounds M15 to M30, in particular M17, M18, M19, M22, M23, M24, M25, M26, M30 and M31.

In the compounds of formulae M1 to M31 the group

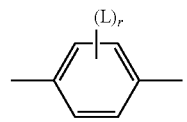

is preferably

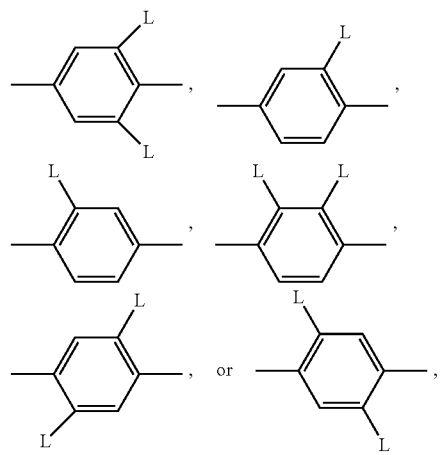

wherein L on each occurrence, identically or differently, has one of the meanings given above or below, and is preferably F, Cl, CN, $NO_2$, $CH_3$, $C_2H_5$, $C(CH_3)_3$, $CH(CH_3)_2$, $CH_2CH(CH_3)C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$ or P-Sp-, very preferably F, Cl, ON, $CH_3$, $C_2H_5$, $OCH_3$, $COCH_3$, $OCF_3$ or P-Sp-, more preferably F, Cl, $CH_3$, $OCH_3$, $COCH_3$ oder $OCF_3$, especially F or $CH_3$.

Besides the polymerizable compounds described above, the LC media for use in the LC displays according to the invention comprise an LC mixture ("host mixture") comprising one or more, preferably two or more LC compounds which are selected from low-molecular-weight compounds that are unpolymerizable. These LC compounds are selected such that they stable and/or unreactive to a polymerization reaction under the conditions applied to the polymerization of the polymerizable compounds.

In principle, any LC mixture which is suitable for use in conventional displays is suitable as host mixture. Suitable LC mixtures are known to the person skilled in the art and are described in the literature, for example mixtures in VA displays in EP 1 378 557 A1 and mixtures for OCB displays in EP 1 306 418 A1 and DE 102 24 046 A1.

The polymerizable compounds of formula I are especially suitable for use in an LC host mixture that comprises one or more mesogenic or LC compounds comprising an alkenyl group (hereinafter also referred to as "alkenyl compounds"), wherein said alkenyl group is stable to a polymerization reaction under the conditions used for polymerization of the compounds of formula I and of the other polymerizable compounds contained in the LC medium. Compared to RMs known from prior art the compounds of formula I do in such an LC host mixture exhibit improved properties, like solubility, reactivity or capability of generating a tilt angle.

Thus, in addition to the polymerizable compounds of formula I, the LC medium according to the present invention comprises one or more mesogenic or liquid crystalline compounds comprising an alkenyl group, ("alkenyl compound"), where this alkenyl group is preferably stable to a polymerization reaction under the conditions used for the polymerization of the polymerizable compounds of formula I or of the other polymerizable compounds contained in the LC medium.

The alkenyl groups in the alkenyl compounds are preferably selected from straight-chain, branched or cyclic alkenyl, in particular having 2 to 25 C atoms, particularly preferably having 2 to 12 C atoms, in which, in addition, one or more non-adjacent CH$_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F and/or Cl.

Preferred alkenyl groups are straight-chain alkenyl having 2 to 7 C atoms and cyclohexenyl, in particular ethenyl, propenyl, butenyl, pentenyl, hexenyl, heptenyl, 1,4-cyclohexen-1-yl and 1,4-cyclohexen-3-yl.

The concentration of compounds containing an alkenyl group in the LC host mixture (i.e. without any polymerizable compounds) is preferably from 5% to 100%, very preferably from 20% to 60%.

Especially preferred are LC mixtures containing 1 to 5, preferably 1, 2 or 3 compounds having an alkenyl group.

The mesogenic and LC compounds containing an alkenyl group are preferably selected from formulae AN and AY as defined below.

Besides the polymerizable component A) as described above, the LC media according to the present invention comprise an LC component B), or LC host mixture, comprising one or more, preferably two or more LC compounds which are selected from low-molecular-weight compounds that are unpolymerizable. These LC compounds are selected such that they stable and/or unreactive to a polymerization reaction under the conditions applied to the polymerization of the polymerizable compounds.

In a first preferred embodiment the LC medium contains an LC component B), or LC host mixture, based on compounds with negative dielectric anisotropy. Such LC media are especially suitable for use in PS-VA and PS—UB-FFS displays. Particularly preferred embodiments of such an LC medium are those of sections a)-z3) below:

a) LC medium wherein the component B) or LC host mixture comprises one or more compounds selected from formulae CY and PY:

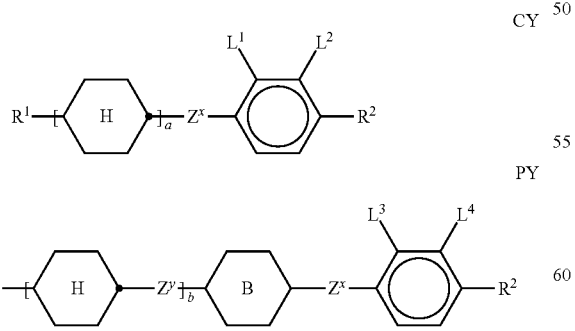

wherein
a denotes 1 or 2,
b denotes 0 or 1,

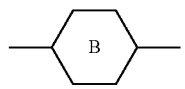

denotes

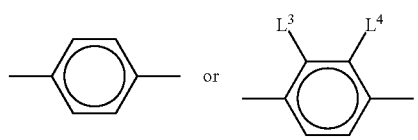

R$^1$ and R$^2$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, preferably alkyl or alkoxy having 1 to 6 C atoms, Z$^x$ and Z$^y$ each, independently of one another, denote —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond, L$^{1-4}$ each, independently of one another, denote F, Cl, OCF$_3$, CF$_3$, CH$_3$, CH$_2$F, CHF$_2$.

Preferably, both L$^1$ and L$^2$ denote F or one of L$^1$ and L$^2$ denotes F and the other denotes Cl, or both L$^3$ and L$^4$ denote F or one of L$^3$ and L$^4$ denotes F and the other denotes Cl.

The compounds of the formula CY are preferably selected from the group consisting of the following sub-formulae:

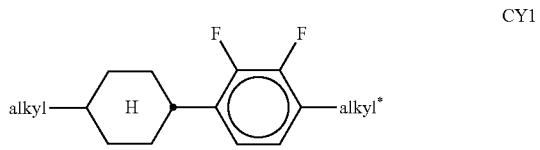

CY1

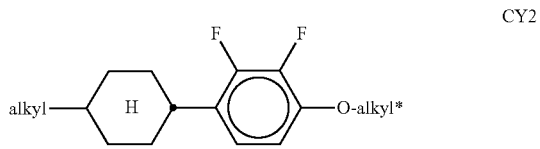

CY2

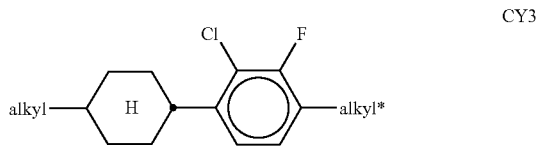

CY3

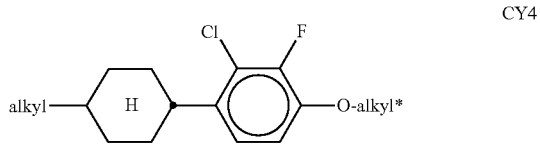

CY4

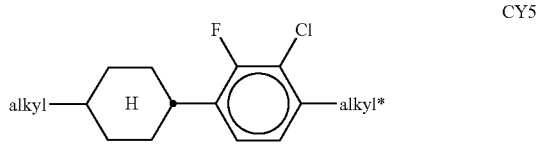

CY5

CY6
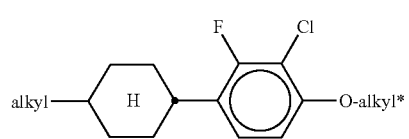
CY7
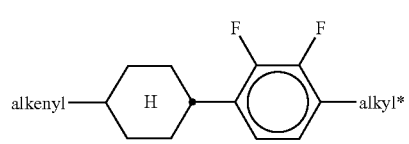
CY8
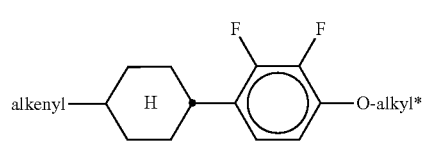
CY9
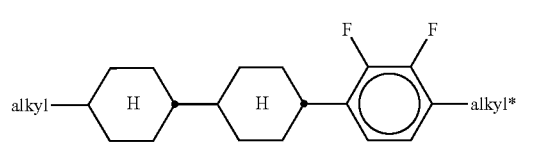
CY10
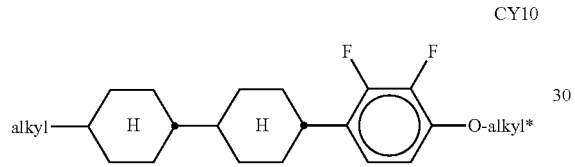
CY11
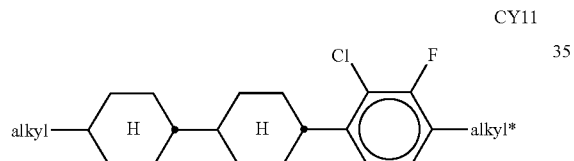
CY12
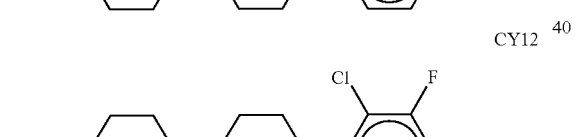
CY13
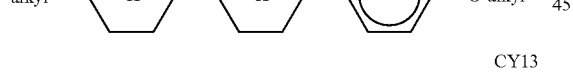
CY14
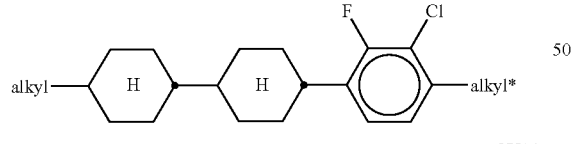
CY15
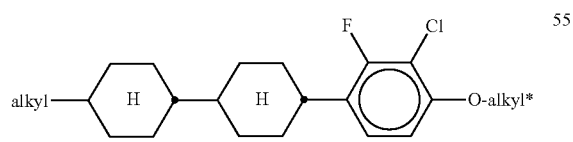
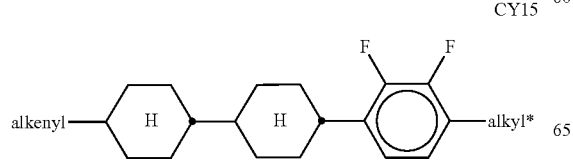
CY16
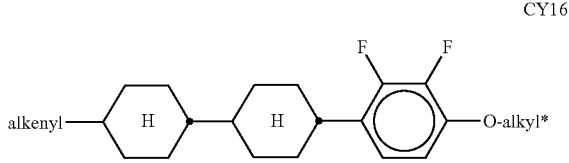
CY17
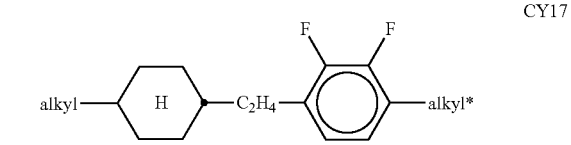
CY18
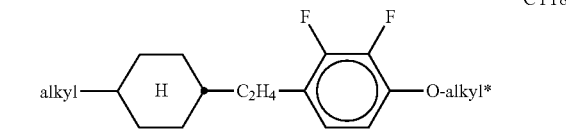
CY19
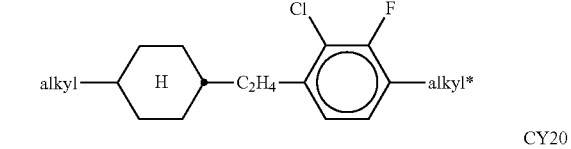
CY20
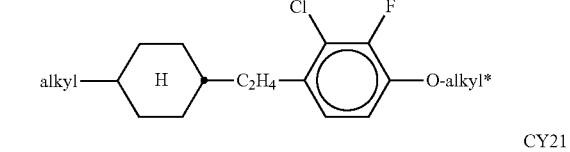
CY21
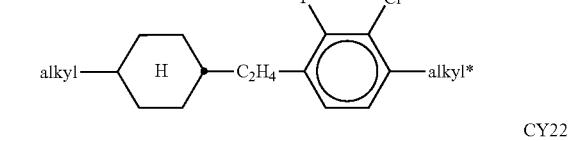
CY22
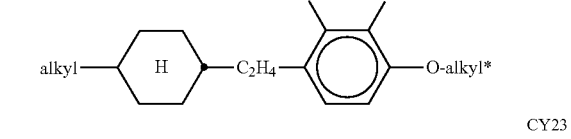
CY23
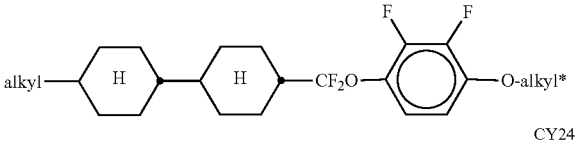
CY24
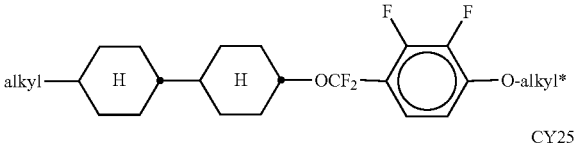
CY25
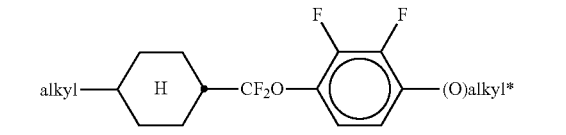
CY26
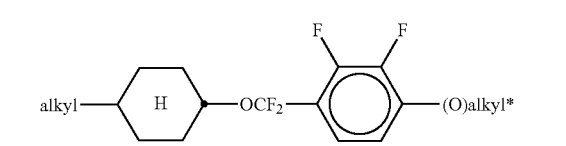

-continued

CY27
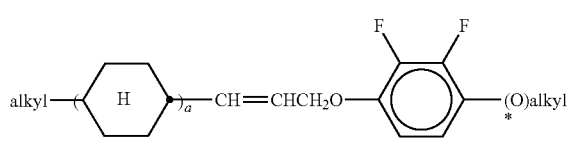

CY28
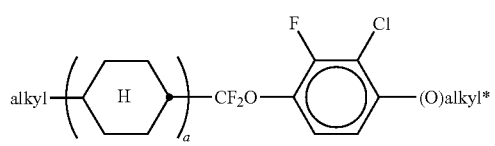

CY29
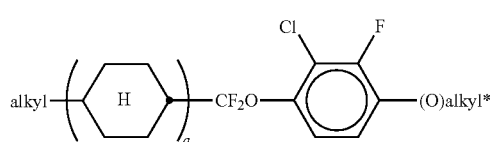

CY30
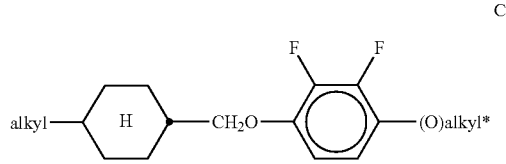

CY31
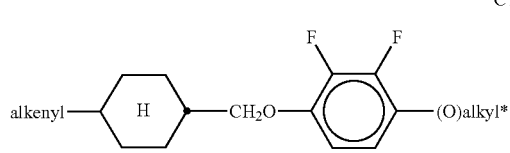

CY32
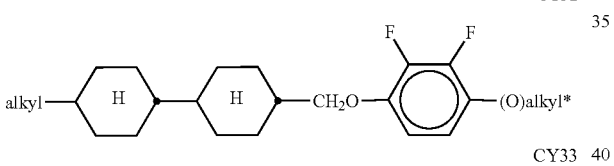

CY33
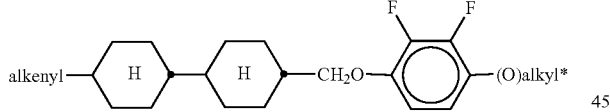

in which a denotes 1 or 2, alkyl and alkyl* each, independently of one another, denote a straight-chain alkyl radical having 1-6 C atoms, and alkenyl denotes a straight-chain alkenyl radical having 2-6 C atoms, and (0) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The compounds of the formula PY are preferably selected from the group consisting of the following sub-formulae:

PY1
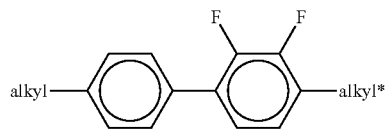

PY2
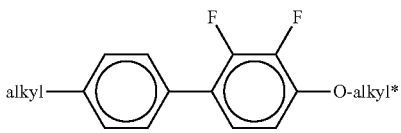

PY3
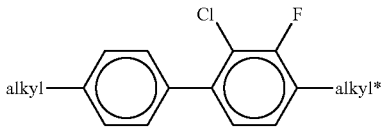

PY4
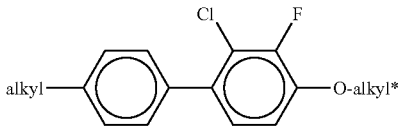

PY5
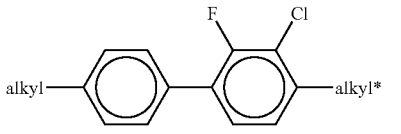

PY6
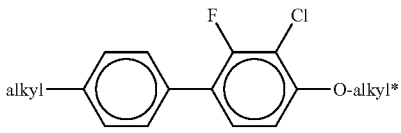

PY7
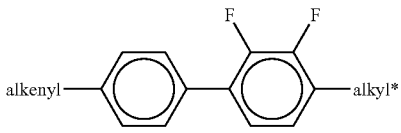

PY8
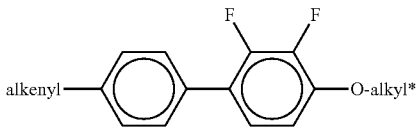

PY9
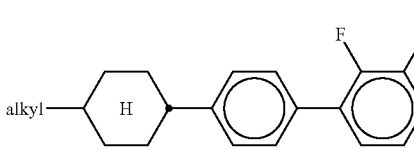

PY10
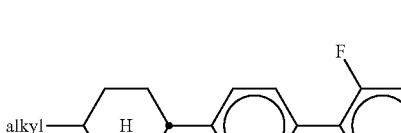

PY11
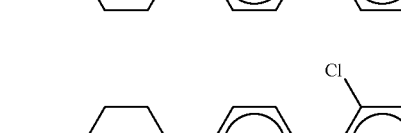

PY12
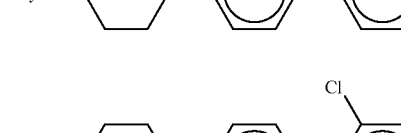

-continued

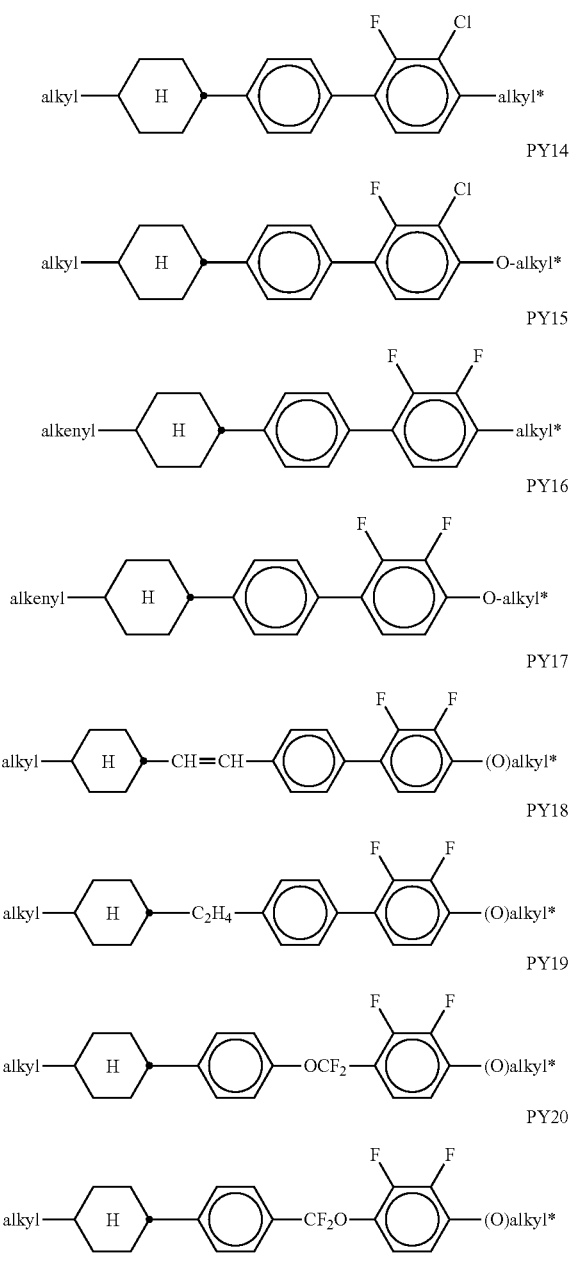

in which alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

b) LC medium wherein the component B) or LC host mixture comprises one or more mesogenic or LC compounds comprising an alkenyl group (hereinafter also referred to as "alkenyl compounds"), wherein said alkenyl group is stable to a polymerization reaction under the conditions used for polymerization of the polymerizable compounds contained in the LC medium.

Preferably the component B) or LC host mixture comprises one or more alkenyl compounds selected from formulae AN and AY

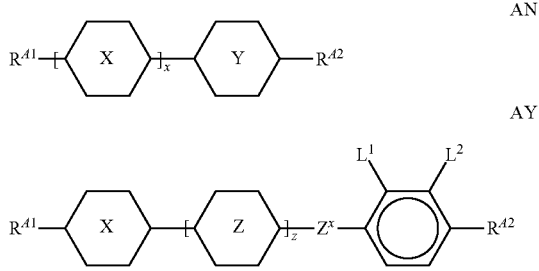

in which the individual radicals, on each occurrence identically or differently, and each, independently of one another, have the following meaning:

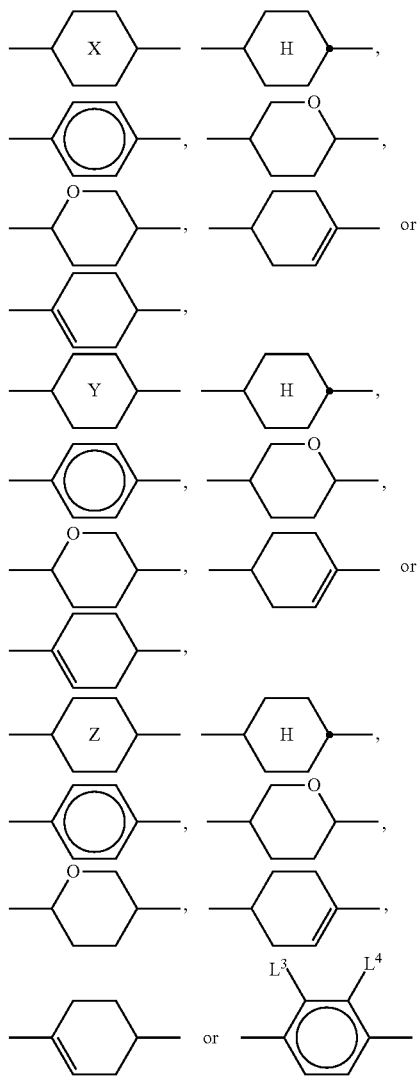

$R^{A1}$ alkenyl having 2 to 9 C atoms or, if at least one of the rings X, Y and Z denotes cyclohexenyl, also one of the meanings of $R^{A2}$, $R^{A2}$ alkyl having 1 to 12 C atoms, in which, in addition, one or two non-adjacent CH$_2$ groups may be replaced by —O—, —CH=CH—, —CO—, —OCO— or —COO— in such a way that O atoms are not linked directly to one another, $Z^x$ —CH$_2$CH$_2$—, —CH=CH—, —CF$_{20}$—, —OCF$_2$—, —CH$_2$O—, —OCH$_2$—, —CO—O—, —O—CO—, —C$_2$F$_4$—, —CF=CF—, —CH=CH—CH$_2$O—, or a single bond, preferably a single bond, $L^{1,2}$ H, F, Cl, OCF$_3$, CF$_3$, CH$_3$, CH$_2$F or CHF$_2$H, preferably H, F or Cl, x 1 or 2, z 0 or 1.

Preferred compounds of formula AN and AY are those wherein $R^{A2}$ is selected from ethenyl, propenyl, butenyl, pentenyl, hexenyl and heptenyl.

In a preferred embodiment the component B) or LC host mixture comprises one or more compounds of formula AN selected from the following sub-formulae:

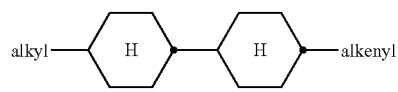
AN1

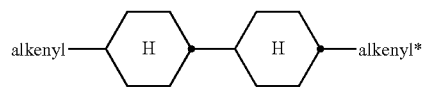
AN2

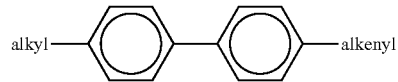
AN3

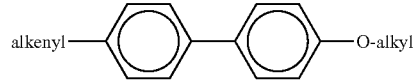
AN4

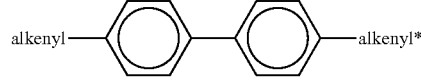
AN5

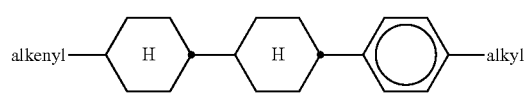
AN6

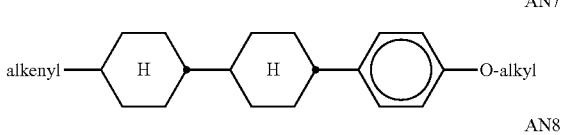
AN7

AN8

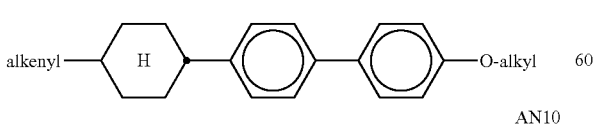
AN9

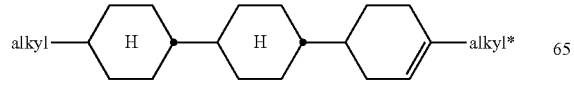
AN10

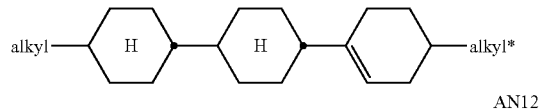
AN11

AN12 in which alkyl and alkyl* each, independently of one another, denote a straight-chain alkyl radical having 1-6 C atoms, and alkenyl and alkenyl* each, independently of one another, denote a straight-chain alkenyl radical having 2-7 C atoms. Alkenyl and alkenyl* preferably denote CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

Preferably the component B) or LC host mixture comprises one or more compounds selected from formulae AN1, AN2, AN3 and AN6, very preferably one or more compounds of formula AN1.

In another preferred embodiment the component B) or LC host mixture comprises one or more compounds of formula AN selected from the following sub-formulae:

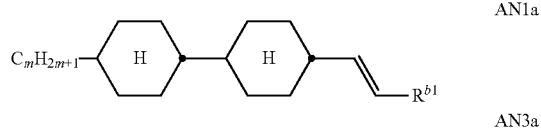
AN1a

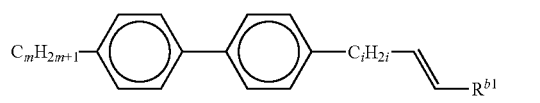
AN3a

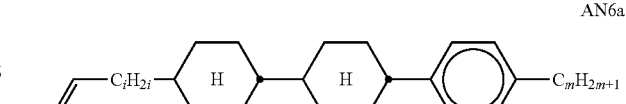
AN6a in which m denotes 1, 2, 3, 4, 5 or 6, i denotes 0, 1, 2 or 3, and $R^{b1}$ denotes H, CH$_3$ or C$_2$H$_5$.

In another preferred embodiment the component B) or LC host mixture comprises one or more compounds selected from the following sub-formulae:

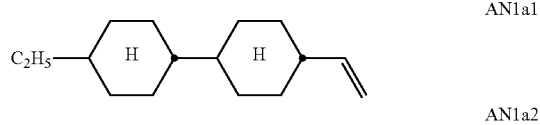
AN1a1

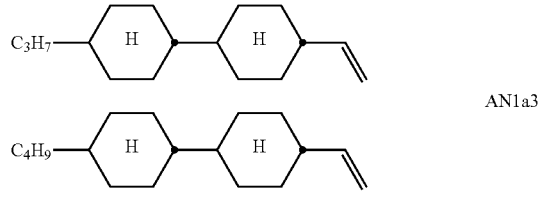
AN1a2

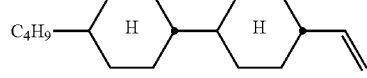
AN1a3

-continued
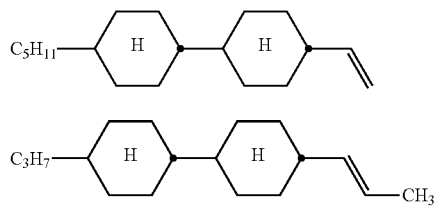
AN1a4
AN1a5
Most preferred are compounds of formula AN1a2 and AN1a5.
In another preferred embodiment the component B) or LC host mixture comprises one or more compounds of formula AY selected from the following sub-formulae:
AY1
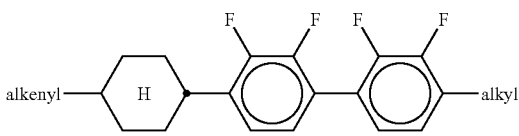
AY2
AY3
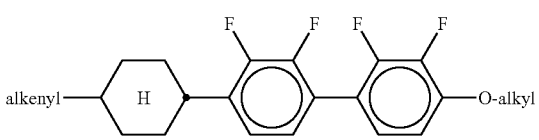
AY4
AY5
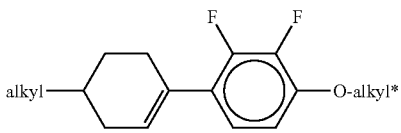
AY6
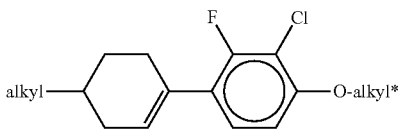
AY7
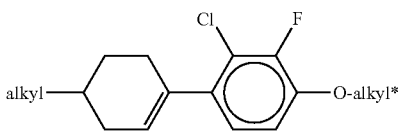
AY8
-continued
AY9
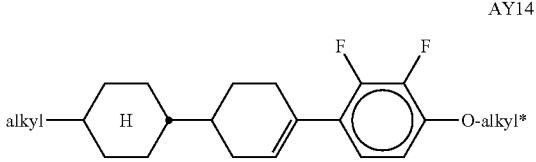
AY10
AY11
AY12
AY13
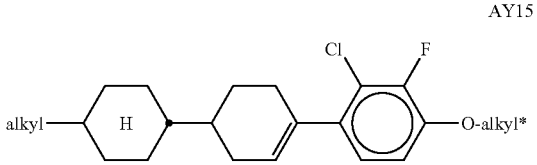
AY14
AY15
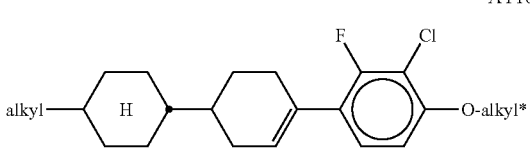
AY16
AY17
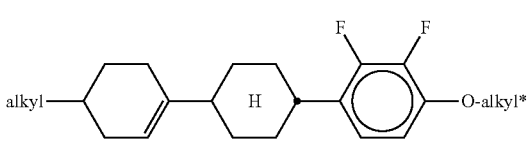
AY18
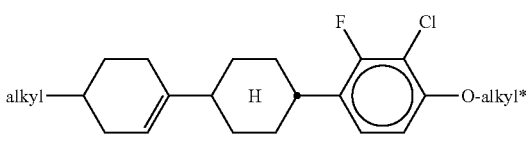

AY19
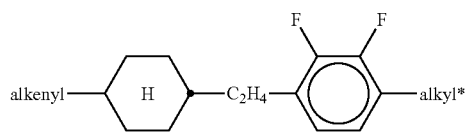

AY20
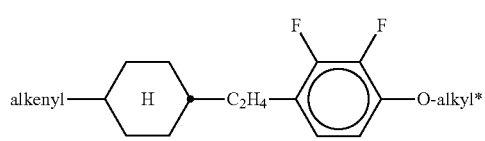

AY21
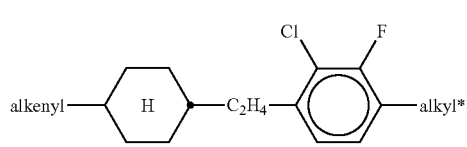

AY22
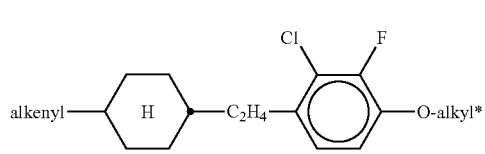

AY23
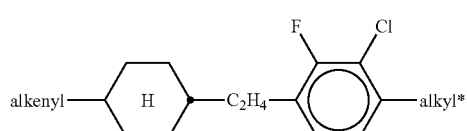

AY24
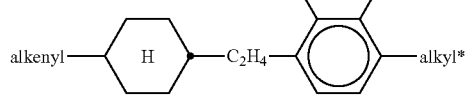

AY25
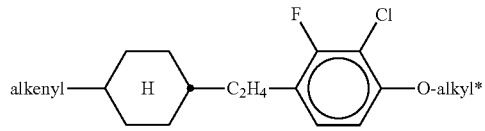

AY26
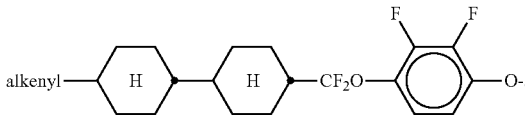

AY27
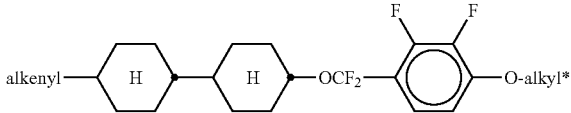

AY28
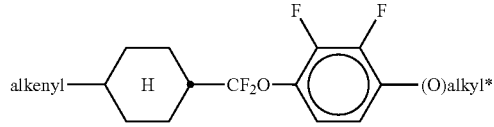

AY29
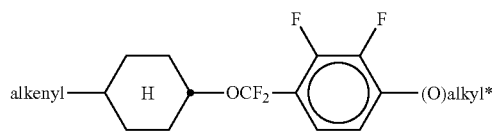

AY30

AY31 in which alkyl and alkyl* each, independently of one another, denote a straight-chain alkyl radical having 1-6 C atoms, "(O)" denotes an O-atom or a single bond, and alkenyl and alkenyl* each, independently of one another, denote a straight-chain alkenyl radical having 2-7 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

In another preferred embodiment the component B) or LC host mixture comprises one or more compounds of formula AY selected from the following sub-formulae:

AY5a
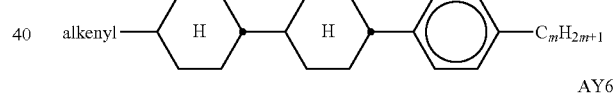

AY6a
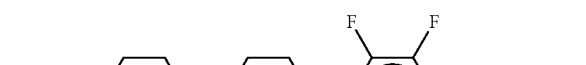

AY9a
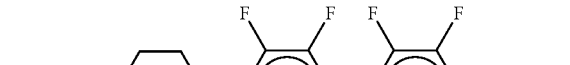

AY10a
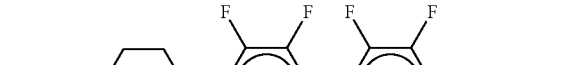

AY11a
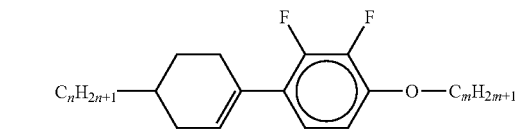

-continued

AY14a
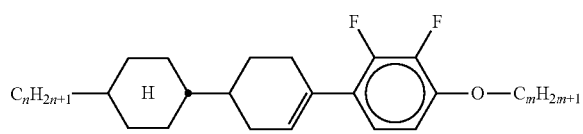

in which m and n each, independently of one another, denote 1, 2, 3, 4, 5 or 6, and alkenyl denotes CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

Preferably the proportion of compounds of formula AN and AY in the LC medium is from 2 to 70% by weight, very preferably from 5 to 60% by weight, most preferably from 10 to 50% by weight.

Preferably the LC medium or LC host mixture contains 1 to 5, preferably 1, 2 or 3 compounds selected from formulae AN and AY.

In another preferred embodiment of the present invention the LC medium comprises one or more compounds of formula AY14, very preferably of AY14a. The proportion of compounds of formula AY14 or AY14a in the LC medium is preferably 3 to 20% by weight.

The addition of alkenyl compounds of formula AN and/or AY enables a reduction of the viscosity and response time of the LC medium.

c) LC medium wherein the component B) or LC host mixture comprises one or more compounds of the following formula:

ZK
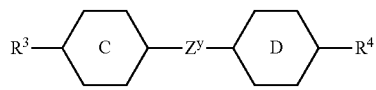

in which the individual radicals have the following meanings:

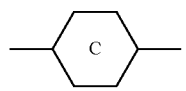

denotes

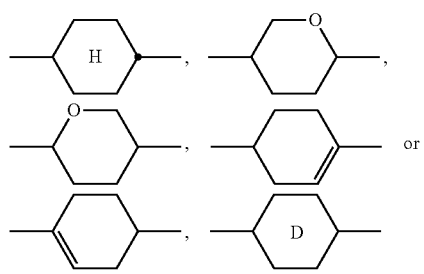

denotes

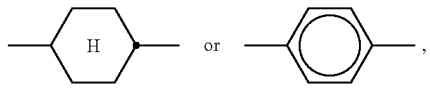

R$^3$ and R$^4$ each, independently of one another, denote alkyl having 1 to 12 C atoms, in which, in addition, one or two non-adjacent CH$_2$ groups may be replaced by —O—, —CH=CH—, —CO—, —O—CO— or —CO—O— in such a way that O atoms are not linked directly to one another, Z$^y$ denotes —CH$_2$CH$_2$—, —CH=CH—, —CF$_{20}$—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond.

The compounds of the formula ZK are preferably selected from the group consisting of the following sub-formulae:

ZK1

ZK2
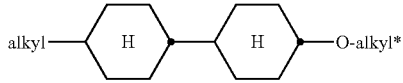

ZK3
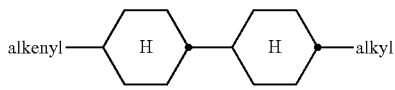

ZK4

ZK5
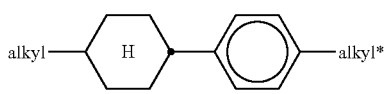

ZK6
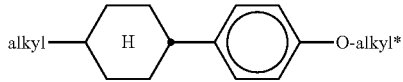

ZK7

ZK8
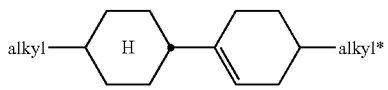

ZK9
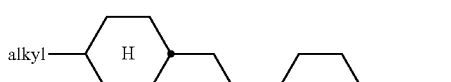

ZK10

in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

Especially preferred are compounds of formula ZK1.

Particularly preferred compounds of formula ZK are selected from the following sub-formulae:

C$_2$H$_5$—[H]—[H]—C$_3$H$_7$  ZK1a

C$_3$H$_7$—[H]—[H]—C$_4$H$_9$  ZK1b

C$_3$H$_7$—[H]—[H]—C$_5$H$_{11}$  ZK1c wherein the propyl, butyl and pentyl groups are straight-chain groups.

Most preferred are compounds of formula ZK1a.

d) LC medium wherein component B) or the LC host mixture additionally comprises one or more compounds of the following formula:

R$^5$—[H]—[E]$_e$—[D]—R$^6$  DK in which the individual radicals on each occurrence, identically or differently, have the following meanings:

R$^5$ and R$^6$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, preferably alkyl or alkoxy having 1 to 6 C atoms,

—[D]— denotes

—[H]— or —[⌬]—, denotes

—[H]—, —[⌬]— or

—[⌬-F]—, and e denotes 1 or 2.

The compounds of the formula DK are preferably selected from the group consisting of the following sub-formulae:

alkyl—[H]—[H]—[⌬]—alkyl*  DK1 alkyl—[H]—[H]—[⌬]—O-alkyl*  DK2 alkenyl—[H]—[H]—[⌬]—alkyl  DK3 alkyl—[H]—[⌬]—[⌬]—alkyl*  DK4 alkyl—[H]—[⌬]—[⌬]—O-alkyl*  DK5 alkenyl—[H]—[⌬]—[⌬]—alkyl  DK6 alkyl—[H]—[⌬-F]—[⌬]—alkyl*  DK7 alkyl—[H]—[⌬-F]—[⌬]—O-alkyl*  DK8 alkyl—[H]—[⌬]—[⌬-F]—[⌬]—alkyl*  DK9

-continued

DK10

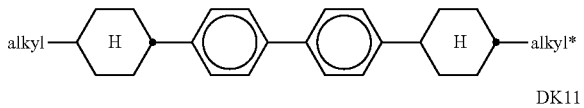

DK11

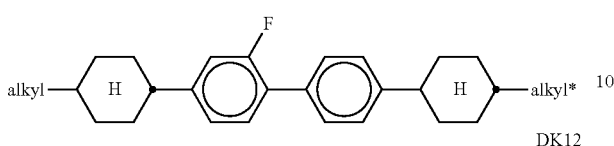

DK12

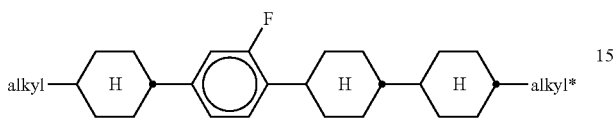

in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

e) LC medium wherein component B) or the LC host mixture additionally comprises one or more compounds of the following formula:

LY

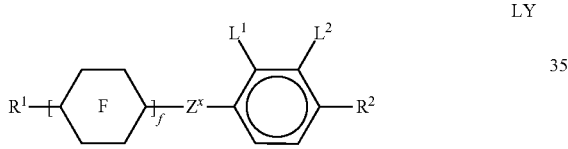

in which the individual radicals have the following meanings:

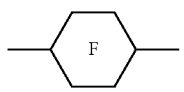

denotes

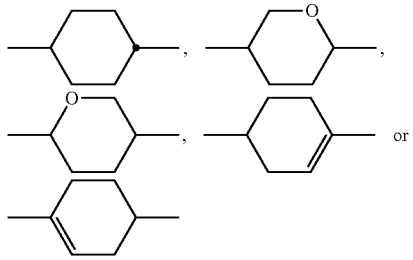

with at least one ring F being different from cyclohexylene,
f denotes 1 or 2,
R$^1$ and R$^2$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, Z$^x$ denotes —CH$_2$CH$_2$—, —CH=CH—, —CF$_{2O}$—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond, L$^1$ and L$^2$ each, independently of one another, denote F, Cl, OCF$_3$, CF$_3$, CH$_3$, CH$_2$F, CHF$_2$.

Preferably, both radicals L$^1$ and L$^2$ denote F or one of the radicals L$^1$ and L$^2$ denotes F and the other denotes Cl.

The compounds of the formula LY are preferably selected from the group consisting of the following sub-formulae:

LY1

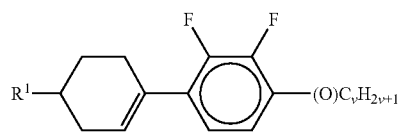

LY2

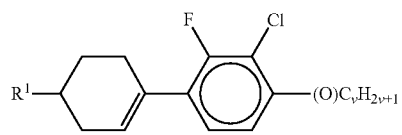

LY3

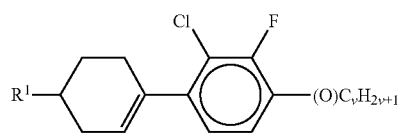

LY4

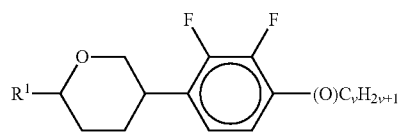

LY5

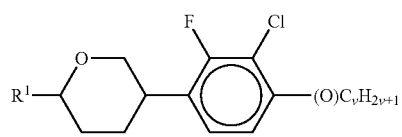

LY6

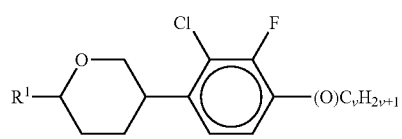

LY7

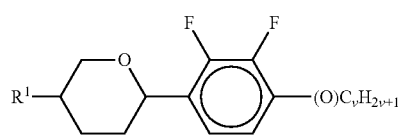

LY8

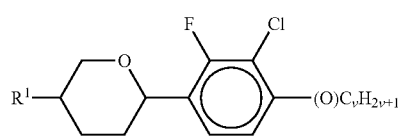

LY9

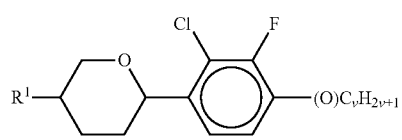

-continued

LY10
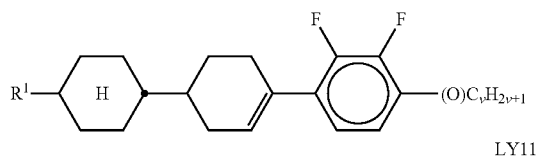

LY11
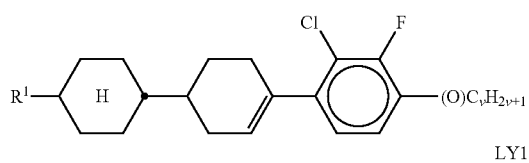

LY12
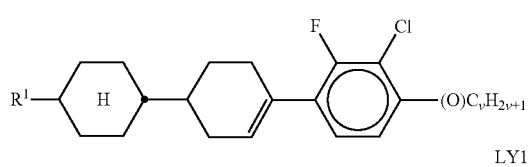

LY13
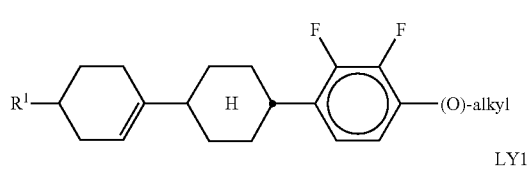

LY14
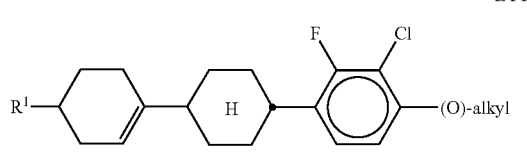

LY15
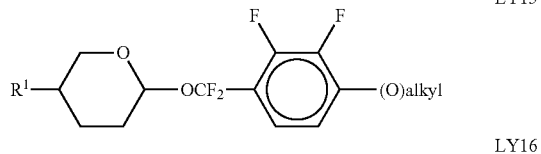

LY16
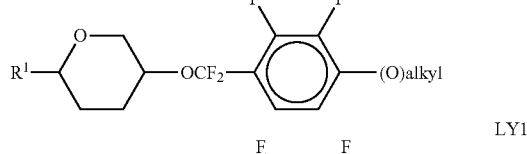

LY17
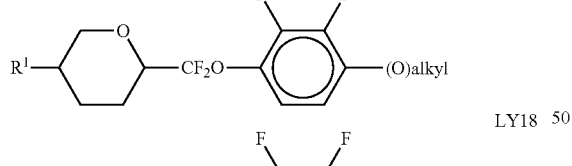

LY18
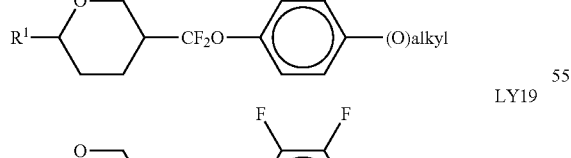

LY19

LY20
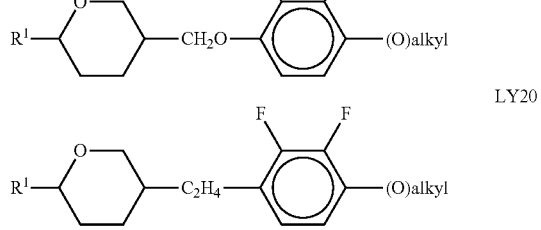

-continued

LY21
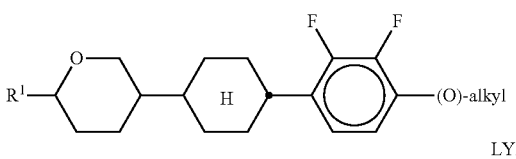

LY22
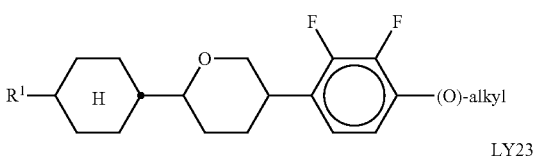

LY23
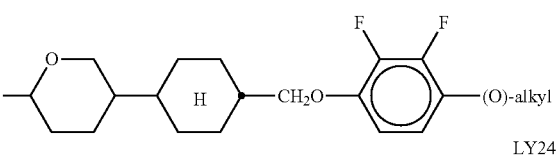

LY24
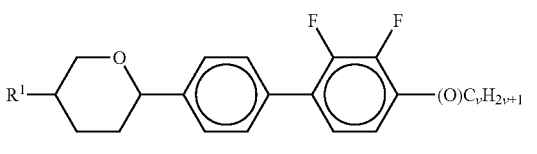

in which $R^1$ has the meaning indicated above, alkyl denotes a straight-chain alkyl radical having 1-6 C atoms, (O) denotes an oxygen atom or a single bond, and v denotes an integer from 1 to 6. $R^1$ preferably denotes straight-chain alkyl having 1 to 6 C atoms or straight-chain alkenyl having 2 to 6 C atoms, in particular $CH_3$, $C_2H_5$, n-$C_3H_7$, n-$C_4H_9$, n-$C_5H_{11}$, $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

f) LC medium wherein component B) or the LC host mixture additionally comprises one or more compounds selected from the group consisting of the following formulae:

G1
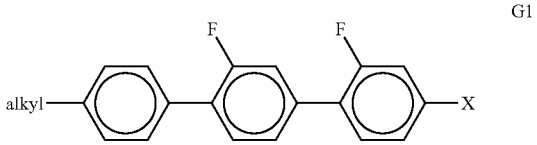

G2
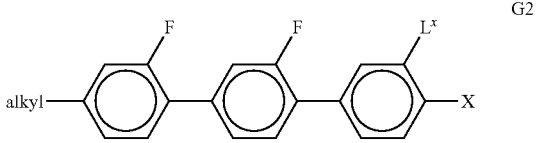

G3
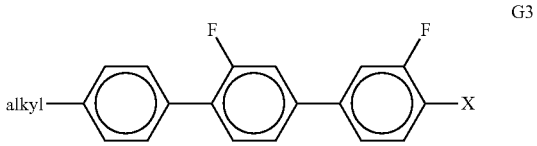

G4
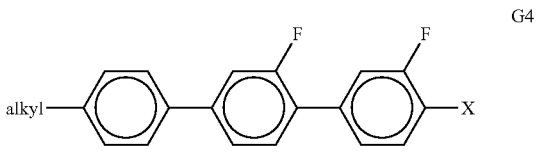

in which alkyl denotes $C_{1-6}$-alkyl, $L^x$ denotes H or F, and X denotes F, Cl, $OCF_3$, $OCHF_2$ or $OCH=CF_2$. Particular preference is given to compounds of the formula G1 in which X denotes F.

g) LC medium wherein component B) or the LC host mixture additionally comprises one or more compounds selected from the group consisting of the following formulae:

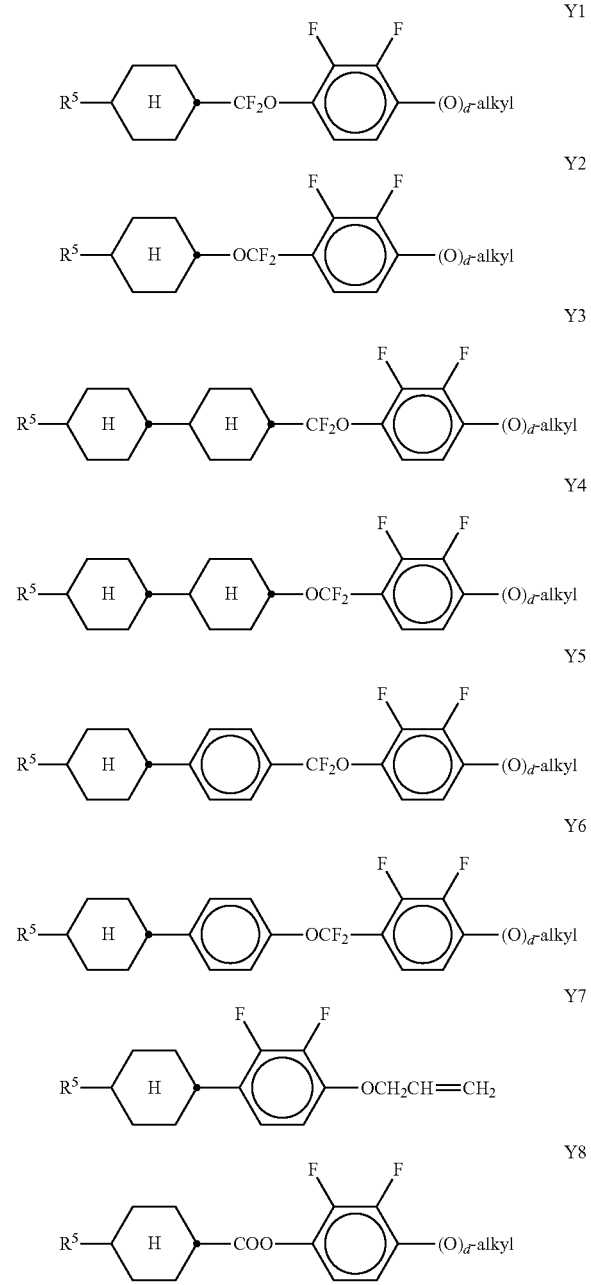

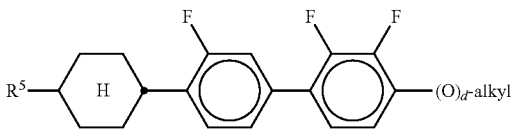

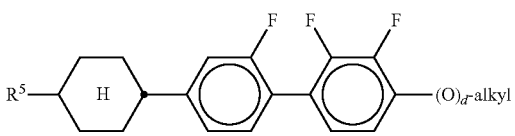

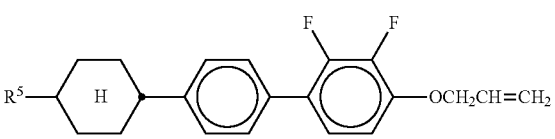

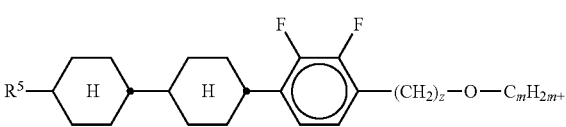

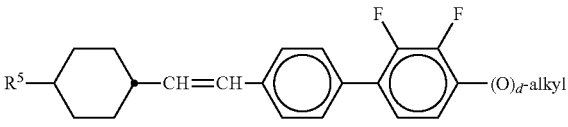

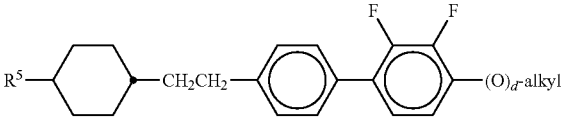

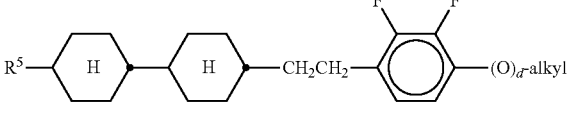

in which $R^5$ has one of the meanings indicated above for $R^1$, alkyl denotes $C_{1-6}$-alkyl, d denotes 0 or 1, and z and m each, independently of one another, denote an integer from 1 to 6. $R^5$ in these compounds is particularly preferably $C_{1-6}$-alkyl or -alkoxy or $C_{2-6}$-alkenyl, d is preferably 1. The LC medium according to the invention preferably comprises one or more compounds of the above-mentioned formulae in amounts of 25% by weight.

h) LC medium wherein component B) or the LC host mixture additionally comprises one or more biphenyl compounds selected from the group consisting of the following formulae:

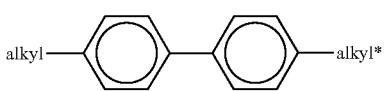

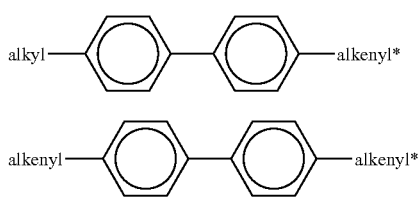

B2

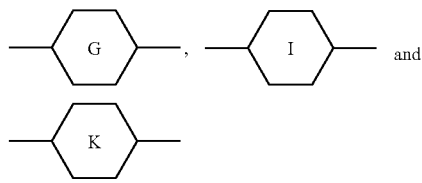

B3 in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The proportion of the biphenyls of the formulae B1 to B3 in the LC host mixture is preferably at least 3% by weight, in particular ≥5% by weight.

The compounds of the formula B2 are particularly preferred.

The compounds of the formulae B1 to B3 are preferably selected from the group consisting of the following sub-formulae:

each, independently of one another, denote

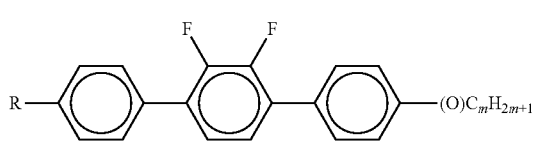

in which $L^5$ denotes F or Cl, preferably F, and $L^6$ denotes F, Cl, $OCF_3$, $CF_3$, $CH_3$, $CH_2F$ or $CHF_2$, preferably F.

The compounds of the formula T are preferably selected from the group consisting of the following sub-formulae:

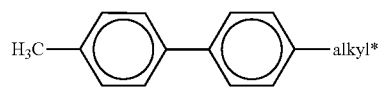

B1a

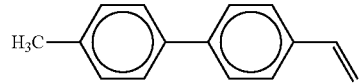

B2a

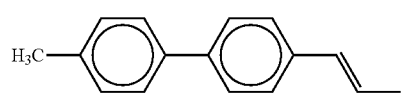

B2b

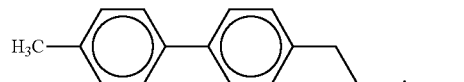

B2c in which alkyl* denotes an alkyl radical having 1-6 C atoms. The medium according to the invention particularly preferably comprises one or more compounds of the formulae B1a and/or B2c.

i) LC medium wherein component B) or the LC host mixture additionally comprises one or more terphenyl compounds of the following formula:

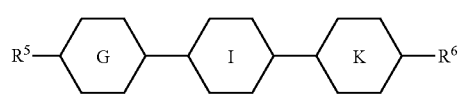

T in which $R^5$ and $R^6$ each, independently of one another, have one of the meanings indicated above, and

T1

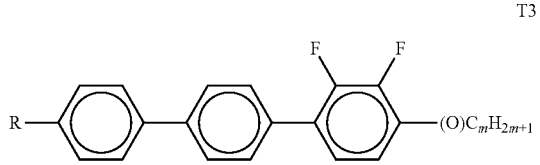

T2

T3

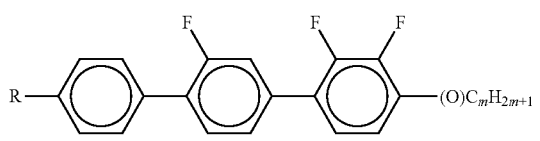

T4

T5

T6
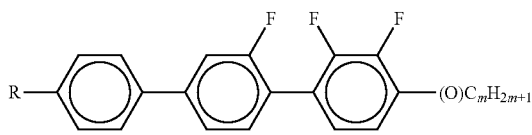
T7
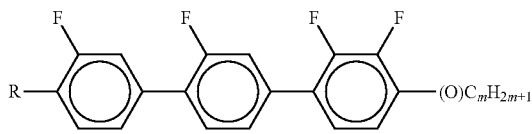
T8
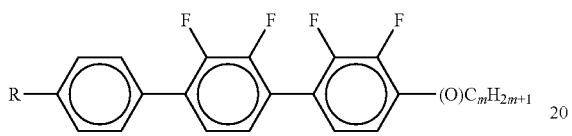
T9
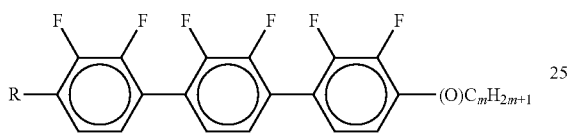
T10
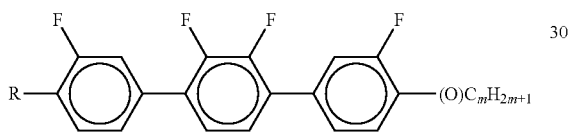
T11
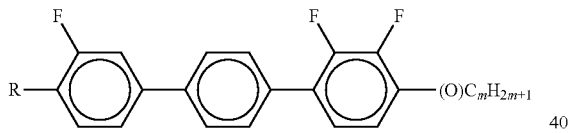
T12
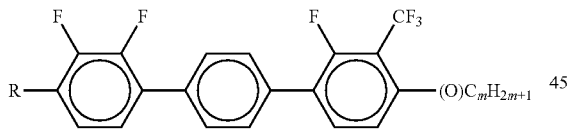
T13
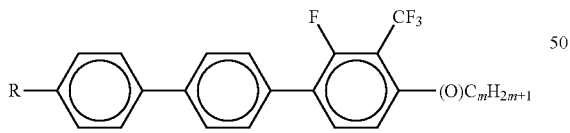
T14
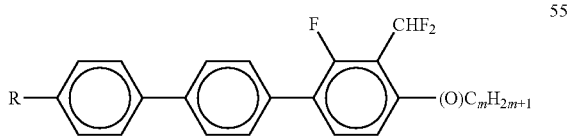
T15
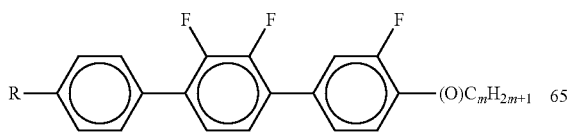
T16
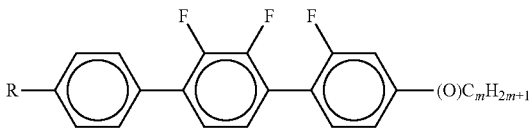
T17
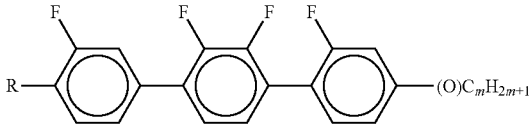
T18
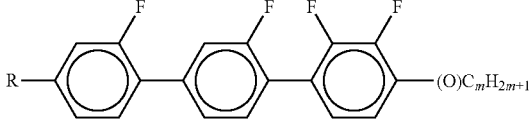
T19
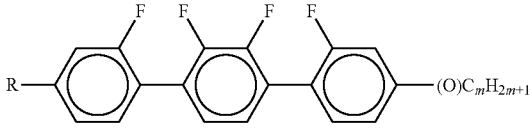
T20
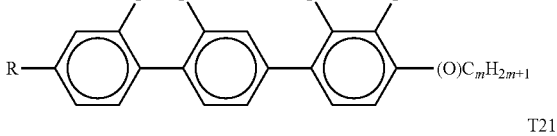
T21
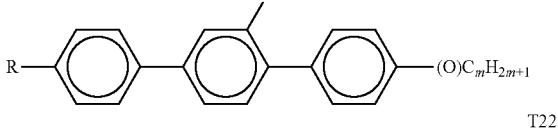
T22
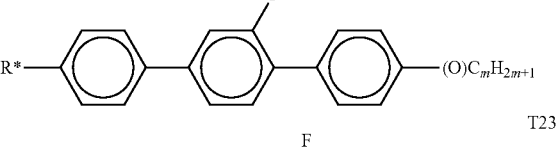
T23
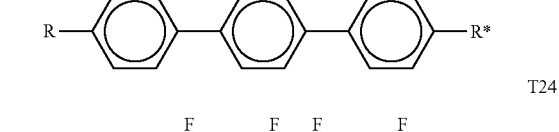
T24
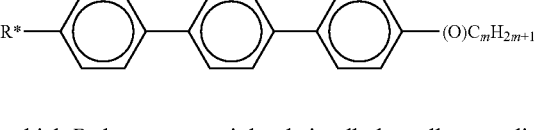
in which R denotes a straight-chain alkyl or alkoxy radical having 1-7 C atoms, R* denotes a straight-chain alkenyl radical having 2-7 C atoms, (O) denotes an oxygen atom or a single bond, and m denotes an integer from 1 to 6. R* preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

R preferably denotes methyl, ethyl, propyl, butyl, pentyl, hexyl, methoxy, ethoxy, propoxy, butoxy or pentoxy.

The LC host mixture according to the invention preferably comprises the terphenyls of the formula T and the preferred sub-formulae thereof in an amount of 0.5-30% by weight, in particular 1-20% by weight.

Particular preference is given to compounds of the formulae T1, T2, T3 and T21. In these compounds, R preferably denotes alkyl, furthermore alkoxy, each having 1-5 C atoms.

The terphenyls are preferably employed in LC media according to the invention if the Δn value of the mixture is to be >0.1. Preferred LC media comprise 2-20% by weight of one or more terphenyl compounds of the formula T, preferably selected from the group of compounds T1 to T22.

k) LC medium wherein component B) or the LC host mixture additionally comprises one or more quaterphenyl compounds selected from the group consisting of the following formulae:

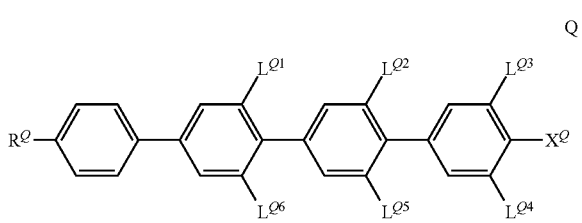

Q wherein
- $R^Q$ is alkyl, alkoxy, oxaalkyl or alkoxyalkyl having 1 to 9 C atoms or alkenyl or alkenyloxy having 2 to 9 C atoms, all of which are optionally fluorinated,
- $X^Q$ is F, Cl, halogenated alkyl or alkoxy having 1 to 6 C atoms or halogenated alkenyl or alkenyloxy having 2 to 6 C atoms,
- $L^{Q1}$ to $L^{Q6}$ independently of each other are H or F, with at least one of $L^{Q1}$ to $L^{Q6}$ being F.

Preferred compounds of formula Q are those wherein $R^Q$ denotes straight-chain alkyl with 2 to 6 C-atoms, very preferably ethyl, n-propyl or n-butyl.

Preferred compounds of formula Q are those wherein $L^{Q3}$ and $L^{Q4}$ are F. Further preferred compounds of formula Q are those wherein $L^{Q3}$, $L^{Q4}$ and one or two of $L^{Q1}$ and $L^{Q2}$ are F.

Preferred compounds of formula Q are those wherein $X^Q$ denotes F or $OCF_3$, very preferably F.

The compounds of formula Q are preferably selected from the following subformulae

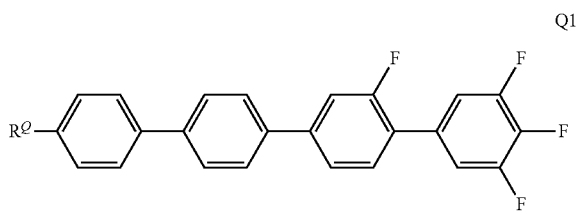

Q1

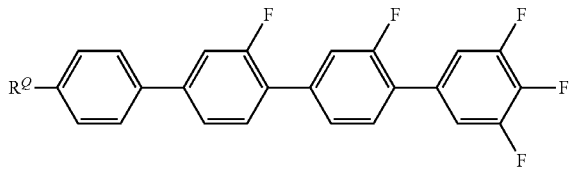

Q2 wherein $R^Q$ has one of the meanings of formula Q or one of its preferred meanings given above and below, and is preferably ethyl, n-propyl or n-butyl.

Especially preferred are compounds of formula Q1, in particular those wherein $R^Q$ is n-propyl.

Preferably the proportion of compounds of formula Q in the LC host mixture is from >0 to ≤5% by weight, very preferably from 0.1 to 2% by weight, most preferably from 0.2 to 1.5% by weight.

Preferably the LC host mixture contains 1 to 5, preferably 1 or 2 compounds of formula Q.

The addition of quaterphenyl compounds of formula Q to the LC host mixture enables to reduce ODF mura, whilst maintaining high UV absorption, enabling quick and complete polymerization, enabling strong and quick tilt angle generation, and increasing the UV stability of the LC medium.

Besides, the addition of compounds of formula Q, which have positive dielectric anisotropy, to the LC medium with negative dielectric anisotropy allows a better control of the values of the dielectric constants $\varepsilon_\parallel$ and $E_\perp$, and in particular enables to achieve a high value of the dielectric constant $\varepsilon_\parallel$ while keeping the dielectric anisotropy Δε constant, thereby reducing the kick-back voltage and reducing image sticking.

l) LC medium wherein component B) or the LC host mixture additionally comprises one or more compounds of formula C:

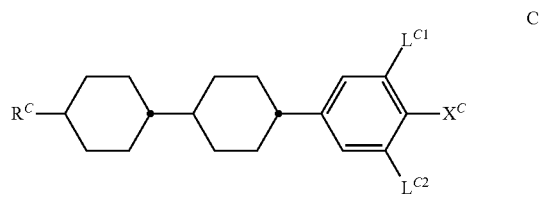

C wherein
- $R^C$ denotes alkyl, alkoxy, oxaalkyl or alkoxyalkyl having 1 to 9 C atoms or alkenyl or alkenyloxy having 2 to 9 C atoms, all of which are optionally fluorinated,
- $X^C$ denotes F, Cl, halogenated alkyl or alkoxy having 1 to 6 C atoms or halogenated alkenyl or alkenyloxy having 2 to 6 C atoms,
- $L^{C1}$, $L^{C2}$ independently of each other denote H or F, with at least one of $L^{C1}$ and $L^{C2}$ being F.

Preferred compounds of formula C are those wherein $R^C$ denotes straight-chain alkyl with 2 to 6 C-atoms, very preferably ethyl, n-propyl or n-butyl.

Preferred compounds of formula C are those wherein $L^{C1}$ and $L^{C2}$ are F.

Preferred compounds of formula C are those wherein $X^C$ denotes F or $OCF_3$, very preferably F.

Preferred compounds of formula C are selected from the following formula

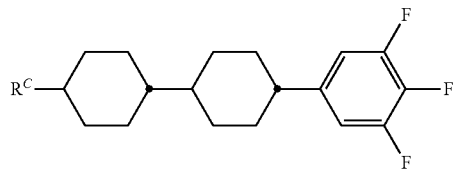
C1 wherein $R^C$ has one of the meanings of formula C or one of its preferred meanings given above and below, and is preferably ethyl, n-propyl or n-butyl, very preferably n-propyl.

Preferably the proportion of compounds of formula C in the LC host mixture is from >0 to ≤10% by weight, very preferably from 0.1 to 8% by weight, most preferably from 0.2 to 5% by weight.

Preferably the LC host mixture contains 1 to 5, preferably 1, 2 or 3 compounds of formula C.

The addition of compounds of formula C, which have positive dielectric anisotropy, to the LC medium with negative dielectric anisotropy allows a better control of the values of the dielectric constants $\varepsilon_\parallel$ and $\varepsilon_\perp$, and in particular enables to achieve a high value of the dielectric constant $\varepsilon_\parallel$ while keeping the dielectric anisotropy $\Delta\varepsilon$ constant, thereby reducing the kick-back voltage and reducing image sticking. Besides, the addition of compounds of formula C enables to reduce the viscosity and the response time of the LC medium.

m) LC medium wherein component B) or the LC host mixture additionally comprises one or more compounds selected from the group consisting of the following formulae:

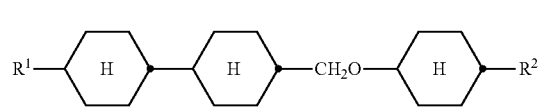
O1

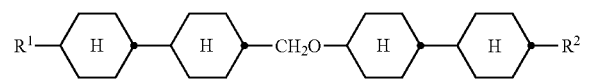
O2

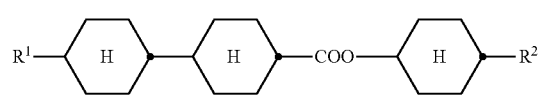
O3

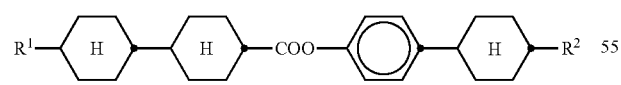
O4

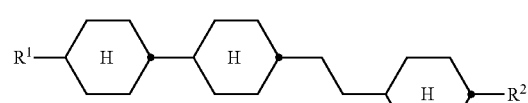
O5

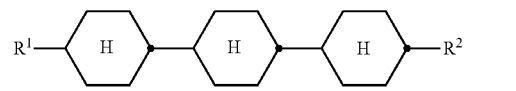
O6

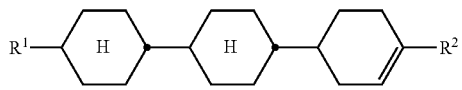
O7

O8

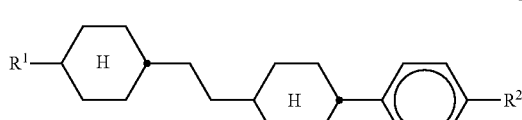
O9

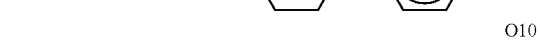
O10

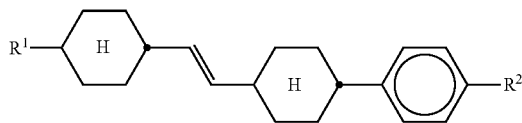
O11 in which $R^1$ and $R^2$ have the meanings indicated above and preferably each, independently of one another, denote straight-chain alkyl having 1 to 6 C atoms or straight-chain alkenyl having 2 to 6 C atoms.

Preferred media comprise one or more compounds selected from the formulae O1, O3 and O4.

n) LC medium wherein component B) or the LC host mixture additionally comprises one or more compounds of the following formula:

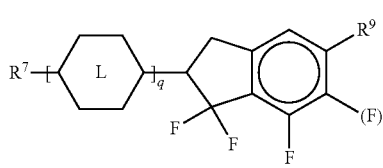
FI in which

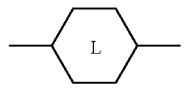

denotes

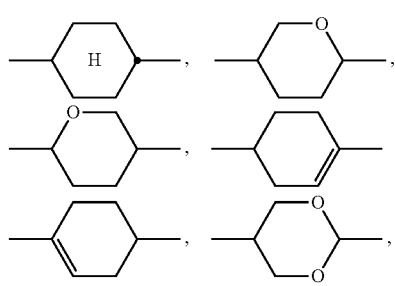

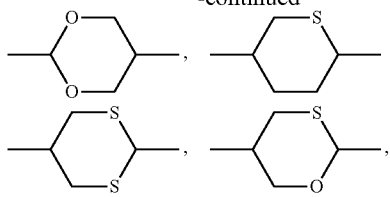

$R^9$ denotes H, $CH_3$, $C_2H_5$ or n-$C_3H_7$, (F) denotes an optional fluorine substituent, and q denotes 1, 2 or 3, and $R^7$ has one of the meanings indicated for $R^1$, preferably in amounts of >3% by weight, in particular 25% by weight and very particularly preferably 5-30% by weight.

Particularly preferred compounds of the formula FI are selected from the group consisting of the following sub-formulae:

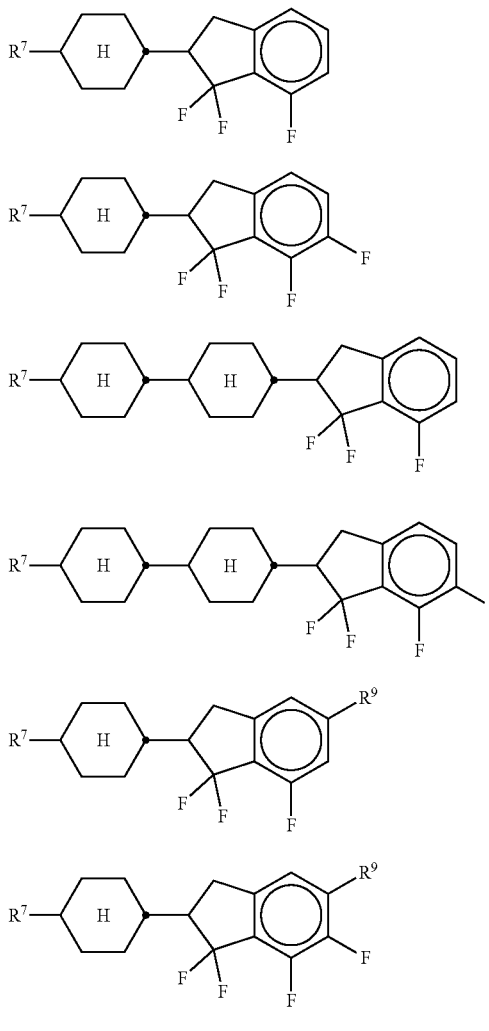

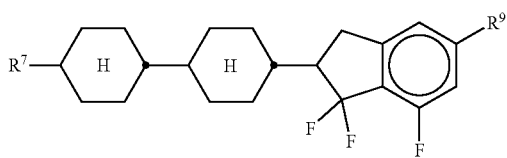

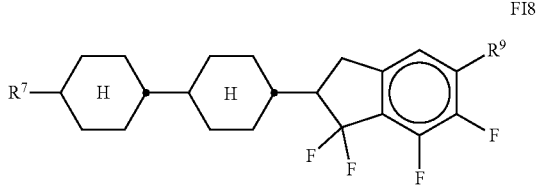

in which $R^7$ preferably denotes straight-chain alkyl, and $R^9$ denotes $CH_3$, $C_2H_5$ or n-$C_3H_7$. Particular preference is given to the compounds of the formulae FI1, FI2 and FI3.

o) LC medium wherein component B) or the LC host mixture additionally comprises one or more compounds selected from the group consisting of the following formulae:

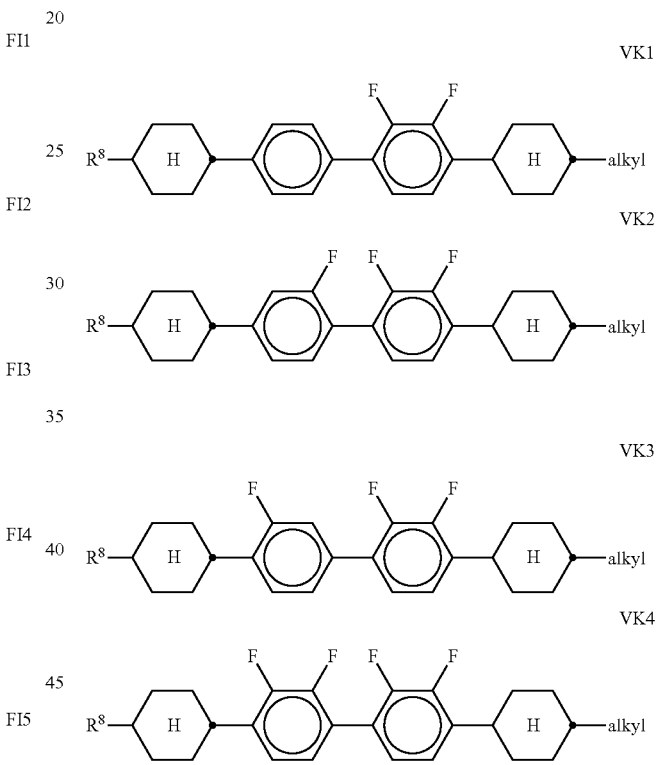

in which $R^8$ has the meaning indicated for $R^1$, and alkyl denotes a straight-chain alkyl radical having 1-6 C atoms.

p) LC medium wherein component B) or the LC host mixture additionally comprises one or more compounds which contain a tetrahydronaphthyl or naphthyl unit, such as, for example, the compounds selected from the group consisting of the following formulae:

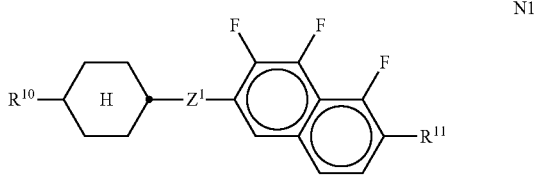

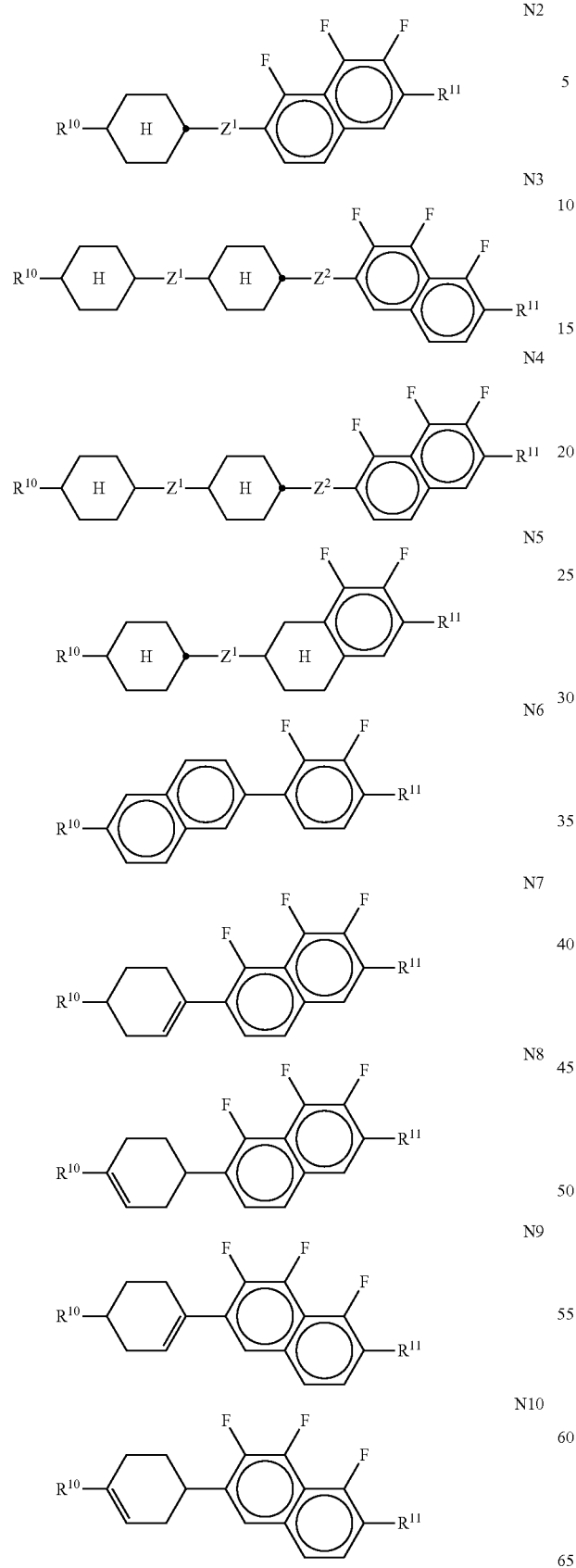

in which
R¹⁰ and R¹¹ each, independently of one another, denote alkyl having 1 to 12 C atoms, where, in addition, one or two non-adjacent CH₂ groups may be replaced by —O—, —CH=CH—, —CO—, —OCO— or —COO— in such a way that O atoms are not linked directly to one another, preferably alkyl or alkoxy having 1 to 6 C atoms, and R¹⁰ and R¹¹ preferably denote straight-chain alkyl or alkoxy having 1 to 6 C atoms or straight-chain alkenyl having 2 to 6 C atoms, and Z¹ and Z² each, independently of one another, denote —C₂H₄—, —CH=CH—, —(CH₂)₄—, —(CH₂)₃O—, —O(CH₂)₃—, —CH=CH—CH₂CH₂—, —CH₂CH₂CH=CH—, —CH₂O—, —OCH₂—, —CO—O—, —O—CO—, —C₂F₄—, —CF=CF—, —CF=CH—, —CH=CF—, —CH₂— or a single bond.

q) LC medium wherein component B) or the LC host mixture additionally comprises one or more difluorodibenzochromans and/or chromans of the following formulae:

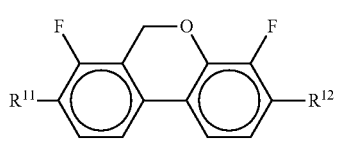

BC

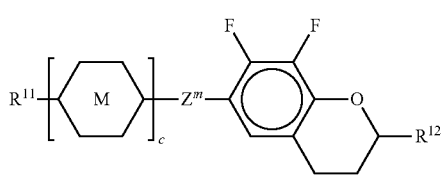

CR

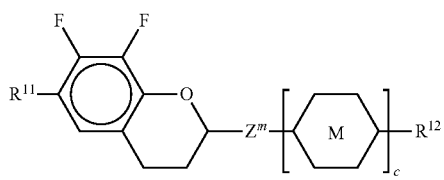

RC in which
R¹¹ and R¹² each, independently of one another, have one of the meanings indicated above for R¹¹,
ring M is trans-1,4-cyclohexylene or 1,4-phenylene,
Zᵐ —C₂H₄—, —CH₂O—, —OCH₂—, —CO—O— or —O—CO—,
c is 0, 1 or 2,
preferably in amounts of 3 to 20% by weight, in particular in amounts of 3 to 15% by weight.

Particularly preferred compounds of the formulae BC, CR and RC are selected from the group consisting of the following sub-formulae:

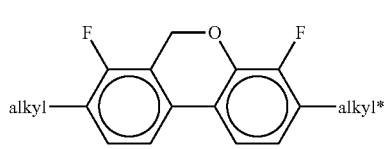

BC1

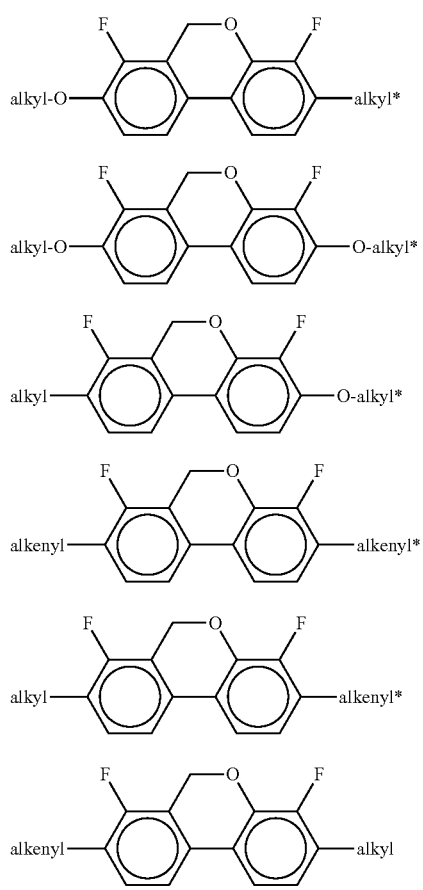
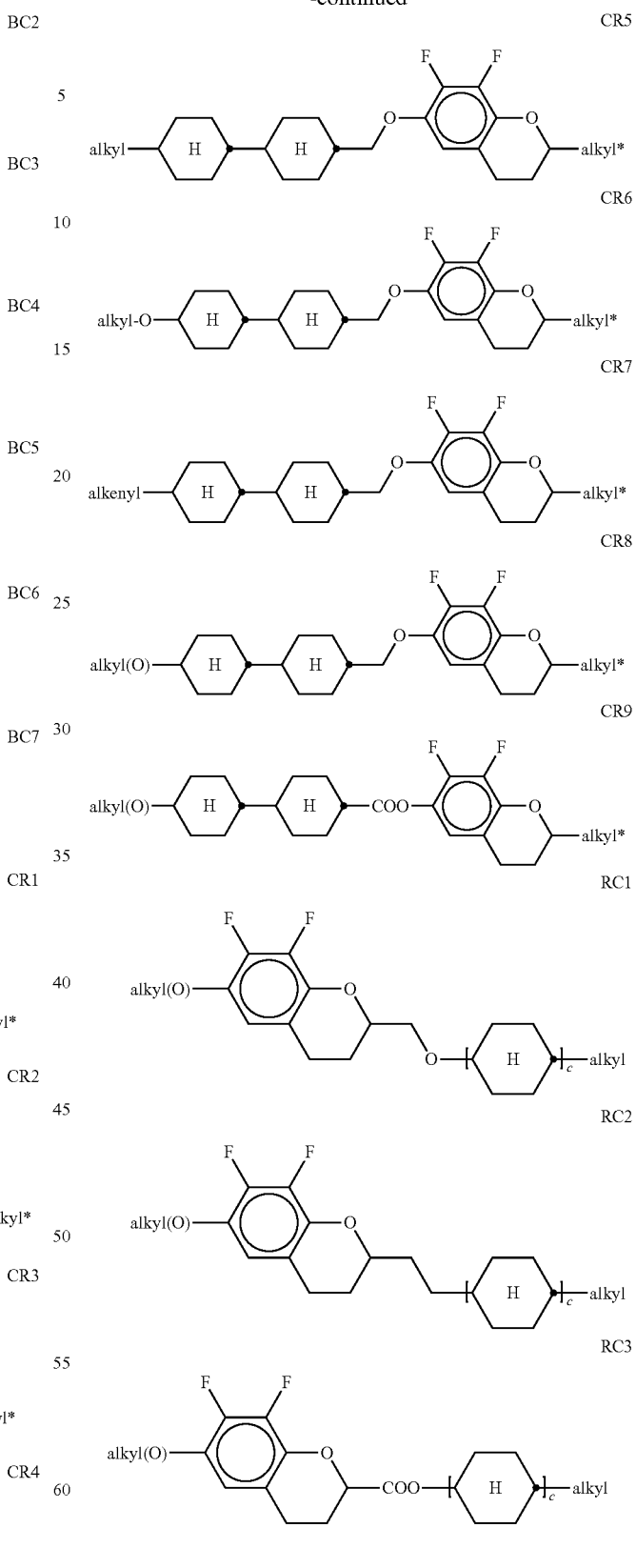
in which alkyl and alkyl* each, independently of one another, denote a straight-chain alkyl radical having 1-6 C atoms, (O) denotes an oxygen atom or a single bond, c is 1 or 2, and alkenyl and alkenyl* each, independently of one another, denote a straight-chain alkenyl radical having 2-6 C atoms. Alkenyl and alkenyl* preferably denote CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

Very particular preference is given to LC host mixtures comprising one, two or three compounds of the formula BC-2.

r) LC medium wherein component B) or the LC host mixture additionally comprises one or more fluorinated phenanthrenes and/or dibenzofurans of the following formulae:

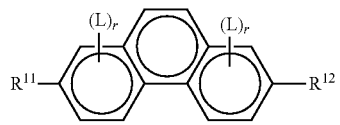

PH

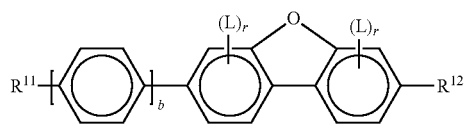

BF in which R$^{11}$ and R$^{12}$ each, independently of one another, have one of the meanings indicated above for R$^{11}$, b denotes 0 or 1, L denotes F, and r denotes 1, 2 or 3.

Particularly preferred compounds of the formulae PH and BF are selected from the group consisting of the following sub-formulae:

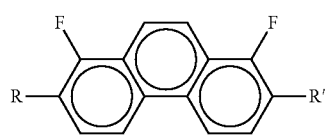

PH1

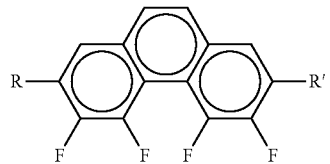

PH2

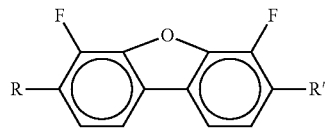

BF1

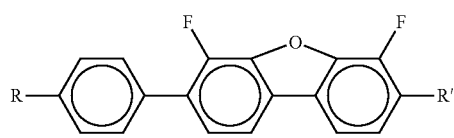

BF2 in which R and R' each, independently of one another, denote a straight-chain alkyl or alkoxy radical having 1-7 C atoms.

s) LC medium wherein component B) or the LC host mixture additionally comprises one or more monocyclic compounds of the following formula

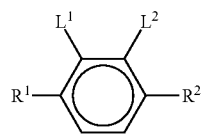

Y wherein

R$^1$ and R$^2$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, preferably alkyl or alkoxy having 1 to 6 C atoms, L$^1$ and L$^2$ each, independently of one another, denote F, Cl, OCF$_3$, CF$_3$, CH$_3$, CH$_2$F, CHF$_2$.

Preferably, both L$^1$ and L$^2$ denote F or one of L$^1$ and L$^2$ denotes F and the other denotes Cl, The compounds of the formula Y are preferably selected from the group consisting of the following sub-formulae:

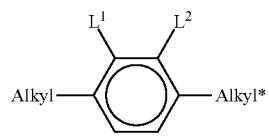

Y1

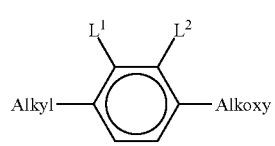

Y2

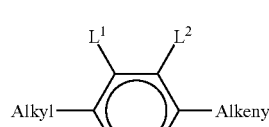

Y3

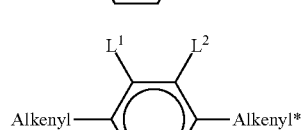

Y4

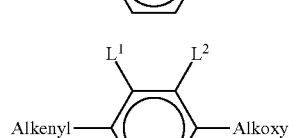

Y5

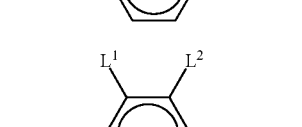

Y6

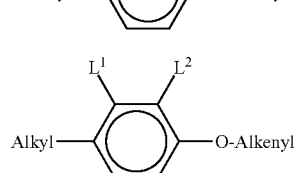

Y7

-continued

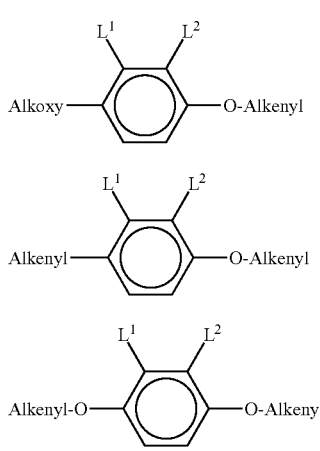

Y8

Y9

Y10 in which, Alkyl and Alkyl* each, independently of one another, denote a straight-chain alkyl radical having 1-6 C atoms, Alkoxy denotes a straight-chain alkoxy radical having 1-6 C atoms, Alkenyl and Alkenyl* each, independently of one another, denote a straight-chain alkenyl radical having 2-6 C atoms, and O denotes an oxygen atom or a single bond. Alkenyl and Alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Particularly preferred compounds of the formula Y are selected from the group consisting of the following subformulae:

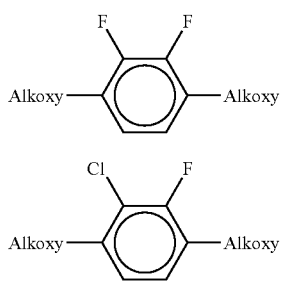

Y6A

Y6B wherein Alkoxy preferably denotes straight-chain alkoxy with 3, 4, or 5 C atoms.

t) LC medium which, apart from the polymerizable compounds as described above and below, does not contain a compound which contains a terminal vinyloxy group ($-O-CH=CH_2$).

u) LC medium wherein component B) or the LC host mixture comprises 1 to 8, preferably 1 to 5, compounds of the formulae CY1, CY2, PY1 and/or PY2. The proportion of these compounds in the LC host mixture as a whole is preferably 5 to 60%, particularly preferably 10 to 35%. The content of these individual compounds is preferably in each case 2 to 20%.

v) LC medium wherein component B) or the LC host mixture comprises 1 to 8, preferably 1 to 5, compounds of the formulae CY9, CY10, PY9 and/or PY10. The proportion of these compounds in the LC host mixture as a whole is preferably 5 to 60%, particularly preferably 10 to 35%. The content of these individual compounds is preferably in each case 2 to 20%.

w) LC medium wherein component B) or the LC host mixture comprises 1 to 10, preferably 1 to 8, compounds of the formula ZK, in particular compounds of the formulae ZK1, ZK2 and/or ZK6. The proportion of these compounds in the LC host mixture as a whole is preferably 3 to 25%, particularly preferably 5 to 45%. The content of these individual compounds is preferably in each case 2 to 20%.

x) LC medium in which the proportion of compounds of the formulae CY, PY and ZK in the LC host mixture as a whole is greater than 70%, preferably greater than 80%.

y) LC medium in which the LC host mixture contains one or more compounds containing an alkenyl group, preferably selected from formulae AN and AY, very preferably selected from formulae AN1, AN3, AN6 and AY14, most preferably from formulae AN1a, AN3a, AN6a and AY14. The concentration of these compounds in the LC host mixture is preferably from 2 to 70%, very preferably from 3 to 55%.

z) LC medium wherein component B) or the LC host mixture contains one or more, preferably 1 to 5, compounds selected of formula PY1-PY8, very preferably of formula PY2. The proportion of these compounds in the LC host mixture as a whole is preferably 1 to 30%, particularly preferably 2 to 20%. The content of these individual compounds is preferably in each case 1 to 20%.

z1) LC medium wherein component B) or the LC host mixture contains one or more, preferably 1, 2 or 3, compounds selected from formulae T1, T2 and T5, very preferably from formula T2. The content of these compounds in the LC host mixture as a whole is preferably 1 to 20%.

z2) LC medium in which the LC host mixture contains one or more compounds selected from formulae CY and PY, one or more compounds selected from formulae AN and AY, and one or more compounds selected from formulae T and Q.

z3) LC medium in which the LC host mixture contains one or more, preferably 1, 2 or 3, compounds of formula BF1, and one or more, preferably 1, 2 or 3, compounds selected from formulae AY14, AY15 and AY16, very preferably of formula AY14. The proportion of the compounds of formula AY14-AY16 in the LC host mixture is preferably from 2 to 35%, very preferably from 3 to 30%. The proportion of the compounds of formula BF1 in the LC host mixture is preferably from 0.5 to 20%, very preferably from 1 to 15%. Further preferably the LC host mixture according to this preferred embodiment contains one or more, preferably 1, 2 or 3 compounds of formula T, preferably selected from formula T1, T2 and T5, very preferably from formula T2 or T5. The proportion of the compounds of formula T in the LC host mixture medium is preferably from 0.5 to 15%, very preferably from 1 to 10%.

In a second preferred embodiment the LC medium contains an LC host mixture based on compounds with positive dielectric anisotropy. Such LC media are especially suitable for use in PS-OCB—, PS-TN-, PS-Posi-VA-, PS-IPS— or PS—FFS-displays.

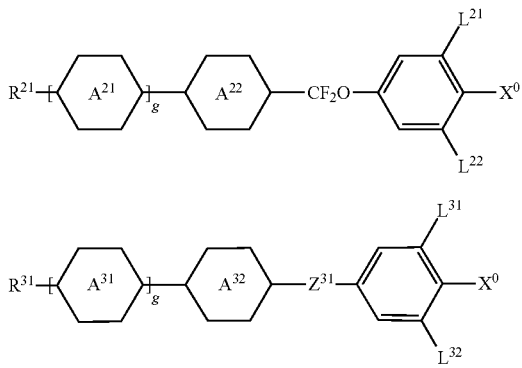

in which the individual radicals have, independently of each other and on each occurrence identically or differently, the following meanings:

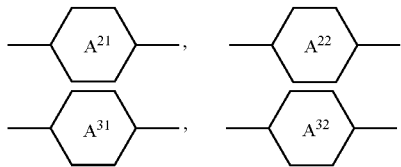

each, independently of one another, and on each occurrence, identically or differently

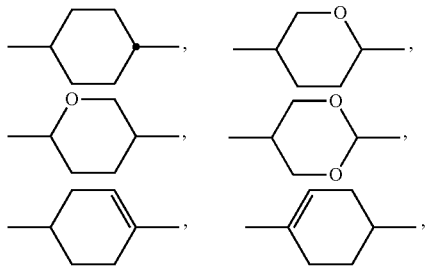

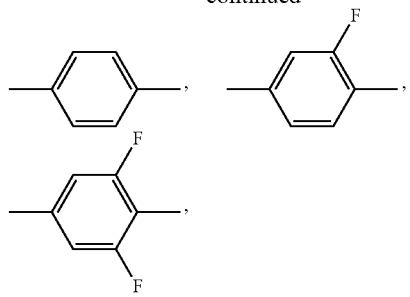

$R^{21}$, $R^{31}$ each, independently of one another, alkyl, alkoxy, oxaalkyl or alkoxyalkyl having 1 to 9 C atoms or alkenyl or alkenyloxy having 2 to 9 C atoms, all of which are optionally fluorinated, $X^0$ F, Cl, halogenated alkyl or alkoxy having 1 to 6 C atoms or halogenated alkenyl or alkenyloxy having 2 to 6 C atoms, $Z^{31}$ —$CH_2CH_2$—, —$CF_2CF_2$—, —COO—, trans-CH=CH—, trans-CF=CF—, —$CH_2O$— or a single bond, preferably —$CH_2CH_2$—, —COO—, trans-CH=CH— or a single bond, particularly preferably —COO—, trans-CH=CH— or a single bond, $L^{21}$, $L^{22}$, $L^{31}$, $L^{32}$ each, independently of one another, H or F, g 0, 1, 2 or 3.

In the compounds of formula A and B, $X^0$ is preferably F, Cl, $CF_3$, $CHF_2$, $OCF_3$, $OCHF_2$, $OCFHCF_3$, $OCFHCHF_2$, $OCFHCHF_2$, $OCF_2CH_3$, $OCF_2CHF_2$, $OCF_2CHF_2$, $OCF_2CF_2CHF_2$, $OCF_2CF_2CHF_2$, $OCFHCF_2CF_3$, $OCFHCF_2CHF_2$, $OCF_2CF_2CF_3$, $OCF_2CF_2CClF_2$, $OCClFCF_2CF_3$ or CH=$CF_2$, very preferably F or $OCF_3$, most preferably F.

In the compounds of formula A and B, $R^{21}$ and $R^{31}$ are preferably selected from straight-chain alkyl or alkoxy with 1, 2, 3, 4, 5 or 6 C atoms, and straight-chain alkenyl with 2, 3, 4, 5, 6 or 7 C atoms.

In the compounds of formula A and B, g is preferably 1 or 2.

In the compounds of formula B, $Z^{31}$ is preferably COO, trans-CH=CH or a single bond, very preferably COO or a single bond.

Preferably component B) of the LC medium comprises one or more compounds of formula A selected from the group consisting of the following formulae:

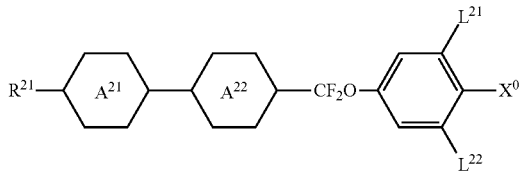

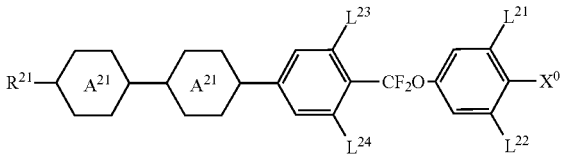

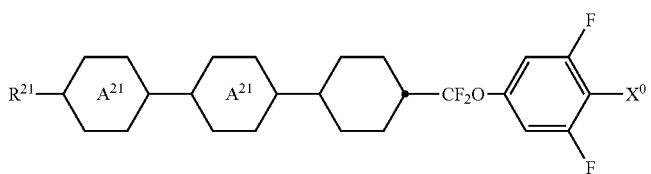

A4

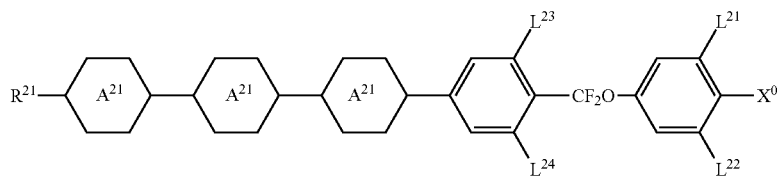

in which $A^{21}$, $R^{21}$, $X^0$, $L^{21}$ and $L^{22}$ have the meanings given in formula A, $L^{23}$ and $L^{24}$ each, independently of one another, are H or F, and $X^0$ is preferably F. Particularly preferred are compounds of formulae A1 and A2.

Particularly preferred compounds of formula A1 are selected from the group consisting of the following subformulae:

A1a

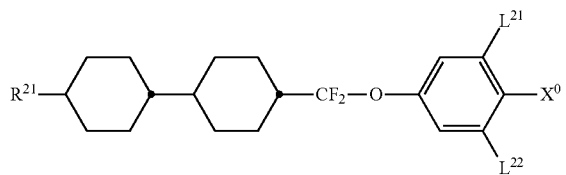

A1b

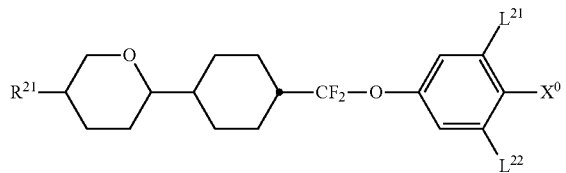

A1c

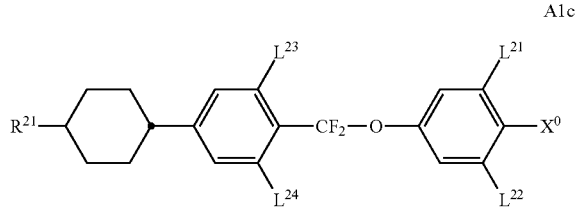

A1d

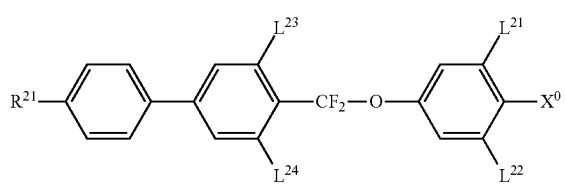

A1e

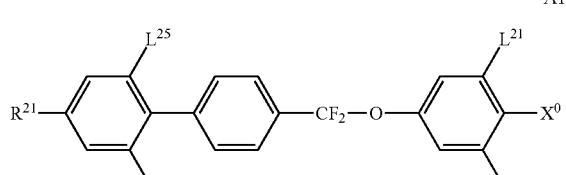

A1f

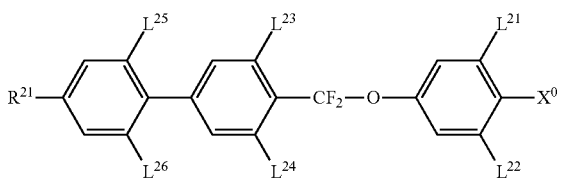

in which $R^{21}$, $X^0$, $L^{21}$ and $L^{22}$ have the meaning given in formula A1, $L^{23}$, $L^{24}$, $L^{25}$ and $L^{26}$ are each, independently of one another, H or F, and $X^0$ is preferably F.

Very particularly preferred compounds of formula A1 are selected from the group consisting of the following subformulae:

A1a1

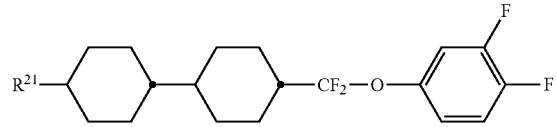

A1a2

A1b1

A1d1

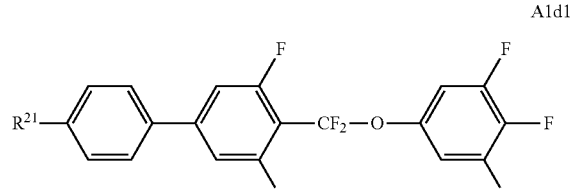

A1e1
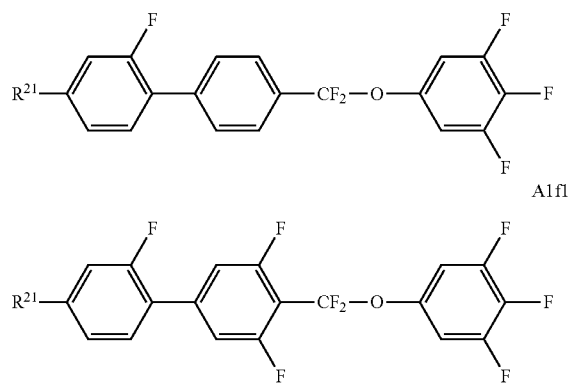

A1f1

In which R²¹ is as defined in formula A1.

Particularly preferred compounds of formula A2 are selected from the group consisting of the following subformulae:

A2a
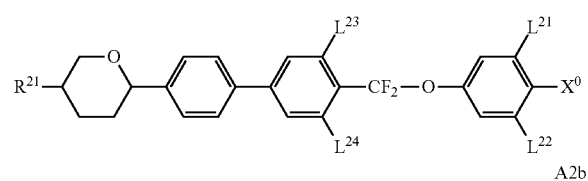

A2b

A2c

A2d
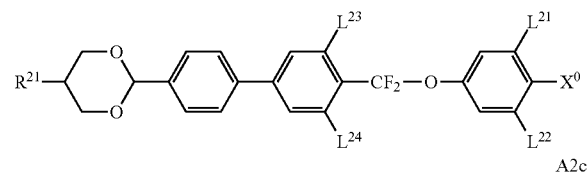

A2e
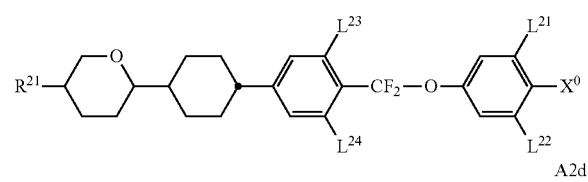

A2f
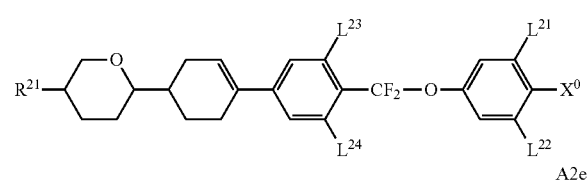

A2g
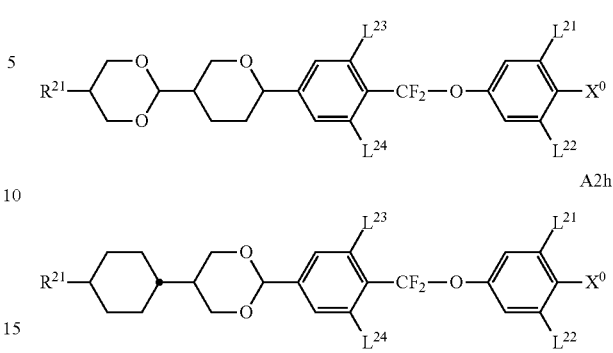

A2h

A2i
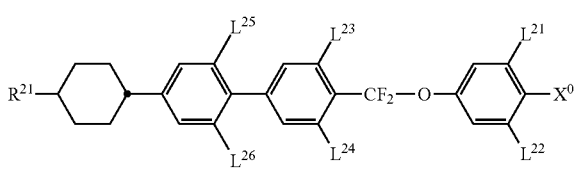

A2k
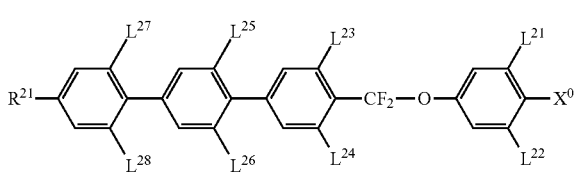

A2l
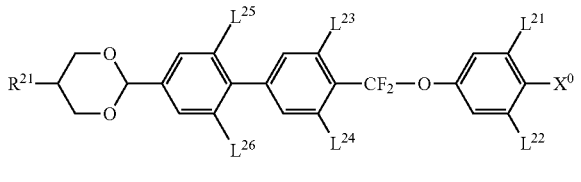

in which R²¹, X⁰, L²¹ and L²² have the meaning given in formula A2, L²³, L²⁴, L²⁵ and L²⁶ each, independently of one another, are H or F, and X⁰ is preferably F.

Very particularly preferred compounds of formula A2 are selected from the group consisting of the following subformulae:

A2a1
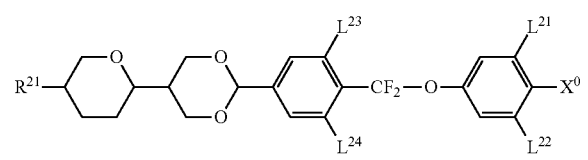

A2c1
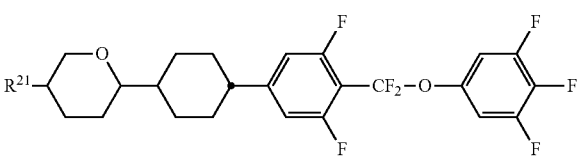

A2d1
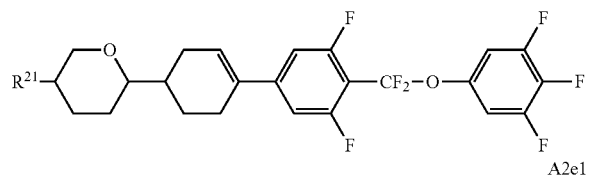

A2e1
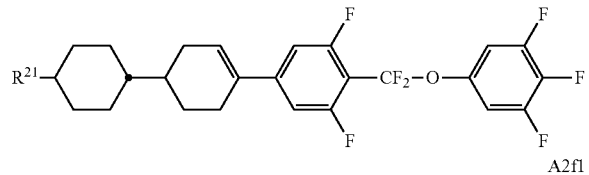

A2f1
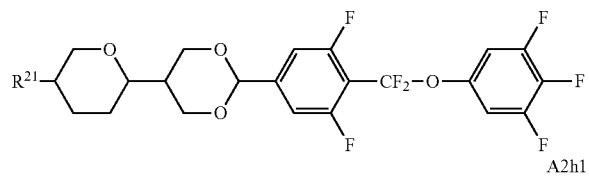

A2h1
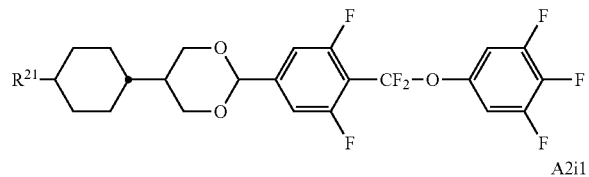

A2i1
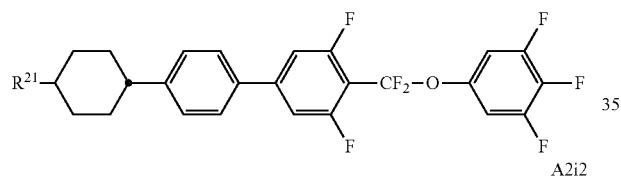

A2i2
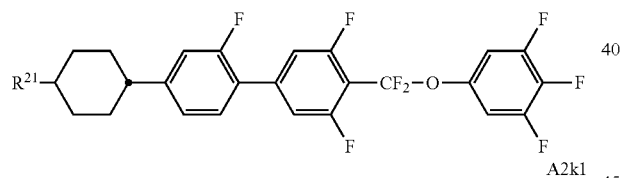

A2k1
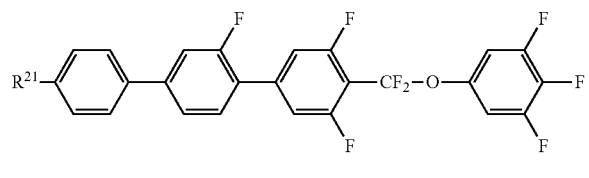

A2k2
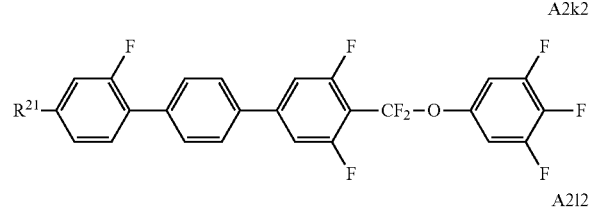

A2l2
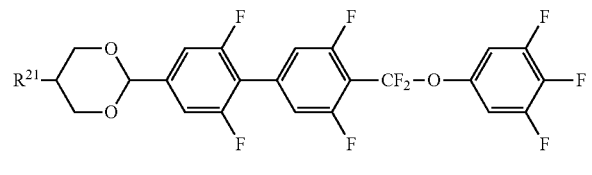

in which $R^{21}$ and $X^0$ are as defined in formula A2.

Particularly preferred compounds of formula A3 are selected from the group consisting of the following subformulae:

A3a
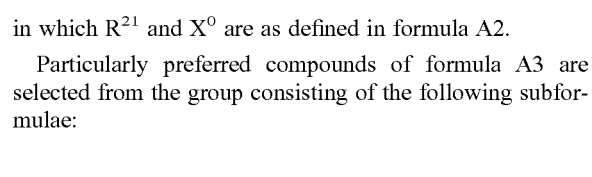

A3b

A3c
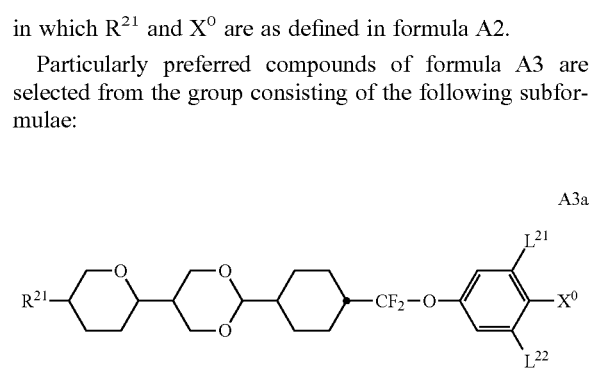

in which $R^{21}$, $X^0$, $L^{21}$ and $L^{22}$ have the meaning given in formula A3, and $X^0$ is preferably F.

Particularly preferred compounds of formula A4 are selected from the group consisting of the following subformulae:

A4a
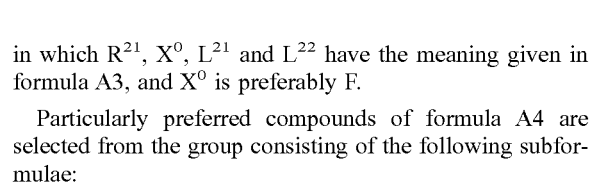

in which $R^{21}$ is as defined in formula A4.

Preferably component B) of the LC medium comprises one or more compounds of formula B selected from the group consisting of the following formulae:

B1
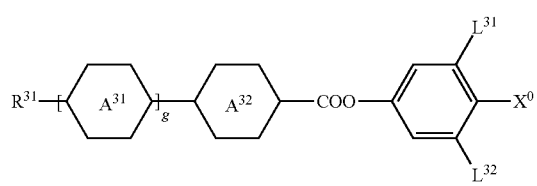

B2
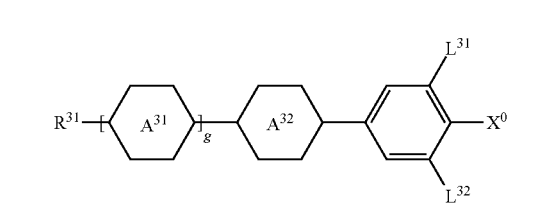

B3
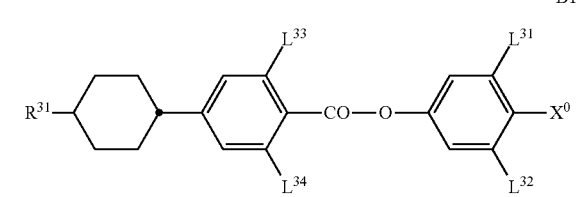

in which g, $A^{31}$, $A^{32}$, $R^{31}$, $X^0$, $L^{31}$ and $L^{32}$ have the meanings given in formula B, and $X^0$ is preferably F. Particularly preferred are compounds of formulae B1 and B2.

Particularly preferred compounds of formula B1 are selected from the group consisting of the following subformulae:

B1a
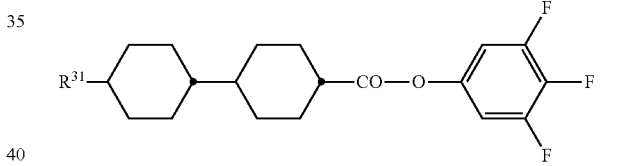

B1b
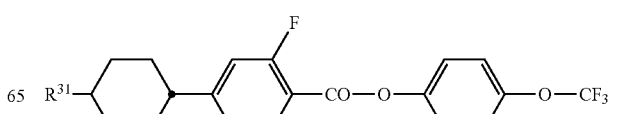

in which $R^{31}$, $X^0$, $L^{31}$ and $L^{32}$ have the meaning given in formula B1, and $X^0$ is preferably F.

Very particularly preferred compounds of formula B1a are selected from the group consisting of the following subformulae:

B1a1
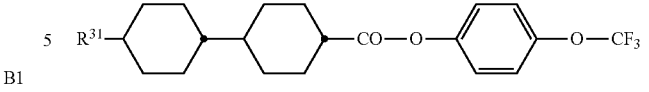

B1a2

B1a3
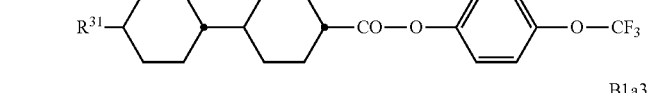

B1a4
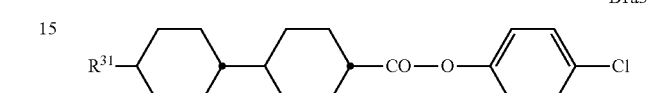

B1a5
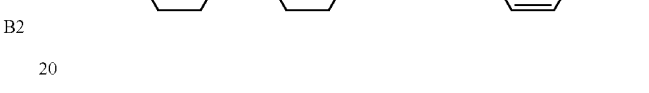

B1a6
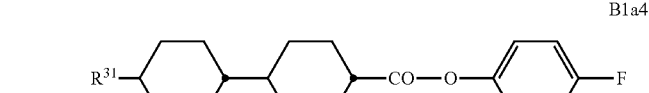

in which $R^{31}$ is as defined in formula B1.

Very particularly preferred compounds of formula B1 b are selected from the group consisting of the following subformulae:

B1b1
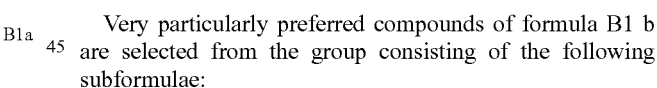

B1b2

B1b3
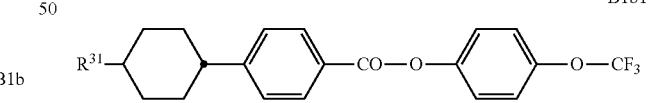

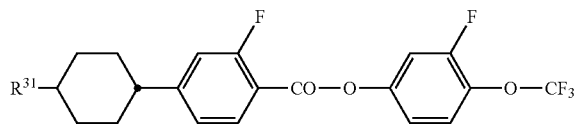

in which R$^{31}$ is as defined in formula B1.

Particularly preferred compounds of formula B2 are selected from the group consisting of the following subformulae:

B2a
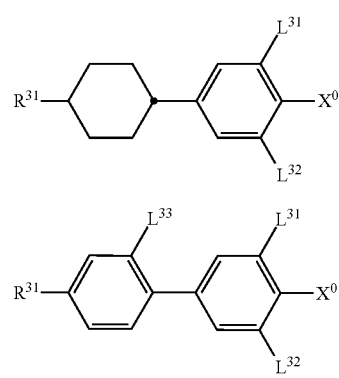

B2b

B2c
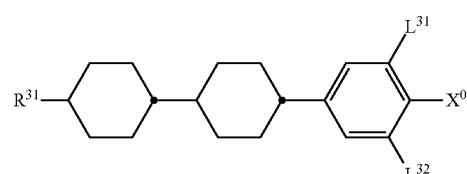

B2d
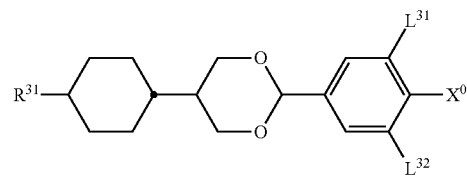

B2e
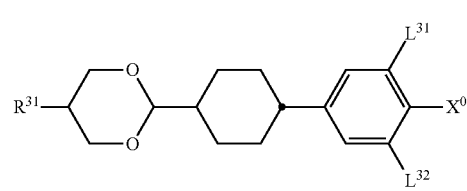

B2f
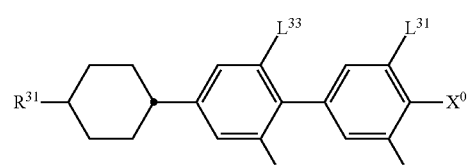

B2g
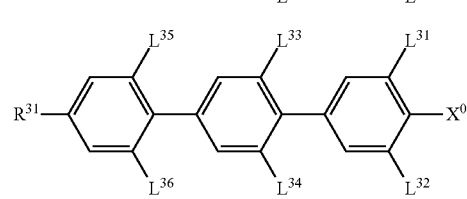

B2h
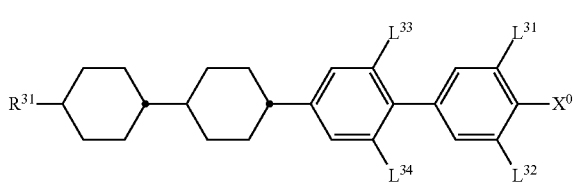

B2i
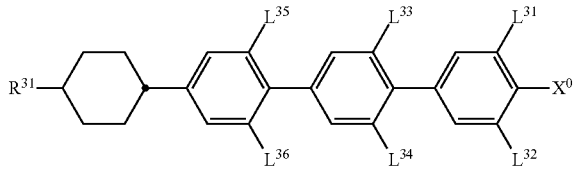

B2k
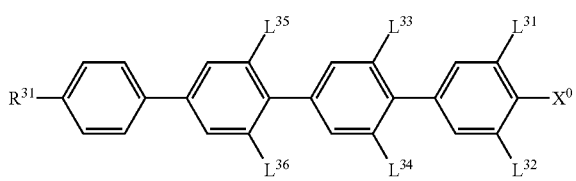

B2l
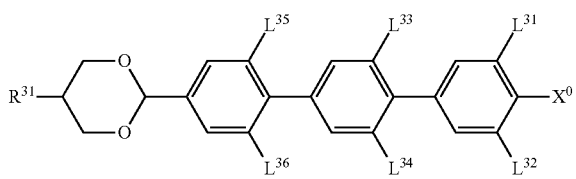

in which R$^{31}$, X$^0$, L$^{31}$ and L$^{32}$ have the meaning given in formula B2, L$^{33}$, L$^{34}$, L$^{35}$ and L$^{36}$ are each, independently of one another, H or F, and X$^0$ is preferably F.

Very particularly preferred compounds of formula B2 are selected from the group consisting of the following subformulae:

B2a1
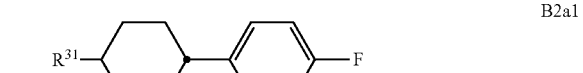

B2a2
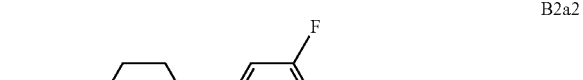

B2a3
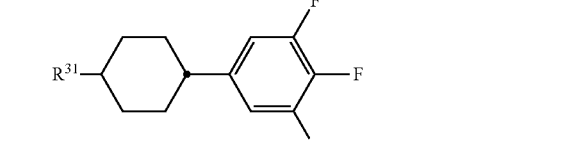

B2a4
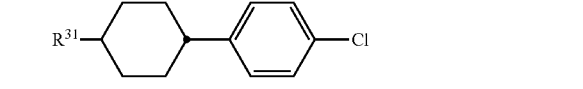

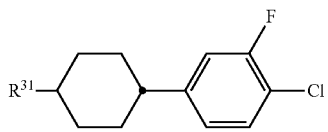
B2a5 in which R³¹ is as defined in formula B2.

Very particularly preferred compounds of formula B2b are selected from the group consisting of the following subformulae

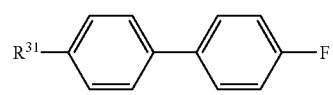
B2b1

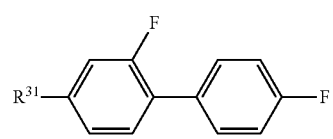
B2b2

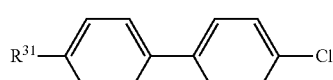
B2b3

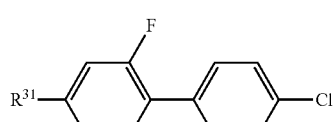
B2b4 in which R³¹ is as defined in formula B2.

Very particularly preferred compounds of formula B2c are selected from the group consisting of the following subformulae:

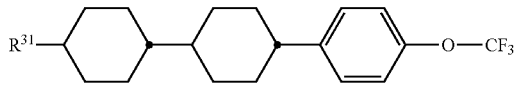
B2c1

B2c2

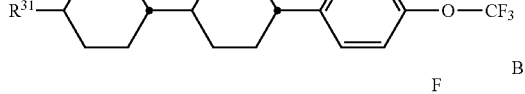
B2c3

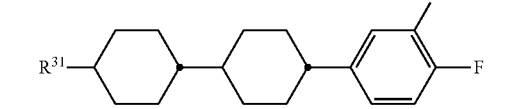
B2c4

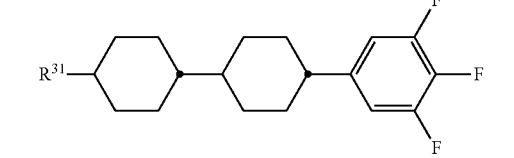

B2c5 in which R³¹ is as defined in formula B2.

Very particularly preferred compounds of formula B2d and B2e are selected from the group consisting of the following subformulae:

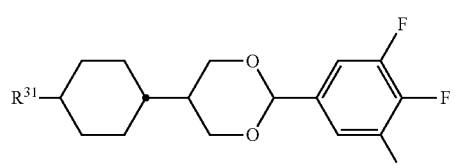
B2d1

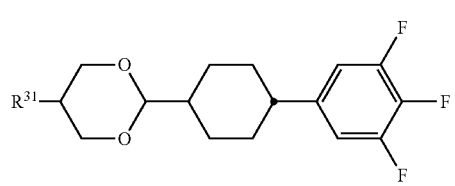
B2e1 in which R³¹ is as defined in formula B2.

Very particularly preferred compounds of formula B2f are selected from the group consisting of the following subformulae:

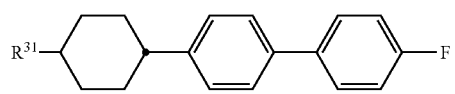
B2f1

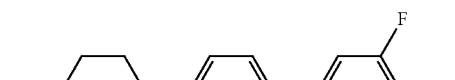
B2f2

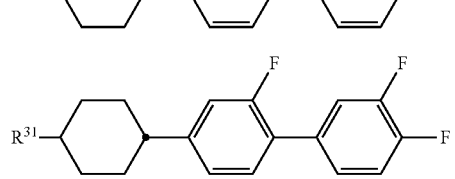
B2f3

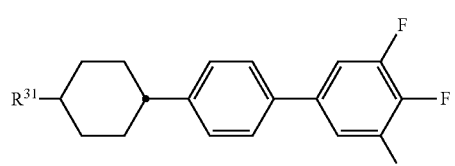
B2f4

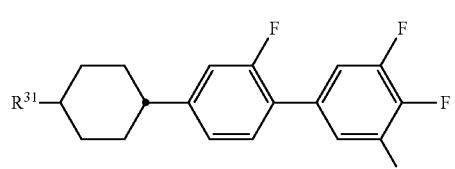
B2f5 in which R³¹ is as defined in formula B2.

Very particularly preferred compounds of formula B2g are selected from the group consisting of the following subformulae:

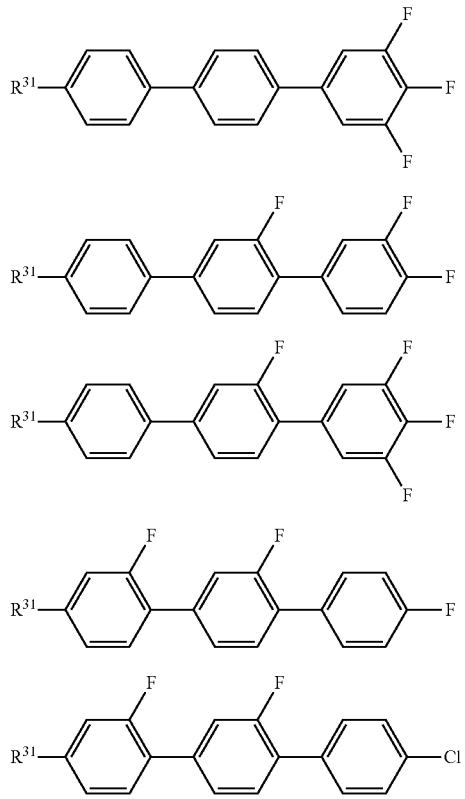

in which $R^{31}$ is as defined in formula B2.

Very particularly preferred compounds of formula B2h are selected from the group consisting of the following subformulae:

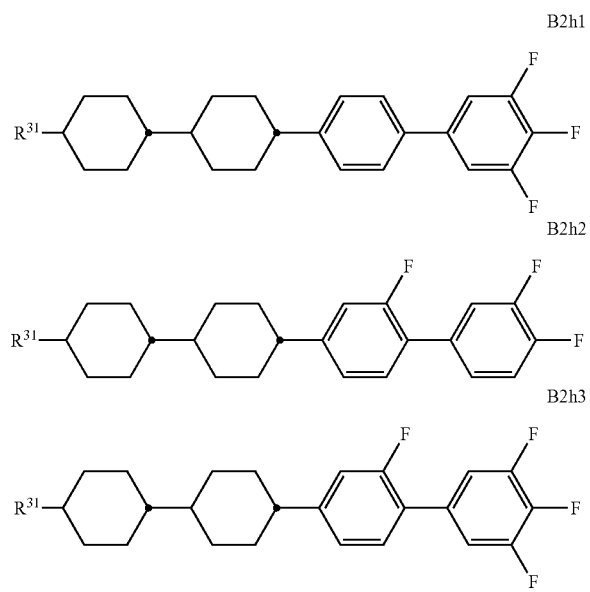

in which $R^{31}$ is as defined in formula B2.

Very particularly preferred compounds of formula B2i are selected from the group consisting of the following subformulae:

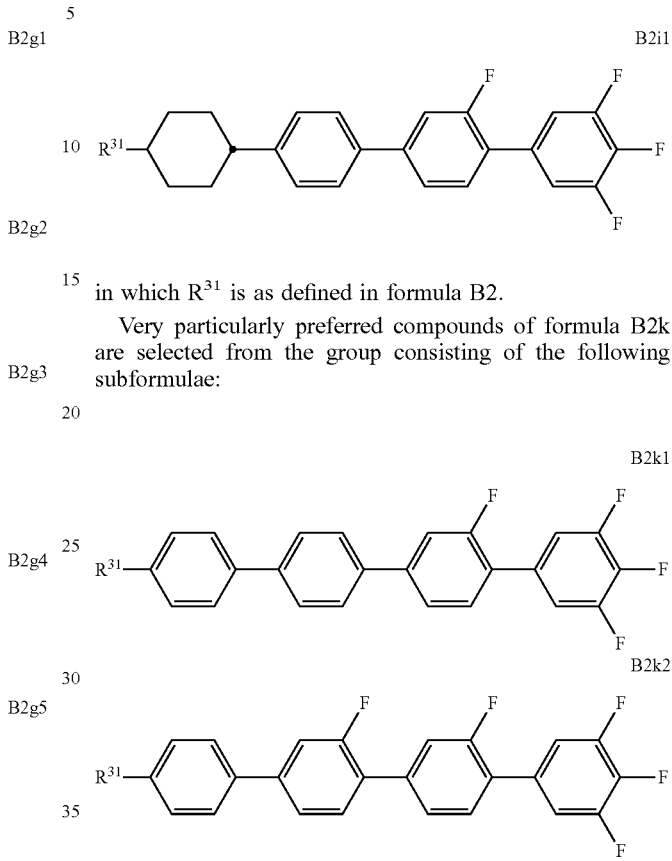

in which $R^{31}$ is as defined in formula B2.

Very particularly preferred compounds of formula B2k are selected from the group consisting of the following subformulae:

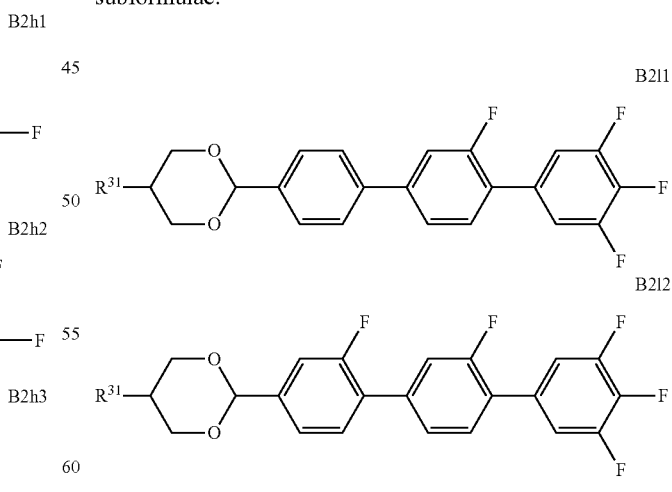

in which $R^{31}$ is as defined in formula B2.

Very particularly preferred compounds of formula B2l are selected from the group consisting of the following subformulae:

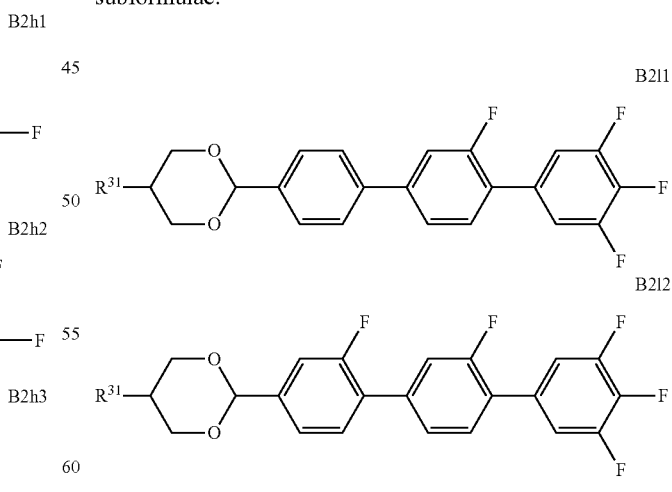

in which $R^{31}$ is as defined in formula B2.

Alternatively to, or in addition to, the compounds of formula B1 and/or B2 component B) of the LC medium may also comprise one or more compounds of formula B3 as defined above.

Particularly preferred compounds of formula B3 are selected from the group consisting of the following subformulae:

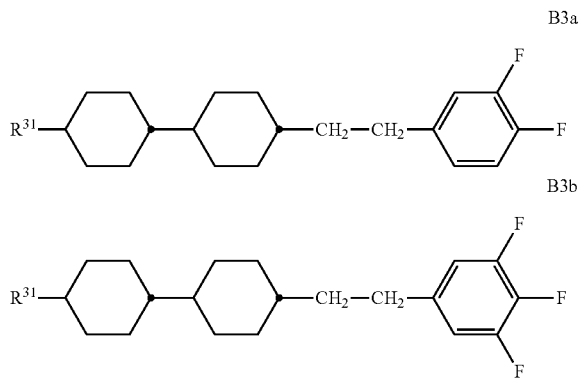

B3a

B3b in which R³¹ is as defined in formula B3.

Preferably component B) of the LC medium comprises, in addition to the compounds of formula A and/or B, one or more compounds of formula C

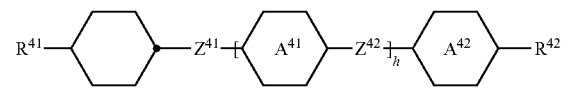

C in which the individual radicals have the following meanings:

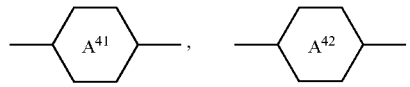

each, independently of one another, and on each occurrence, identically or differently

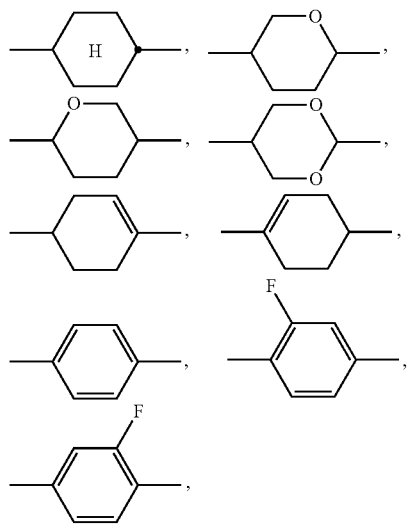

$R^{41}$, $R^{42}$ each, independently of one another, alkyl, alkoxy, oxaalkyl or alkoxyalkyl having 1 to 9 C atoms or alkenyl or alkenyloxy having 2 to 9 C atoms, all of which are optionally fluorinated, $Z^{41}$, $Z^{42}$ each, independently of one another, —CH₂CH₂—, —COO—, trans-CH=CH—, trans-CF=CF—, —CH₂O—, —CF₂O—, —C≡C— or a single bond, preferably a single bond, h 0, 1, 2 or 3.

In the compounds of formula C, $R^{41}$ and $R^{42}$ are preferably selected from straight-chain alkyl or alkoxy with 1, 2, 3, 4, 5 or 6 C atoms, and straight-chain alkenyl with 2, 3, 4, 5, 6 or 7 C atoms.

In the compounds of formula C, h is preferably 0, 1 or 2.

In the compounds of formula C, $Z^{41}$ and $Z^{42}$ are preferably selected from COO, trans-CH=CH and a single bond, very preferably from COO and a single bond.

Preferred compounds of formula C are selected from the group consisting of the following subformulae:

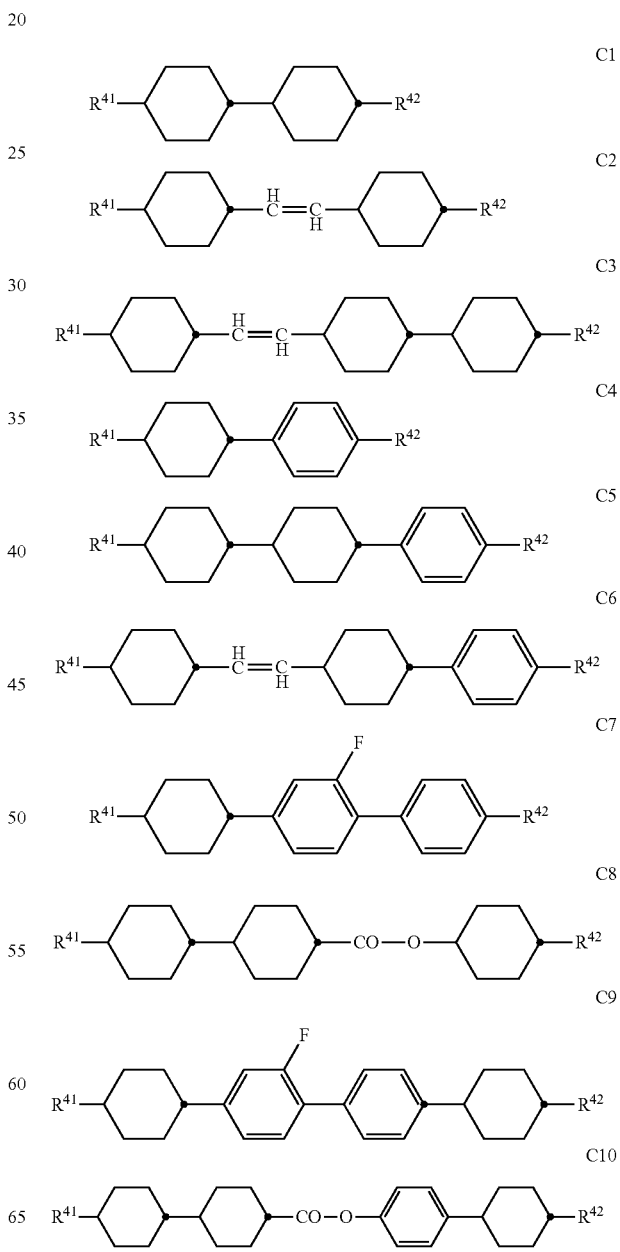

-continued

C11
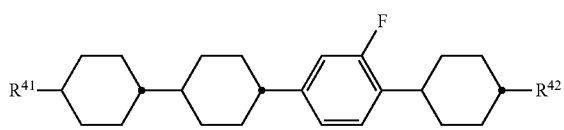

C12
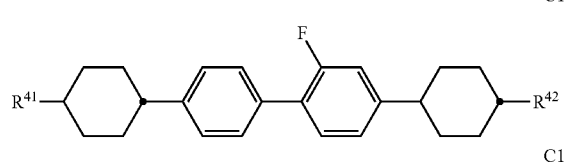

C13
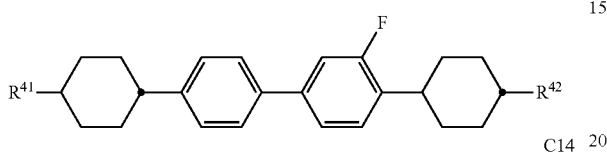

C14
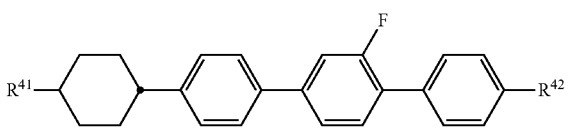

wherein $R^{41}$ and $R^{42}$ have the meanings given in formula C, and preferably denote each, independently of one another, alkyl, alkoxy, fluorinated alkyl or fluorinated alkoxy with 1 to 7 C atoms, or alkenyl, alkenyloxy, alkoxyalkyl or fluorinated alkenyl with 2 to 7 C atoms.

Further preferably component B) of the LC medium comprises, in addition to the compounds of formula A and/or B, one or more compounds of formula D D
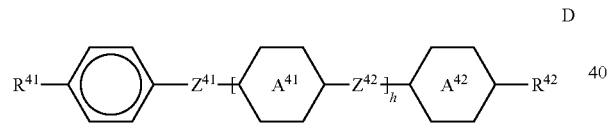

in which $A^{41}$, $A^{42}$, $Z^{41}$, $Z^{42}$, $R^{41}$, $R^{42}$ and h have the meanings given in formula C or one of the preferred meanings given above.

Preferred compounds of formula D are selected from the group consisting of the following subformulae:

D1
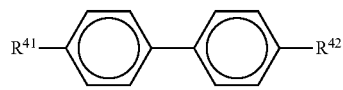

D2
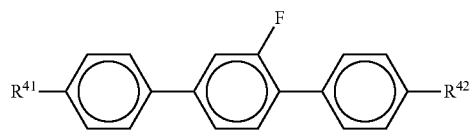

in which $R^{41}$ and $R^{42}$ have the meanings given in formula D and $R^{41}$ preferably denotes alkyl bedeutet, and in formula D1 $R^{42}$ preferably denotes alkenyl, particularly preferably —(CH$_2$)$_2$—CH═CH—CH$_3$, and in formula D2 $R^{42}$ preferably denotes alkyl, —(CH$_2$)$_2$—CH═CH$_2$ or —(CH$_2$)$_2$—CH═CH—CH$_3$.

Further preferably component B) of the LC medium comprises, in addition to the compounds of formula A and/or B, one or more compounds of formula E containing an alkenyl group E
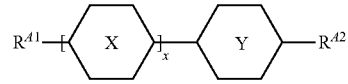

in which the individual radicals, on each occurrence identically or differently, each, independently of one another, have the following meaning:

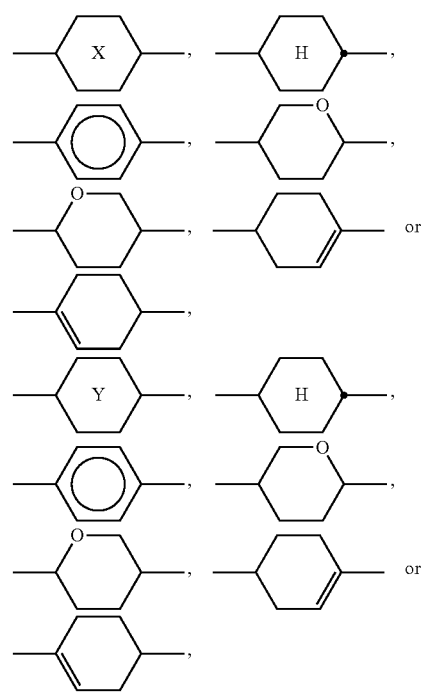

$R^{A1}$ alkenyl having 2 to 9 C atoms or, if at least one of the rings X, Y and Z denotes cyclohexenyl, also one of the meanings of $R^{A2}$, $R^{A2}$ alkyl having 1 to 12 C atoms, in which, in addition, one or two non-adjacent CH$_2$ groups may be replaced by —O—, —CH═CH—, —CO—, —OCO— or —COO— in such a way that O atoms are not linked directly to one another, x 1 or 2.

$R^{A2}$ is preferably straight-chain alkyl or alkoxy having 1 to 8 C atoms or straight-chain alkenyl having 2 to 7 C atoms.

Preferred compounds of formula E are selected from the following sub-formulae:

E1
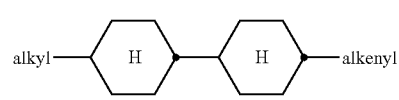

E2
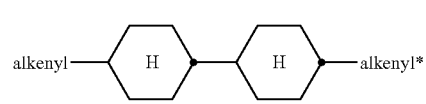

-continued

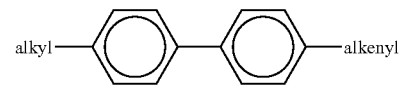
E3

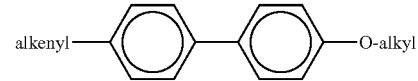
E4

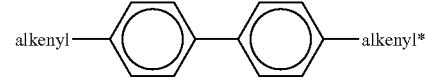
E5

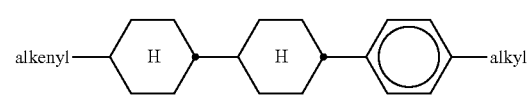
E6

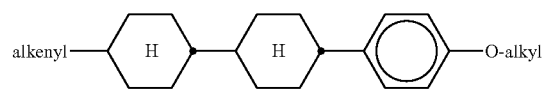
E7

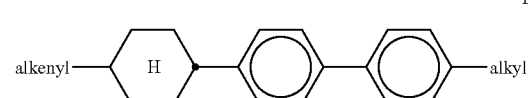
E8

E9

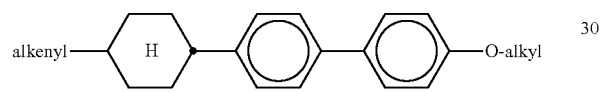
E10

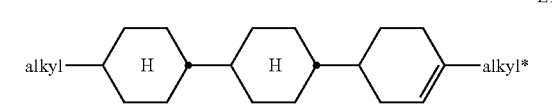
E10

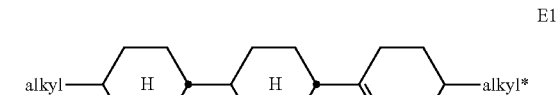
E11

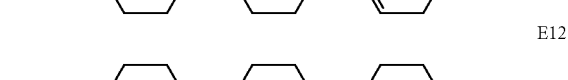
E12

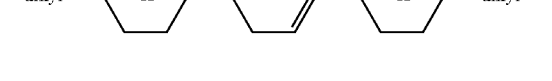

in which alkyl and alkyl* each, independently of one another, denote a straight-chain alkyl radical having 1-6 C atoms, and alkenyl and alkenyl* each, independently of one another, denote a straight-chain alkenyl radical having 2-7 C atoms. Alkenyl and alkenyl* preferably denote CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

Very preferred compounds of the formula E are selected from the following sub-formulae:

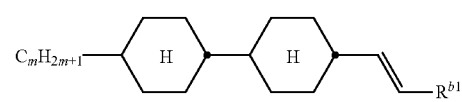
E1a

-continued

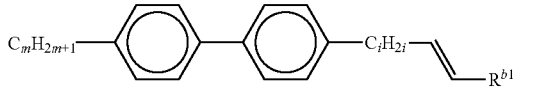
E3a

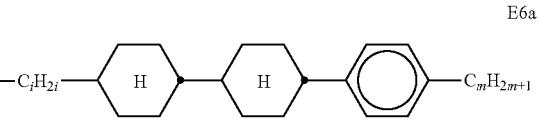
E6a in which m denotes 1, 2, 3, 4, 5 or 6, i denotes 0, 1, 2 or 3, and R$^{b}$1 denotes H, CH$_3$ or C$_2$H$_5$.

Very particularly preferred compounds of the formula E are selected from the following sub-formulae:

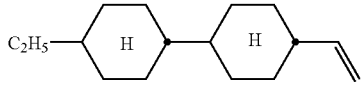
E1a1

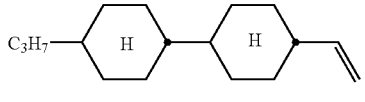
E1a2

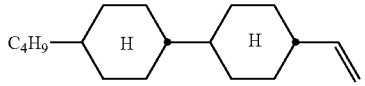
E1a3

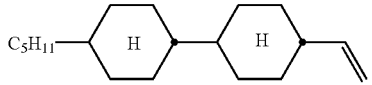
E1a4

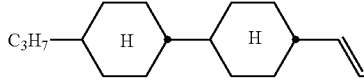
E1a5

E3a1

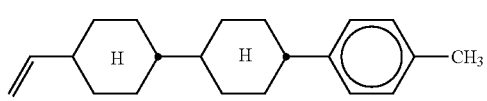
E6a1

Most preferred are compounds of formula E1a2, E1a5, E3a1 and E6a1.

Further preferably component B) of the LC medium comprises, in addition to the compounds of formula A and/or B, one or more compounds of formula F

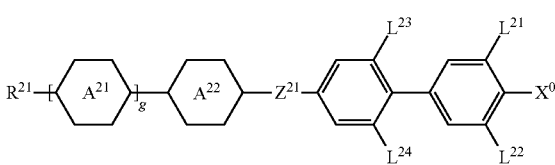
F in which the individual radicals have, independently of each other and on each occurrence identically or differently, the following meanings:

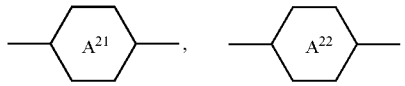

denote

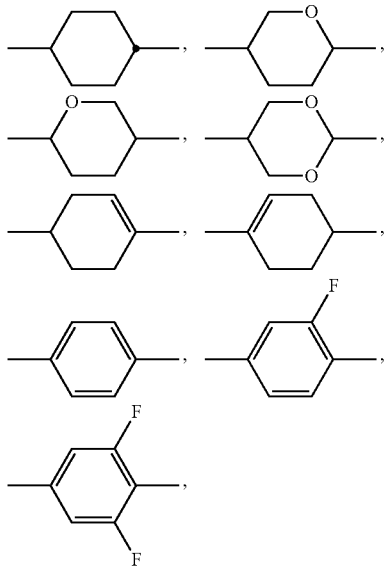

$R^{21}$, $R^{31}$ each, independently of one another, alkyl, alkoxy, oxaalkyl or alkoxyalkyl having 1 to 9 C atoms or alkenyl or alkenyloxy having 2 to 9 C atoms, all of which are optionally fluorinated, $X^0$ F, Cl, halogenated alkyl or alkoxy having 1 to 6 C atoms or halogenated alkenyl or alkenyloxy having 2 to 6 C atoms, $Z^{21}$ —$CH_2CH_2$—, —$CF_2CF_2$—, —COO—, trans-CH=CH—, trans-CF=CF—, —$CH_2O$— or a single bond, preferably —$CH_2CH_2$—, —COO—, trans-CH=CH— or a single bond, particularly preferably —COO—, trans-CH=CH— or a single bond, $L^{21}$, $L^{22}$, $L^{23}$, $L^{24}$ each, independently of one another, H or F, g 0, 1, 2 or 3.

Particularly preferred compounds of formula F are selected from the group consisting of the following formulae:

F1

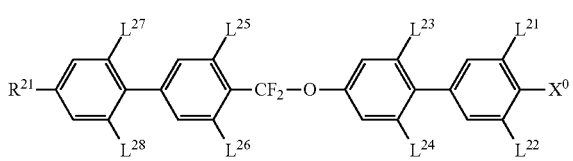

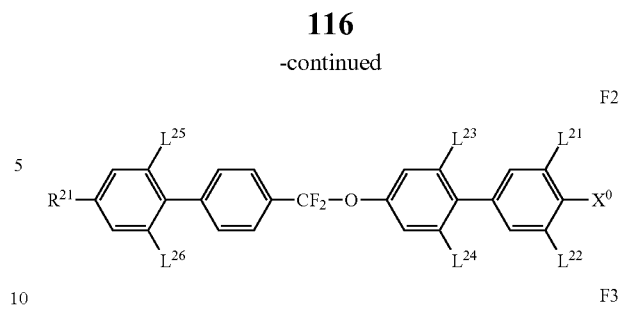

in which $R^{21}$, $X^0$, $L^{21}$ and $L^{22}$ have the meaning given in formula F, $L^{25}$ and $L^{26}$ are each, independently of one another, H or F, and $X^0$ is preferably F.

Very particularly preferred compounds of formula $F_1$-$F_3$ are selected from the group consisting of the following subformulae:

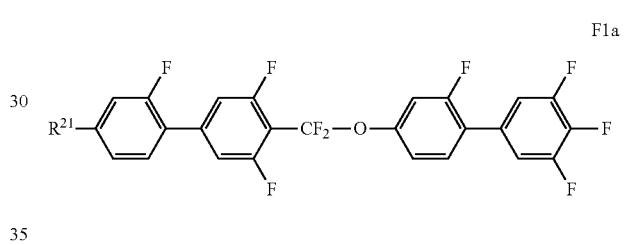

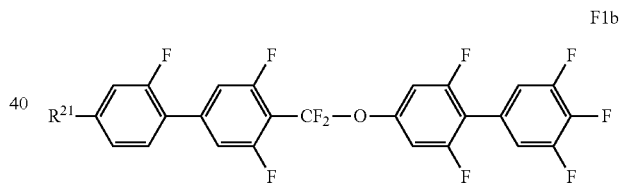

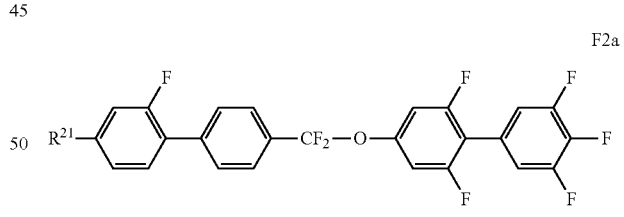

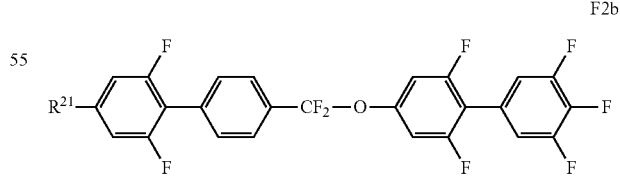

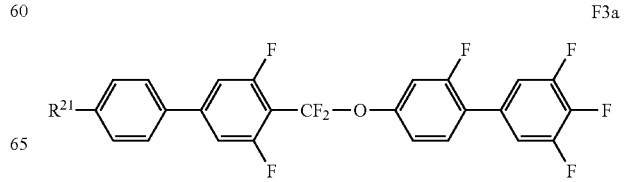

-continued

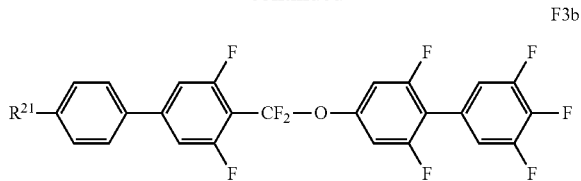
F3b

In which $R^{21}$ is as defined in formula $F_1$.

The concentration of the compounds of formula A and B in the LC host mixture is preferably from 2 to 60%, very preferably from 3 to 45%, most preferably from 4 to 35%.

The concentration of the compounds of formula C and D in the LC host mixture is preferably from 2 to 70%, very preferably from 5 to 65%, most preferably from 10 to 60%.

The concentration of the compounds of formula E in the LC host mixture is preferably from 5 to 50%, very preferably from 5 to 35%.

The concentration of the compounds of formula F in the LC host mixture is preferably from 2 to 30%, very preferably from 5 to 20%.

Further preferred embodiments of this second preferred embodiment of the present invention are listed below, including any combination thereof.

2a) The LC host mixture comprises one or more compounds of formula A and/or B with high positive dielectric anisotropy, preferably with $\Delta\varepsilon>15$.

2b) The LC host mixture comprises one or more compounds selected from the group consisting of formulae A1a2, A1b1, A1d1, A1f1, A2a1, A2h1, A2I2, A2k1, B2h3, B2I1, F1a. The proportion of these compounds in the LC host mixture is preferably from 4 to 40%, very preferably from 5 to 35%.

2c) The LC host mixture comprises one or more compounds selected from the group consisting of formulae B2c1, B2c4, B2f4, C14. The proportion of these compounds in the LC host mixture is preferably from 4 to 40%, very preferably from 5 to 35%.

2d) The LC host mixture comprises one or more compounds selected from the group consisting of formulae C3, C4, C5, C9 and D2. The proportion of these compounds in the LC host mixture is preferably from 8 to 70%, very preferably from 10 to 60%.

2e) The LC host mixture comprises one or more compounds selected from the group consisting of formulae G1, G2 and G5, preferably G1a, G2a and G5a. The proportion of these compounds in the LC host mixture is preferably from 4 to 40%, very preferably from 5 to 35%.

2f) The LC host mixture comprises one or more compounds selected from the group consisting of formulae E1, E3 and E6, preferably E1a, E3a and E6a, very preferably E1a2, E1a5, E3a1 and E6a1. The proportion of these compounds in the LC host mixture is preferably from 5 to 60%, very preferably from 10 to 50%.

The combination of compounds of the preferred embodiments mentioned above with the polymerized compounds described above causes low threshold voltages, low rotational viscosities and very good low-temperature stabilities in the LC media according to the invention at the same time as constantly high clearing points and high HR values, and allows the rapid establishment of a particularly low pretilt angle in PSA displays. In particular, the LC media exhibit significantly shortened response times, in particular also the grey-shade response times, in PSA displays compared with the media from the prior art.

The LC media and LC host mixtures of the present invention preferably have a nematic phase range of at least 80 K, particularly preferably at least 100 K, and a rotational viscosity ≤250 mPa·s, preferably <200 mPa·s, at 20° C.

In the VA-type displays according to the invention, the molecules in the layer of the LC medium in the switched-off state are aligned perpendicular to the electrode surfaces (homeotropically) or have a a tilted homeotropic alignment. On application of an electrical voltage to the electrodes, a realignment of the LC molecules takes place with the longitudinal molecular axes parallel to the electrode surfaces.

LC media according to the invention based on compounds with negative dielectric anisotropy according to the first preferred embodiment, in particular for use in displays of the PS-VA and PS—UB-FFS type, have a negative dielectric anisotropy $\Delta\varepsilon$, preferably from −0.5 to −10, in particular from −2.5 to −7.5, at 20° C. and 1 kHz.

The birefringence $\Delta n$ in LC media according to the invention for use in displays of the PS-VA and PS—UB-FFS type is preferably below 0.16, particularly preferably from 0.06 to 0.14, very particularly preferably from 0.07 to 0,12.

In the OCB-type displays according to the invention, the molecules in the layer of the LC medium have a "bend" alignment. On application of an electrical voltage, a realignment of the LC molecules takes place with the longitudinal molecular axes perpendicular to the electrode surfaces.

LC media according to the invention for use in displays of the PS—OCB, PS-TN, PS—IPS, PS-posi-VA and PS-FFS type are preferably those based on compounds with positive dielectric anisotropy according to the second preferred embodiment, and preferably have a positive dielectric anisotropy $\Delta\varepsilon$ from +4 to +17 at 20° C. and 1 kHz.

The birefringence $\Delta n$ in LC media according to the invention for use in displays of the PS-OCB type is preferably from 0.14 to 0.22, particularly preferably from 0.16 to 0.22.

The birefringence $\Delta n$ in LC media according to the invention for use in displays of the PS-TN-, PS-posi-VA-, PS-IPS- oder PS-FFS-type is preferably from 0.07 to 0.15, particularly preferably from 0.08 to 0.13.

LC media according to the invention, based on compounds with positive dielectric anisotropy according to the second preferred embodiment, for use in displays of the PS-TN-, PS-posi-VA-, PS-IPS- oder PS-FFS-type, preferably have a positive dielectric anisotropy $\Delta\varepsilon$ from +2 to +30, particularly preferably from +3 to +20, at 20° C. and 1 kHz.

The LC media according to the invention may also comprise further additives which are known to the person skilled in the art and are described in the literature, such as, for example, polymerization initiators, inhibitors, stabilizers, surface-active substances or chiral dopants. These may be polymerizable or non-polymerizable. Polymerizable additives are accordingly ascribed to the polymerizable component or component A). Non-polymerizable additives are accordingly ascribed to the non-polymerizable component or component B).

In a preferred embodiment the LC media contain one or more chiral dopants, preferably in a concentration from 0.01 to 1%, very preferably from 0.05 to 0.5%. The chiral dopants are preferably selected from the group consisting of compounds from Table B below, very preferably from the group consisting of R- or S-1011, R- or S-2011, R- or S-3011, R- or S-4011, and R- or S-5011.

In another preferred embodiment the LC media contain a racemate of one or more chiral dopants, which are preferably selected from the chiral dopants mentioned in the previous paragraph.

Furthermore, it is possible to add to the LC media, for example, 0 to 15% by weight of pleochroic dyes, furthermore nanoparticles, conductive salts, preferably ethyldimethyldodecylammonium 4-hexoxybenzoate, tetrabutyl-ammonium tetraphenylborate or complex salts of crown ethers (cf., for example, Haller et al., Mol. Cryst. Liq. Cryst. 24, 249-258 (1973)), for improving the conductivity, or substances for modifying the dielectric anisotropy, the viscosity and/or the alignment of the nematic phases. Substances of this type are described, for example, in DE-A 22 09 127, 22 40 864, 23 21 632, 23 38 281, 24 50 088, 26 37 430 and 28 53 728.

The individual components of the preferred embodiments a)-z) of the LC media according to the invention are either known or methods for the preparation thereof can readily be derived from the prior art by the person skilled in the relevant art, since they are based on standard methods described in the literature. Corresponding compounds of the formula CY are described, for example, in EP-A-0 364 538. Corresponding compounds of the formula ZK are described, for example, in DE-A-26 36 684 and DE-A-33 21 373.

The LC media which can be used in accordance with the invention are prepared in a manner conventional per se, for example by mixing one or more of the above-mentioned compounds with one or more polymerizable compounds as defined above, and optionally with further liquid-crystalline compounds and/or additives. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

It goes without saying to the person skilled in the art that the LC media according to the invention may also comprise compounds in which, for example, H, N, O, Cl, F have been replaced by the corresponding isotopes like deuterium etc.

The following examples explain the present invention without restricting it. However, they show the person skilled in the art preferred mixture concepts with compounds preferably to be employed and the respective concentrations thereof and combinations thereof with one another. In addition, the examples illustrate which properties and property combinations are accessible.

The following abbreviations are used:
(n, m, z: in each case, independently of one another, 1, 2, 3, 4, 5 or 6)

TABLE A

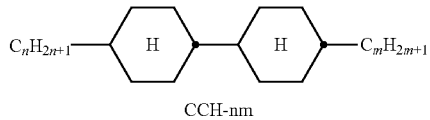

CCH-nm

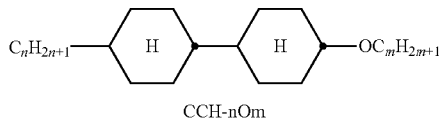

CCH-nOm

TABLE A-continued

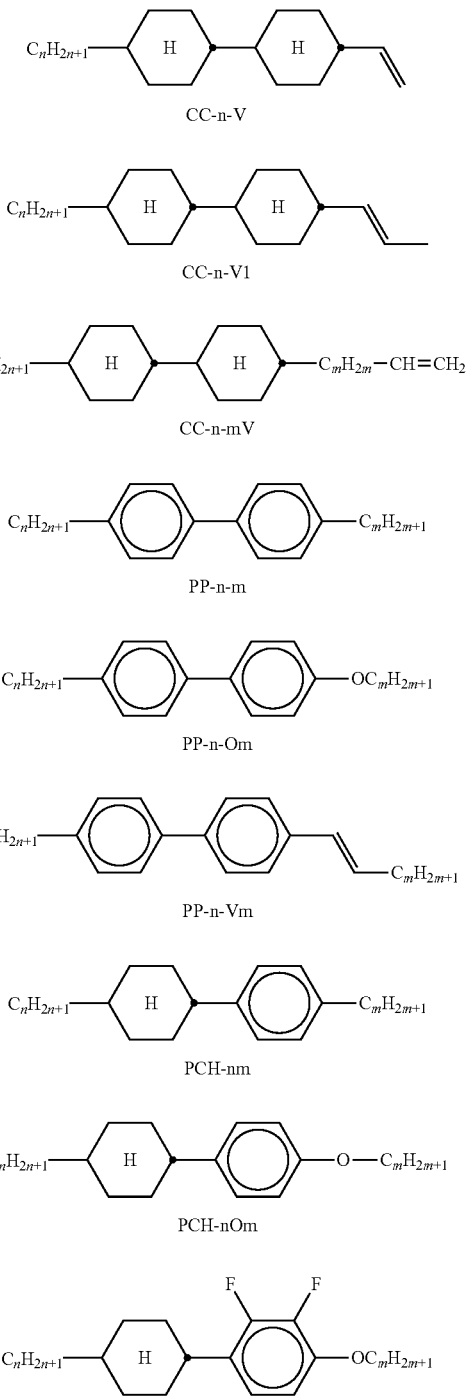

CC-n-V

CC-n-V1

CC-n-mV

PP-n-m

PP-n-Om

PP-n-Vm

PCH-nm

PCH-nOm

CY-n-Om

CY-n-m

TABLE A-continued
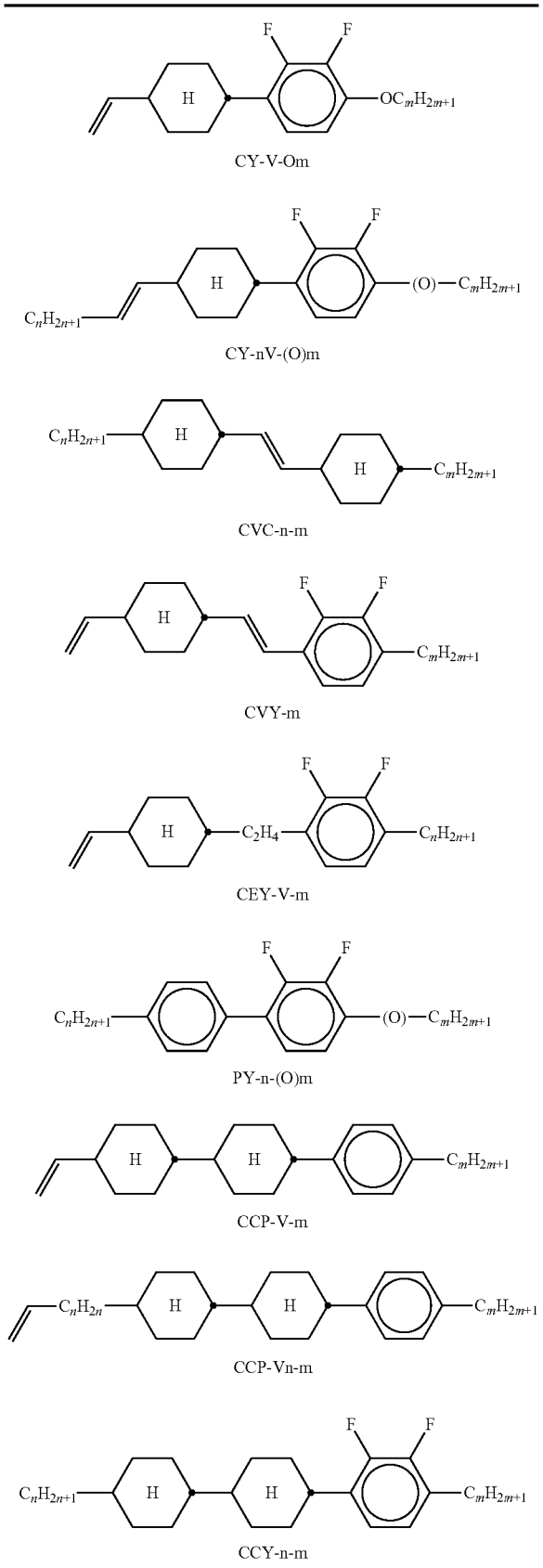
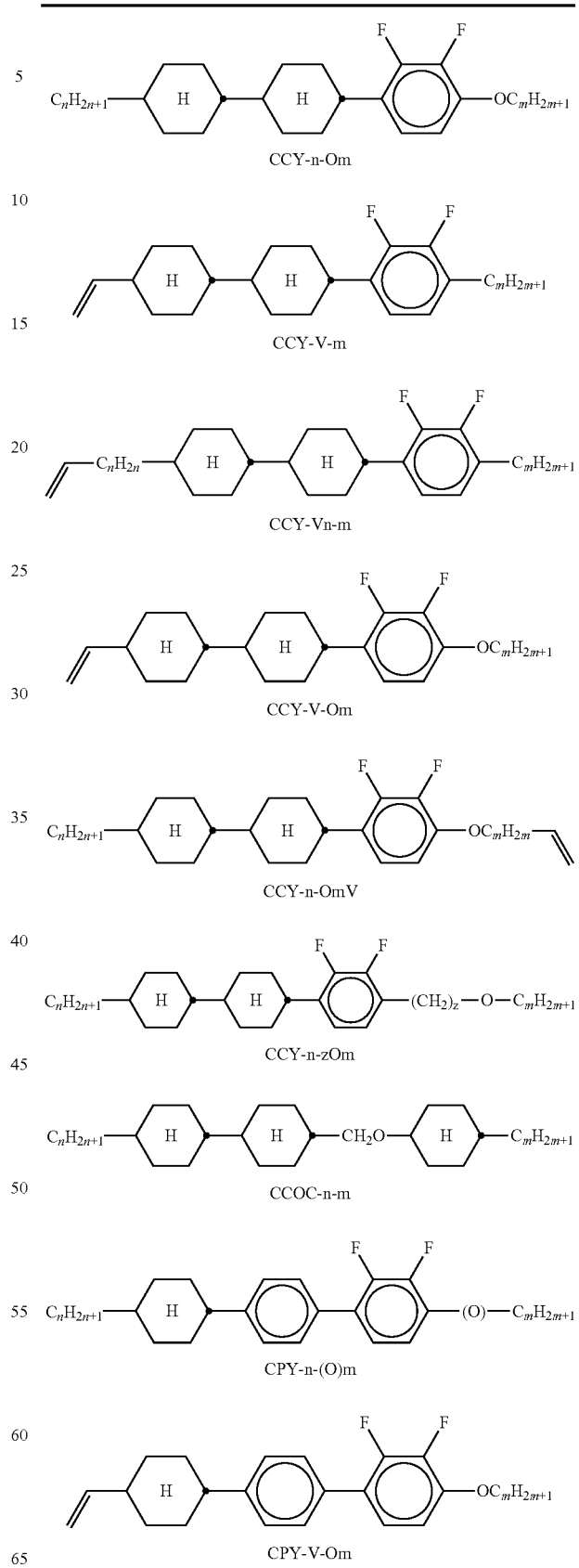

TABLE A-continued
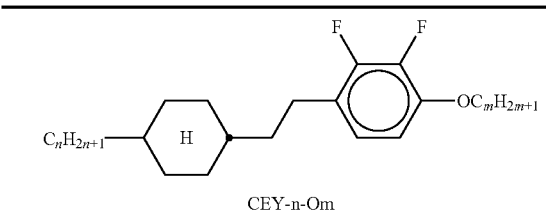
CEY-n-Om
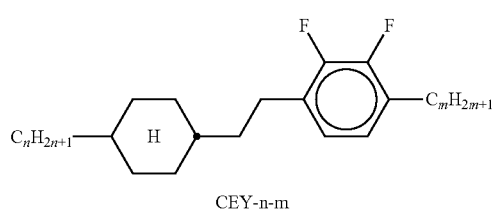
CEY-n-m
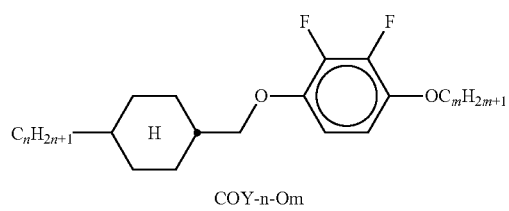
COY-n-Om
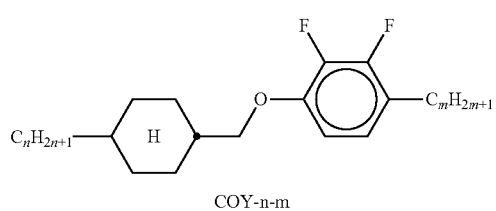
COY-n-m
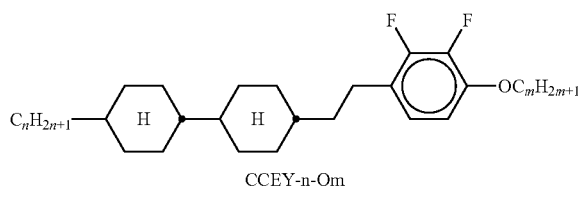
CCEY-n-Om
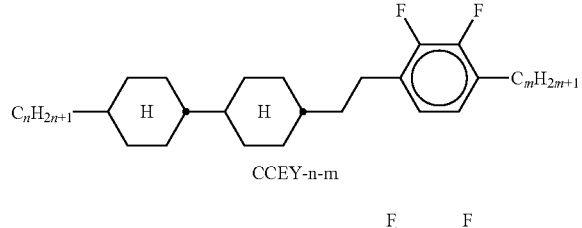
CCEY-n-m
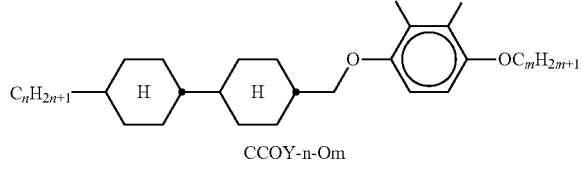
CCOY-n-Om
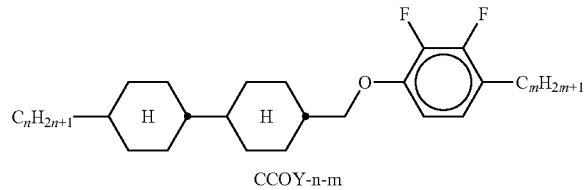
CCOY-n-m
TABLE A-continued
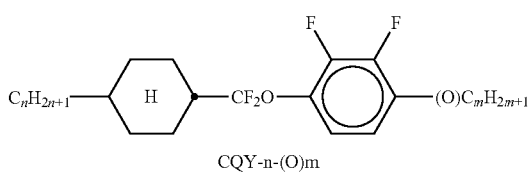
CQY-n-(O)m
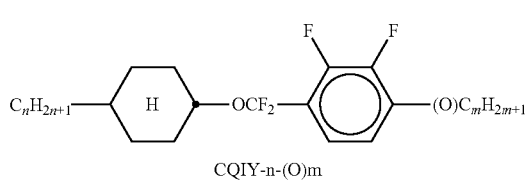
CQIY-n-(O)m
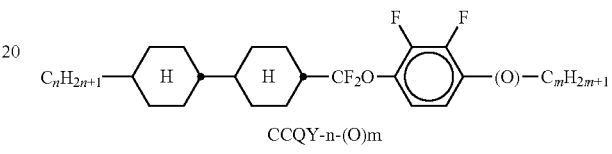
CCQY-n-(O)m
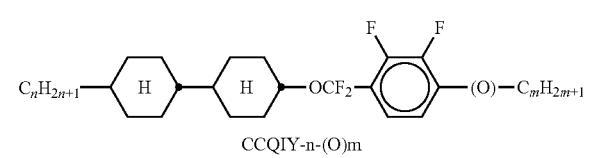
CCQIY-n-(O)m
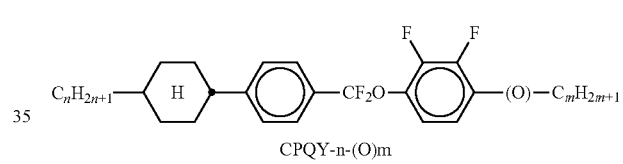
CPQY-n-(O)m
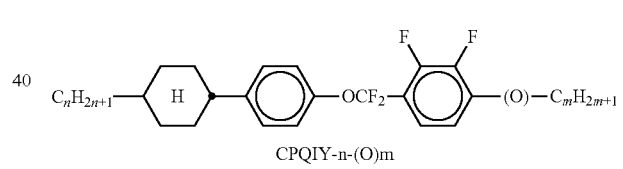
CPQIY-n-(O)m
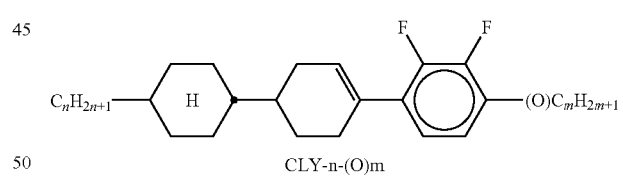
CLY-n-(O)m
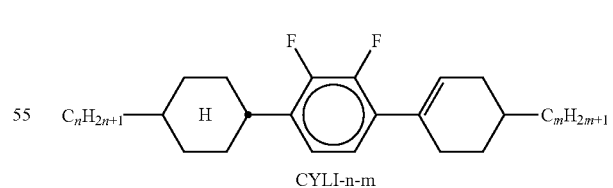
CYLI-n-m
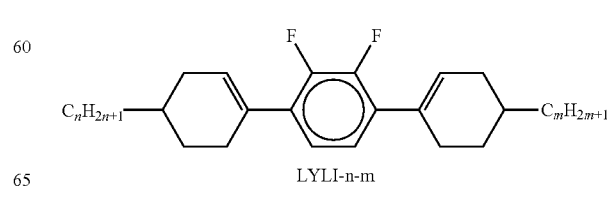
LYLI-n-m TABLE A-continued LY-n-(O)m PGIGI-n-F PGP-n-m PYP-n-(O)m PYP-n-mV YPY-n-m YPY-n-mV BCH-nm BCH-nmF CPYP-n-(O)m CPGP-n-m CCZPC-n-m CGCC-n-m CPYC-n-m CYYC-n-m CCYY-n-m CPYG-n-(O)m CBC-nm CBC-nmF

TABLE A-continued

CNap-n-Om

CCNap-n-Om

CENap-n-Om

CTNap-n-Om

CETNap-n-Om

CK-n-F

DFDBC-n(O)-(O)m

C-DFDBC-n-(O)m

In a preferred embodiment of the present invention, the LC media according to the invention comprise one or more compounds selected from the group consisting of compounds from Table A.

TABLE B

Table B sows possible chiral dopants which can be added to the LC media according to the invention

C 15

CB 15

CM 21

R/S-811

CM 44

CM 45

CM 47

129
TABLE B-continued

Table B sows possible chiral dopants which can be added to the LC media according to the invention

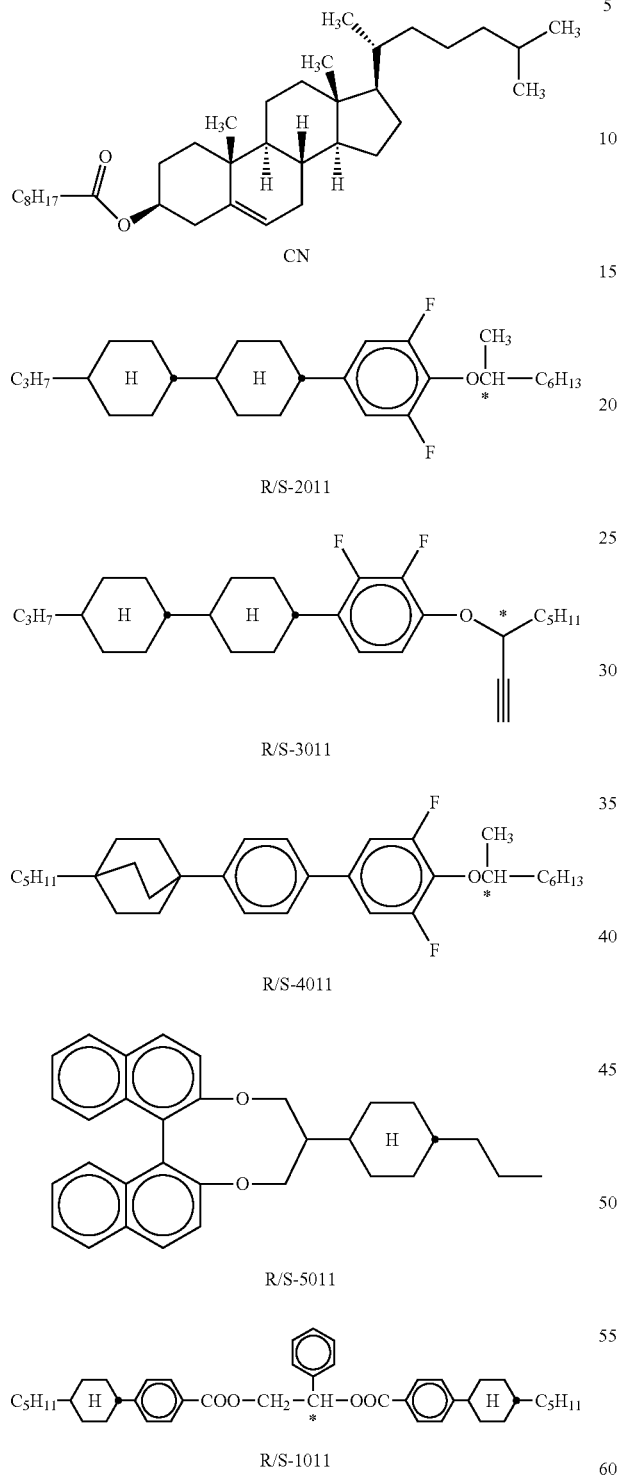

130
TABLE C

Table C shows possible stabilizers which can be added to the LC media according to the invention.
(n here denotes an integer from 1 to 12, preferably 1, 2, 3, 4, 5, 6, 7 or 8, terminal methyl groups are not shown).

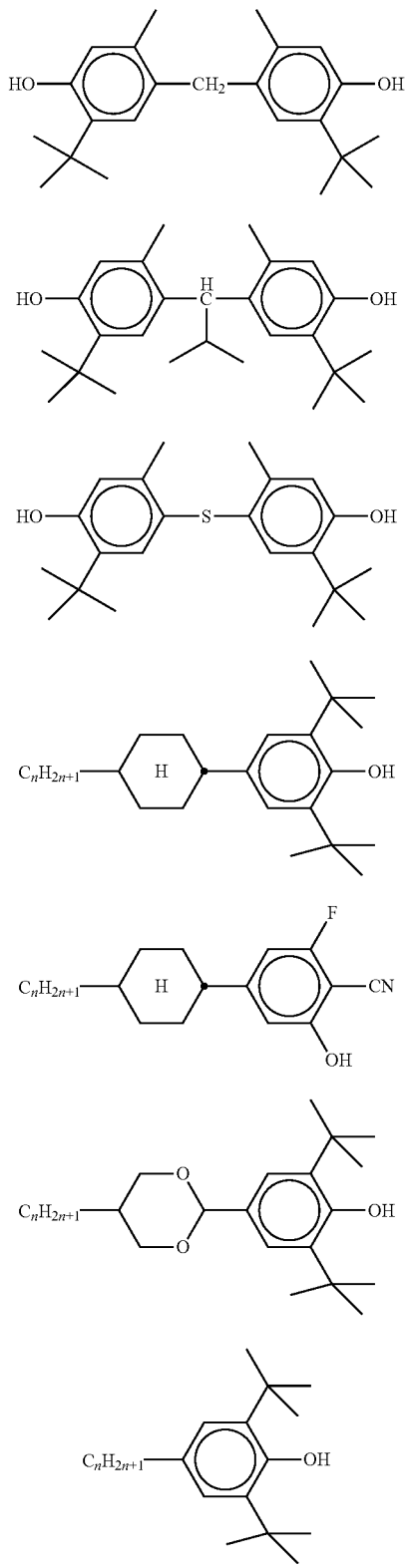

The LC media preferably comprise 0 to 10% by weight, in particular 0.01 to 5% by weight, particularly preferably 0.1 to 3% by weight, of dopants. The LC media preferably comprise one or more dopants selected from the group consisting of compounds from Table B.

TABLE C-continued

Table C shows possible stabilizers which can be added to the LC media according to the invention.
(n here denotes an integer from 1 to 12, preferably 1, 2, 3, 4, 5, 6, 7 or 8, terminal methyl groups are not shown).

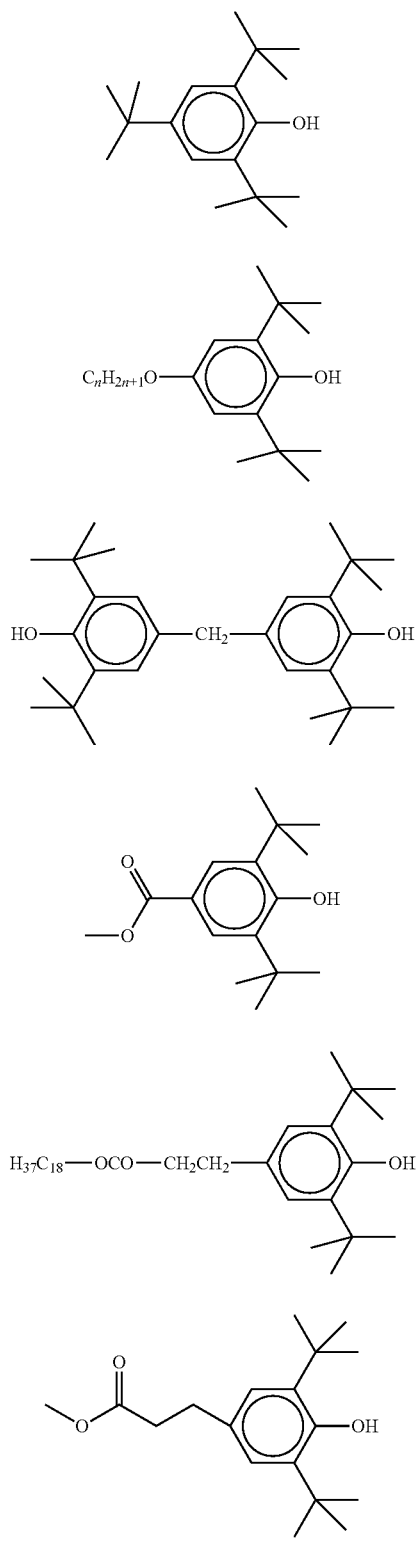

TABLE C-continued

Table C shows possible stabilizers which can be added to the LC media according to the invention.
(n here denotes an integer from 1 to 12, preferably 1, 2, 3, 4, 5, 6, 7 or 8, terminal methyl groups are not shown).

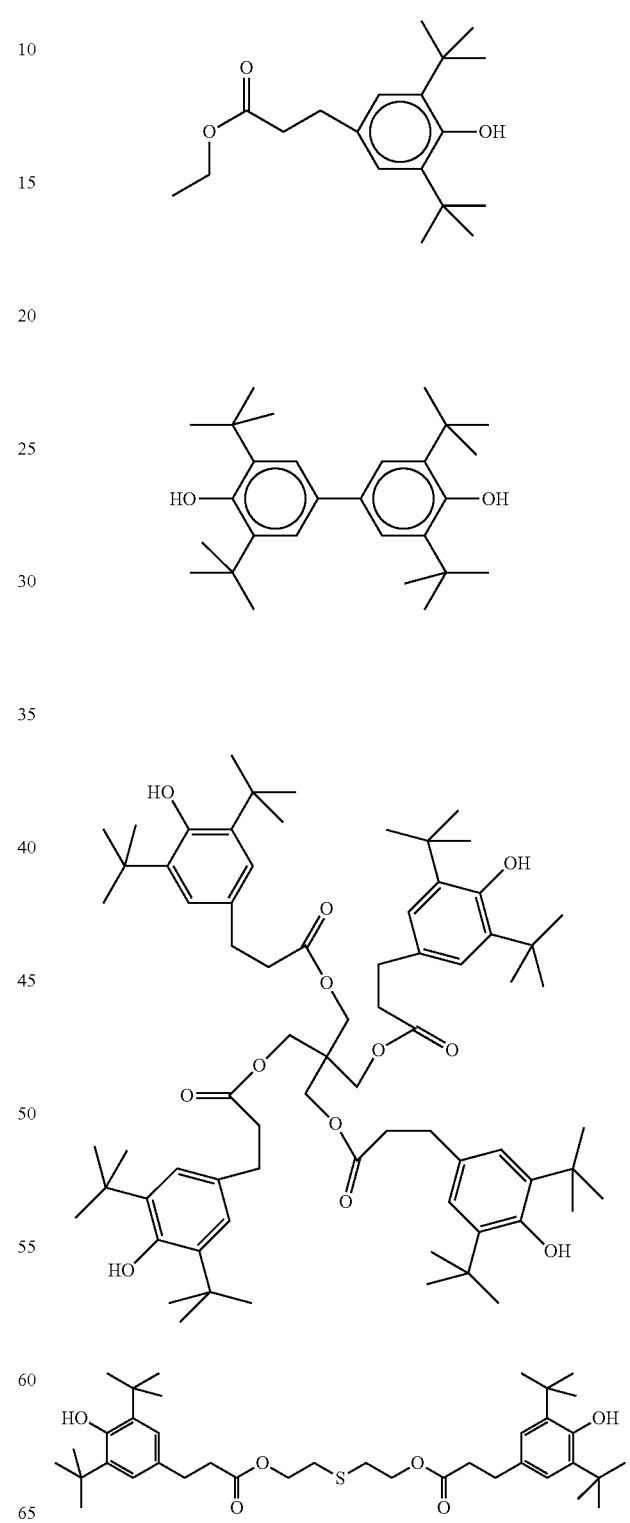

TABLE C-continued

Table C shows possible stabilizers which can be added to the LC media according to the invention.
(n here denotes an integer from 1 to 12, preferably 1, 2, 3, 4, 5, 6, 7 or 8, terminal methyl groups are not shown).

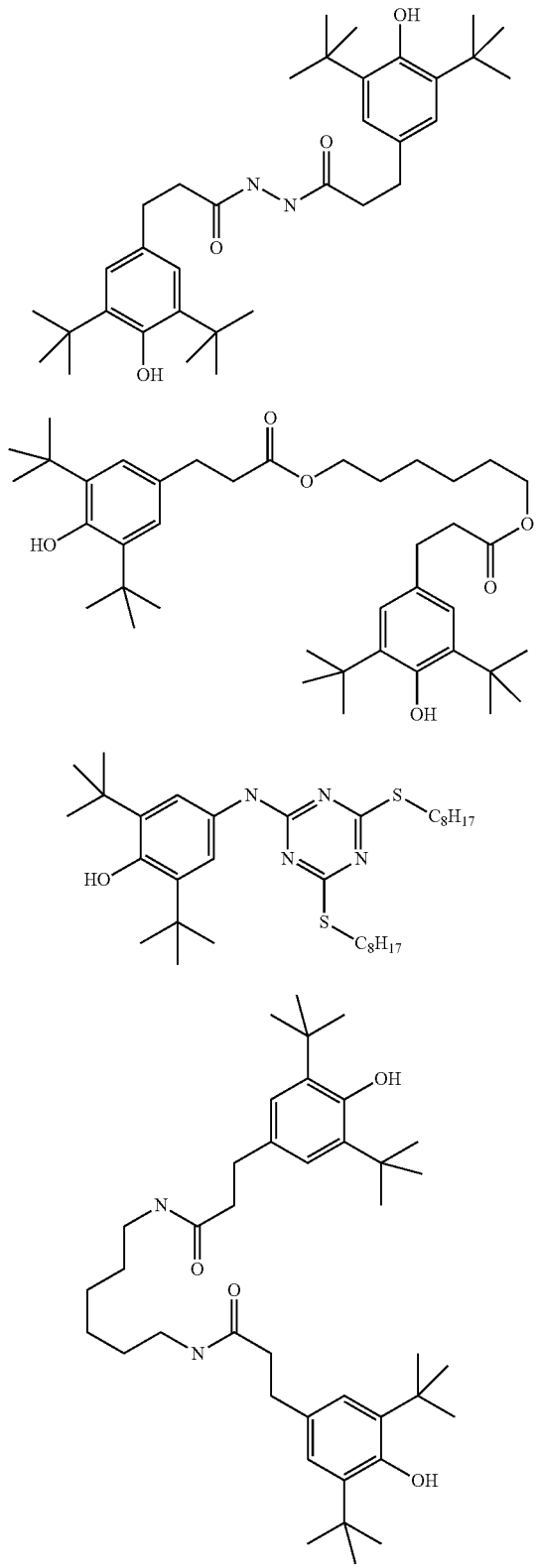

TABLE C-continued

Table C shows possible stabilizers which can be added to the LC media according to the invention.
(n here denotes an integer from 1 to 12, preferably 1, 2, 3, 4, 5, 6, 7 or 8, terminal methyl groups are not shown).

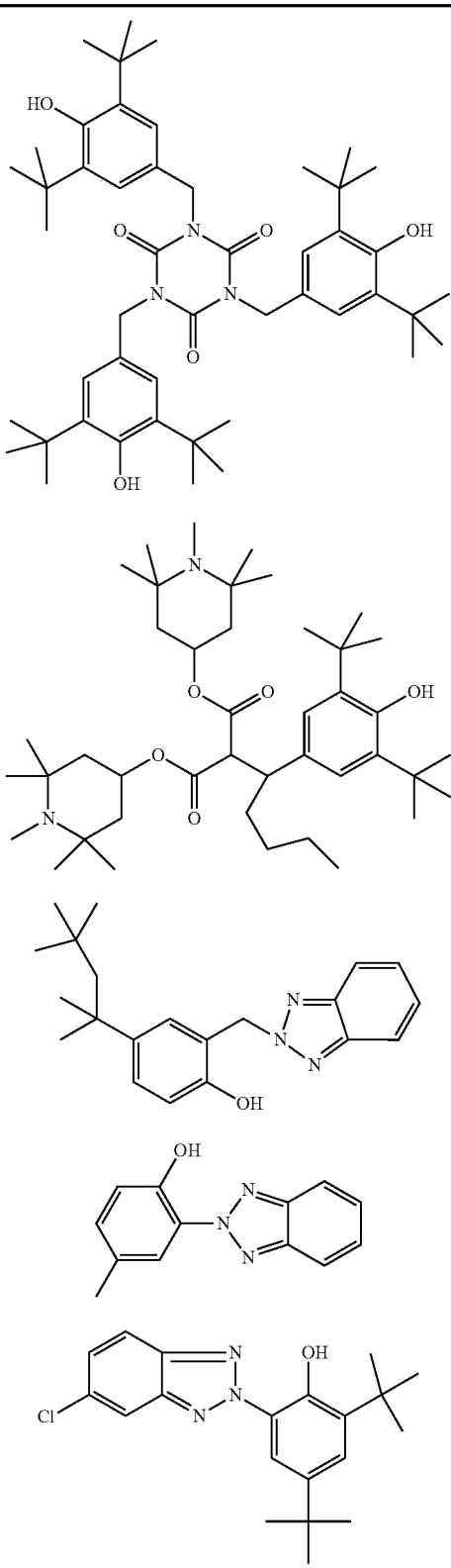

TABLE C-continued
Table C shows possible stabilizers which can be added to the LC media according to the invention.
(n here denotes an integer from 1 to 12, preferably 1, 2, 3, 4, 5, 6, 7 or 8, terminal methyl groups are not shown).
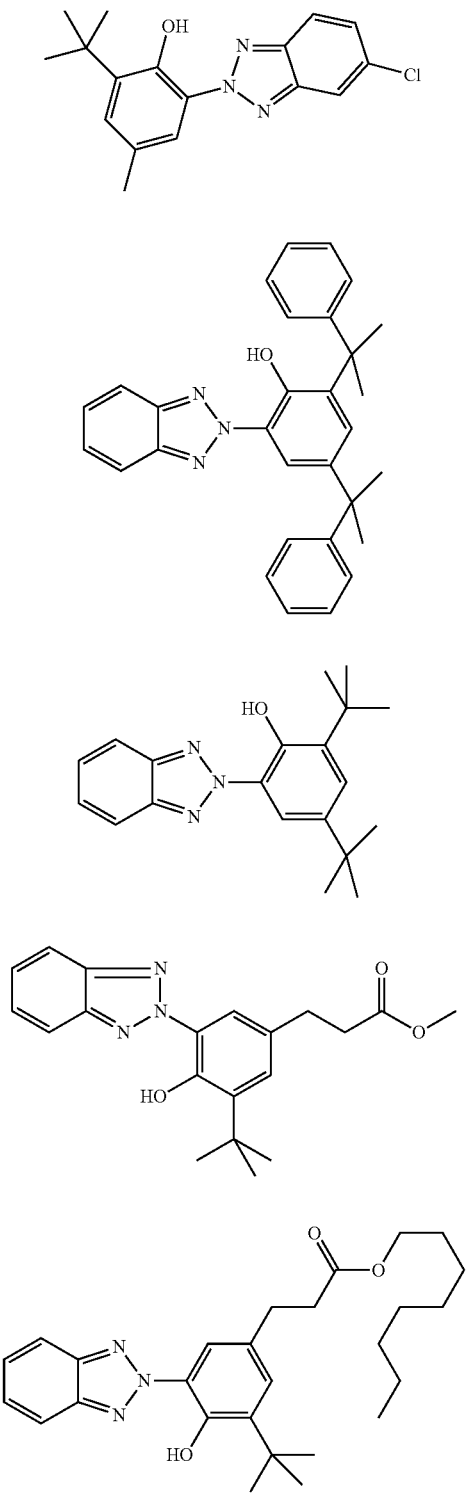
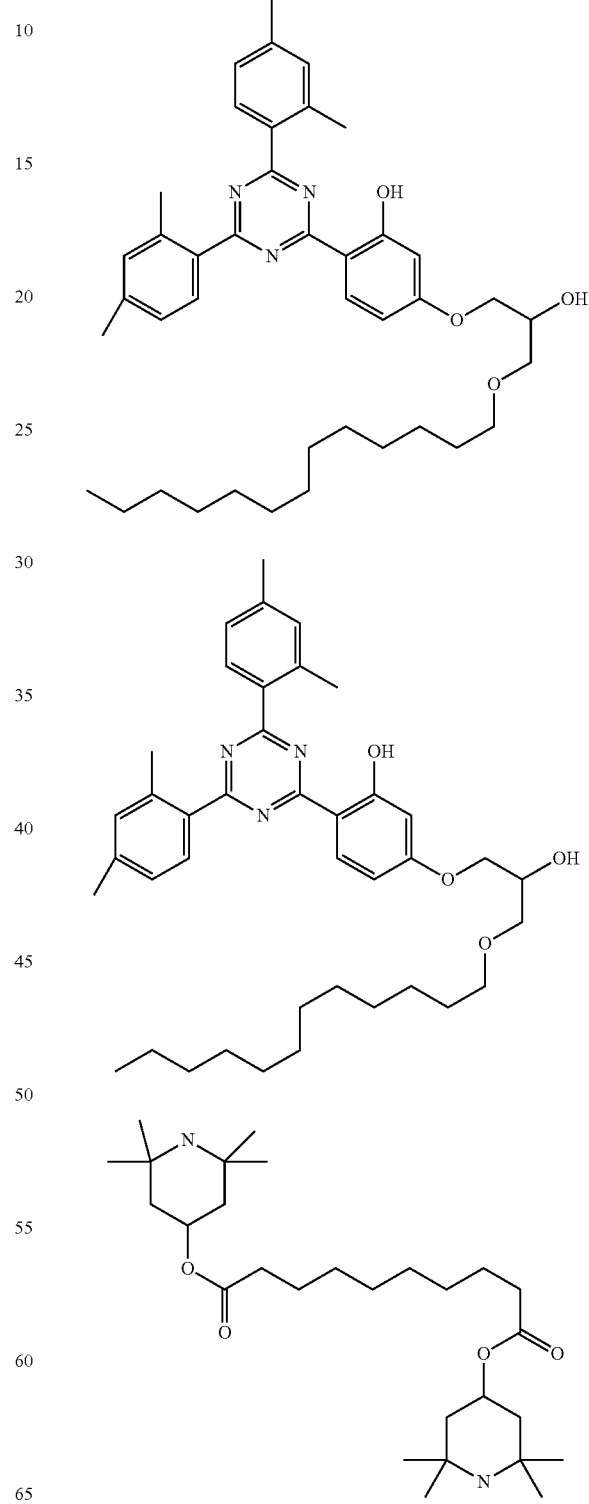

TABLE C-continued

Table C shows possible stabilizers which can be added to the LC media according to the invention.
(n here denotes an integer from 1 to 12, preferably 1, 2, 3, 4, 5, 6, 7 or 8, terminal methyl groups are not shown).

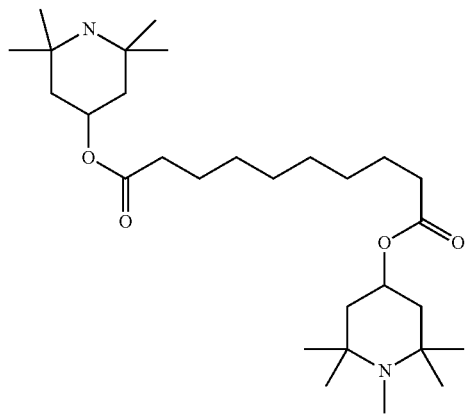

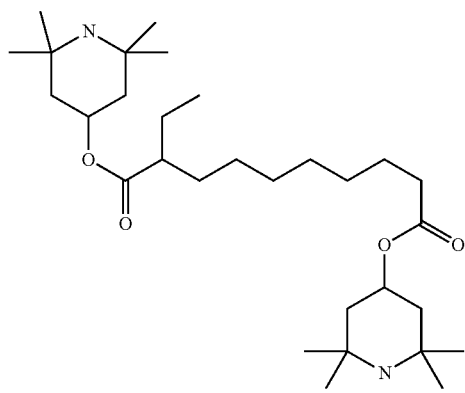

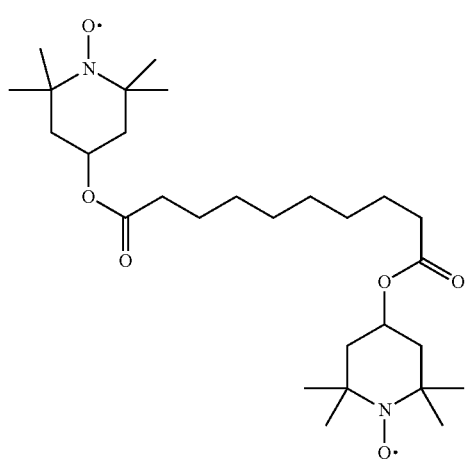

TABLE C-continued

Table C shows possible stabilizers which can be added to the LC media according to the invention.
(n here denotes an integer from 1 to 12, preferably 1, 2, 3, 4, 5, 6, 7 or 8, terminal methyl groups are not shown).

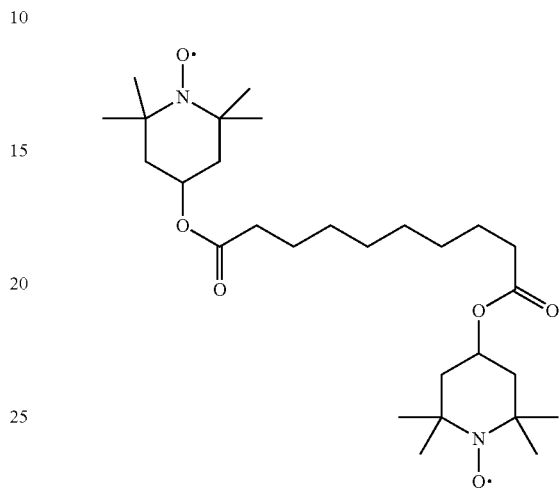

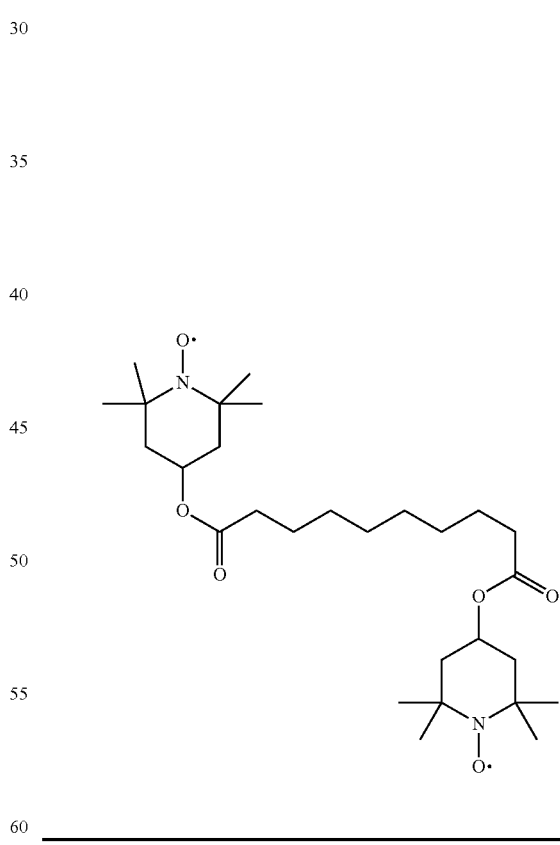

The LC media preferably comprise 0 to 10% by weight, in particular 1 ppm to 5% by weight, particularly preferably 1 ppm to 1% by weight, of stabilizers. The LC media preferably comprise one or more stabilizers selected from the group consisting of compounds from Table C.

TABLE D
Table D shows illustrative compounds which can be used in the LC media in accordance with the present invention, preferably as reactive mesogenic compounds.
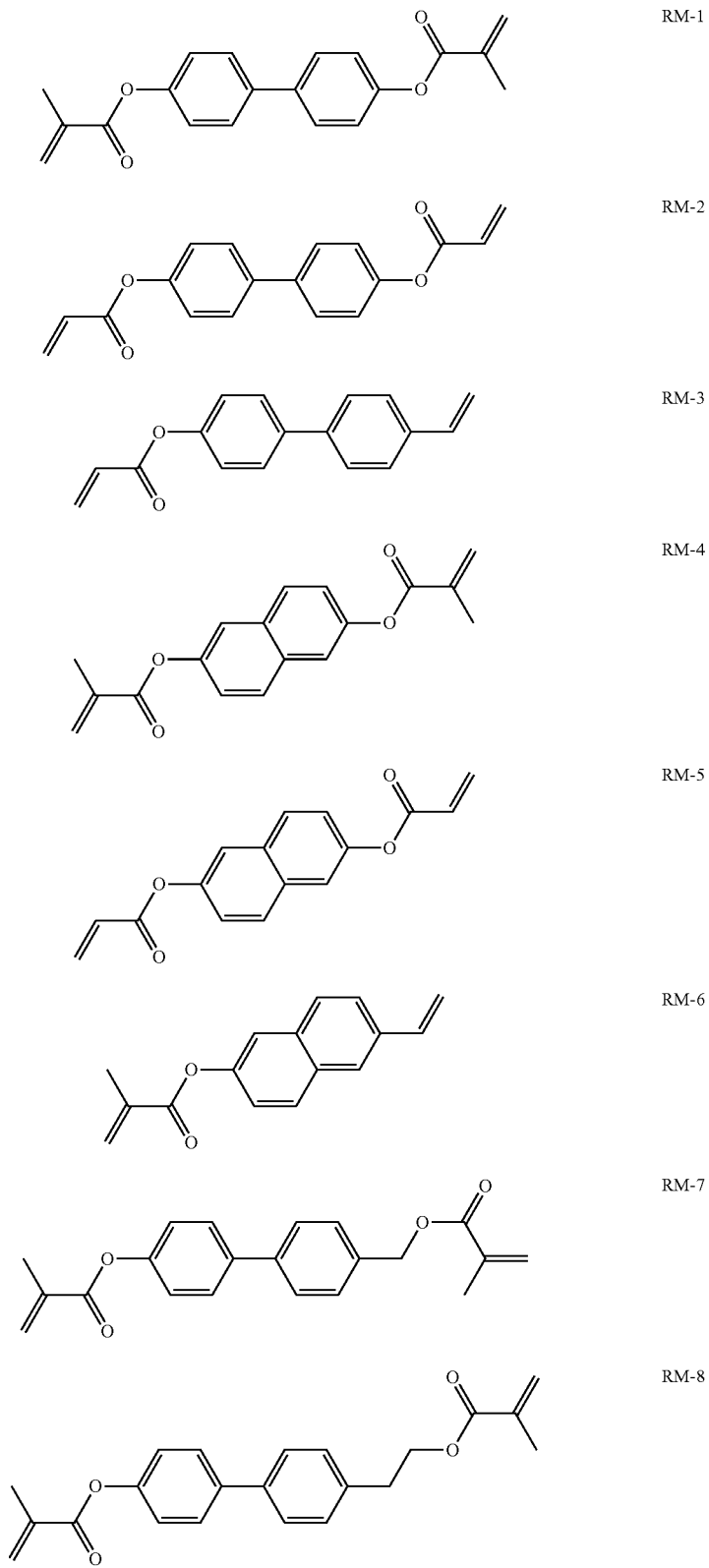
RM-1
RM-2
RM-3
RM-4
RM-5
RM-6
RM-7
RM-8

TABLE D-continued
Table D shows illustrative compounds which can be used in the LC media in accordance with the present invention, preferably as reactive mesogenic compounds.
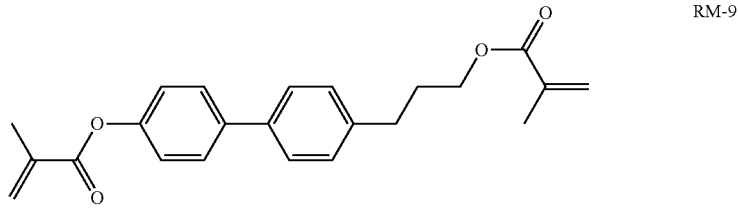 RM-9
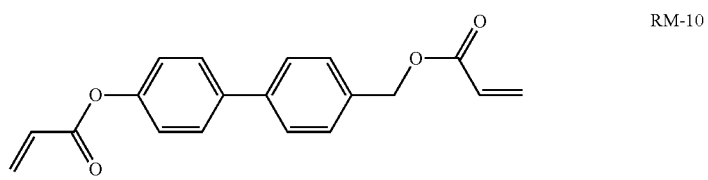 RM-10
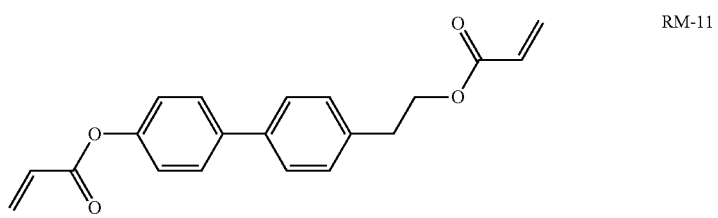 RM-11
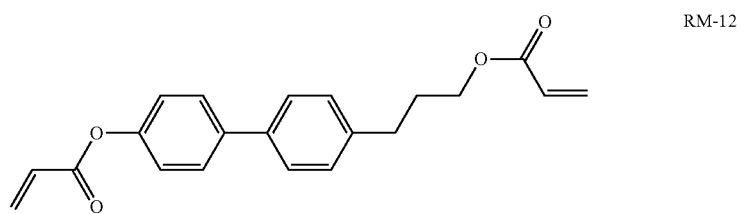 RM-12
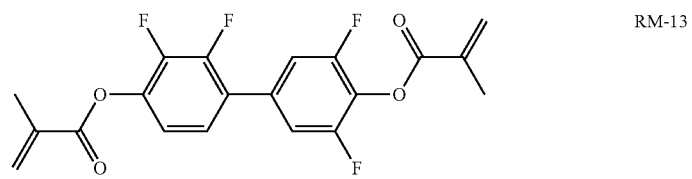 RM-13
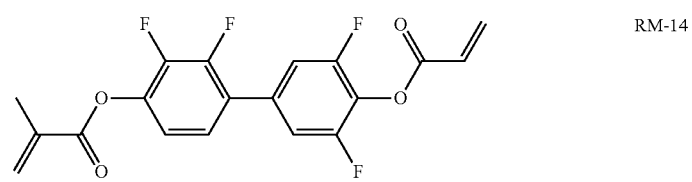 RM-14
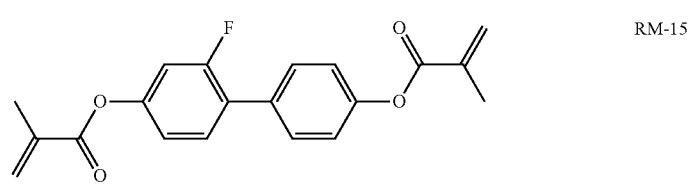 RM-15
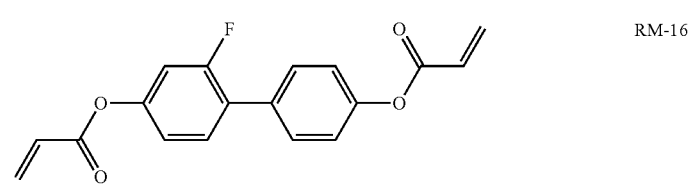 RM-16

TABLE D-continued
Table D shows illustrative compounds which can be used in the LC media in accordance with the present invention, preferably as reactive mesogenic compounds.
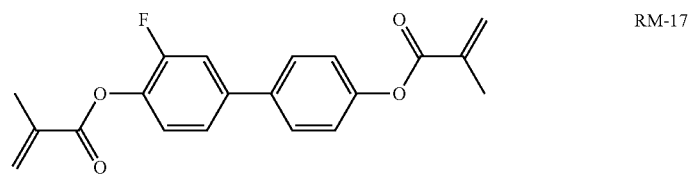 RM-17
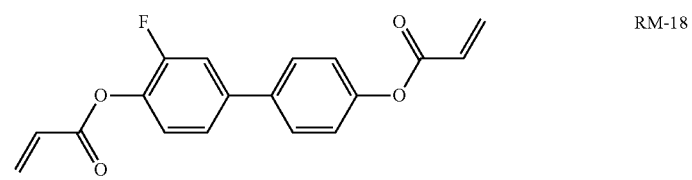 RM-18
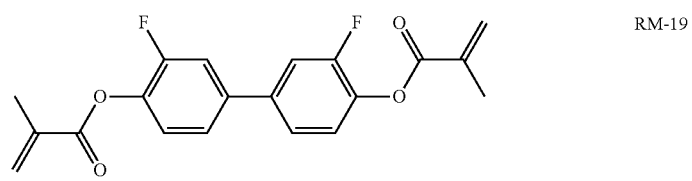 RM-19
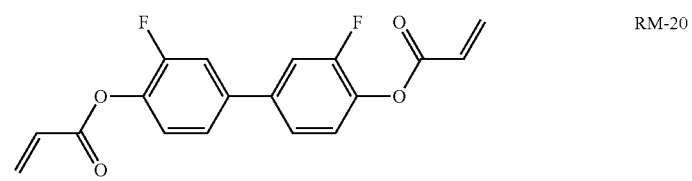 RM-20
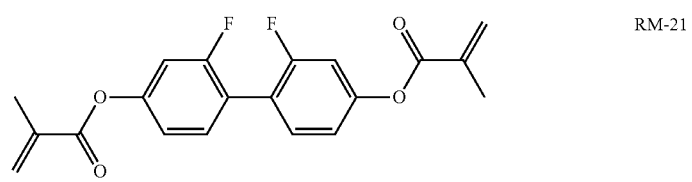 RM-21
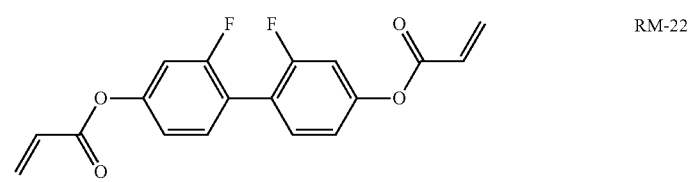 RM-22
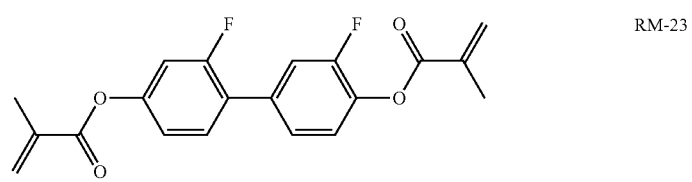 RM-23
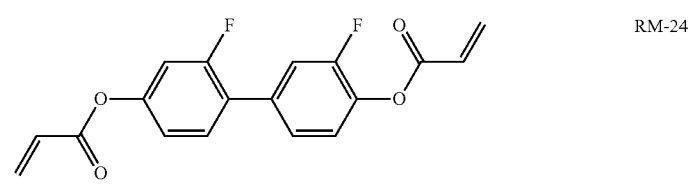 RM-24

TABLE D-continued
Table D shows illustrative compounds which can be used in the LC media in accordance with the present invention, preferably as reactive mesogenic compounds.
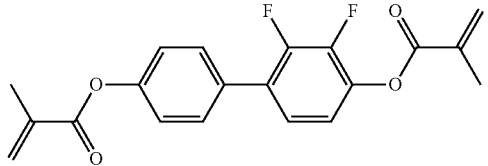 [SMILES: C=C(C)C(=O)Oc1ccc(-c2ccc(OC(=O)C(=C)C)cc2)cc1]
RM-25
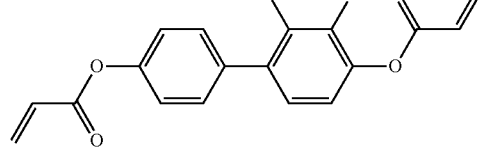
RM-26
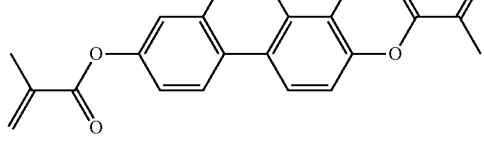
RM-27
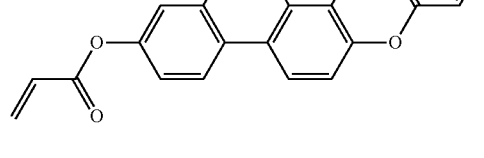
RM-28
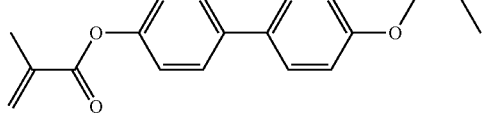
RM-29
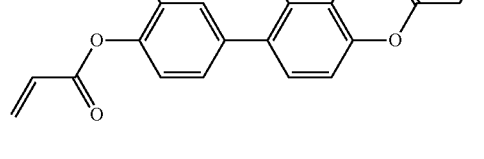
RM-30
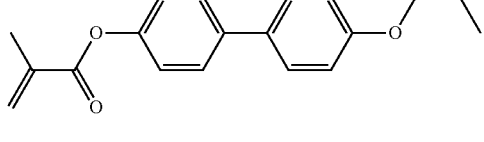
RM-31
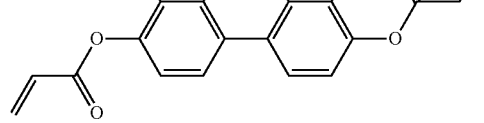
RM-32

TABLE D-continued
Table D shows illustrative compounds which can be used in the LC media in accordance with the present invention, preferably as reactive mesogenic compounds.
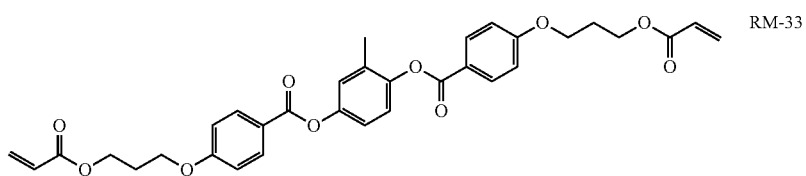
RM-33
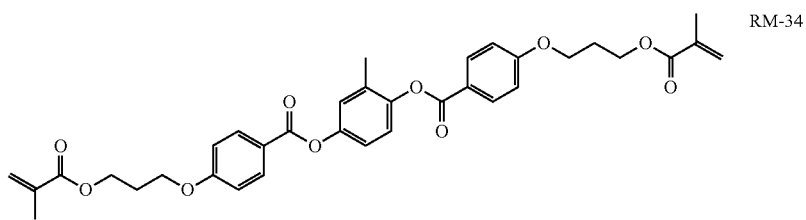
RM-34
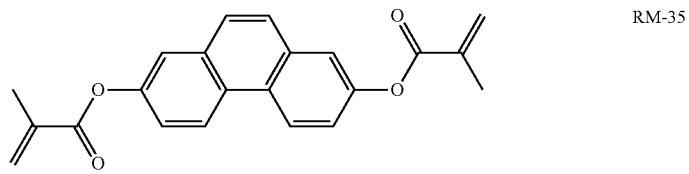
RM-35
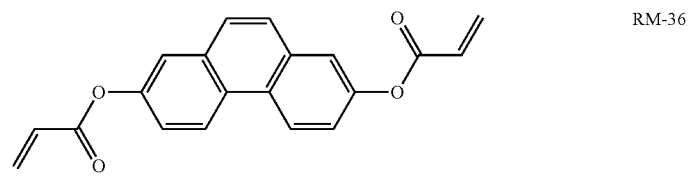
RM-36
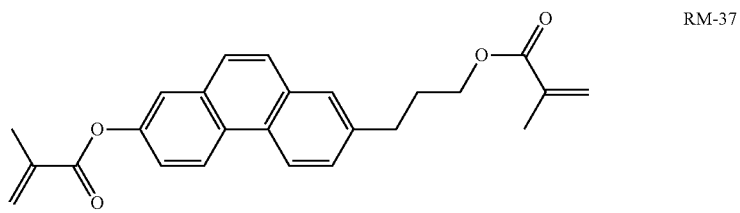
RM-37
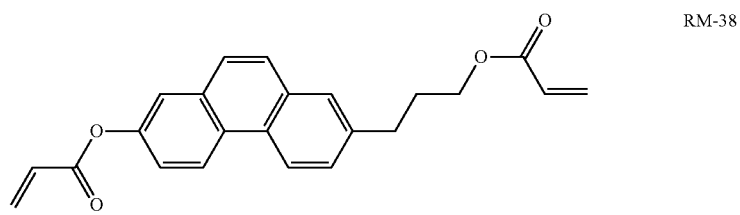
RM-38
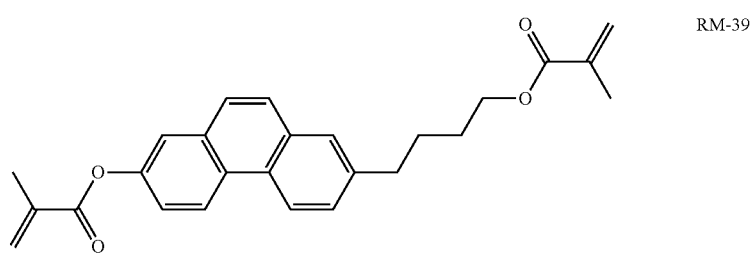
RM-39

TABLE D-continued
Table D shows illustrative compounds which can be used in the LC media in accordance with the present invention, preferably as reactive mesogenic compounds.
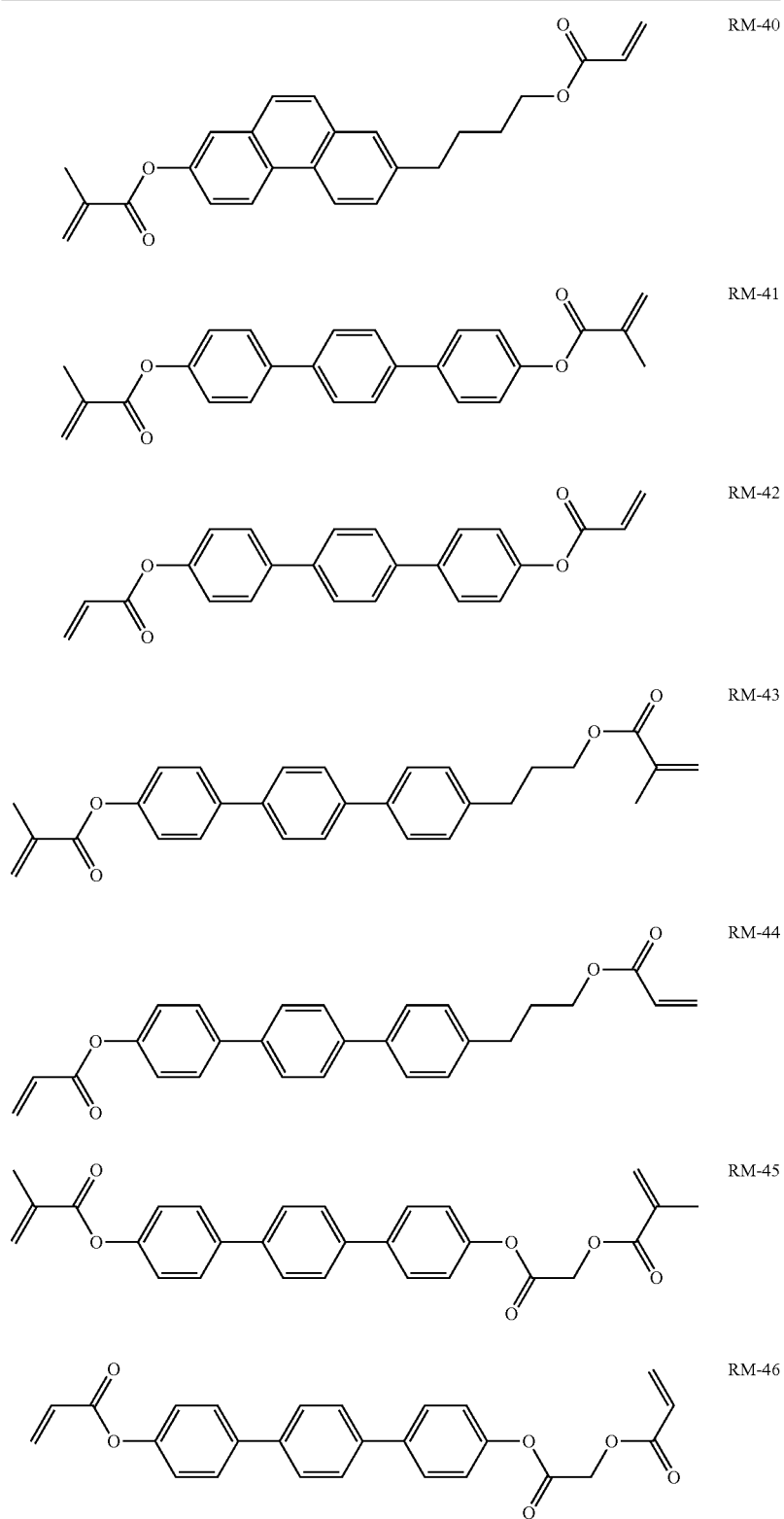

TABLE D-continued
Table D shows illustrative compounds which can be used in the LC media in accordance with the present invention, preferably as reactive mesogenic compounds.
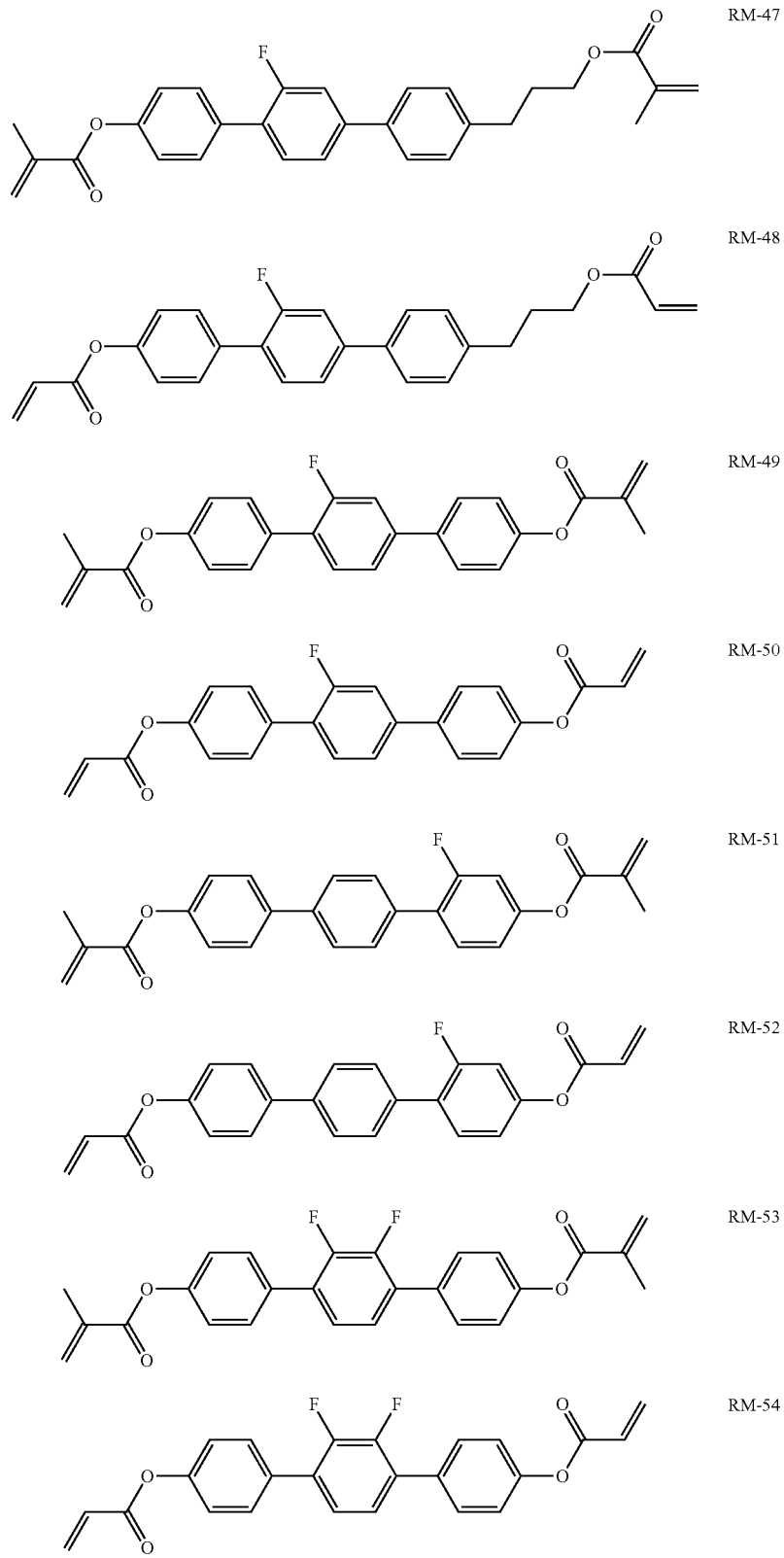

TABLE D-continued
Table D shows illustrative compounds which can be used in the LC media in accordance with the present invention, preferably as reactive mesogenic compounds.
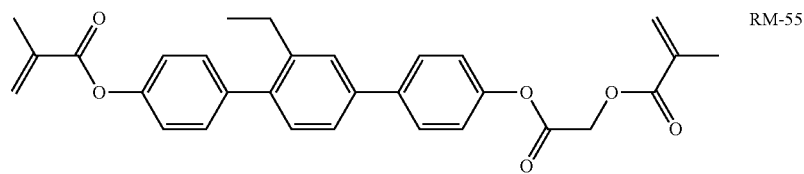 RM-55
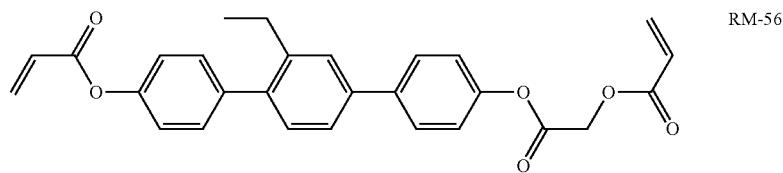 RM-56
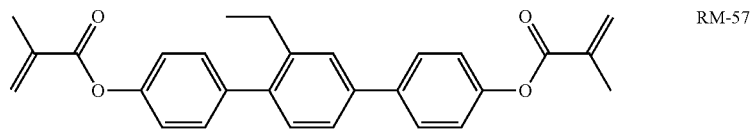 RM-57
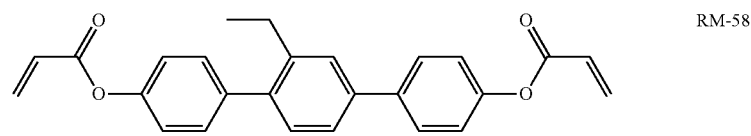 RM-58
RM-59
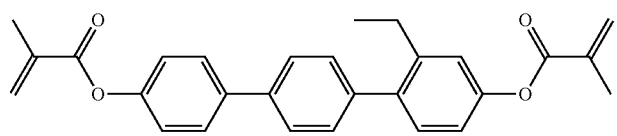 [SMILES: C=C(C)C(=O)Oc1ccc(-c2ccc(-c3ccc(OC(=O)C(=C)C)cc3CC)cc2)cc1] 
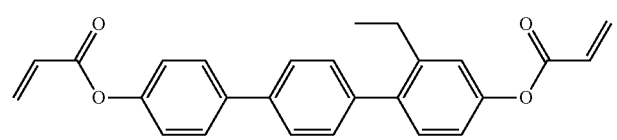 [SMILES: C=CC(=O)Oc1ccc(-c2ccc(-c3ccc(OC(=O)C=C)cc3CC)cc2)cc1] RM-60
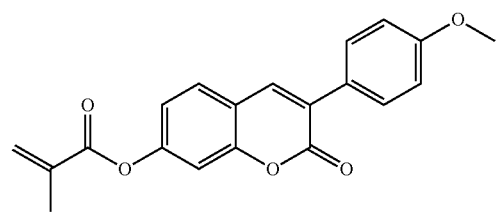 [SMILES: C=C(C)C(=O)Oc1ccc2cc(-c3ccc(OC)cc3)c(=O)oc2c1] RM-61
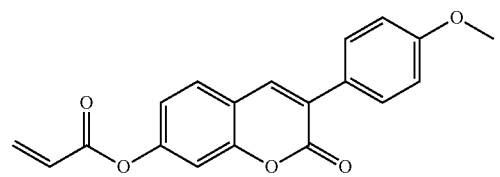 [SMILES: C=CC(=O)Oc1ccc2cc(-c3ccc(OC)cc3)c(=O)oc2c1] RM-62

TABLE D-continued
Table D shows illustrative compounds which can be used in the LC media in accordance with the present invention, preferably as reactive mesogenic compounds.
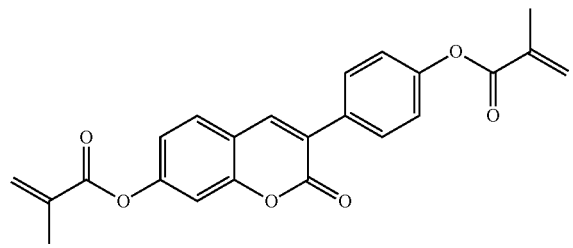 [SMILES: C=C(C)C(=O)Oc1ccc(-c2cc3ccc(OC(=O)C(=C)C)cc3oc2=O)cc1]
RM-63
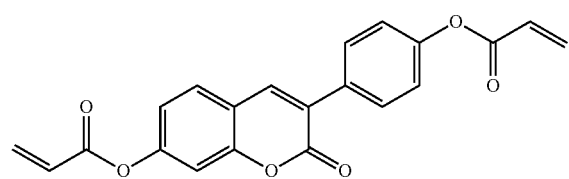 [SMILES: C=CC(=O)Oc1ccc(-c2cc3ccc(OC(=O)C=C)cc3oc2=O)cc1]
RM-64
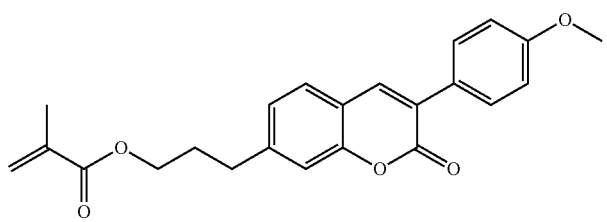 [SMILES: C=C(C)C(=O)OCCCc1ccc2cc(-c3ccc(OC)cc3)c(=O)oc2c1]
RM-65
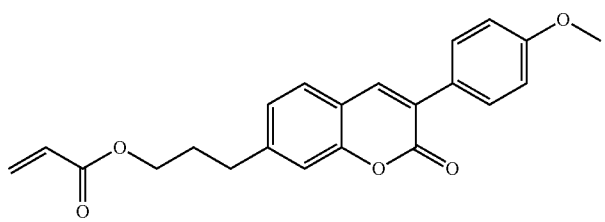 [SMILES: C=CC(=O)OCCCc1ccc2cc(-c3ccc(OC)cc3)c(=O)oc2c1]
RM-66
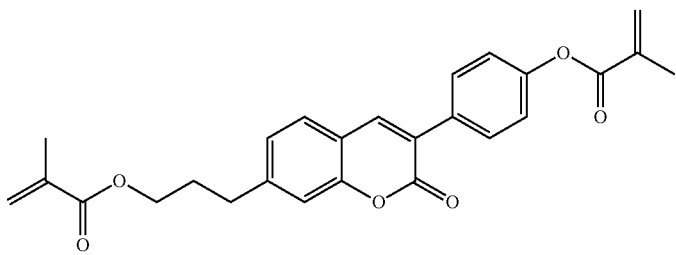 [SMILES: C=C(C)C(=O)OCCCc1ccc2cc(-c3ccc(OC(=O)C(=C)C)cc3)c(=O)oc2c1]
RM-67
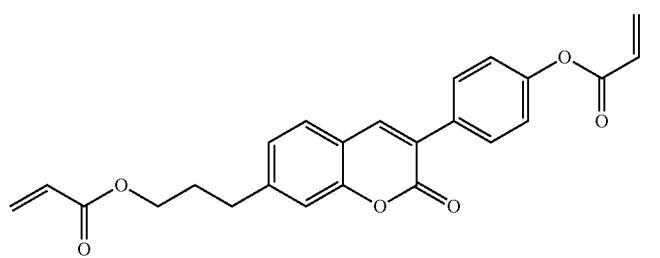 [SMILES: C=CC(=O)OCCCc1ccc2cc(-c3ccc(OC(=O)C=C)cc3)c(=O)oc2c1]
RM-68

TABLE D-continued
Table D shows illustrative compounds which can be used in the LC media in accordance with the present invention, preferably as reactive mesogenic compounds.
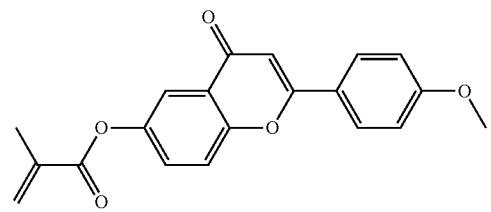 [SMILES: C=C(C)C(=O)Oc1ccc2oc(-c3ccc(OC)cc3)cc(=O)c2c1]
RM-69
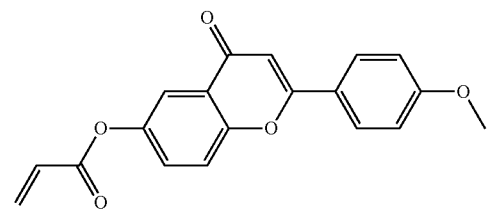 [SMILES: C=CC(=O)Oc1ccc2oc(-c3ccc(OC)cc3)cc(=O)c2c1]
RM-70
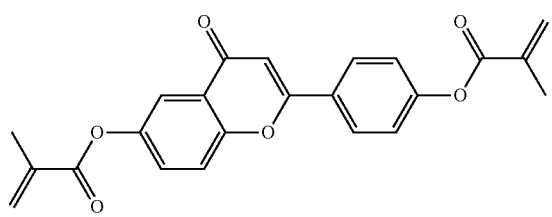 [SMILES: C=C(C)C(=O)Oc1ccc(-c2cc(=O)c3cc(OC(=O)C(=C)C)ccc3o2)cc1]
RM-71
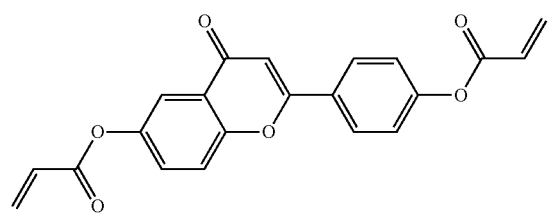 [SMILES: C=CC(=O)Oc1ccc(-c2cc(=O)c3cc(OC(=O)C=C)ccc3o2)cc1]
RM-72
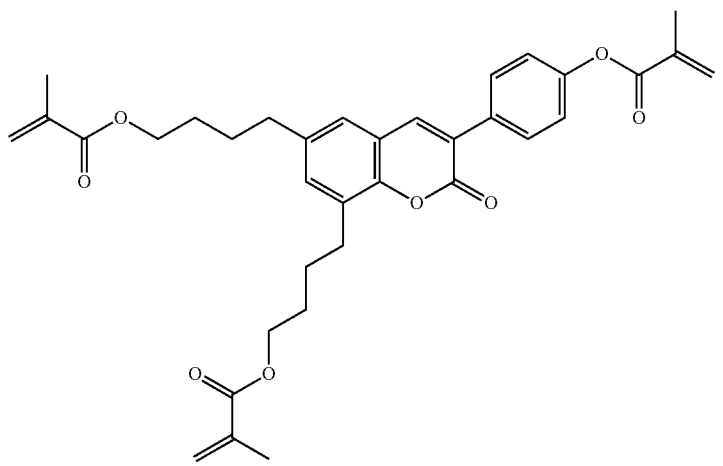 [SMILES: C=C(C)C(=O)OCCCCc1cc(CCCCOC(=O)C(=C)C)c2oc(=O)c(-c3ccc(OC(=O)C(=C)C)cc3)cc2c1]
RM-73

TABLE D-continued
Table D shows illustrative compounds which can be used in the LC media in accordance with the present invention, preferably as reactive mesogenic compounds.
RM-74
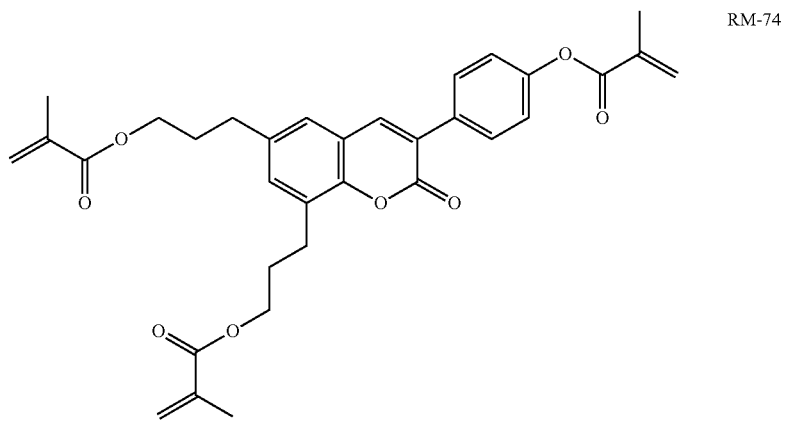
RM-75
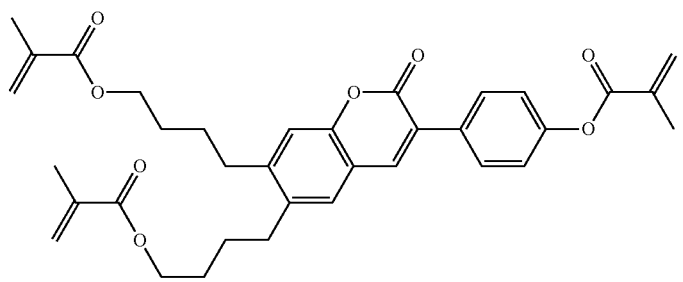 [SMILES: C=C(C)C(=O)OCCCCc1cc2cc(-c3ccc(OC(=O)C(=C)C)cc3)c(=O)oc2cc1CCCCOC(=O)C(=C)C]
RM-76
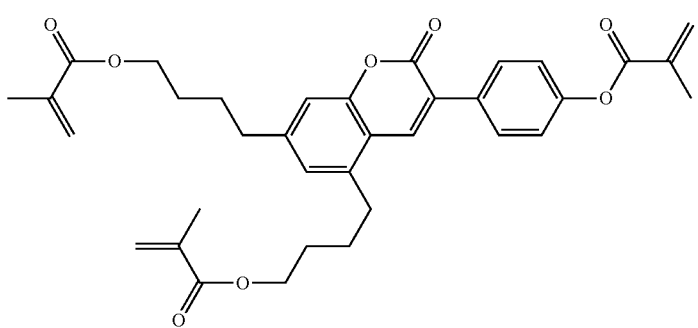 [SMILES: C=C(C)C(=O)OCCCCc1cc(CCCCOC(=O)C(=C)C)c2cc(-c3ccc(OC(=O)C(=C)C)cc3)c(=O)oc2c1]
RM-77
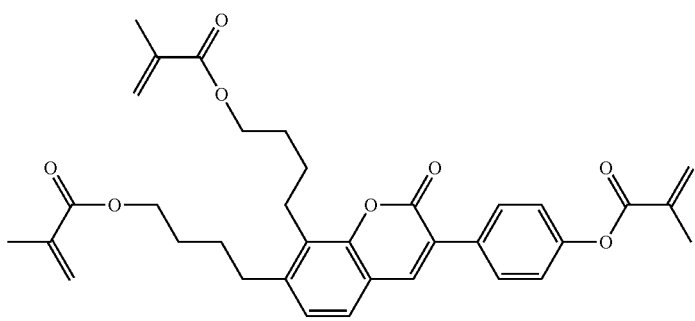 [SMILES: C=C(C)C(=O)OCCCCc1ccc2cc(-c3ccc(OC(=O)C(=C)C)cc3)c(=O)oc2c1CCCCOC(=O)C(=C)C]

TABLE D-continued
Table D shows illustrative compounds which can be used in the LC media in accordance with the present invention, preferably as reactive mesogenic compounds.
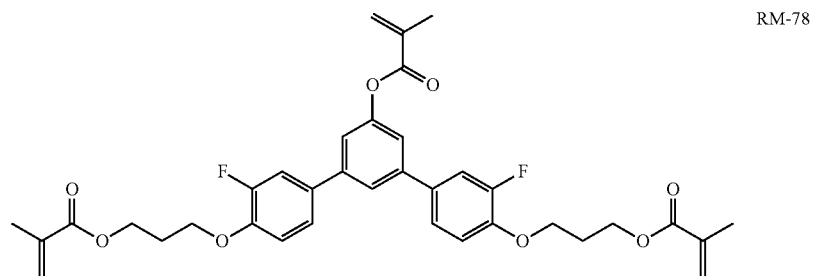
RM-78
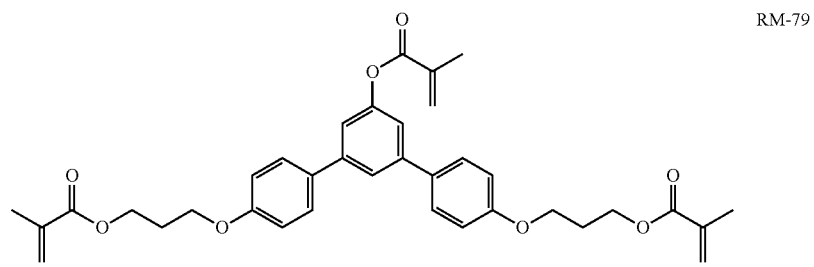
RM-79
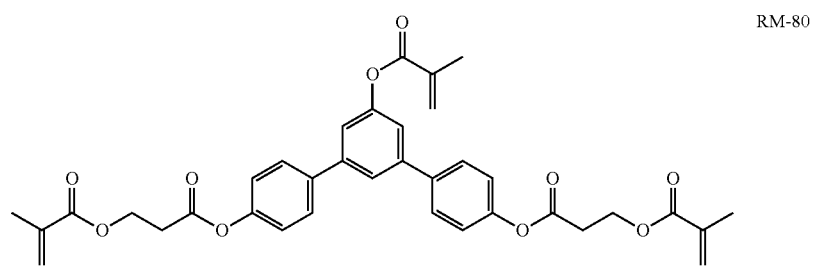
RM-80
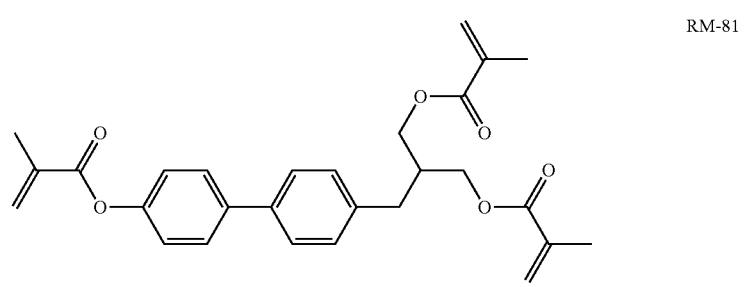
RM-81
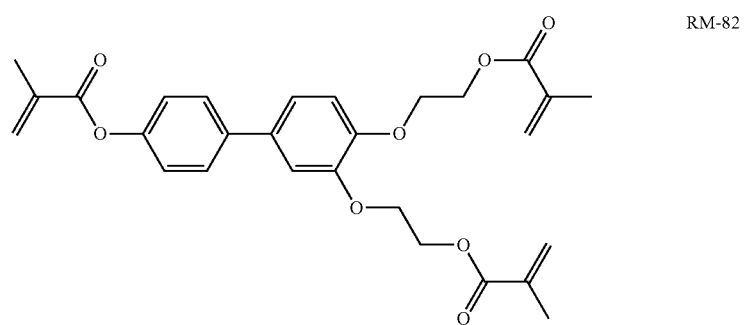
RM-82

TABLE D-continued

Table D shows illustrative compounds which can be used in the LC media in accordance with the present invention, preferably as reactive mesogenic compounds.

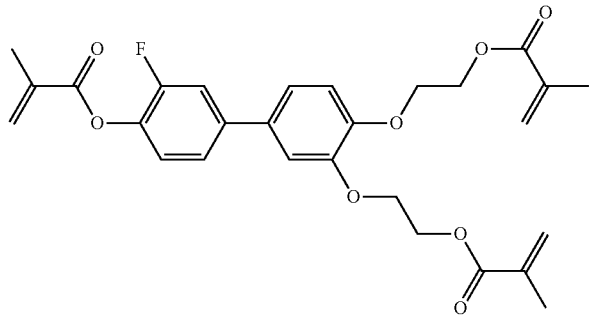 [SMILES: C=C(C)C(=O)OCCOc1ccc(-c2ccc(OC(=O)C(=C)C)c(F)c2)cc1OCCOC(=O)C(=C)C]
RM-83

In a preferred embodiment of the present invention, the mesogenic media comprise one or more compounds selected from the group of the compounds from Table D.

In addition, the following abbreviations and symbols are used:

$V_0$ threshold voltage, capacitive [V] at 20° C.,
$n_e$ extraordinary refractive index at 20° C. and 589 nm,
$n_o$ ordinary refractive index at 20° C. and 589 nm,
$\Delta n$ optical anisotropy at 20° C. and 589 nm,
$\varepsilon\perp$ dielectric permittivity perpendicular to the director at 20° C. and 1 kHz,
$\varepsilon\|$ dielectric permittivity parallel to the director at 20° C. and 1 kHz,
$\Delta\varepsilon$ dielectric anisotropy at 20° C. and 1 kHz,
cl.p., T(N,I) clearing point [° C.],
$\gamma_1$ rotational viscosity at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN].

Unless explicitly noted otherwise, all concentrations in the present application are quoted in % by weight and relate to the corresponding mixture as a whole, comprising all solid or liquid-crystalline components, without solvents. Unless explicitly noted otherwise, the expression "x % of compound Y are added to the mixture" means that the concentration of compound Y in the final mixture, i.e. after its addition, is x %.

Unless explicitly noted otherwise, all temperature values indicated in the present application, such as, for example, for the melting point T(C,N), the transition from the smectic (S) to the nematic (N) phase T(S,N) and the clearing point T(N,I), are quoted in degrees Celsius (° C.). M.p. denotes melting point, cl.p.=clearing point. Furthermore, C=crystalline state, N=nematic phase, S=smectic phase and I=isotropic phase. The data between these symbols represent the transition temperatures.

All physical properties are and have been determined in accordance with "Merck Liquid Crystals, Physical Properties of Liquid Crystals", Status November 1997, Merck KGaA, Germany, and apply for a temperature of 20° C., and $\Delta n$ is determined at 589 nm and $\Delta\varepsilon$ at 1 kHz, unless explicitly indicated otherwise in each case.

The term "threshold voltage" for the present invention relates to the capacitive threshold ($V_0$), also known as the Freedericks threshold, unless explicitly indicated otherwise. In the examples, the optical threshold may also, as generally usual, be quoted for 10% relative contrast ($V_{10}$).

Unless stated otherwise, the process of polymerizing the polymerizable compounds in the PSA displays as described above and below is carried out at a temperature where the LC medium exhibits a liquid crystal phase, preferably a nematic phase, and most preferably is carried out at room temperature.

Unless stated otherwise, methods of preparing test cells and measuring their electrooptical and other properties are carried out by the methods as described hereinafter or in analogy thereto.

The display used for measurement of the capacitive threshold voltage consists of two plane-parallel glass outer plates at a separation of 25 μm, each of which has on the inside an electrode layer and an unrubbed polyimide alignment layer on top, which effect a homeotropic edge alignment of the liquid-crystal molecules.

The display or test cell used for measurement of the tilt angles consists of two plane-parallel glass outer plates at a separation of 4 μm, each of which has on the inside an electrode layer and a polyimide alignment layer on top, where the two polyimide layers are rubbed antiparallel to one another and effect a homeotropic edge alignment of the liquid-crystal molecules.

The polymerizable compounds are polymerized in the display or test cell by irradiation with UV light of defined intensity for a prespecified time, with a voltage simultaneously being applied to the display (usually 10 V to 30 V alternating current, 1 kHz). In the examples, unless indicated otherwise, a metal halide lamp and an intensity of 100 mW/cm² is used for polymerization. The intensity is measured using a standard meter (Hoenle UV-meter high end with UV sensor).

The tilt angle is determined by crystal rotation experiment (Autronic-Melchers TBA-105). A low value (i.e. a large deviation from the 90° angle) corresponds to a large tilt here.

Unless stated otherwise, the term "tilt angle" means the angle between the LC director and the substrate, and "LC director" means in a layer of LC molecules with uniform orientation the preferred orientation direction of the optical main axis of the LC molecules, which corresponds, in case of calamitic, uniaxially positive birefringent LC molecules, to their molecular long axis.

The VHR value is measured as follows: 0.3% of a polymerizable monomeric compound is added to the LC host mixture, and the resultant mixture is introduced into VA-VHR test cells which comprise an unrubbed VA-polyimide alignment layer. The LC-layer thickness d is approx.

4 μm, unless stated otherwise. The VHR value is determined after 5 min at 100° C. before and after UV exposure at 1 V, 60 Hz, 64 is pulse (measuring instrument: Autronic-Melchers VHRM-105).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding EP application No. 15001706.9, filed Jun. 9, 2015, is incorporated by reference herein.

EXAMPLE 1

Polymerizable monomeric compound 1 is prepared as follows.

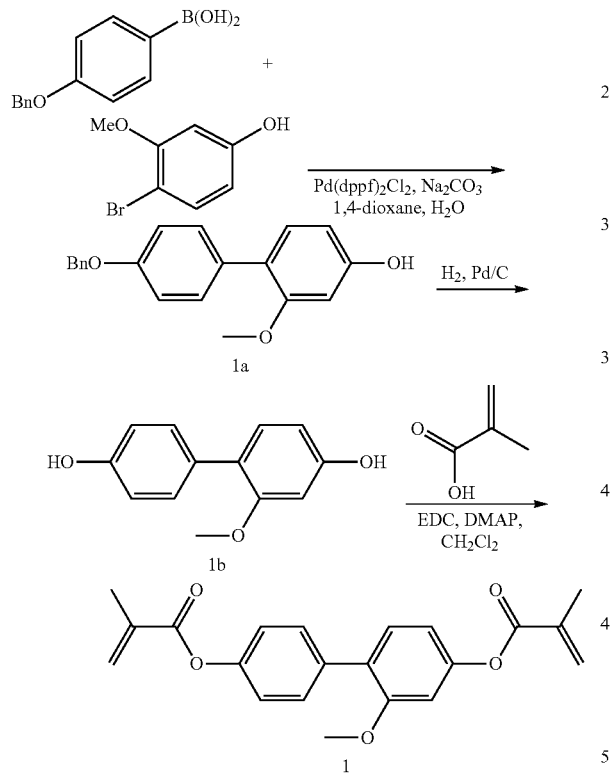

1a: To a solution of 4-bromo-3-methoxylphenol (10.00 g, 49.2 mmol) and 4-benzyloxyphenylboronic acid (13.00 g, 54.2 mmol) in 170 ml 1,4-dioxane was added sodium carbonate (10.44 g, 98.5 mmol) and 40 ml distilled water. After thoroughly degassing with argon, [1,1'-bis(diphenylphosphino)ferrocene]-dichloropalladium(II) (1.08 g, 1.50 mmol) is added. The reaction mixture is heated to reflux and stirred overnight. After cooling to room temperature, the reaction mixture is carefully neutralized with 2 M HCl. The aqueous phase is separated and extracted with ethyl acetate. The organic phase is combined, dried over anhydrous sodium sulfate, and filtrated through silica gel. After removing solvent in vacuo, the obtained crude product is recrystallized from heptane/toluene solvent mixture to provide the product as off-white crystal (8.6 g).

1b: A solution of 1a (6.54 g, 21.0 mmol) in tetrahydrofuran (70 ml) is treated with palladium (5%) on activated charcoal (2.0 g) and submitted to hydrogenation for 17 hs. The catalyst is then filtered off, and the remaining solution is concentrated in vacuo. The residue is recrystallized from toluene/heptane solvent mixture to 1b as off-white solid (4.3 g).

1: Methacrylic acid (3.56 g, 41.5 mmol) and 4-(dimethylamino)pyridine (0.17 g, 1.4 mmol) is added to a suspension of 1b (3.0 g, 13.9 mmol) in 40 ml dichloromethane. The reaction mixture is treated dropwise at 0° C. with a solution of N-(3-dimethylaminopropyl)-N'-ethylcarbodiimide (6.44 g, 41.5 mmol) in dichloromethane (20 ml) and stirred for 20 h at room temperature. After removing solvent in vacuo, the oily residue is purified by silica gel chromatography with dichcloromethane/ethyl acetate 20:1 as eluent. The obtained product is recrystallized from acetonitril to afford white crystals of 1 (2.1 g, mp. 105° C.).

EXAMPLE 2

Polymerizable monomeric compound 2 is prepared from the commercially available 3-fluoro-4-benzyloxylphenyl boronic acid in analogy to Example 1 as follows.

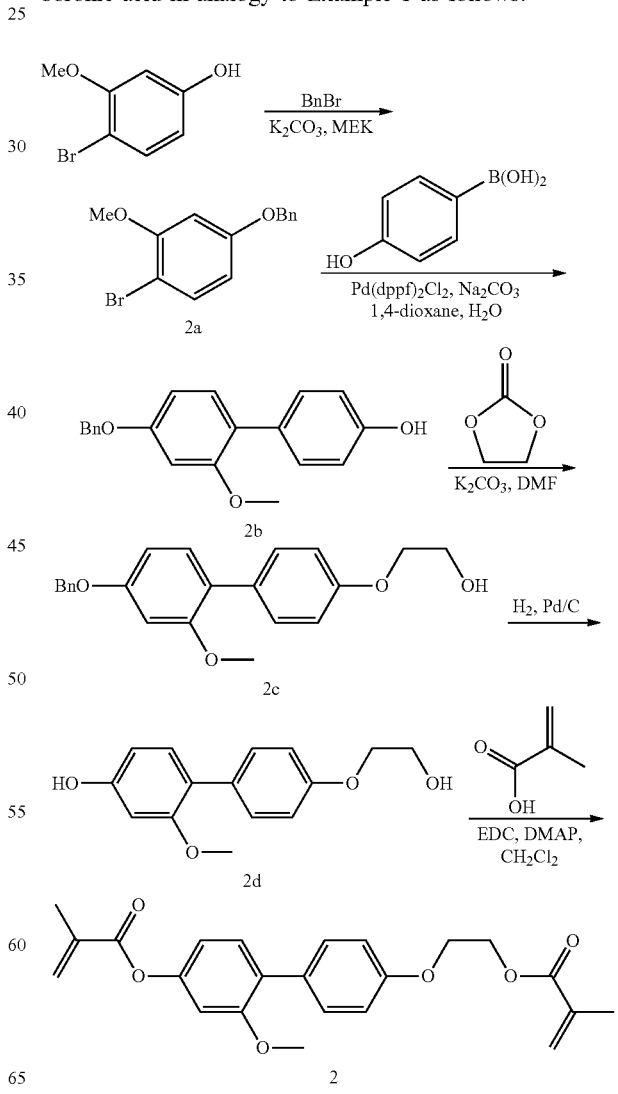

2a: To a solution of 4-bromo-3-methoxyphenol (15.00 g, 70.2 mmol) in 135 ml ethyl methylketone is added potassium carbonate (11.60 g. 84.0 mmol) in several portions. The reaction mixture is heated to reflux, to which benzylbromide (10.0 ml, 84.0 mmol) is added dropwise, and stirred overnight while refluxing. After cooling to room temperature, the reaction mixture is filtrated. The solid residue is washed thoroughly with aceton. After removing solvent in vacuo, the oily residue is purified by silica gel chromatography with heptane/ethyl acetate 9:1 as eluent to provide 2a as yellowish oil (23.6 g).

2b: To a solution of 2a (23.50 g, 80.1 mmol) and 4-hydoxylphenyl boronic acid (12.2 g, 88.2 mmol) in 275 ml 1,4-dioxane was added 65 ml dist. water and sodium carbonate (17.00 g, 160.3 mmol). The resulted suspension is degassed carefully with argon., [1,1'-bis(diphenylphosphino)ferrocene]-(II) (1.76 g, 2.4 mmol) is then added. The reaction mixture is heated to reflux and stirred overnight. After cooling to room temperature, the reaction mixture is neutralized carefully with 2 M HCl acid. The aqueous phase is extracted with methyl t-butyl ether. The organic phase is combined and washed with sat. aq. NaCl solution, dried over sodium sulfate. After removing solvent, the solid residue is purified by column chromatography with THF/toluene 9:1 as eluent and further recrystallized from hepane/toluene 1:1 to provide 2b as off-white solid (11.7 g).

2c: To a solution of 2b (11.7 g, 37.4 mmol) and ethylenecarbonate (3.46 g. 39.2 mmol) in DMF (120 ml) is added dry potassium carbonate (0.52 g, 3.7 mmol). The reaction mixture is refluxed overnight. After cooling to room temperature, the reaction mixture is added into 100 ml water and neutralized carefully with 2 M HCl. The aqueous phase is extracted with ethylacetate. The organic phase is combined and washed with sat. aq. NaCl solution, dried over sodium sulfate. After removing solvent, the solid residue is recrystallized with heptane/ethyl acetate 1:1 to provide 2c as yellowish solid (13.6 g).

2d: A suspension of 2c (13.4 g, 37.4 mmol) in tetrahydrofuran (150 ml) is treated with palladium (5%) on activated charcoal (4.3 g) and submitted to hydrogenation for 30 hs. The catalyst is then filtered off. After removing solvent, 2d is obtained as solid (8.5 g). 2: Methacrylic acid (7.8 g, 91.4 mmol) and 4-(dimethylamino)pyridine (0.40 g, 3.3 mmol) is added to a suspension of 2d (8.50 g, 32.7 mmol) in dichloromethane (90 ml). The reaction mixture is treated dropwise at 0° C. with a solution of N-(3-dimethylaminopropyl)-N'-ethylcarbodiimide (15.2 g, 98.9 mmol) in dichloromethane (60 ml) and stirred for 20 hs at room temperature. The reaction mixture is concentrated in vacuo, and the oily residue is purified by column chromatography on silica gel with dichloromethane as eluent. The obtained product is recrystallized from ethanol to afford white crystals of 2 (3.7 g, mp. 74° C.).

EXAMPLE 3

Polymerizable monomeric compound 3 is prepared as follows.

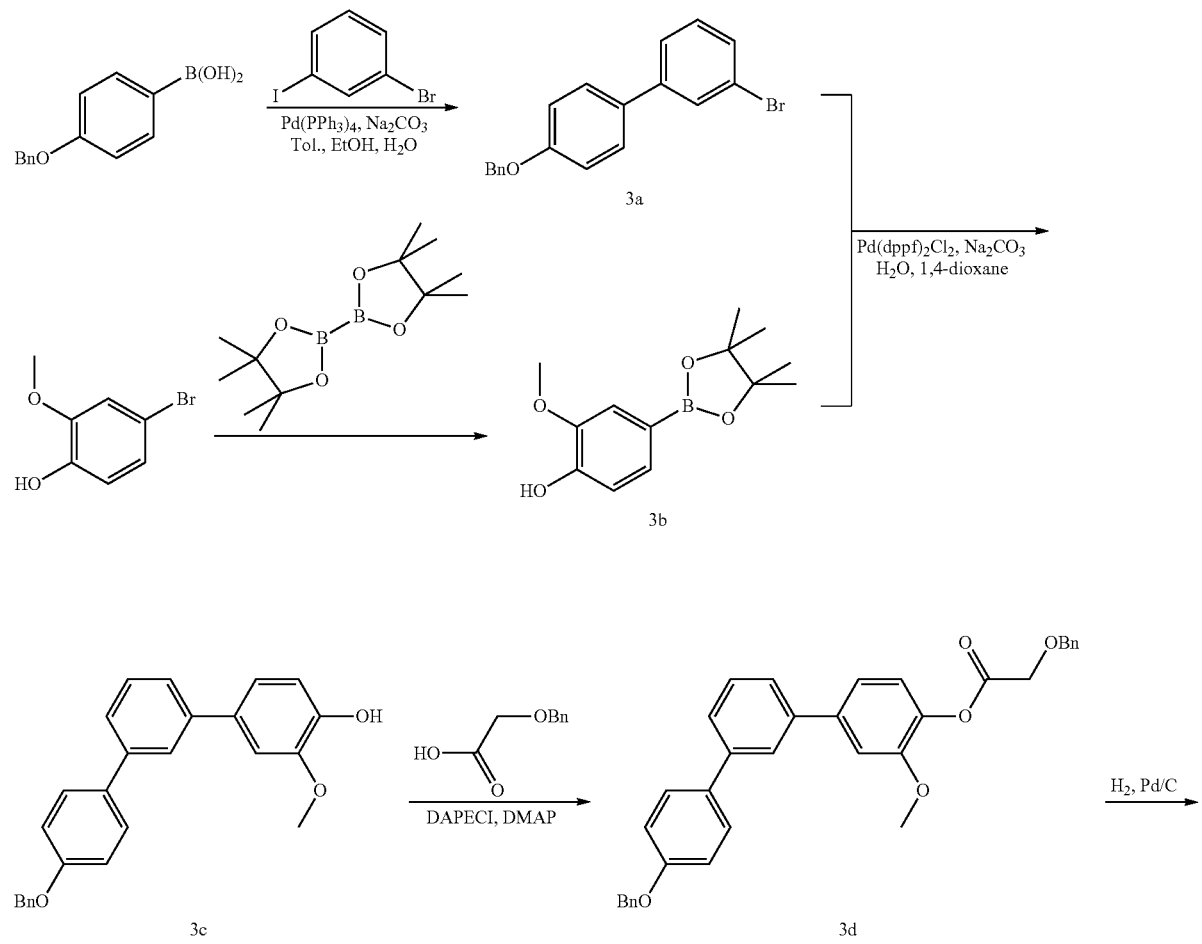

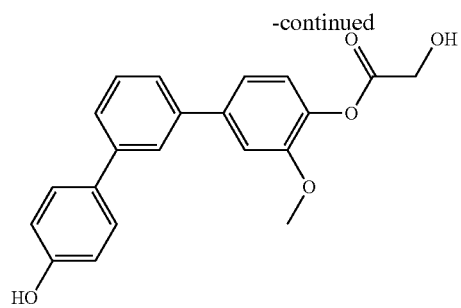
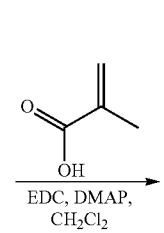

3e

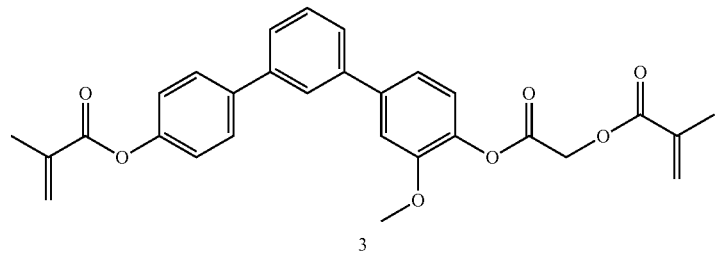

3

3a: To a solution of 1-bromo-3-iodobenzene (100.0 g, 346.0 mmol) and 4-benzyloxylphenyl boronic acid (77.41 g, 340.0 mmol) in 1000 ml toluene was added 500 ml dist. water and 250 ml ethanol. Sodium carbonate (101.0 g, 604.4 mmol) is added. The resulted suspension is degassed carefully with argon. Tetrakis(triphenylphosphine)palladium(0) (14.4 g, 12.4 mmol) is then added. The reaction mixture is heated to reflux and stirred overnight. After cooling to room temperature, the reaction mixture is neutralized carefully with 2 M HCl acid. The aqueous phase is extracted with ethylacetate. The organic phase is combined and washed with sat. aq. NaCl solution, dried over sodium sulfate. After removing solvent in vacuo, the solid residue is purified by column chromatography with heptane/ethyl acetate 4:1 as eluent. The crude product is further recrystallized from toluene to provide 3a as yellowish solid (80.6 g).

3b: To a solution of 4-bromo-2-methoxylohenol (25.00 g, 120.6 mmol) and bis(pinacolato)diboron (27.6 g, 108.6 mmol) in 350 ml 1,4-dioxane was added sodium acetate (35.5 g, 362.0 mmol). After thoroughly degassing with argon, [1,1'-bis(diphenylphosphino)ferrocene]dichloropalladium(II) (2.67 g, 3.62 mmol) is added. The reaction mixture is heated to reflux and stirred for 4 hours. After cooling to room temperature, 200 ml dist. water is added. The aqueous phase is separated and extracted with ethyl acetate. The organic phase is combined and dried over anhydrous sodium sulfate, and filtrated through silica gel. After removing solvent in vacuo, the crude product is recrystallized from toluene/ethyl acetate 9:1 to provide 3b as yellowish solid (12.1 g)

3c: To a solution of 3a (10.0 g, 28.4 mmol) and 3b (8.25 g, 31.2 mmol) in 100 ml 1,4-dioxane was added 25 ml dist. water. Sodium carbonate (6.04 g, 56.8 mmol) is added. The resulted suspension is degassed carefully with argon, [1,1'-bis(diphenylphosphino)ferrocene]dichloropalladium(II) (0.63 g, 0.85 mmol) is then added. The reaction mixture is heated to reflux and stirred overnight. After cooling to room temperature, the reaction mixture is neutralized carefully with 2 M HCl acid. The aqueous phase is extracted with ethylacetate. The organic phase is combined and washed with sat. aq. NaCl solution, dried over sodium sulfate. After removing solvent in vacuo, the solid residue is purified by column chromatography with heptane/ethyl acetate mixture as eluent. The crude product is further recrystallized from ethanol to provide 3c as grayisch solid (6.03 g).

3d: To a solution of 3c (6.03 g, 14.9 mmol) in 60 ml dichloromethane are added 4-(dimethylamino)pyridine (0.18 g, 1.50 mmol) and N-(3-dimethylaminopropyl)-N'-ethylcarbodiimidhydrochlorid (DAPECI) (4.00 g, 20.8 mmol). The reaction mixture is stirred at room temperature overnight. 200 ml water is added. The aqueous phase is extracted with dichloromethane. The organic phase is combined and dried over anhydrous sodium sulfate. After removing solvent in vacuo, the solid residue is purified by column chromatography with dichloromethane as eluent to provide 3d as off-white solid (4.5 g).

3e: A solution of 3d (4.5 g, 8.43 mmol) in tetrahydrofuran (45 ml) is treated with palladium (5%) on activated charcoal (3.0 g) and submitted to hydrogenation for 20 hs. The catalyst is then filtered off, and the remaining solution is concentrated in vacuo. The residue is recrystallized from toluene/heptane solvent mixture to provide 3e as yellowish oil (3.04 g).

3: Methacrylic acid (2.21 ml, 26.0 mmol) and 4-(dimethylamino)pyridine (0.11 g, 0.86 mmol) is added to a suspension of 3e (3.04 g, 8.6 mmol) in dichloromethane (40 ml). The reaction mixture is treated dropwise at 0° C. with a solution of N-(3-dimethylaminopropyl)-N'-ethylcarbodiimide (4.6 g, 26.0 mmol) in dichloromethane (30 ml) and stirred for 20 hs at room temperature. The reaction mixture is concentrated in vacuo, and the oily residue is purified by column chromatography on silica gel with heptane/ethyl acetate mixture as eluent. The obtained product is recrystallized from heptane/ethanol 1:1 to afford white crystals of 3 (1.6 g, mp. 88° C.).

EXAMPLE 4

Polymerizable monomeric compound 4 is prepared as follows.

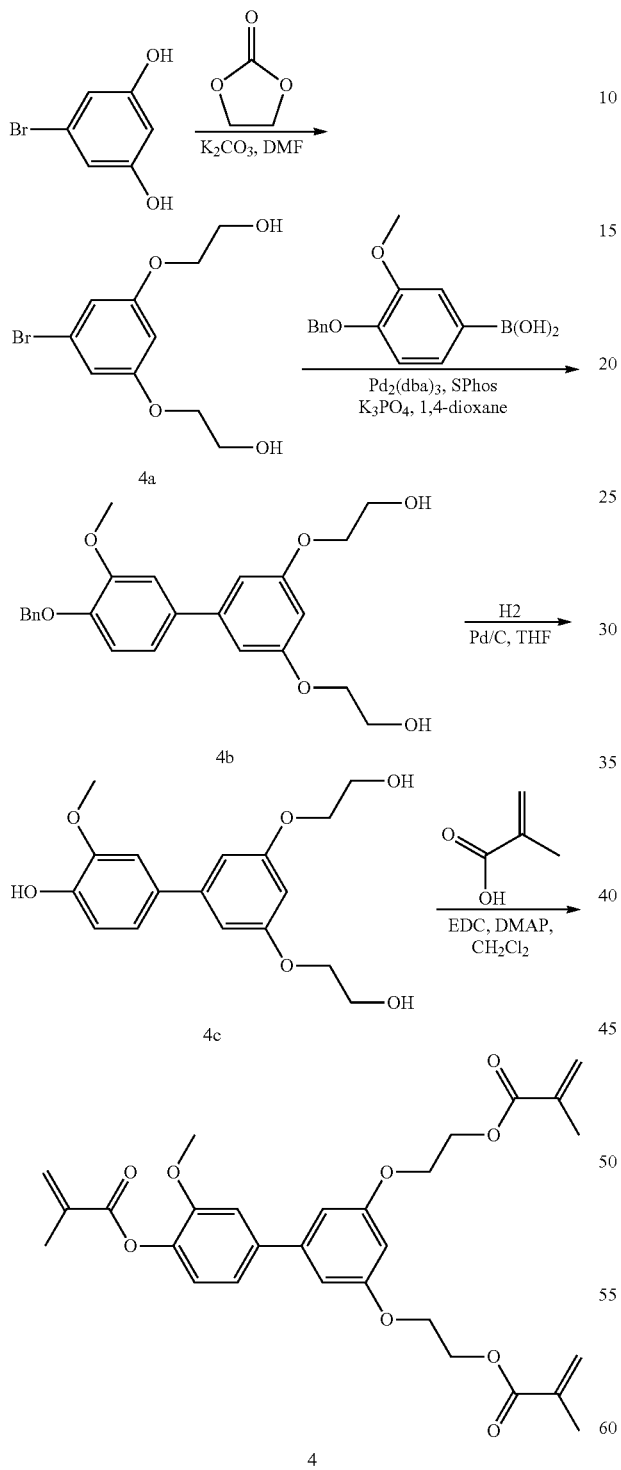

4a

4b

4c

4

4a: To a solution of 5-bromoresorcinol (26.00 g, 135.4 mmol) and ethylenecarbonate (29.00 g. 329.3 mmol) in 400 ml DMF is added dry potassium carbonate (3.75 g, 27.1 mmol). The reaction mixture is refluxed overnight. After cooling to room temperature, the reaction mixture is added into 1000 ml water and neutralized carefully with 2 M HCl. The aqueous phase is extracted with ethyl acetate. The organic phase is combined and washed with sat. aq. NaCl solution, dried over sodium sulfate. After removing solvent in vacuo, the solid residue is recrystallized with heptane/ ethyl acetate 4:1 to provide 4a as white solid (24.3 g).

4b: To a solution of 4a (5.60 g, 20.1 mol) and 4-benzyloxyl-3-methoxyl-phenyl boronic acid (5.7 g, 22.0 mmol) in 120 ml 1,4-dioxane was added 23.1 g (100.2 mmol) potassium phosphate. The resulted suspension is degassed carefully with argon. Tris(dibenzylidene acetone)dipalladium(0) (0.37 g, 0.4 mmol) and 2-dicyclohexylphosphine-2',6'-dimethoxylbiphenyl (SPhos) (0.68 g, 1.6 mmol) is then added. The reaction mixture is heated to reflux and stirred overnight. After cooling to room temperature 200 ml dist. water and 150 ml ethylacetate is added, and the mixture is neutralized carefully with 6 M HCl acid under cooling to pH-4. The aqueous phase is extracted with ethylacetate. The organic phase is combined and washed with sat. aq. NaCl solution, dried over sodium sulfate. After removing solvent in vacuo, the solid residue is purified by column chromatography with ethylacetate as eluent, and the obtained crude product is recrystallized from heptane/toluene 1:1 to provide 4b as white solid (3.7 g).

4c: A solution of 4b (3.6 g, 7.48 mmol) in 36 ml tetrahydrofuran is treated with palladium (5%) on activated charcoal (0.5 g) and submitted to hydrogenation for 19 hs. The catalyst is then filtered off, and the remaining solution is concentrated in vacuo. The oily residue is purified by column chromatography on silica gel with ethyl acetate as eluent to provide 4c as light yellow oil (2.5 g).

4: Methacrylic acid (2.68 g, 31.2 mmol) and 4-(dimethylamino)pyridine (0.1 g, 0.82 mmol) is added to a suspension of 4c (2.5 g, 7.8 mmol) in 50 ml dichloromethane. The reaction mixture is treated dropwise at 0° C. with a solution of N-(3-dimethylaminopropyl)-N'-ethylcarbodiimide (4.97 g, 32.0 mmol) in 20 ml dichloromethane and stirred for 20 h at room temperature. After removing solvent in vacuo, the oily residue is purified by silica gel chromatography with heptane/ethyl acetate 7:3 as eluent to afford 4 as colorless oil (2.0 g).

EXAMPLES 5-14

The following polymerizable monomeric compounds are prepared in analogy to the methods described in Examples 1-4.

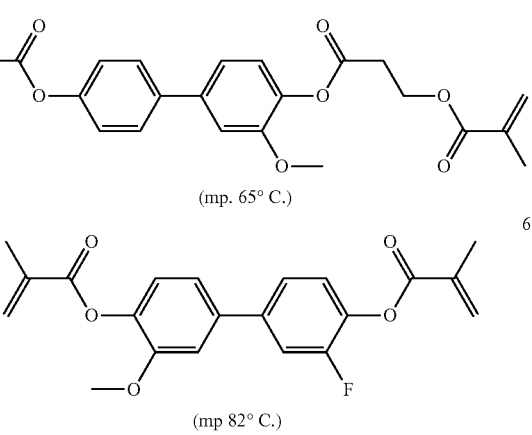

5

(mp. 65° C.)

6

(mp 82° C.)

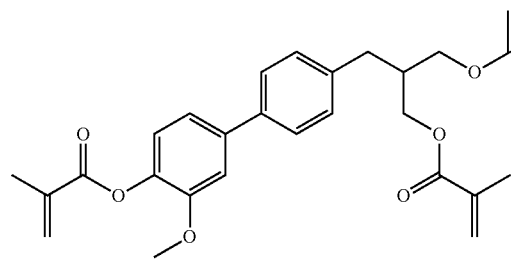
7
(oil)

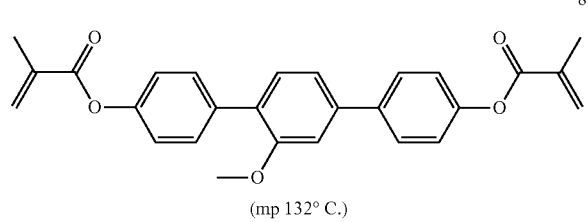
8
(mp 132° C.)

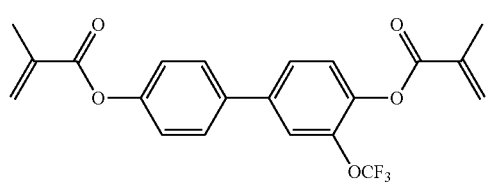
9
(mp. 82° C.)

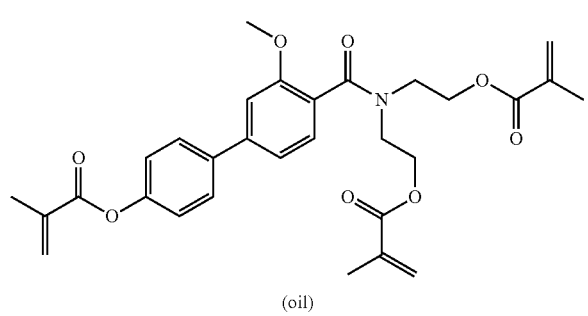
10
(oil)

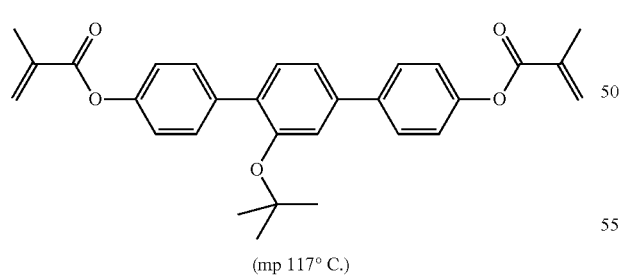
11
(mp 117° C.)

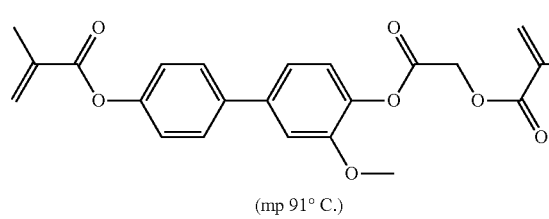
12
(mp 91° C.)

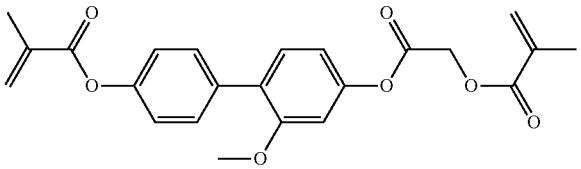
13
(mp 75° C.)

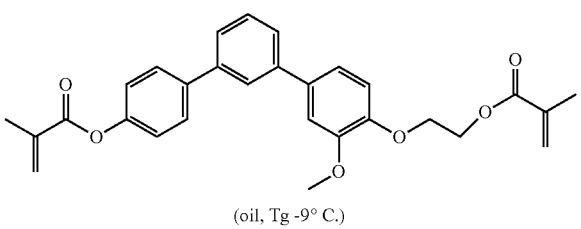
14
(oil, Tg -9° C.)

Mixture Example 1

The nematic LC host mixture N1 is formulated as follows.

| | | | |
|---|---|---|---|
| CCH-501 | 9.00% | cl.p. | 70.0° C. |
| CCH-35 | 14.00% | Δn | 0.0825 |
| PCH-53 | 8.00% | Δε | −3.5 |
| CY-3-O4 | 14.00% | $\varepsilon_\parallel$ | 3.5 |
| CY-5-O4 | 13.00% | $K_3/K_1$ | 1.00 |
| CCY-2-1 | 9.00% | $\gamma_1$ | 141 mPa s |
| CCY-3-1 | 9.00% | $V_0$ | 2.10 V |
| CCY-3-O2 | 8.00% | | |
| CCY-5-O2 | 8.00% | | |
| CPY-2-O2 | 8.00% | | |

Mixture Example 2

The nematic LC host mixture N2 is formulated as follows.

| | | | |
|---|---|---|---|
| CY-3-O2 | 18.00% | cl.p. | +74.5° C. |
| CPY-2-O2 | 10.00% | Δη | 0.1021 |
| CPY-3-O2 | 10.00% | Δε | −3.1 |
| CCY-3-O2 | 9.00% | $\varepsilon_\parallel$ | 3.5 |
| CCY-4-O2 | 4.00% | $K_3/K_1$ | 1.16 |
| PYP-2-3 | 9.00% | $\gamma_1$ | 86 mPa s |
| CC-3-V | 40.00% | $V_0$ | 2.29 V |

Mixture Example 3

The nematic LC host mixture N3 is formulated as follows.

| | | | |
|---|---|---|---|
| CC-3-V1 | 9.00% | cl.p. | 75.4° C. |
| CCH-23 | 14.00% | Δn | 0.1055 |
| CCH-34 | 6.00% | Δε | −2.8 |
| CCH-35 | 6.00% | $\varepsilon_\parallel$ | 3.30 |
| CCP-3-1 | 7.00% | $K_3/K_1$ | 1.07 |
| CCY-3-O1 | 5.00% | $\gamma_1$ | 102 mPa s |
| CCY-3-O2 | 10.00% | $V_0$ | 2.67 |
| CPY-3-O2 | 12.00% | | |
| CY-3-O2 | 9.50% | | |
| PP-1-2V1 | 8.50% | | |
| PY-3-O2 | 12.00% | | |
| PY-4-O2 | 1.00% | | |

Mixture Example 4

The nematic LC host mixture N4 is formulated as follows.

| | | | |
|---|---|---|---|
| CC-3-V | 35.50% | cl.p. | +75.1° C. |
| CC-3-V1 | 10.00% | Δn | 0.1096 |
| CCP-3-1 | 1.50% | Δε | −3.1 |
| CLY-3-O2 | 10.00% | $\varepsilon_\parallel$ | 3.51 |
| CLY-3-O3 | 3.00% | $K_3/K_1$ | 1.115 |
| CPY-2-O2 | 9.00% | $\gamma_1$ | 84 mPa s |
| CPY-3-O2 | 10.50% | $V_0$ | 2.37 |
| PY-3-O2 | 16.50% | | |
| PYP-2-3 | 1.00% | | |
| B-2O—O5 | 3.00% | | |

Polymerizable Mixture Example A

Polymerizable mixtures are prepared by adding one of polymerizable compounds 1 to 14 of Examples 1 to 14, respectively, to nematic LC host mixtures N1 and N2 at a concentration of 0.3% by weight.

For comparison purposes further polymerizable mixtures are prepared by adding polymerizable compound C0 of prior art, which has two different polymerizable groups, or one of polymerizable compounds C1-C14 of prior art, which do not contain an alkoxy substituent, respectively, to nematic LC host mixtures N1 and N2 at a concentration of 0.3% by weight.

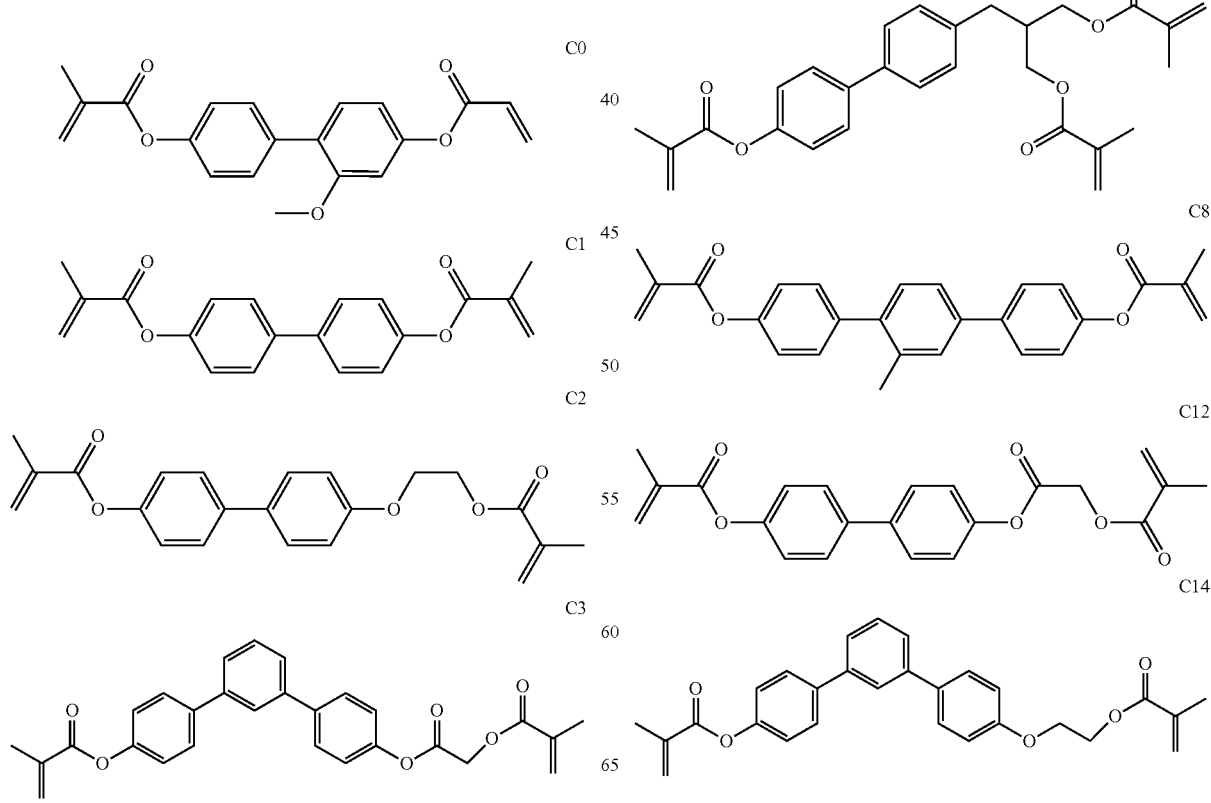

The composition of the polymerizable mixtures is shown in Table 1.

TABLE 1

Polymerizable mixture composition

| Mix. No. | P11 | P12 | P13 | P14 | P15 | P16 | P17 | P18 | P112 | P113 | P114 |
|---|---|---|---|---|---|---|---|---|---|---|---|
| LC Host | N1 | N1 | N1 | N1 | N1 | N1 | N1 | N1 | N1 | N1 | N1 |
| RM | 1 | 2 | 3 | 4 | 5 | 6 | 7 | 8 | 12 | 13 | 14 |

| Mix. No. | C10 | C11 | C12 | C13 | C14 | C15 | C16 | C17 | C18 | C112 | C114 |
|---|---|---|---|---|---|---|---|---|---|---|---|
| LC Host | N1 | N1 | N1 | N1 | N1 | N1 | N1 | N1 | N1 | N1 | N1 |
| RM | C0 | C1 | C2 | C3 | C4 | C5 | C6 | C7 | C8 | C12 | C14 |

| Mix. No. | P21 | P22 | P23 | P24 | P25 | P26 | P27 | P28 | P212 | P213 | P214 |
|---|---|---|---|---|---|---|---|---|---|---|---|
| LC Host | N2 | N2 | N2 | N2 | N2 | N2 | N2 | N2 | N2 | N2 | N2 |
| RM | 1 | 2 | 3 | 4 | 5 | 6 | 7 | 8 | 12 | 13 | 14 |

| Mix. No. | C20 | C21 | C22 | C23 | C24 | C25 | C26 | C27 | C28 | C212 | C214 |
|---|---|---|---|---|---|---|---|---|---|---|---|
| LC Host | N2 | N2 | N2 | N2 | N2 | N2 | N2 | N2 | N2 | N2 | N2 |
| RM | C0 | C1 | C2 | C3 | C4 | C5 | C6 | C7 | C8 | C12 | C14 |

Polymerizable Mixture Example B

Polymerizable mixtures are prepared by adding polymerizable compound $C_1$ of prior art or polymerizable compound 1 of Example 1, respectively, to nematic LC host mixtures N3 and N4 at a concentration of 0.3% by weight.

The composition of the polymerizable mixtures is shown in Table 2.

TABLE 2

Polymerizable mixture composition

| Mix. No. | C31 | C41 | P31 | P41 |
|---|---|---|---|---|
| LC Host | N3 | N4 | N3 | N4 |
| RM | C1 | C1 | 1 | 1 |

Use Example A

Polymerizable mixtures C10-C114 and C20-C214, which contain RM C0 of prior art with two different polymerizable groups or one of RMs C1-C14 of prior art without an alkoxy substituent, are compared with polymerizable mixtures P11-P114 and P21-C214, which contain one of RMs 1-14 according to the invention with an alkoxy substituent and two identical polymerizable groups.

Residual RM

The polymerization speed is measured by determining the residual content of residual, unpolymerized RM (in % by weight) in the mixture after UV exposure at a given intensity and lamp spectrum.

For this purpose the polymerizable mixtures are inserted into electrooptic test cells. The test cells comprise two soda-lime glass substrates with an ITO electrode layer of approx. 200 nm thickness and a VA-polyimide alignment layer (JALS-2096-R1) of approx. 30 nm thickness. The LC layer thickness is approx. 25 µm.

The test cells are irradiated with UV light having an intensity of 100 mW/cm$^2$ (metal halide lamp with a 320 nm cut-off filter) for the time indicated, causing polymerization of the RM.

The mixture is then rinsed out of the test cell using MEK (methyl ethyl ketone) and the residual amount of unreacted RM is measured by HPLC. The results are shown in Table 3.

TABLE 3

Residual monomer content

| Mixture | Residual RM (%) after Exposure Time (min) | | | | Mixture | Residual RM (%) after Exposure Time (min) | | |
|---|---|---|---|---|---|---|---|---|
| | 0 | 2 | 4 | 6 | | 0 | 2 | 6 |
| C10 | 0.300 | 0.247 | 0.160 | 0.081 | C20 | 0.300 | 0.204 | 0.059 |
| P11 | 0.300 | 0.192 | 0.107 | 0.044 | P21 | 0.300 | 0.136 | 0.034 |
| C11 | 0.300 | 0.264 | 0.203 | 0.173 | C21 | 0.300 | 0.185 | 0.067 |
| P12 | 0.300 | 0.201 | 0.149 | 0.121 | P22 | 0.300 | 0.168 | 0.057 |
| C12 | 0.300 | 0.275 | 0.209 | 0.153 | C22 | 0.300 | 0.210 | 0.069 |
| P13 | 0.300 | 0.238 | 0.165 | 0.103 | P23 | 0.300 | 0.197 | 0.091 |
| C13 | 0.300 | 0.283 | 0.231 | 0.190 | C23 | 0.300 | 0.223 | 0.123 |
| P14 | 0.300 | 0.121 | 0.103 | 0.077 | P24 | 0.300 | 0.105 | 0.030 |
| C14 | 0.300 | 0.265 | 0.160 | 0.091 | C24 | 0.300 | 0.176 | 0.055 |
| P15 | 0.300 | 0.266 | 0.200 | 0.155 | P25 | 0.300 | 0.196 | 0.100 |
| C15 | 0.300 | 0.286 | 0.264 | 0.230 | C25 | 0.300 | 0.229 | 0.134 |
| P16 | 0.300 | 0.245 | 0.195 | 0.148 | P26 | 0.300 | 0.188 | 0.079 |
| C16 | 0.300 | 0.276 | 0.241 | 0.225 | C26 | 0.300 | 0.214 | 0.108 |
| P17 | 0.300 | 0.256 | 0.177 | 0.138 | P27 | 0.300 | 0.198 | 0.080 |
| C17 | 0.300 | 0.296 | 0.222 | 0.197 | C27 | 0.300 | 0.215 | 0.110 |

TABLE 3-continued

Residual monomer content

| Mixture | Residual RM (%) after Exposure Time (min) | | | | Mixture | Residual RM (%) after Exposure Time (min) | | |
|---|---|---|---|---|---|---|---|---|
| | 0 | 2 | 4 | 6 | | 0 | 2 | 6 |
| P18 | 0.300 | 0.107 | 0.051 | 0.029 | P28 | 0.300 | 0.095 | 0.022 |
| C18 | 0.300 | 0.227 | 0.141 | 0.091 | C28 | 0.300 | 0.189 | 0.066 |
| P112 | 0.300 | 0.275 | 0.194 | 0.143 | P212 | 0.300 | 0.192 | 0.095 |
| P113 | 0.300 | 0.246 | 0.173 | 0.114 | P213 | 0.300 | 0.202 | 0.088 |
| C112 | 0.300 | 0.277 | 0.221 | 0.212 | C212 | 0.300 | 0.212 | 0.128 |
| P114 | 0.300 | 0.243 | 0.185 | 0.121 | P214 | 0.300 | 0.204 | 0.079 |
| C114 | 0.300 | 0.291 | 0.237 | 0.197 | C214 | 0.300 | 0.224 | 0.124 |

It can be seen that the polymerizable mixtures P11-P114 and P21-P214 containing alkoxy-substituted RMs 1-14 according to the present invention show a significantly faster polymerization and lower amount of residual RM, compared to corresponding polymerizable mixtures C10-C114 and C20-C214 containing RMs C0-C14 of prior art.

Tilt Angle Generation

For measuring the tilt angle generation the polymerizable mixtures are inserted into electrooptic test cells. The test cells comprise two soda-lime glass substrates with an ITO electrode layer of approx. 200 nm thickness and a VA-polyimide alignment layer (JALS-2096-R1) of approx. 30 nm thickness which is rubbed antiparallel. The LC-layer thickness d is approx. 6 μm.

The test cells are irradiated with UV light having an intensity of 100 mW/cm² (metal halide lamp with a 320 nm cut-off filter) for the time indicated, with application of a voltage of 24 $V_{RMS}$ (alternating current), causing polymerization of the RM.

The tilt angle is determined before and after UV irradiation by a crystal rotation experiment (Autronic-Melchers TBA-105). The results are shown in Table 4.

TABLE 4

Tilt angles

| Mixture | Tilt Angle (°) after Exposure Time (min) | | | Mixture | Tilt Angle (°) after Exposure Time (min) | | |
|---|---|---|---|---|---|---|---|
| | 0 | 2 | 6 | | 0 | 2 | 6 |
| C10 | 89.5 | 83.6 | 74.3 | P112 | 89.9 | 80.2 | 74.7 |
| P11 | 88.6 | 80.2 | 73.0 | P113 | 89.7 | 79.4 | 72 |
| C11 | 89.6 | 84.9 | 77.5 | C112 | 88.7 | 84.3 | 77.8 |
| P12 | 89.1 | 80.4 | 67.3 | P114 | 89.8 | 83.8 | 72.4 |
| C12 | 88.0 | 84.0 | 73.8 | C114 | 89.5 | 85.7 | 75.6 |
| P13 | 89.7 | 82.9 | 71.1 | | | | |
| C13 | 88.6 | 77.7 | 70.4 | | | | |
| P14 | 89.1 | 83.4 | 75.0 | | | | |
| C14 | 88.9 | 82.7 | 71.1 | | | | |
| P15 | 88.7 | 83.3 | 74.6 | | | | |
| C15 | 89.0 | 84.5 | 78.7 | | | | |
| P16 | 88.7 | 83.5 | 77.3 | | | | |
| C16 | 88.0 | 86.2 | 77.4 | | | | |
| P17 | 89.6 | 81.6 | 74.7 | | | | |
| C17 | 88.1 | 82.9 | 73.5 | | | | |
| P18 | 89.7 | 77.5 | 74.0 | | | | |
| C18 | 88.7 | 77.4 | 66.2 | | | | |
| C20 | 89.5 | 85.0 | 76.4 | P212 | 89.6 | 81.7 | 78.4 |
| P21 | 88.6 | 77.5 | 74.7 | P213 | 89.9 | 81.1 | 78.7 |
| C21 | 88.8 | 77.2 | 70.3 | C212 | 88.7 | 80.4 | 77.2 |
| P22 | 88.3 | 78.0 | 73.9 | P214 | 89.7 | 79.2 | 74.8 |
| C22 | 88.9 | 77.8 | 77.3 | C214 | 89.4 | 81.5 | 76.9 |
| P23 | 89.5 | 81.2 | 76.5 | | | | |
| C23 | 88.6 | 79.8 | 75.6 | | | | |
| P24 | 88.8 | 76.8 | 70.9 | | | | |
| C24 | 88.7 | | 71.8 | | | | |
| P25 | 88.4 | 81.3 | 77.4 | | | | |
| C25 | 88.9 | 81.1 | 77.9 | | | | |
| P26 | 88.5 | 81.0 | 76.6 | | | | |
| C26 | 88.8 | 81.5 | 73.9 | | | | |
| P27 | 88.8 | 77.7 | 72.9 | | | | |
| C27 | 88.2 | 77.6 | 73.3 | | | | |
| P28 | 89.3 | 81.7 | 80.9 | | | | |
| C28 | 88.5 | 78.2 | 74.5 | | | | |

It can be seen that polymerizable mixtures P11-P114 and P21-P214 containing alkoxy-substituted RMs 1-14 according to the present invention show a tilt angle generation that is in most cases comparable to, and in some even stronger and faster than, that of corresponding polymerizable mixtures C10-C114 and C20-C214 containing RMs C0-C14 of prior art.

Voltage Holding Ratio (VHR)

For measuring the VHR the polymerizable mixtures are inserted into electrooptic test cells. The test cells comprise two AF glass substrates with an ITO electrode layer of approx. 20 nm thickness and a VA-polyimide alignment layer (PI-4) of approx. 100 nm thickness. The LC layer thickness is approx. 4 μm.

The VHR is measured at 100° C. with application of a voltage of 1 V/60 Hz. For the sun-test the test cells are irradiated at 20° C. for 2 h with light having an intensity of 750 W/m² using a CPs/CPS+ type lamp. For the UV test the test cells are irradiated for 10 min with UV light having an intensity of 100 mW/cm² (metal halide lamp with a 320 nm cut-off filter).

The results are shown in Table 5.

TABLE 5

VHR values

| Mixture | VHR (%) | | Mixture | VHR (%) | | |
|---|---|---|---|---|---|---|
| | no illumination | Suntest | | no illumination | Suntest | UV Test |
| C10 | 99.2 | 97.7 | C20 | 98.8 | 45.2 | 33.1 |
| P11 | 98.7 | 98.3 | P21 | 97.5 | 73.0 | 76.8 |
| C11 | 98.2 | 97.6 | C21 | 98.3 | 85.6 | 74.8 |
| P12 | 98.6 | 97.5 | P22 | 81.2 | 84.1 | 70.1 |
| C12 | 99.3 | 99.2 | C22 | 98.7 | 91.7 | 86.8 |
| P13 | 99.2 | 98.8 | P23 | 98.7 | 93.7 | 90.8 |
| C13 | 98.2 | 98.2 | C23 | 98.4 | 89.6 | 88.6 |
| P14 | 97.4 | 98.1 | P24 | 96.4 | 91.9 | 93.4 |
| C14 | 99.2 | 99.3 | C24 | 98.8 | 97.4 | 96.5 |
| P15 | 98.0 | 98.2 | P25 | 98.5 | 91.1 | 87.7 |
| C15 | 99.1 | 98.7 | C25 | 98.4 | 90.5 | 88.9 |
| P16 | 98.8 | 98.2 | P26 | 97.2 | 72.7 | 81.7 |
| C16 | 98.9 | 98.1 | C26 | 97.9 | 84.9 | 78.3 |
| P17 | 98.5 | 98.1 | P27 | 97.6 | 89.8 | 90.4 |
| C17 | 98.6 | 98.8 | C27 | 97.2 | 94.3 | 94.1 |
| P18 | 99.1 | 98.5 | P28 | 98.7 | 68.9 | 61.0 |
| C18 | 98.8 | 98.0 | C28 | 98.3 | 89.8 | 83.5 |
| P112 | 99.1 | 98.6 | P212 | 98.8 | 92.0 | 89.5 |
| P113 | 99.1 | 98.4 | P213 | 98.7 | 91.5 | 88.7 |
| C112 | 99.1 | 98.8 | C212 | 99.0 | 93.1 | 92.4 |
| P114 | 98.5 | 98.2 | P214 | 97.8 | 89.1 | 81.9 |
| C114 | 98.9 | 98.6 | C214 | 98.4 | 91.4 | 86.9 |

It can be seen that polymerizable mixtures P11-P114 and P21-P214 containing alkoxy-substituted RMs 1-14 according to the present invention invention show a VHR after suntest or UV test that is in most cases comparable to, and in some even higher than, that of corresponding polymerizable mixtures C10-C114 and C20-C214 containing RMs C0-C14 of prior art.

Use Example B

Polymerizable mixtures C31 and D41, which contain RM C1 of to prior art without an alkoxy substituent, are compared with polymerizable mixtures P31 and P41, which contain the RM 1 according to the present invention having an alkoxy substituent.

Residual RM

The polymerization speed is measured by determining the residual content of residual, unpolymerized RM (in % by weight) in the mixture after UV exposure at a given intensity and lamp spectrum as described in Use Example A, but using a UV intensity of 3.5 mW/cm$^2$/UV C-type lamp).

The results are shown in Table 6.

TABLE 6

Residual monomer content

| Mixture | Residual RM (%) after Exposure Time (min) | |
| --- | --- | --- |
| | 0 | 10 |
| C31 | 0.300 | 0.114 |
| P31 | 0.300 | 0.046 |
| C41 | 0.300 | 0.038 |
| P41 | 0.300 | 0.012 |

It can be seen that polymerizable mixtures P31 and P41 containing alkoxy-substituted RM1 according to the present invention show a significantly faster polymerization and lower amount of residual RM, compared to polymerizable mixtures C31 and C41 containing RM C1 of prior art.

In conclusion, the use examples demonstrate that the polymerizable compounds and polymerizable mixtures according to the present invention show in particular a quick polymerization with low amount of residual RM, while maintaining sufficient pretilt angle generation and sufficient VHR values after suntest or UV exposure for display applications.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A liquid crystalline medium comprising one or more compounds of formulae I1-3-1, I1-3-2, I1-4-1 or I1-4-2

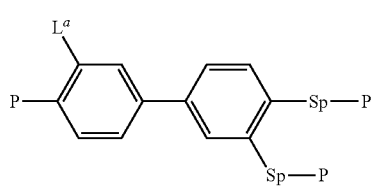

I1-3-1

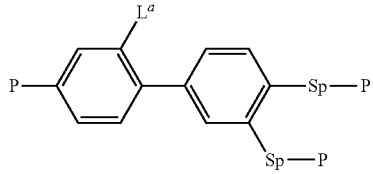

I1-3-2

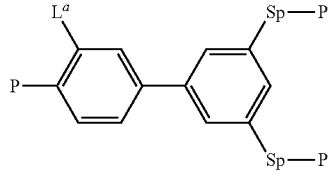

I1-4-1

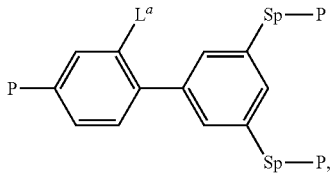

I1-4-2 wherein L$^a$ is a straight-chain alkoxy group with 1 to 12 C atoms or a branched alkoxy group with 3 to 12 atoms, and is optionally fluorinated, P denotes acrylate or methacrylate, and all groups P that are present have the same meaning, Sp, is —(CH$_2$)$_{p2}$—O—, —(CH$_2$)$_{p2}$—O—, —(CH$_2$)$_{p2}$—CO—O—, or —(CH$_2$)$_{p2}$—O—CO—, wherein p2 is 2, 3, 4, 5 or 6, and the O-atom or the CO-group, respectively, is connected to the aromatic ring, one or more compounds of the formulae CY and/or PY:

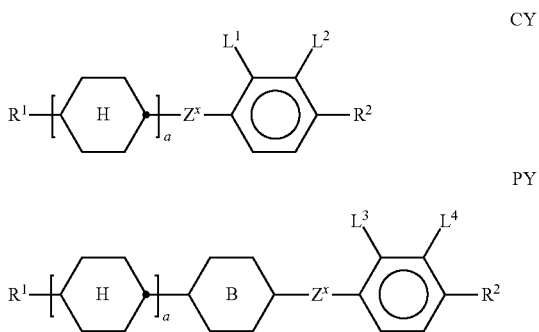

in which the individual radicals have the following meanings:

a denotes 1 or 2, b denotes 0 or 1,

denotes

<img: benzene ring with bonds> or <img: benzene ring with L³, L⁴ substituents>

R¹ and R² each, independently of one another, denote alkyl having 1 to 12 C atoms, where, in addition, one or two non-adjacent CH₂ groups may be replaced by —O—, —CH=CH—, —CO—, —O—CO— or —CO—O— in such a way that 0 atoms are not linked directly to one another, $Z^X$ denotes —CH=CH—, —CH₂O—, —OCH₂—, —CF₂O—, —OCF₂—, —O—, —CH₂—, —CH₂CH₂— or a single bond, $L^{1-4}$ each, independently of one another, denote F, Cl, OCF₃, CF₃, CH₃, CH₂F, CHF₂ and one or more compounds of formulae AN1 or ZK1:

alkyl—[H]—[H]—alkenyl    AN1 in which alkyl denotes a straight-chain alkyl radical having 1-6 C atoms, and alkenyl denotes a straight-chain alkenyl radical having 2-7 C atoms, alkyl—[H]—[H]—alkyl*    ZK1 in which alkyl and alkyl* each, independently of one another, denote a straight-chain alkyl radical having 1-6 C atoms.

2. The liquid crystalline medium according to claim 1, further comprising one or more additional compounds of the following formulae:

$R^{A1}$—[X]ₓ—[Y]—$R^{A2}$    AN or $R^{A1}$—[X]—[Z]_z—$Z^x$—[ring with L¹, L²]—$R^{A2}$    AY in which the individual radicals, on each occurrence identically or differently, each, independently of one another, have the following meaning:

[X] is

[H], [benzene], [pyran-O], [pyran-O], [cyclohexene] or [cyclohexene],

[Y] is

[H], [benzene], [pyran-O], [pyran-O], [cyclohexene] or [cyclohexene],

[Z] is

[H], [benzene], [pyran-O], [pyran-O], [cyclohexene], [cyclohexene] or [benzene with L³, L⁴]

$R^{41}$ is alkenyl having 2 to 9 C atoms or, if at least one of the rings X, Y and Z denotes cyclohexenyl, also one of the meanings of $R^{42}$, $R^{42}$ is alkyl having 1 to 12 C atoms, in which, in addition, one or two non-adjacent $CH_2$ groups may be replaced by —O—, —CH=CH—, —CO—, —OCO— or —COO— in such a way that 0 atoms are not linked directly to one another, $Z^x$ is —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH=CH—$CH_2O$—, or a single bond, $L^{1-4}$ each, independently of one another, are H, F, Cl, $OCF_3$, $CF_3$, $CH_3$, $CH_2F$ or $CHF_2H$, x is 1 or 2, z is 0 or 1.

3. The liquid crystalline medium according to claim 1, further comprising one or more additional compounds of the following formula:

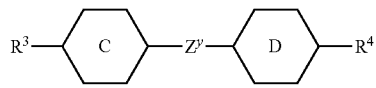

in which the individual radicals have the following meanings:

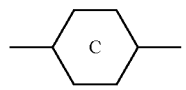

denotes

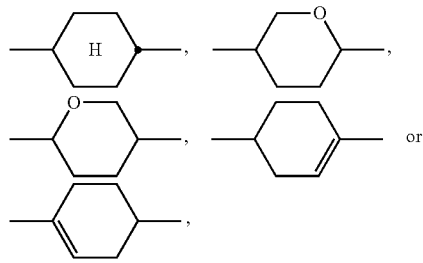

denotes

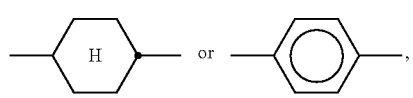

$R^3$ and $R^4$ each, independently of one another, denote alkyl having 1 to 12 C atoms, in which, in addition, one or two non-adjacent $CH_2$ groups may be replaced by —O—, —CH=CH—, —CO—, —O—CO— or —CO—O— in such a way that 0 atoms are not linked directly to one another, $Z^Y$ denotes —$CH_2CH_2$—, —CH=CH—, —$CF_2O$—, —$OCF_2$—, —$CH_2O$—, —$OCH_2$—, —COO—, —OCO—, —$C_2F_4$—, —CF=CF— or a single bond.

4. The liquid crystalline medium according to claim 1, wherein the polymerizable compounds of formula I1-3-1, I1-3-2, I1-4-1 or I1-4-2 are polymerized.

5. A process of preparing an liquid crystalline medium of claim 1, comprising mixing one or more mesogenic or liquid-crystalline compounds with one or more compounds of formula I1-3-1, I1-3-2, I1-4-1 or I1-4-2 and optionally with further liquid-crystalline compounds and/or additives.

6. A liquid crystalline display comprising a liquid crystalline medium as defined in claim 1.

7. The liquid crystalline display of claim 6, which is a PSA display.

8. The liquid crystalline display of claim 7, which is a PS-VA, PS-OCB, PS-IPS, PS-FFS, PS-UB-FFS, PS-poli-VA or PS-TN display.

9. A liquid crystalline display of comprising two substrates, at least one which is transparent to light, an electrode provided on each substrate or two electrodes provided on only one of the substrates, and located between the substrates a layer of an liquid crystalline medium according to claim 1, wherein the polymerizable compounds are polymerized between the substrates of the display.

10. A process for the production of a liquid crystalline display according to claim 9, comprising providing the liquid crystalline medium comprising one or more polymerizable compounds between the substrates of the display, and polymerizing the polymerizable compounds.

11. A process for preparing a compound of formula

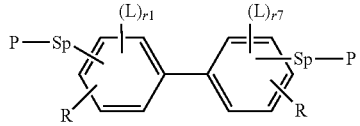

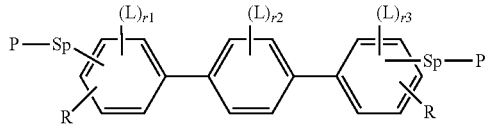

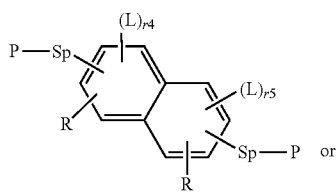

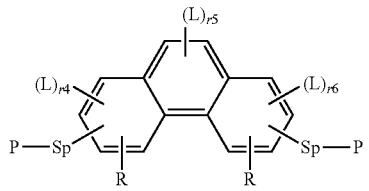

by esterification of a compound of the formula

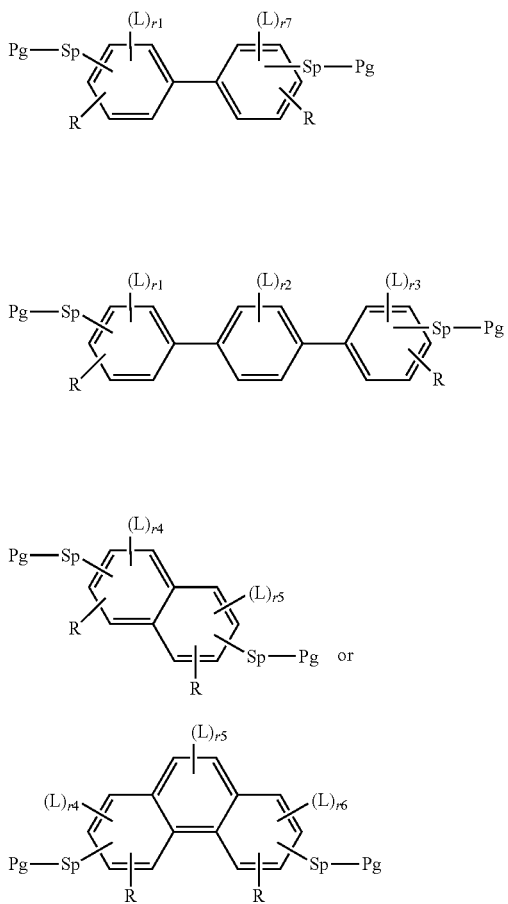

wherein

L is on each occurrence identically or differently F, Cl, —CN, P—Sp—, or straight chain alkyl having 1 to 25 C atoms, or branched or cyclic alkyl having 3 to 25 C atoms, wherein one or more non-adjacent CH$_2$-groups are optionally replaced by —O—, —S—, —CO—, —CO—O—, —O—CO—O—CO—O— in such a manner that O- and/or S-atoms are not directly connected with each other, and wherein one or more H atoms are each optionally replaced by F or Cl, or L has the meaning of L$^a$, Sp is a spacer group that is optionally substituted by one or more groups P, or a single bond, P is a polymerizable group, r1, r3, r7 are independently of each other 0, 1, 2 or 3, r2 is 0, 1, 2, 3 or 4, r4, r5, r6 are independently of each other 0, 1 or 2, with r1+r7≥1, r1+r2+r3 1, r4+r5 1, r1+r3+r4 1, R denotes H, and Pg denotes OH, and wherein one R is H and one R is Sp-Pg, or one Sp group is substituted by one or more Pg groups such that Sp-Pg corresponds to Sp(Pg), with s being ≥2, using corresponding acids, acid derivatives, or halogenated compounds containing a group P, in the presence of a dehydrating reagent.

12. A liquid crystalline medium comprising one or more polymerizable compounds of formula I1-4

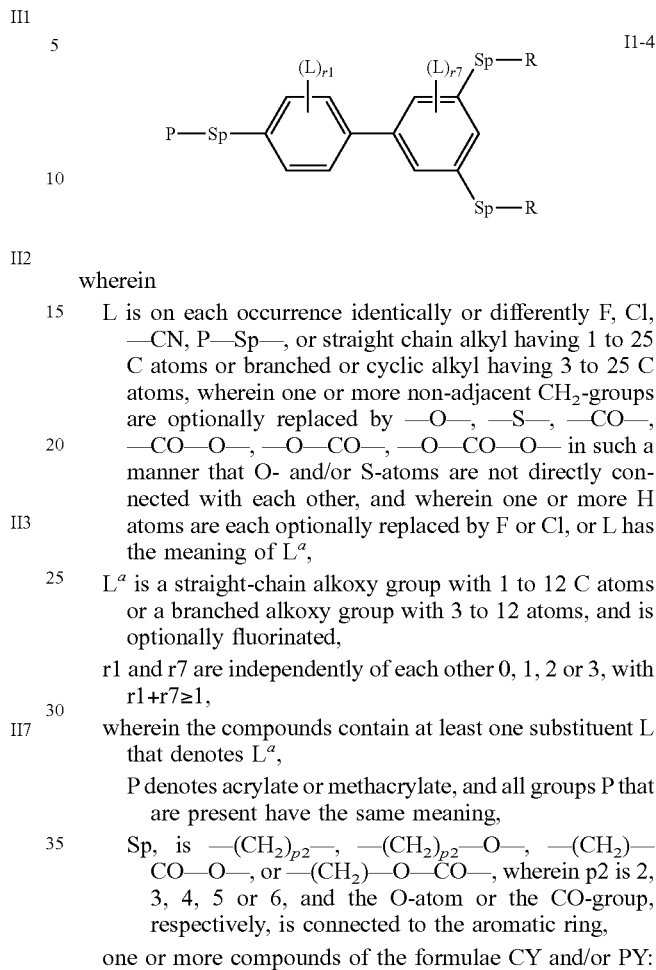

wherein

L is on each occurrence identically or differently F, Cl, —CN, P—Sp—, or straight chain alkyl having 1 to 25 C atoms or branched or cyclic alkyl having 3 to 25 C atoms, wherein one or more non-adjacent CH$_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F or Cl, or L has the meaning of L$^a$, L$^a$ is a straight-chain alkoxy group with 1 to 12 C atoms or a branched alkoxy group with 3 to 12 atoms, and is optionally fluorinated, r1 and r7 are independently of each other 0, 1, 2 or 3, with r1+r7≥1, wherein the compounds contain at least one substituent L that denotes L$^a$, P denotes acrylate or methacrylate, and all groups P that are present have the same meaning, Sp, is —(CH$_2$)$_{p2}$—, —(CH$_2$)$_{p2}$—O—, —(CH$_2$)—CO—O—, or —(CH$_2$)—O—CO—, wherein p2 is 2, 3, 4, 5 or 6, and the O-atom or the CO-group, respectively, is connected to the aromatic ring, one or more compounds of the formulae CY and/or PY:

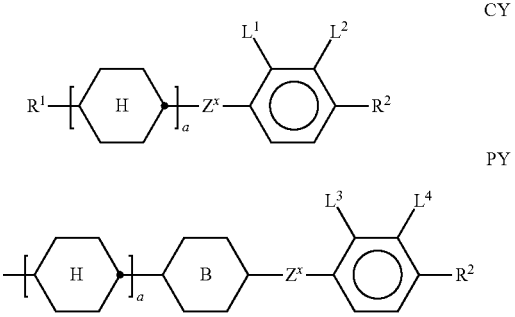

in which the individual radicals have the following meanings:

a denotes 1 or 2, b denotes 0 or 1,

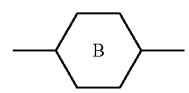

denotes

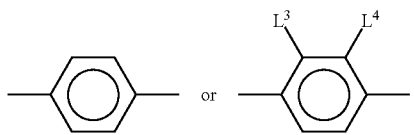

R¹ and R² each, independently of one another, denote alkyl having 1 to 12 C atoms, where, in addition, one or two non-adjacent CH₂ groups may be replaced by —O—, —CH=CH—, —CO—, —O—CO— or —CO—O— in such a way that O atoms are not linked directly to one another, $Z^X$ denotes —CH=CH—, —CH₂O—, —OCH₂—, —CF₂O—, —OCF₂—, —O—, —CH₂—, —CH₂CH₂— or a single bond, $L^{1-4}$ each, independently of one another, denote F, Cl, OCF₃, CF₃, CH₃, CH₂F, CHF₂ and one or more compounds of formulae AN1 or ZK1:

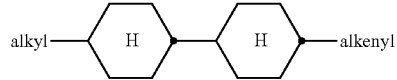

in which alkyl denotes a straight-chain alkyl radical having 1-6 C atoms, and alkenyl denotes a straight-chain alkenyl radical having 2-7 C atoms,

in which alkyl and alkyl* each, independently of one another, denote a straight-chain alkyl radical having 1-6 C atoms.

* * * * *